(12) United States Patent
Soriani et al.

(10) Patent No.: US 10,279,026 B2
(45) Date of Patent: May 7, 2019

(54) ANTIGENS AND ANTIGEN COMBINATIONS

(71) Applicant: GlaxoSmithKline Biologicals SA, Rixensart (BE)

(72) Inventors: Marco Soriani, Siena (IT); Maria Scarselli, Siena (IT); Nathalie Norais, Rapolano Terme (IT); Danilo Gomes Moriel, Brisbane (AU); Silvia Rossi Paccani, Murlo (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 24 days.

(21) Appl. No.: 14/396,881

(22) PCT Filed: Apr. 24, 2013

(86) PCT No.: PCT/EP2013/058459
§ 371 (c)(1),
(2) Date: Oct. 24, 2014

(87) PCT Pub. No.: WO2013/160335
PCT Pub. Date: Oct. 31, 2013

(65) Prior Publication Data
US 2015/0202279 A1    Jul. 23, 2015

(30) Foreign Application Priority Data

Apr. 26, 2012  (GB) .................................. 1207385.4
Dec. 21, 2012  (EP) .................................... 12199079

(51) Int. Cl.
| | | |
|---|---|---|
| A61K 39/102 | (2006.01) | |
| A61K 39/095 | (2006.01) | |
| C07K 14/285 | (2006.01) | |
| A61K 39/02 | (2006.01) | |
| C12R 1/21 | (2006.01) | |
| A61K 39/00 | (2006.01) | |

(52) U.S. Cl.
CPC .......... A61K 39/102 (2013.01); A61K 39/095 (2013.01); A61K 39/099 (2013.01); C07K 14/285 (2013.01); C12R 1/21 (2013.01); A61K 2039/55505 (2013.01); A61K 2039/55566 (2013.01); Y02A 50/466 (2018.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,057,540 A | 10/1991 | Kensil et al. | |
| 5,707,829 A | 1/1998 | Jacobs et al. | |
| 5,916,588 A | 6/1999 | Popescu et al. | |
| 6,090,406 A | 7/2000 | Popescu et al. | |
| 6,207,646 B1 | 3/2001 | Krieg et al. | |
| 6,239,116 B1 | 5/2001 | Krieg et al. | |
| 6,429,199 B1 | 8/2002 | Krieg et al. | |
| 7,749,518 B2* | 7/2010 | Masignani | A61K 39/102 424/185.1 |
| 9,943,584 B2* | 4/2018 | Dunkley | A61K 9/20 |

FOREIGN PATENT DOCUMENTS

| | | |
|---|---|---|
| EP | 0372501 A2 | 6/1990 |
| EP | 0378881 B1 | 6/1993 |
| EP | 0427347 B1 | 2/1995 |
| EP | 0471177 B1 | 10/1995 |
| EP | 0735898 A1 | 10/1996 |
| EP | 0761231 A1 | 3/1997 |
| EP | 0835318 A2 | 4/1998 |
| EP | 0626169 B1 | 7/1999 |
| GB | 2276169 A | 9/1994 |
| WO | WO-90/14837 A1 | 12/1990 |
| WO | WO-91/01146 A1 | 2/1991 |
| WO | WO-93/17712 A2 | 9/1993 |
| WO | WO-94/00153 A1 | 1/1994 |
| WO | WO-94/03208 A1 | 2/1994 |
| WO | WO-98/40100 A1 | 9/1998 |
| WO | WO-98/57659 A1 | 12/1998 |
| WO | WO-98/58668 A2 | 12/1998 |
| WO | WO-99/11241 A1 | 3/1999 |
| WO | WO-99/27960 A1 | 6/1999 |
| WO | WO-99/40936 A2 | 8/1999 |
| WO | WO-99/44636 A2 | 9/1999 |
| WO | WO-99/52549 A1 | 10/1999 |
| WO | WO-00/55191 A2 | 9/2000 |
| WO | WO-00/56360 A2 | 9/2000 |
| WO | WO-00/61761 A2 | 10/2000 |
| WO | WO-01/72337 A1 | 10/2001 |
| WO | WO-02/24729 A2 | 3/2002 |
| WO | WO-02/28889 A2 | 4/2002 |
| WO | WO-02/34771 A2 | 5/2002 |
| WO | WO-2002/062378 A2 | 8/2002 |
| WO | WO-03/024480 A2 | 3/2003 |
| WO | WO-03/024481 A2 | 3/2003 |
| WO | WO-2005/111066 A2 | 11/2005 |
| WO | WO-2006/110603 A1 | 10/2006 |
| WO | WO-2010/092176 A2 | 8/2010 |

OTHER PUBLICATIONS

Patist A1, Zoerb H. Colloids Surf B Biointerfaces. Feb. 10, 2005;40(2):107-13.*
Beignon et al. (2002) "The LTR72 mutant of heat-labile enterotoxin of *Escherichia coli* enhances the ability of peptide antigens to elicit CD4(+) T cells and secrete gamma interferon after coapplication onto bare skin." Infect Immun 70:3012-3019.
Bernadac A., et al. (1998) "*Escherichia coli* tol-pal mutants form outer membrane vesicles." Journal of Bacteriology 180 (18):4872-4878.

(Continued)

Primary Examiner — Jana A Hines
Assistant Examiner — Khatol S Shahnan Shah
(74) Attorney, Agent, or Firm — Birch, Stewart, Kolasch & Birch, LLP

(57) ABSTRACT

NTHI protein antigens have been identified and found to be conserved across several *Haemophilus influenzae* pathogenic strains. They have been isolated, cloned from a reference strain and tested for immunogenicity. Methods for immunization and vaccines derived thereof are also disclosed.

9 Claims, 5 Drawing Sheets
Specification includes a Sequence Listing.

(56) References Cited

OTHER PUBLICATIONS

Brandt et al. (2006) "Evaluation of anti-pneumococcal capsular antibodies as adjunctive therapy in experimental pneumococcal meningitis." J Antimicrob Chemother. 58(6):1291-4.

Brusic et al. (1998) "Prediction of MHC class II-binding peptides using an evolutionary algorithm and artificial neural network." Bioinformatics 14(2):121-30.

Bublil et al. (2007) "Stepwise prediction of conformational discontinuous B-cell epitopes using the Mapitope algorithm." Proteins 68(1):294-304.

Carter (1994) "Epitope mapping of a protein using the Geysen (PEPSCAN) procedure." Methods Mol Biol 36:207-23.

Chanyangam M. et al., (1991) "Contribution of a 28-kilodalton membrane protein to the virulence of Haemophilus influenzae." Infection and Immunity, vol. 59 (2), 600-608.

Cheeseman M. T. et al. (2011) "HIF-VEGF pathways are critical for chronic otitis media in Junbo and Jeff mouse mutants." PLoS Genetics 7 (10):e1002336.

Chen et al. (2007) "Prediction of linear B-cell epitopes using amino acid pair antigenicity scale." Amino Acids 33(3):423-8.

Davenport et al. (1995) "An empirical method for the prediction of T-cell epitopes." Immunogenetics 42:392-297.

Ercoli, et al. (2015) "LytM proteins play a crucial role in cell separation, outer membrane composition, and pathogenesis in nontypeable Haemophilus influenzae." MBio. 6(2):e02575.

Feller & de la Cruz (1991) "Identifying antigenic T-cell sites." Nature 349(6311):720-1.

Ferretti et al. (2001) "Complete genome sequence of an M1 strain of *Streptococcus pyogenes*." PNAS USA 98: 4658-4663.

Fleischmann et al. (1995) "Whole-genome random sequencing and assembly of Haemophilus influenzae Rd." Science 269:496-512.

Gerber et al. (2001) "Human papillomavirus virus-like particles are efficient oral immunogens when coadministered with *Escherichia coli* heat-labile enterotoxin mutant R192G or CpG DNA." J Virol 75:4752-4760.

Geysen et al. (1984) "Use of peptide synthesis to probe viral antigens for epitopes to a resolution of a single amino acid." PNAS USA 81:3998-4002.

Gustafsson et al. (1996) "A controlled trial of a two-component acellular, a five-component acellular, and a whole-cell pertussis vaccine." N. Engl. J. Med. 334:349-355.

Hallstrom T et al. (2009) "Nontypeable Haemophilus influenzae protein E binds vitronectin and is important for serum resistance." J Immunol. 183(4):2593-601.

Hogg et al. (2007) "Characterization and modeling of the Haemophilus influenzae core and supragenomes based on the complete genomic sequences of Rd and 12 clinical nontypeable strains." Genome Biology 8:R103.

Hopp (1993) "Retrospective: 12 years of antigenic determinant predictions, and more." Peptide Research 6:183-190.

Huston et al., (1988) "Protein engineering of antibody binding sites: recovery of specific activity in an anti-digoxin single-chain Fv analogue produced in *Escherichia coli*." Proc. Natl. Acad. Sci. U.S.A. 85:5879-83.

Inbar et al., (1972) "Localization of antibody-combining sites within the variable portions of heavy and light chains." Proc. Natl. Acad. Sci. U.S.A. 69:2659-62.

Jameson, B A et al. (1988) "The antigenic index: a novel algorithm for predicting antigenic determinants." CABIOS 4(1):181-186.

Jedrzejas (2001) "Pneumococcal virulence factors: structure and function." Microbiol Mol Biol Rev 65:187-207.

Kuroda et al. (2001) "Whole genome sequencing of meticillin-resistant *Staphylococcus aureus*." Lancet 357(9264):1225-1240; see also pp. 1218-1219.

Kwok et al. (2001) "Rapid epitope identification from complex class-II-restricted T-cell antigens." Trends Immunol 22:583-88.

Kyd J M et al. (1998) "Potential of a novel protein, OMP26, from nontypeable Haemophilus influenzae to enhance pulmonary clearance in a rat model." Infect Immun. 66(5):2272-8.

Li et al. (2003) "Identification and characterization of genomic loci unique to the Brazilian purpuric fever clonal group of H. influenzae biogroup aegyptius: functionality explored using meningococcal homology." Mol Microbiol 47:1101-1111.

Loosmore S M et al. (1998) "The Haemophilus influenzae HtrA protein is a protective antigen." Infect Immun. 66(3):899-906.

Lundstrom et al. (2008) "Structural analysis of the lipopolysaccharide from nontypeable Haemophilus influenzae strain R2846." Biochemistry, 47 (22):6025-38.

Maksyutov & Zagrebelnaya (1993) "ADEPT: a computer program for prediction of protein antigenic determinants." Comput Appl Biosci 9(3):291-7.

Mason et al. (2003) "Nontypeable Haemophilus influenzae gene expression induced in vivo in a chinchilla model of otitis media." Infect Immun 71:3454-3462.

McCluskie et al. (2002) "Parenteral and mucosal prime-boost immunization strategies in mice with hepatitis B surface antigen and CpG DNA." FEMS Immunology and Medical Microbiology 32:179-185.

Meister et al. (1995) "Two novel T cell epitope prediction algorithms based on MHC-binding motifs; comparison of predicted and published epitopes from *Mycobacterium tuberculosis* and HIV protein sequences." Vaccine 13(6):581-91.

Munson R.S.; Granoff D.M (1985) "Purification and partial characterization of outer membrane proteins P5 and P6 from Haemophilus influenzae type b." Infection and Immunity 49 (3):544-549.

Murphy et al. (2009) "Current and Future Prospects for a Vaccine for Nontypeable Haemophilus influenzae." Current Infectious Disease report, 11:177-182.

Niikura et al. (2002) "Chimeric recombinant hepatitis E virus-like particles as an oral vaccine vehicle presenting foreign epitopes." Virology 293:273-280.

Ogunniyi et al. (2001) "Protection against *Streptococcus pneumoniae* elicited by immunization with pneumolysin and CbpA." Infect Immun 69:5997-6003.

Pinto et al. (2003) "Cellular immune responses to human papillomavirus (HPV)-16 L1 in healthy volunteers immunized with recombinant HPV-16 L1 virus-like particles." J Infect Dis 188:327-338.

Poggio, et al. (2010) "A protein critical for cell constriction in the Gram-negative bacterium Caulobacter crescentus localizes at the division site through its peptidoglycan-binding LysM domains." Mol Microbiol. 77(1):74-89.

Ronander, et al. (2009) "Nontypeable Haemophilus influenzae adhesin protein E: characterization and biological activity." The Journal of Infectious Diseases 199(4):522-531.

Ryan et al. (1999) "Mutants of *Escherichia coli* heat-labile toxin act as effective mucosal adjuvants for nasal delivery of an acellular pertussis vaccine: differential effects of the nontoxic AB complex and enzyme activity on Th1 and Th2 cells." Infect Immun 67:6270-6280.

Scharton-Kersten et al. (2000) "Transcutaneous immunization with bacterial ADP-ribosylating exotoxins, subunits, and unrelated adjuvants." Infect Immun 68:5306-5313.

Tong et al. (2007) "Methods and protocols for prediction of immunogenic epitopes." Brief Bioinform. 8(2):96-108.

Tsurui & Takahashi (2007) "Prediction of T-cell epitope." J Pharmacol Sci. 105(4):299-316.

Uehara T. et al., (2010) "Daughter cell separation is controlled by cytokinetic ring-activated cell wall hydrolysis." The EMBO Journal, 29(8):1412-1422.

Webb DC et al. (2007) "Investigation of the potential of a 48 kDa protein as a vaccine candidate for infection against nontypable Haemophilus influenzae." Vaccine; 25(20):4012-9.

Welling et al. (1985) "Prediction of sequential antigenic regions in proteins." FEBS Lett. 188:215-218.

Zwijnenburg et al. (2001) "Experimental pneumococcal meningitis in mice: a model of intranasal infection." J Infect Dis 183:1143-6.

Yi et al. (Jan. 1997) "Importance of an Immunodominant Surface-Exposed Loop on Outer Membrane Protein P2 of Nontypeable *Haemophilus influenzae*." Infect Immun 65(1):150-155.

\* cited by examiner

SEQUENCE LISTING

<160> NUMBER OF SEQ ID NOS: 131

<210> SEQ ID NO 1
<211> LENGTH: 277
<212> TYPE: PRT
<213> ORGANISM: Unknown

<220> FEATURE:
<223> OTHER INFORMATION: Description of Unknown:
      Bacteria <Prokaryote> sequence
<220> FEATURE:
<223> OTHER INFORMATION: NT018

<400> SEQUENCE: 1

```
Lys His Gly Gln Lys Arg Asp Asp Leu Asn Lys Ala Leu Tyr Phe Ser
1               5                   10                  15

Arg Leu Glu Glu Ile Glu Gln Asp Asn Ser Gln Gly Leu Val Glu Asn
            20                  25                  30

Val Glu Gln Leu Lys Gln Glu Leu Gln Lys Thr Leu Leu Asp Asp Val
        35                  40                  45

Pro Ser Lys Val Gln Glu Asn Val Asp Tyr Ser Gly Lys Ser Tyr Gly
    50                  55                  60

Lys Ile Trp Phe Val Ser Gly Val Leu Ala Leu Gly Ile Ile Ala Gly
65                  70                  75                  80

Ser Ser Tyr Phe Met Val Gly Ser Trp Gln Ala Glu Ser Met Leu Glu
                85                  90                  95

Gln Thr Tyr Ala Lys Leu Pro Tyr Phe Phe Asp Arg Met Lys Asp Glu
            100                 105                 110

Asp Lys Asn Pro Phe Ser Asp Ala Glu Met Gln Gln Phe Ser Ile Ala
        115                 120                 125

Leu Arg Ile Asp Leu Gln Lys Asn Pro Thr Asp Ala Lys Lys Trp Trp
    130                 135                 140

Met Leu Gly Gln Ile Gly Met Asn Leu Gly Asp Ala Arg Leu Ala Phe
145                 150                 155                 160

Asp Ser Tyr Gln Lys Ala Asn Lys Leu Glu Pro Asp Asn Val Gln Tyr
                165                 170                 175

Lys Leu Gly Tyr Ala Arg Ile Leu Met Phe Ser Glu Asp Ala Thr Asp
            180                 185                 190

Lys Leu Lys Gly Gly Asn Leu Leu Arg Glu Val Ile Arg Gln Glu His
        195                 200                 205

Thr Asn Ile Glu Ala Leu Ser Leu Leu Ala Phe Arg Tyr Phe Glu Thr
    210                 215                 220

Glu Asp Tyr Lys Met Ala Ala Val Thr Trp Ala Met Met Leu Arg Leu
225                 230                 235                 240

Met Pro Lys Asp Asp Glu Arg Val Pro Leu Ile Glu Lys Ser Ile Arg
                245                 250                 255

Thr Ala Arg Asp Ala Leu Glu Ala Gln Asn Glu Glu Lys Ser Lys Ser
            260                 265                 270

Ile Thr Pro Glu Lys
        275
```

<210> SEQ ID NO 2
<211> LENGTH: 160
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT024

```
<400> SEQUENCE: 2

Met Lys Thr Ile Asp Ile Thr Ala Asn Ser Lys Met Asp Asp Gln Ala
1               5                   10                  15

Arg Met Asn Leu Ala Gln Glu Phe Ala Asn Lys Gln Gln Trp Ser Ser
            20                  25                  30

Val Phe Asp Ile Met Tyr Pro Met Ala Leu Glu Gly Asn Thr Thr Ala
        35                  40                  45

Gln Ser Asn Leu Gly Met Leu Tyr Asn Leu Gly Arg Gly Thr Val Arg
    50                  55                  60

Asp Tyr Glu Lys Ala Tyr Trp Trp Phe Ser Glu Ala Ala Glu Lys Gly
65                  70                  75                  80

Ser Val Lys Gly Leu Asn Asn Leu Gly Val Met Tyr Leu Arg Gly Asp
                85                  90                  95

Tyr Val Lys Gln Asn Thr Glu Gln Ala Ile Lys Leu Phe Glu Arg Thr
                100                 105                 110

Ala Arg Ala Lys Asp Thr Asp Ala Met Met Met Leu Ser Asn Ile Tyr
                115                 120                 125

Arg Leu Gln Asn Gln Pro Glu Lys Ser Leu Glu Trp Leu Lys Lys Ala
    130                 135                 140

Ala Glu Leu Gly Asn Lys Glu Ala Lys Gln Arg Leu Ser Ser Gln Pro
145                 150                 155                 160

<210> SEQ ID NO 3
<211> LENGTH: 102
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT032

<400> SEQUENCE: 3

Gly Phe Asn Gly Asn Asn Ser Gln Gly Gly Phe Gln Gln Thr Ala Pro
1               5                   10                  15

Ala Ala Ile Ser Val Lys Gln Ala Leu Ser Ala Ala Asp Asn Ser Met
            20                  25                  30

Ile Thr Leu Val Gly Asn Ile Thr Gln Gln Ile Asp Asp Asp Glu Phe
        35                  40                  45

Trp Phe Thr Asp Gly Thr Gly Gln Ile Lys Ile Glu Ile Lys Lys Arg
    50                  55                  60

Val Trp Asn Gly Leu Asn Val Asp Ser Lys Asp Lys Val Lys Ile Tyr
65                  70                  75                  80

Gly Lys Leu Asp Asn Glu Ala Phe Glu Lys Ala Glu Leu Asp Val Leu
                85                  90                  95

Arg Val Glu Lys Ala Glu
            100

<210> SEQ ID NO 4
<211> LENGTH: 259
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT038
```

<400> SEQUENCE: 4

```
Lys Gln Asp Gly Ser Ala Asp Met Asp Lys Val Lys Asn Gly Glu
1               5                   10                  15
Leu Val Lys Thr Lys Val Lys Leu Val Ser Ala Asn Gly Thr Asn Pro
            20                  25                  30
Val Lys Ile Ser Asn Val Ala Glu Gly Thr Glu Asp Thr Asp Ala Val
            35                  40                  45
Ser Phe Lys Gln Leu Lys Ala Leu Gln Asn Lys Gln Val Thr Leu Ser
        50                  55                  60
Ala Ser Asn Ala Tyr Ala Asn Gly Gly Ser Asp Ala Asp Val Gly Lys
65                  70                  75                  80
Val Thr Gln Thr Leu Ser Asn Gly Leu Asn Phe Lys Phe Lys Ser Thr
                85                  90                  95
Asp Gly Glu Leu Leu Asn Ile Lys Ala Asp Lys Asp Thr Val Thr Ile
            100                 105                 110
Thr Arg Ala Ser Gly Ala Asn Gly Ala Ala Thr Asp Ala Asp Lys
            115                 120                 125
Ile Lys Val Ala Ser Asp Gly Ile Ser Ala Gly Asn Lys Ala Val Lys
        130                 135                 140
Asn Val Ala Ala Gly Glu Ile Ser Ala Thr Ser Thr Asp Ala Ile Asn
145                 150                 155                 160
Gly Ser Gln Leu Tyr Ala Val Ala Lys Gly Val Thr Asn Leu Ala Gly
                165                 170                 175
Gln Val Asn Lys Val Gly Lys Arg Ala Asp Ala Gly Thr Ala Ser Ala
            180                 185                 190
Leu Ala Ala Ser Gln Leu Pro Gln Ala Ser Met Pro Gly Lys Ser Met
        195                 200                 205
Val Ser Ile Ala Gly Ser Ser Tyr Gln Gly Gln Ser Gly Leu Ala Ile
        210                 215                 220
Gly Val Ser Arg Ile Ser Asp Asn Gly Lys Leu Ile Ile Arg Leu Ser
225                 230                 235                 240
Gly Thr Thr Asn Ser Gln Gly Lys Thr Gly Val Ala Ala Gly Val Gly
                245                 250                 255
Tyr Gln Trp
```

<210> SEQ ID NO 5
<211> LENGTH: 521
<212> TYPE: PRT
<213> ORGANISM: Unknown
<220> FEATURE:
<223> OTHER INFORMATION: Description of Unknown:
    Bacteria <Prokaryote> sequence
<220> FEATURE:
<223> OTHER INFORMATION: NT067

<400> SEQUENCE: 5

```
Val Ile Val Pro Glu Gly Thr Gln Leu Asp Glu Lys Gln His Ile Val
1               5                   10                  15
Ile Asn Asn Gly Ala Glu Pro Gln Ser Phe Asn Pro His Lys Thr Glu
            20                  25                  30
Gly Val Pro Glu Ser Asn Val Ala Tyr Gln Leu Leu Glu Gly Leu Val
            35                  40                  45
Thr Ser Asp Ser Glu Gly Lys Leu Gln Pro Gly Ala Ala Glu Ser Trp
        50                  55                  60
Glu Asn Thr Pro Asp Phe Lys Thr Trp Thr Phe His Leu Arg Lys Asp
65                  70                  75                  80
```

```
Ala Lys Trp Ser Asn Gly Asp Pro Val Thr Ala His Asp Phe Val Phe
                85                  90                  95
Ala Trp Arg Arg Leu Val Asp Pro Ala Thr Ala Pro Tyr Ala Ser
        100                 105                 110
Tyr Leu Ser Tyr Leu Gln Val Glu Asn Ala Gln Asp Ile Ile Asp Gly
            115                 120                 125
Lys Lys Lys Pro Ala Glu Leu Gly Val Glu Ala Lys Asp Asp Tyr Thr
130                 135                 140
Phe Val Val His Ala Thr Asn Pro Val Pro Tyr Ala Val Ser Leu Thr
145                 150                 155                 160
Thr His Gln Ser Leu Leu Pro Leu Pro Gln Lys Val Val Glu Lys Leu
                165                 170                 175
Gly Asp Ala Trp Val Lys Lys Glu Asn Tyr Val Gly Asn Gly Ala Tyr
            180                 185                 190
Lys Leu Ala Asn His Ile Ile Asn Glu Lys Ile Glu Phe Glu Arg Asn
            195                 200                 205
Pro Leu Tyr Trp Asn Asp Lys Glu Thr Val Ile Asn Ser Ala Thr Phe
    210                 215                 220
Leu Ala Ile Glu Asn Pro Ser Thr Asp Val Ala Arg Tyr Arg Ala Gly
225                 230                 235                 240
Asp Leu Asp Met Thr Ser Tyr Gly Leu Pro Pro Glu Gln Phe Ala Lys
                245                 250                 255
Leu Lys Lys Glu Leu Leu Gly Glu Val Tyr Val Thr Arg Thr Leu Gly
            260                 265                 270
Thr Tyr Ser Tyr Glu Leu Asn Asn Lys Lys Ala Pro Phe Asp Asn Val
        275                 280                 285
Asn Ile Arg Lys Ala Leu Asn Leu Ser Leu Asp Arg Asn Val Ile Thr
    290                 295                 300
Asp Lys Val Leu Gly Gln Gly Gln Thr Pro Thr Tyr Val Phe Thr Pro
305                 310                 315                 320
Thr Tyr Ile Glu Glu Gly His Leu Ile Gln Gln Pro Ala Tyr Ser Lys
                325                 330                 335
Glu Pro Met Ala Gln Arg Asn Glu Glu Ala Ile Lys Leu Leu Glu Glu
            340                 345                 350
Ala Gly Tyr Ser Lys Ala Asn Pro Leu Lys Phe Ser Ile Leu Tyr Asn
        355                 360                 365
Thr Asn Glu Asn His Lys Lys Val Ala Ile Ala Ala Ser Met Trp
    370                 375                 380
Lys Ala Asn Thr Lys Gly Leu Ile Asp Val Lys Leu Glu Asn Gln Glu
385                 390                 395                 400
Trp Lys Thr Tyr Ile Asp Ser Arg Arg Ala Gly Arg Tyr Asp Val Ala
                405                 410                 415
Arg Ala Gly Trp His Ala Asp Tyr Asn Gln Ala Thr Thr Phe Gly Asn
            420                 425                 430
Tyr Phe Leu Ser Asn Ser Asn Asn Thr Ala Lys Tyr Ala Asn Pro
        435                 440                 445
Glu Tyr Asp Lys Ala Met Ala Glu Ser Tyr Ala Ala Thr Asp Ala Glu
    450                 455                 460
Gly Arg Ala Lys Ala Tyr Ala Lys Ala Glu Ile Leu Gly Lys Asp
465                 470                 475                 480
Tyr Gly Ile Val Pro Ile Phe Asn Tyr Val Asn Pro Arg Leu Val Lys
                485                 490                 495
Pro Tyr Val Lys Gly Tyr Ser Gly Lys Asp Pro Gln Asp His Ile Tyr
```

Leu Arg Asn Leu Tyr Ile Ile Lys His
        515                 520

<210> SEQ ID NO 6
<211> LENGTH: 252
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT001

<400> SEQUENCE: 6

Lys Glu Asp Lys Lys Pro Glu Ala Ala Val Ala Pro Leu Lys Ile Lys
1               5                   10                  15

Val Gly Val Met Ser Gly Pro Glu His Gln Val Ala Glu Ile Ala Ala
            20                  25                  30

Lys Val Ala Lys Glu Lys Tyr Gly Leu Asp Val Gln Phe Val Glu Phe
        35                  40                  45

Asn Asp Tyr Ala Leu Pro Asn Glu Ala Val Ser Lys Gly Asp Leu Asp
50                  55                  60

Ala Asn Ala Met Gln His Lys Pro Tyr Leu Asp Glu Asp Ala Lys Ala
65                  70                  75                  80

Lys Asn Leu Asn Asn Leu Val Ile Val Gly Asn Thr Phe Val Tyr Pro
                85                  90                  95

Leu Ala Gly Tyr Ser Lys Lys Ile Lys Asn Val Asn Glu Leu Gln Asp
            100                 105                 110

Gly Ala Lys Val Val Pro Asn Asp Pro Thr Asn Arg Gly Arg Ala
        115                 120                 125

Leu Ile Leu Leu Glu Lys Gln Gly Leu Ile Lys Leu Lys Asp Ala Asn
130                 135                 140

Asn Leu Leu Ser Thr Val Leu Asp Ile Val Glu Asn Pro Lys Lys Leu
145                 150                 155                 160

Asn Ile Thr Glu Val Asp Thr Ser Val Ala Ala Arg Ala Leu Asp Asp
                165                 170                 175

Val Asp Leu Ala Val Val Asn Asn Thr Tyr Ala Gly Gln Val Gly Leu
            180                 185                 190

Asn Ala Gln Asp Asp Gly Val Phe Val Glu Asp Lys Asp Ser Pro Tyr
        195                 200                 205

Val Asn Ile Ile Val Ser Arg Thr Asp Asn Lys Asp Ser Lys Ala Val
    210                 215                 220

Gln Asp Phe Val Lys Ser Tyr Gln Thr Glu Glu Val Tyr Gln Glu Ala
225                 230                 235                 240

Gln Lys His Phe Lys Asp Gly Val Val Lys Gly Trp
                245                 250

<210> SEQ ID NO 7
<211> LENGTH: 243
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT016

<400> SEQUENCE: 7

```
Ser Ser Gly Ser Lys Asp Val Glu Gln Ala Ser Val Asn Glu Leu Tyr
1               5                   10                  15

Thr Lys Gly Thr Thr Ser Leu Gln Glu Gly Ser Tyr Ser Glu Ala Ile
            20                  25                  30

Arg Tyr Leu Lys Ala Thr Thr Glu Arg Phe Pro Gly Ser Val Tyr Gln
        35                  40                  45

Glu Gln Ala Met Leu Asp Leu Ile Tyr Ala Asn Tyr Lys Thr Gln Asp
    50                  55                  60

Tyr Thr Gln Val Leu Leu Met Val Asp Ser Phe Leu His Gln Phe Pro
65                  70                  75                  80

Gln Ser Pro Asn Gln Ala Tyr Ala Val Tyr Met Ala Gly Leu Thr Asn
                85                  90                  95

Ala Ala Thr Gly Asp Asn Phe Ile Gln Asp Phe Phe Gly Ile Asp Arg
            100                 105                 110

Ala Thr Arg Glu Thr Thr Ser Met Arg Thr Ala Phe Ser Asn Phe Gln
        115                 120                 125

Asn Leu Val Arg Val Phe Pro Asn Ser Pro Tyr Ser Gln Asp Ala Leu
    130                 135                 140

Ala Arg Met Ala Tyr Ile Lys Asp Ala Leu Ala Arg His Glu Leu Glu
145                 150                 155                 160

Ile Ala Lys Phe Tyr Ala Lys Arg Lys Ala Trp Val Ala Val Ala Asn
                165                 170                 175

Arg Val Val Gly Met Leu Lys Gln Tyr Pro Asp Thr Lys Ala Thr Tyr
            180                 185                 190

Glu Gly Leu Phe Leu Met Gln Ala Ala Tyr Glu Lys Met Gly Leu Thr
        195                 200                 205

Ala Leu Ala Asn Asp Thr Gln Lys Ile Ile Asp Ala Asn Lys Asp Lys
    210                 215                 220

Thr Phe Ala Pro Ile Glu Lys Pro Asn Glu Pro Asp Leu Lys Val Pro
225                 230                 235                 240

Ala Val Lys

<210> SEQ ID NO 8
<211> LENGTH: 337
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT052

<400> SEQUENCE: 8

Asp Thr Leu Glu Gln Gln Phe Gln Gln Gly Leu Glu Ala Thr Lys Arg
1               5                   10                  15

Gly Asp Tyr Gln Thr Ala Phe Lys Leu Trp Leu Pro Leu Ala Glu Gln
            20                  25                  30

Gly Asn Ala Ser Ile Gln Phe Asn Leu Gly Leu Met Tyr Lys Lys Gly
        35                  40                  45

Gln Gly Ile Lys Gln Asp Asp Phe Glu Ala Val Lys Trp Tyr Arg Lys
    50                  55                  60

Ala Ala Glu Gln Gly Val Ala Asp Ala Gln Leu Asn Leu Gly Asn Met
65                  70                  75                  80

Tyr Ala Lys Gly Leu Gly Val Lys Gln Asp Asp Val Glu Ala Val Lys
                85                  90                  95

Trp Tyr Arg Gln Ala Ala Glu Gln Gly Asn Ala Lys Ala Gln Phe Asn
```

-continued

```
            100                 105                 110
Leu Gly Leu Met Tyr Asp Asn Gly Arg Gly Val Lys Gln Asp Tyr Phe
        115                 120                 125
Glu Ala Val Lys Trp Phe Arg Lys Ala Ala Glu Gln Gly Tyr Ala Asp
    130                 135                 140
Ala Gln Phe Asn Leu Gly Asn Met Tyr Tyr Asn Gly His Gly Val Lys
145                 150                 155                 160
Gln Asp Asp Phe Glu Ala Val Lys Trp Tyr Arg Lys Ala Ala Glu Gln
                165                 170                 175
Gly Tyr Ala Asp Ala Gln Phe Asn Leu Gly Asn Met Tyr Tyr Asn Gly
            180                 185                 190
His Gly Val Lys Gln Asp Asp Phe Glu Ala Val Lys Trp Tyr Arg Lys
        195                 200                 205
Ala Ala Glu Gln Gly His Ala Lys Ala Gln Tyr Asn Leu Gly Asn Met
    210                 215                 220
Tyr Ala Asn Gly Arg Gly Val Lys Gln Asp Tyr Phe Glu Ala Val Lys
225                 230                 235                 240
Trp Tyr Arg Lys Ala Ala Glu Gln Gly Tyr Ala Asp Ala Gln Ala Asn
                245                 250                 255
Leu Gly Ser Ala Tyr Ser Ala Gly His Gly Val Arg Gln Asp Tyr Ile
            260                 265                 270
Glu Ala Val Lys Trp Phe Lys Lys Ala Ala Glu Asn Gly Ser Ala Asp
        275                 280                 285
Gly Gln Phe Lys Leu Gly Leu Val Tyr Leu Ile Gly Gln Gly Ile Gln
    290                 295                 300
Lys Asp Arg Thr Leu Ala Lys Glu Trp Leu Gly Lys Ala Cys Asp Asn
305                 310                 315                 320
Gly Asn Gln Asn Gly Cys Glu Tyr Tyr Gly Leu Asn Arg Gly Glu
                325                 330                 335
Arg

<210> SEQ ID NO 9
<211> LENGTH: 143
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT002

<400> SEQUENCE: 9

Cys Ser Ser Phe Gln Asn Asp Asp Tyr Ala Met Asn Tyr Lys Gly Gln
1               5                   10                  15
Ile Gly Asp Pro Ile Met Ala Ile Ala Met Leu Ser Glu Gln Gln His
            20                  25                  30
Glu Trp Ala Gly Thr Pro Tyr Val Leu Gly Gly Val Ser Arg Arg Gly
        35                  40                  45
Val Asp Cys Ser Gly Phe Val Gln Lys Thr Phe Phe Asp Arg Phe Asn
    50                  55                  60
Leu Arg Leu Pro Arg Ser Thr Val Glu Gln Ala Asn Tyr Gly Lys His
65                  70                  75                  80
Val Arg Lys Glu His Ile Gln Thr Gly Asp Leu Ile Phe Phe Lys Thr
                85                  90                  95
Gly Leu Gly Pro Asn Gly Tyr His Val Gly Ile Tyr Val Lys Glu Asp
            100                 105                 110
```

```
Lys Phe Leu His Ala Ser Thr Arg Gly Gly Val Val Tyr Ser Ser Met
        115                 120                 125

Asn Asn Pro Tyr Trp Ser Lys Ala Phe Trp Gln Val Arg Arg Ile
        130                 135                 140

<210> SEQ ID NO 10
<211> LENGTH: 146
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT026

<400> SEQUENCE: 10

Val Pro Leu Trp Lys Thr Asp Ser Pro Lys Thr Ile Leu Ala Lys Glu
1               5                   10                  15

Gln His Arg Leu Tyr Leu Phe Leu Arg Gln Ile Gln Ala Arg Ala Glu
            20                  25                  30

Asn Ser Ser Glu Val Trp Phe Leu Leu Ile Asn Arg Asn Leu Ala Thr
        35                  40                  45

Gln Gln Trp Cys Leu Thr Ala Gln Val Lys Asn Asn Gln Thr Cys Asp
    50                  55                  60

Cys Leu Asn Pro Ile Asn Cys Pro Lys Glu Val Tyr Ala His Phe Tyr
65                  70                  75                  80

Tyr Pro Tyr Phe Pro Asn Lys Thr Met Ile Gln Ser His His Ile Tyr
                85                  90                  95

Pro Lys Glu Ile Thr Arg Phe Asp Gly Ile Arg Asn Thr Ile Val Thr
            100                 105                 110

Arg Cys Phe Ile Leu Gln Ala Glu Asn Glu Arg Thr Leu Phe Leu Phe
        115                 120                 125

Phe Asn Val Gly Ser Ile Arg Leu Lys Thr Asn Gln Phe Asp Ser Ala
    130                 135                 140

Cys Asn
145

<210> SEQ ID NO 11
<211> LENGTH: 556
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT009

<400> SEQUENCE: 11

Glu Gln Thr Val Asp Ile Glu Val Gln Gly Ile Arg Gly Phe Arg Ala
1               5                   10                  15

Val Arg Asn Thr Asp Leu Asn Val His Leu Ile Asn Lys Glu Glu Met
            20                  25                  30

Asp Gly Ser Glu Arg Tyr Gln His Leu Val Thr Lys Ala Val Asp Arg
        35                  40                  45

Gly Leu Arg Val Phe Gly Tyr Tyr Asp Ser Ser Val Arg Phe Glu Arg
    50                  55                  60

Lys Gln Arg Gln Gly Lys Arg Asp Leu Leu Ile Ala His Val Thr Pro
65                  70                  75                  80

Gly Glu Pro Thr Lys Ile Ala Gly Thr Asp Val Gln Ile Glu Gly Glu
```

```
                        85                  90                  95
Ala Ala Gln Asp Glu Asn Phe Asn Ala Leu Arg Lys Asn Leu Pro Lys
            100                 105                 110

Asp Gly Val Leu Val Glu His Gln Thr Tyr Asp Asp Tyr Lys Thr Ala
            115                 120                 125

Ile Ser Arg Leu Ala Leu Asn Arg Gly Tyr Phe Asp Gly Glu Phe Lys
            130                 135                 140

Ile Ser Arg Leu Glu Ile Ser Pro Glu Thr His Gln Ala Trp Trp Arg
145                 150                 155                 160

Met Leu Phe Asp Ser Gly Val Arg Tyr His Tyr Gly Asn Ile Thr Phe
                165                 170                 175

Ser His Ser Gln Ile Arg Asp Asp Tyr Leu Asn Asn Ile Leu Asn Ile
                180                 185                 190

Lys Ser Gly Asp Pro Tyr Leu Met Asn Asn Leu Ser Asp Leu Thr Ser
                195                 200                 205

Asp Phe Ser Ser Ser Asn Trp Phe Asn Ser Val Leu Val Gln Pro Asn
            210                 215                 220

Ile Asn His Lys Ser Lys Thr Val Asp Ile Glu Ile Ile Leu Tyr Pro
225                 230                 235                 240

Arg Lys Lys Asn Ala Met Glu Leu Gly Val Gly Phe Asp Thr Asp Gly
                245                 250                 255

Gly Val His Gly Gln Ile Gly Trp Thr Lys Pro Trp Ile Asn Ser Arg
                260                 265                 270

Gly His Ser Leu Arg Ser Asn Leu Tyr Leu Ser Ala Pro Lys Gln Thr
                275                 280                 285

Leu Glu Ala Thr Tyr Arg Ile Pro Leu Leu Lys Asn Pro Leu Asn Tyr
            290                 295                 300

Tyr Tyr Asp Phe Ala Val Gly Trp Glu Gly Lys Glu Asn Asp Thr
305                 310                 315                 320

Asn Thr Arg Ala Leu Thr Leu Ser Ala Leu Arg Tyr Trp Asn Asn Ala
                325                 330                 335

Arg Gly Trp Gln Tyr Phe Gly Gly Leu Arg Ala Arg Tyr Asp Ser Phe
                340                 345                 350

Thr Gln Ala Asp Ile Thr Asp Lys Thr Leu Leu Tyr Pro Thr Val
                355                 360                 365

Gly Phe Thr Arg Thr Arg Leu Arg Gly Gly Ser Phe Ala Thr Trp Gly
            370                 375                 380

Asp Val Gln Lys Ile Thr Phe Asp Leu Ser Lys Arg Ile Trp Leu Ser
385                 390                 395                 400

Glu Ser Ser Phe Ile Lys Val Gln Ala Ser Ser Ala Trp Ile Arg Thr
                405                 410                 415

Tyr Ala Glu Asn His Arg Ile Val Ala Arg Ala Glu Ile Gly Tyr Leu
                420                 425                 430

His Thr Lys Asp Ile Glu Lys Ile Pro Pro Thr Leu Arg Phe Phe Ala
                435                 440                 445

Gly Gly Asp Arg Ser Val Arg Gly Tyr Gly Tyr Lys Lys Ile Ala Pro
            450                 455                 460

Lys Asn Lys Asn Gly Lys Leu Val Gly Gly Ser Arg Leu Leu Thr Gly
465                 470                 475                 480

Ser Leu Glu Tyr Gln Tyr Gln Val Tyr Pro Asn Trp Trp Ala Ala Thr
                485                 490                 495

Phe Val Asp Ser Gly Leu Val Ala Asp Asn Tyr Thr Ala Lys Glu Leu
            500                 505                 510
```

Arg Tyr Gly Ala Gly Val Gly Val Arg Trp Ala Ser Pro Val Gly Ala
         515                 520                 525

Ile Lys Phe Asp Ile Ala Thr Pro Ile Arg Asp Lys Asp Asn Ser Lys
    530                 535                 540

Asn Ile Gln Phe Tyr Ile Gly Leu Gly Thr Glu Ile
545                 550                 555

<210> SEQ ID NO 12
<211> LENGTH: 126
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT025

<400> SEQUENCE: 12

Ile Ile Ala Ile Leu Ala Thr Ile Ala Ile Pro Ser Tyr Gln Asn Tyr
1               5                   10                  15

Thr Lys Lys Ala Ala Val Ser Glu Leu Leu Gln Ala Ser Ala Pro Tyr
            20                  25                  30

Lys Ala Asp Val Glu Leu Cys Val Tyr Ser Thr Asn Glu Thr Thr Asn
        35                  40                  45

Cys Thr Gly Gly Lys Asn Gly Ile Ala Ala Asp Ile Thr Thr Ala Lys
    50                  55                  60

Gly Tyr Val Lys Ser Val Thr Thr Ser Asn Gly Ala Ile Thr Val Lys
65                  70                  75                  80

Gly Asp Gly Thr Leu Ala Asn Met Glu Tyr Ile Leu Gln Ala Thr Gly
                85                  90                  95

Asn Ala Ala Thr Gly Val Thr Trp Thr Thr Thr Cys Lys Gly Thr Asp
            100                 105                 110

Ala Ser Leu Phe Pro Ala Asn Phe Cys Arg Ser Val Thr Lys
        115                 120                 125

<210> SEQ ID NO 13
<211> LENGTH: 162
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT028

<400> SEQUENCE: 13

Pro Arg Thr Val Ser His Gln Val Ile Ser Glu Asn Asp Asp Ile Gln
1               5                   10                  15

Leu Thr Gly Leu Ile Asn Asn Leu Glu Lys Asp Asn Arg Thr Gly Ile
            20                  25                  30

Phe His Lys Val Arg Thr Asn Arg Ser Ala Leu Met Gly Asp Lys
        35                  40                  45

Ala Leu Ala Ser Val Tyr Asn Glu Trp Val Gly Thr Arg Tyr Arg Met
    50                  55                  60

Gly Gly Thr Thr Lys Arg Gly Ile Asp Cys Ser Ala Phe Met Gln Thr
65                  70                  75                  80

Thr Phe Ser Glu Val Phe Gly Ile Glu Leu Pro Arg Ser Thr Ala Glu
                85                  90                  95

Gln Arg His Leu Gly Arg Lys Ile Asn Lys Ser Glu Leu Lys Lys Gly

Asp Leu Val Phe Phe Arg Lys Asn Asn His Val Gly Val Tyr Ile Gly
            115                 120                 125

Asn Asn Gln Phe Met His Ala Ser Thr Gly Gln Gly Val Thr Ile Ser
        130                 135                 140

Ser Leu Asp Glu Lys Tyr Trp Ala Arg Thr Tyr Thr Gln Ser Arg Arg
145                 150                 155                 160

Ile Met

<210> SEQ ID NO 14
<211> LENGTH: 895
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT029

<400> SEQUENCE: 14

Ser Thr Pro Asp Leu Pro Gln Asn His Lys Ile Ile Thr Gly Thr Ala
1               5                   10                  15

Thr Val Ser His Thr Glu Asn Glu Met Thr Ile Lys Gln Thr Thr Pro
            20                  25                  30

Thr Thr Gln Ile Asn Trp Asp Ser Phe Asn Ile Gly Lys Asp Lys Glu
        35                  40                  45

Val Lys Phe Glu Gln Pro Ser Thr Ser Ala Val Ala Tyr Asn Arg Val
    50                  55                  60

Thr Gly Gly Asn Ala Ser His Ile Gln Gly Lys Leu Thr Ala Asn Gly
65              70                  75                  80

Lys Val Tyr Leu Ala Asn Pro Asn Gly Val Ile Thr Lys Gly Ala
                85                  90                  95

Glu Ile Asn Val Ala Gly Leu Leu Ala Thr Thr Lys Asp Leu Glu Arg
            100                 105                 110

Ile Ser Glu Asn Gly Asn Thr Asn Thr Asn Lys Phe Thr Arg Lys Ala
        115                 120                 125

Lys Glu Gly Lys Val Leu Thr Glu Gly Gln Val Ile Asn Glu Gly Glu
    130                 135                 140

Ile Lys Ala Lys Asp Phe Val Val Leu Asn Gly Asp Glu Val Ile Asn
145                 150                 155                 160

Lys Gly Asn Ile Asn Val Glu Lys Asn Ser Thr Ile Asn Gly Glu Val
                165                 170                 175

Tyr Leu Ser Ser Ser Asn Asn Phe Thr Phe Thr Leu Ser Asp Ser Gly
            180                 185                 190

Ile Ser Val Ala Leu Glu Asp Asn Thr Val Gln Gly Ile Val Lys Asn
        195                 200                 205

Glu Gly Ile Val Lys Asn Glu Gly Ser Ile Lys Ala Gly Glu Ile Thr
    210                 215                 220

Leu Ser Ala Lys Gly Arg Lys Glu Ala Leu Asp Ser Leu Val Val Asn
225                 230                 235                 240

Asn Gly Val Leu Glu Ala Thr Lys Val Ser Asn Arg Lys Gly Lys Ile
                245                 250                 255

Val Leu Ser Ala Asp Asp Val Gln Leu Asn Asn Asn Ser Asp Ile Lys
            260                 265                 270

Gly Glu Ile Val Asn Phe Gly Thr Glu Val Thr Ser Asn Glu Asp Lys
        275                 280                 285

-continued

```
Lys Leu Lys Ile Thr Ser Gln Thr Gly Ser Lys Val Thr Ser Pro Lys
    290                 295                 300

Ile Asn Phe Lys Gly Lys Ser Val Asn Ile Lys Gly Asp Phe Gly Arg
305                 310                 315                 320

Glu Asp Asn Thr Thr Tyr Tyr Asp Asp Glu His Lys Lys Leu Lys Thr
                325                 330                 335

Glu Val Asn Ile Asp Val Pro Asn Thr Glu Asn Ile Gln Ile Ala Asp
            340                 345                 350

Lys Asp Asn Ala Gly Thr Asp Ser Phe Ile Gln Thr Gly Ala Leu Ser
        355                 360                 365

Ser Leu Leu Ala Asn Asn Gly Lys Val Asn Leu Lys Gly Lys Asp Val
    370                 375                 380

Asn Ile Ser Gly Asn Ile Asn Ile Asn Ser Phe Arg Gly Thr Asp Ser
385                 390                 395                 400

Leu Leu Lys Leu Thr Asn Lys Gly His Ile Asn Ile Asn His Ala Asp
                405                 410                 415

Ile His Ser Lys Gly Arg Leu Phe Phe Ile Thr Ser Leu Gln Asn Asp
            420                 425                 430

Val Asp Phe Gln Ser Asn Ile Thr Ile Thr Asp Ser Lys Ile Asn Leu
        435                 440                 445

Gly Asn Gly Ala Met Gly Leu Gly Arg Ser Val Asn Glu Asn Asp Leu
    450                 455                 460

Asp Arg Trp Arg Arg Thr Glu Tyr Ser Gln Arg Lys Lys Phe Asn Val
465                 470                 475                 480

Asn Met Arg Asn Val Val Phe Asp Gln Val Asp Val Val Ala
                485                 490                 495

Gly Gly Phe Lys Glu Val Asn Leu Asn Asn Ile Val Ala Thr Gly Gln
            500                 505                 510

Thr Asn Phe Tyr Ile Asp Gly Val Ser Arg Asn Arg Asn Gly Val
        515                 520                 525

Ser Ser Lys Tyr Glu Tyr Gly Val Leu Asp Leu Asp Lys Arg Thr Gln
    530                 535                 540

Leu Ser Glu Leu Asp Gln Arg Arg Arg Trp Gly Tyr Tyr Pro Asp
545                 550                 555                 560

Leu Asp Leu Asp Met Asn Lys Ala Tyr Trp His Arg Phe Asp Met Phe
                565                 570                 575

Ala Ser Lys Asn Thr Gly Arg Ser Thr Ile Lys Asp Thr Glu Ile Asn
            580                 585                 590

Ile Ser Asn Ser Lys Ile Asn Leu Lys Asn Gly Phe Val His Leu Leu
        595                 600                 605

Ala Glu Lys Ile Lys Leu Asp Asn Ser Lys Ile Asp Ile Thr Phe Asp
    610                 615                 620

Lys Asp Asn Ser Gln Asp Ile Ser Thr Gln Ile Asn Arg Leu Gly Met
625                 630                 635                 640

Asn Gly Lys Val Ser Met Val Asn Ser His Ile Lys Ile Val Gly Asp
                645                 650                 655

Glu Lys Ile Asp Ile Ser Ala Lys Ala Pro Tyr Ala Thr Met Phe Leu
            660                 665                 670

Ile Gly Glu Leu Ile Gly Glu Lys Ser Ser Ile Phe Val Lys Ser His
        675                 680                 685

Gln Gly Tyr Thr Phe Arg Thr Asp Gly Asp Thr Lys Ile Ala Gly Lys
    690                 695                 700
```

```
Asn Ser Lys Asp Asp Leu Lys Ile Thr Ala Ile Asn Thr Gly Gly Arg
705                 710                 715                 720

Thr Gly Lys Glu Val Ile Ile Asn Gly Ala Pro Gly Ser Ile Asp Asn
            725                 730                 735

Asp Ala Asn Ile Ala Asn Met Ala Phe Thr Ile Gly Asp Asn Ala Asn
        740                 745                 750

Thr Lys Thr Thr Ile Glu Asn Ala Asp Ile Thr Ala Leu Ala Pro Asn
    755                 760                 765

Gly Gly Thr Ala Tyr Leu Ser Ser Lys Gly Val Glu Ile Glu Val Asn
770                 775                 780

Pro Asn Ser Asn Phe Thr Phe Phe Glu Leu Pro Arg Glu Lys Asn Phe
785                 790                 795                 800

Asn Gln Thr Lys Ile Asn Gly Asp Ser Thr Lys Leu Ser Glu Arg Gly
            805                 810                 815

Phe Ala Arg Leu Tyr Asp Lys Ile Asn Gly Val Arg Ala Ser Asn Leu
        820                 825                 830

Ser Ala Glu Gln Leu Asn Val Thr Asp Ser Ser Glu Lys Ile Ile Asn
    835                 840                 845

Thr Lys Leu Val Ser Ser Leu Asp Val Glu Lys Leu Val Ser Val Ala
850                 855                 860

Val Cys Asp Ala Gly Lys Gly Cys Glu Glu Gln Gln Phe Gly Asp Lys
865                 870                 875                 880

Gly Asn Asn Thr Lys Val Ser Val Gly Glu Leu Glu Ala Glu Gln
            885                 890                 895

<210> SEQ ID NO 15
<211> LENGTH: 165
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT031

<400> SEQUENCE: 15

Cys Ile Ala Pro Pro Lys Gly Leu Glu Lys Glu Arg Phe Ser Ile Asn
1               5                   10                  15

Ser Tyr Arg Glu Ile Ser Pro Gln Asp Leu Thr Cys His Cys Asn Thr
            20                  25                  30

Val Arg Leu Gly Gly Lys Ile Val Asn Thr Thr Val Leu Ala Asn Gln
        35                  40                  45

Thr Lys Ile Glu Val Leu Ser Leu Pro Val Ser Ser Ile Ser Gly Lys
    50                  55                  60

Pro Phe Val Glu Leu Gln Ser Asp Gly Arg Phe Ile Val Tyr Phe Asn
65                  70                  75                  80

Gly Phe Val Glu Pro Glu Asn Leu Lys Glu Arg Tyr Ile Thr Val Gly
                85                  90                  95

Gly Gln Leu Thr Gly Thr Glu Lys Gly Lys Ile Glu Gln Ala Asp Tyr
            100                 105                 110

Thr Tyr Pro Val Val Gln Ala Asp Lys Tyr Arg Ile Trp Thr Leu Ser
        115                 120                 125

Thr Thr Tyr Asn Tyr Pro Thr Asp Asp Trp Asp Glu Asp Asp Asp Trp
    130                 135                 140

Gly Phe Phe Arg Trp Arg His Arg Pro Trp Tyr Val Gln Pro Glu Ile
145                 150                 155                 160
```

```
His Tyr Tyr Leu Asn
            165

<210> SEQ ID NO 16
<211> LENGTH: 117
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT015

<400> SEQUENCE: 16

Ala Gln Asn Ala Asn Val Thr Thr Pro Gln Thr Gln Lys Met Gln Val
1               5                   10                  15

Glu Lys Val Asp Lys Ala Leu Gln Lys Gly Glu Ala Asp Arg Tyr Leu
            20                  25                  30

Cys Gln Asp Asp Lys Val Val Arg Val His Ala Thr His Lys Lys
        35                  40                  45

Tyr Lys Lys Asn Leu His Tyr Val Thr Val Thr Phe Gln Gly Val Ser
    50                  55                  60

Glu Lys Leu Thr Leu Met Ile Ser Glu Arg Gly Lys Asn Tyr Ala Asn
65                  70                  75                  80

Ile Arg Trp Met Trp Gln Glu Arg Asp Asp Phe Ser Thr Leu Lys Thr
                85                  90                  95

Asn Leu Gly Glu Ile Leu Ala Thr Gln Cys Val Ser Gln Thr Ser Glu
            100                 105                 110

Arg Leu Ser Gly Gln
        115

<210> SEQ ID NO 17
<211> LENGTH: 134
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT023

<400> SEQUENCE: 17

Asn Thr Asp Ile Phe Ser Gly Asp Val Tyr Ser Ala Ser Gln Ala Lys
1               5                   10                  15

Glu Ala Arg Ser Ile Thr Tyr Gly Thr Ile Val Ser Val Arg Pro Val
            20                  25                  30

Lys Ile Gln Ala Asp Asn Gln Gly Val Val Gly Thr Leu Gly Gly Gly
        35                  40                  45

Ala Leu Gly Gly Ile Ala Gly Ser Thr Ile Gly Gly Arg Gly Gln
    50                  55                  60

Ala Ile Ala Ala Val Gly Ala Ile Gly Gly Ala Ile Ala Gly Ser
65                  70                  75                  80

Lys Ile Glu Glu Lys Met Ser Gln Val Asn Gly Ala Glu Leu Val Ile
                85                  90                  95

Lys Lys Asp Asp Gly Gln Glu Ile Val Val Gln Lys Ala Asp Ser
            100                 105                 110

Ser Phe Val Ala Gly Arg Arg Val Arg Ile Val Gly Gly Ser Ser
        115                 120                 125

Leu Asn Val Ser Val Leu
    130
```

<210> SEQ ID NO 18
<211> LENGTH: 315
<212> TYPE: PRT
<213> ORGANISM: Unknown
<220> FEATURE:
<223> OTHER INFORMATION: Description of Unknown:
     Bacteria <Prokaryote> sequence
<220> FEATURE:
<223> OTHER INFORMATION: NT100

<400> SEQUENCE: 18

Ile Lys Lys Asn Glu Asn Asn Ala Tyr Gln Phe Asn His Leu Lys
1               5                   10                  15

Thr Leu Gly Leu Tyr Ile Gln Asn Thr Thr Tyr Phe Thr Asp Asn Phe
            20                  25                  30

Ile Ile Thr Gly Gly Leu Arg Tyr Glu Tyr Phe Asp Gln Val Val Gly
        35                  40                  45

Arg Ser Thr Leu Lys Asn Ile Arg Ser Gly Tyr Leu Ala Gln Lys Asp
    50                  55                  60

Gly Lys Leu Leu Tyr Gln Leu Gly Ser Val Tyr Lys Phe Thr Pro Asn
65                  70                  75                  80

Ile Ala Thr Phe Phe Asn His Ala Glu Ser Phe Arg Pro Gln Asn Asn
                85                  90                  95

Arg Thr Leu Ile Ile Asn Gly Glu Leu Pro Ala Glu Gln Gly Lys Ser
            100                 105                 110

Phe Glu Thr Gly Leu Lys Tyr Glu Asn Ala Tyr Leu Asn Ala Thr Val
        115                 120                 125

Ala Leu Phe Asn Ile Asn Lys Arg Asn Val Ala Glu Thr Val Asn Val
    130                 135                 140

Asn Gly Thr Asn Glu Leu Gln Ile Val Gly Lys Gln Arg Ser Arg Gly
145                 150                 155                 160

Ile Glu Phe Asp Leu Asn Gly Gln Leu Thr Asp Asn Leu Ser Ile Ala
                165                 170                 175

Ala Asn Tyr Thr Tyr Thr Lys Val Lys Asn Leu Glu Asn His Asn Asn
            180                 185                 190

Lys Leu Ala Val Gly Lys Gln Leu Ser Gly Val Pro Lys His Gln Ala
        195                 200                 205

Ser Leu Phe Leu Ala Tyr Asn Ile Gly Glu Phe Asp Phe Gly Asn Ile
    210                 215                 220

Arg Val Gly Gly Gly Ala Arg Tyr Leu Gly Ser Trp Tyr Ala Tyr Asn
225                 230                 235                 240

Asn Thr Tyr Thr Lys Ala Tyr Lys Leu Pro Gln Ala Ile Val Tyr Asp
                245                 250                 255

Ala Phe Ile Ala Tyr Asp Thr Lys Ile Ser Gly Lys Lys Val Ser Phe
            260                 265                 270

Gln Leu Asn Gly Lys Asn Leu Ser Asn Lys Val Tyr Ser Pro Ser Thr
        275                 280                 285

Ser Gly Asn Ala Ser Arg Thr Leu Ile Pro Val Ala Leu Gly Tyr Ala
    290                 295                 300

Arg Glu Val Ile Leu Asn Thr Lys Ile Glu Phe
305                 310                 315

<210> SEQ ID NO 19
<211> LENGTH: 212
<212> TYPE: PRT
<213> ORGANISM: Unknown

```
<220> FEATURE:
<223> OTHER INFORMATION: Description of Unknown:
      Bacteria <Prokaryote> sequence
<220> FEATURE:
<223> OTHER INFORMATION: NT040

<400> SEQUENCE: 19

Ser Ile Ser His Phe Tyr Val Gln Ile Gln Thr Gln Asn Gln Gln Met
1               5                   10                  15

Leu Leu His Leu Lys Leu Gln Ala Glu Leu Gln Arg Thr Leu Gln Leu
            20                  25                  30

Ile Gly Lys Asp Leu Arg Arg Leu Gly Phe Arg Ala Leu Asn Ala Lys
        35                  40                  45

Leu Thr Glu Ser Asn Leu Ser Leu Phe Glu Leu Asp Glu Gln Gly Thr
    50                  55                  60

Ala Ile Phe Ile Ser Gln Glu Asp Asn Ala Pro Pro Asn Ser Cys Val
65                  70                  75                  80

Leu Phe Phe Tyr Asp Leu Asn Lys Asn Gly Cys Ile Gly Lys Gly Ser
                85                  90                  95

Pro Lys Thr Cys Met Lys Lys Gly Lys Asn Thr Ser Lys Ser Ser Thr
            100                 105                 110

Glu Glu Leu Phe Gly Tyr Lys Val Ser Asn Lys Met Ile Lys Thr Lys
        115                 120                 125

Leu Thr Tyr Gln Ser Val Ile Pro Thr Asn Cys Thr Ala Glu Thr Cys
    130                 135                 140

Lys Arg Ala Phe Gln Gln Thr Ala Cys Asn Ala Gly Gly Gly Trp Ala
145                 150                 155                 160

Asp Leu Leu Asp Asn Asn Glu Tyr Glu Ile Thr Arg Leu Gln Phe Asn
                165                 170                 175

Trp Leu Ile Glu Gly Lys Gly Leu Glu Ile Lys Leu Lys Gly Asn Leu
            180                 185                 190

Lys Gln Thr Pro Asn Ile Ser Tyr Glu Thr Ser Leu Val Val Ala Leu
        195                 200                 205

Trp Asn Gln Lys
    210

<210> SEQ ID NO 20
<211> LENGTH: 630
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT048

<400> SEQUENCE: 20

Ser Gly Gly Gly Gly Ser Phe Asp Val Asp Val Ser Asn Pro Ser
1               5                   10                  15

Ser Ser Lys Pro Arg Tyr Gln Asp Thr Ser Ser Arg Thr Lys
            20                  25                  30

Ser Lys Leu Glu Asn Leu Ser Ile Pro Ser Leu Gly Gly Met Lys
        35                  40                  45

Leu Val Ala Gln Asn Leu Arg Asp Arg Thr Lys Pro Ser Leu Leu Asn
    50                  55                  60

Glu Asp Asp Tyr Met Ile Phe Ser Ser Leu Ser Thr Ile Lys Ala Asp
65                  70                  75                  80

Val Glu Lys Glu Asn Lys His Tyr Thr Ser Pro Val Gly Ser Ile Asp
```

```
                    85                  90                  95
Glu Pro Ser Thr Thr Asn Pro Lys Glu Asn Asp His Gly Gln Arg Tyr
                100                 105                 110
Val Tyr Ser Gly Leu Tyr Tyr Ile Pro Ser Trp Asn Leu Asn Asp Leu
                115                 120                 125
Lys Asn Asn Lys Tyr Tyr Ser Gly Tyr Tyr Gly Tyr Ala Tyr Tyr
            130                 135                 140
Phe Gly Lys Gln Thr Ala Thr Thr Leu Pro Val Asn Gly Lys Val Thr
145                 150                 155                 160
Tyr Lys Gly Thr Trp Ser Phe Ile Thr Ala Ala Glu Asn Gly Lys Arg
                165                 170                 175
Tyr Pro Leu Leu Ser Asn Gly Ser Gln Ala Tyr Phe Arg Arg Ser Ala
                180                 185                 190
Ile Pro Glu Asp Ile Asp Leu Glu Val Lys Asn Asp Glu Asn Arg Glu
                195                 200                 205
Lys Gly Leu Val Ser Glu Phe Ser Ala Asp Phe Gly Thr Lys Lys Leu
                210                 215                 220
Thr Gly Gly Leu Phe Tyr Thr Lys Arg Gln Thr His Ile Gln Asn His
225                 230                 235                 240
Glu Lys Lys Lys Leu Tyr Asp Ile Asp Ala His Ile Tyr Ser Asn Arg
                245                 250                 255
Phe Arg Gly Lys Val Asn Pro Thr Gln Lys Asp Ser Lys Glu His Pro
                260                 265                 270
Phe Thr Ser Glu Gly Thr Leu Glu Gly Phe Tyr Gly Pro Glu Gly
                275                 280                 285
Gln Glu Leu Gly Gly Lys Phe Leu Ala Gly Asp Lys Lys Val Phe Gly
                290                 295                 300
Val Phe Ser Ala Lys Gly Thr Glu Glu Asn Lys Lys Leu Pro Lys Glu
305                 310                 315                 320
Thr Leu Ile Asp Gly Lys Leu Thr Thr Phe Ser Thr Lys Thr Thr Asp
                325                 330                 335
Ala Lys Thr Asn Ala Thr Ala Asn Ala Thr Thr Ser Thr Ala Ala Asn
                340                 345                 350
Thr Thr Thr Asp Thr Thr Ala Asn Thr Ile Thr Asp Ala Glu Asn Phe
                355                 360                 365
Lys Thr Lys Asp Ile Ser Ser Phe Gly Glu Ala Asp Tyr Leu Leu Ile
                370                 375                 380
Asp Asn Tyr Pro Val Pro Leu Leu Pro Glu Ser Gly Asp Phe Ile Ser
385                 390                 395                 400
Ser Lys His His Thr Val Gly Lys Lys Thr Tyr Gln Val Lys Ala Cys
                405                 410                 415
Cys Ser Asn Leu Ser Tyr Val Lys Phe Gly Met Tyr Tyr Glu Val Pro
                420                 425                 430
Pro Lys Glu Glu Glu Lys Asp Lys Glu Lys Lys Glu Lys Glu Lys Glu
                435                 440                 445
Lys Gln Ala Thr Asn Leu Ser Asn Thr Tyr Tyr Gln Phe Leu Leu Gly
                450                 455                 460
Leu Arg Thr Pro Ser Ser Glu Ile Pro Lys Gly Gly Ser Ala Lys Tyr
465                 470                 475                 480
Leu Gly Ser Trp Phe Gly Tyr Leu Ser Asp Gly Ser Thr Ser Tyr Ser
                485                 490                 495
Pro Ser Gly Asp Lys Lys Arg Glu Asn Asn Ala Leu Ala Glu Phe Asn
                500                 505                 510
```

Val Asn Phe Ala Asp Lys Thr Leu Lys Gly Gln Leu Lys Arg His Asp
           515                  520                  525

Asn Gln Asn Thr Val Phe Thr Ile Asp Ala Thr Phe Lys Ser Gly Lys
  530                  535                  540

Asn Asn Phe Thr Gly Thr Ala Thr Ala Asn Asn Val Ala Ile Asp Pro
545                  550                  555                  560

Gln Ser Thr Gln Gly Thr Ser Asn Val Asn Phe Thr Ala Thr Val Asn
           565                  570                  575

Gly Ala Phe Tyr Gly Pro Asn Ala Thr Glu Leu Gly Gly Tyr Phe Thr
                580                  585                  590

Tyr Asn Gly Asn Pro Thr Asp Lys Ser Ser Ser Thr Val Pro Ser Ser
        595                  600                  605

Ser Asn Ser Lys Asn Ala Arg Ala Ala Val Val Phe Gly Ala Arg Gln
           610                  615                  620

Gln Val Glu Thr Thr Lys
625                  630

<210> SEQ ID NO 21
<211> LENGTH: 157
<212> TYPE: PRT
<213> ORGANISM: Unknown
<220> FEATURE:
<223> OTHER INFORMATION: Description of Unknown:
     Bacteria <Prokaryote> sequence
<220> FEATURE:
<223> OTHER INFORMATION: NT053

<400> SEQUENCE: 21

Ala Asp Ser Ser Asp Lys Thr Trp Gln Leu Gln Thr Gly Gln Gly Leu
1                  5                  10                  15

Asp Ala Lys Arg Gly Gln Val Asn Asn Gln Phe Thr Gln Val Asp Thr
           20                  25                  30

Arg Leu Asn Arg Thr Asp Leu Arg Ile Asn Arg Val Gly Ala Ser Ala
        35                  40                  45

Thr Ala Leu Ala Ser Leu Lys Pro Ala Gln Leu Gly Glu Asp Asp Lys
  50                  55                  60

Phe Ala Leu Ser Leu Gly Val Gly Ser Tyr Lys Asn Ala Gln Ala Met
65                  70                  75                  80

Ala Met Gly Ala Val Phe Lys Pro Ala Glu Asn Val Leu Leu Asn Val
           85                  90                  95

Ala Gly Ser Phe Ser Gly Ser Glu Lys Ile Val Gly Ala Gly Val Ser
          100                  105                  110

Trp Lys Phe Gly Ser Lys Ser Lys Pro Ala Val Ser Thr Gln Ser Ala
        115                  120                  125

Val Asn Ser Ala Glu Val Leu Gln Leu Arg Gln Glu Ile Ser Ala Met
  130                  135                  140

Gln Lys Glu Leu Ala Glu Leu Lys Lys Ala Leu Arg Lys
145                 150                  155

<210> SEQ ID NO 22
<211> LENGTH: 505
<212> TYPE: PRT
<213> ORGANISM: Unknown
<220> FEATURE:
<223> OTHER INFORMATION: Description of Unknown:
     Bacteria <Prokaryote> sequence
<220> FEATURE:
<223> OTHER INFORMATION: NT066

```
<400> SEQUENCE: 22

Phe Lys Lys Ser Leu Ile Val Ala Ala Ser Phe Ala Ser Leu Ser Leu
1               5                   10                  15

Phe Asn Ser Ala Thr Ala Glu Leu Val Tyr Lys Pro Leu Glu Gln Pro
            20                  25                  30

Val Glu Pro Ala Lys Pro Asp Leu Lys Ile Glu Ser Val Asn Glu Lys
        35                  40                  45

Phe Ala Glu Lys Tyr Pro Asn Gln Tyr Asn Ser Trp Arg Ser Thr Ala
    50                  55                  60

Asn Gly Asp Gly Glu Asn Ile Ile Tyr Ala Asp Glu Glu Asn Pro Arg
65                  70                  75                  80

Leu Ile Val Leu Trp Gly Gly Tyr Ala Phe Ala Lys Glu Tyr Asn Ala
                85                  90                  95

Pro Arg Gly His Phe Tyr Ala Val Thr Asp Val Arg Asn Ile Leu Arg
            100                 105                 110

Thr Gly Ala Pro Lys Thr Ala Asn Asp Gly Pro Gln Ala Met Ala Cys
        115                 120                 125

Trp Thr Cys Lys Gly Pro Asp Val Pro Arg Leu Ile Ala Glu Trp Gly
    130                 135                 140

Glu Lys Asp Tyr Phe Asn Ala Lys Trp Ala Lys Gly Pro Glu Ile
145                 150                 155                 160

Val Asn Ser Ile Gly Cys Ala Asp Cys His Asp Thr Thr Ser Lys Asp
                165                 170                 175

Phe Ala Glu Gly Lys Pro Ala Leu Arg Ile Ala Arg Pro His Ile Leu
            180                 185                 190

Arg Ala Leu Asp Ala Leu Glu Lys Ala Thr Ala Glu Lys Asp Lys Ala
        195                 200                 205

Glu Gly Arg Pro His Asn Asn Leu Ser Phe Asn Thr Ala Ala Arg Thr
    210                 215                 220

Glu Lys Arg Ala Glu Ile Cys Ala Asn Cys His Val Glu Tyr Tyr Phe
225                 230                 235                 240

Ser Gly Asp Ile Lys Gln Val Thr Phe Pro Trp Asp Asn Gly Gln Thr
                245                 250                 255

Val Asp Asp Ile Glu Lys Tyr Tyr Asp Asp Ile Gly Phe Thr Asp Trp
            260                 265                 270

Thr His Ser Leu Ser Lys Ala Pro Met Leu Lys Ala Gln His Pro Asp
        275                 280                 285

Phe Glu Ile Trp Ser Leu Gly Met His Gly Lys Asn Gly Val Thr Cys
    290                 295                 300

Val Asp Cys His Met Pro Lys Val Gln Gly Ala Asp Gly Lys Val Tyr
305                 310                 315                 320

Thr Asp His Gln Ile Gln Asn Pro Phe Glu Ala Phe Asp Ser Thr Cys
                325                 330                 335

Ala Asn Cys His Asp Gln Ser Lys Glu Lys Leu Arg Asp Ile Val Thr
            340                 345                 350

Ser Arg Lys Lys Glu Val Lys Asp Val Met Gly Arg Leu Glu Asp Gln
        355                 360                 365

Val Val Lys Ala His Phe Glu Ala Lys Glu Ala Trp Asp Ala Gly Ala
    370                 375                 380

Thr Lys Lys Glu Met Glu Ala Ala Leu Met Asp Ile Arg His Ala Gln
385                 390                 395                 400

Trp Arg Trp Asp Tyr Thr Ala Ala Ser His Gly Gly His Met His Ala
                405                 410                 415
```

```
Pro Glu Val Val Leu Arg Val Leu Ala Ser Gly Leu Asp Lys Val Ala
            420                 425                 430

Asp Ala Arg Thr Lys Leu Ala Val Ile Leu Thr Lys His Gly Val Lys
            435                 440                 445

Thr Pro Val Gln Ile Pro Asp Ile Ser Thr Ala Asp Lys Ala Trp Lys
            450                 455                 460

Val Met Gly Ile Asp Ile Glu Lys Glu Arg Lys Ala Lys Glu Glu Phe
465                 470                 475                 480

Leu Lys Thr Val Val Pro Gln Trp Glu Gln Gln Ala Arg Glu Lys Gly
                485                 490                 495

Leu Leu Val Asp Pro Pro Ala Gln Lys
            500                 505

<210> SEQ ID NO 23
<211> LENGTH: 429
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT097

<400> SEQUENCE: 23

Ala Ala Phe Gln Leu Ala Glu Val Ser Thr Ser Gly Leu Gly Arg Ala
1               5                   10                  15

Tyr Ala Gly Glu Ala Ala Ile Ala Asp Asn Ala Ser Val Val Ala Thr
            20                  25                  30

Asn Pro Ala Leu Met Ser Leu Phe Lys Thr Ala Gln Phe Ser Thr Gly
            35                  40                  45

Gly Val Tyr Ile Asp Ser Arg Ile Asn Met Asn Gly Asp Val Asn Ser
    50                  55                  60

Tyr Leu Asn Ser Gly Ser Met Ala Leu Thr Lys Tyr Gly Ser Ala Ser
65              70                  75                  80

Gln Arg Asn Val Val Pro Gly Ala Phe Val Pro Asn Leu Tyr Phe Val
                85                  90                  95

Ala Pro Val Asn Asp Lys Phe Ala Leu Gly Ala Gly Met Asn Val Asn
            100                 105                 110

Phe Gly Leu Lys Ser Glu Tyr Asp Asp Ser Tyr Asp Ala Gly Val Phe
            115                 120                 125

Gly Gly Lys Thr Asp Leu Asn Ala Ile Asn Leu Asn Leu Ser Gly Ala
    130                 135                 140

Tyr Arg Val Ile Glu Gly Leu Ser Leu Gly Leu Gly Val Asn Ala Val
145                 150                 155                 160

Tyr Ala Asn Ala Gln Val Glu Arg Asn Ala Gly Ile Ile Ala Asp Ser
                165                 170                 175

Leu Gln Asp Ser Gln Val Lys Gly Ala Leu Lys Ile Val Asp Ser Thr
            180                 185                 190

Asn Lys Ala Pro Asp Arg Leu Thr Ser Lys Asp Lys Ser Val Val Ser
            195                 200                 205

Leu Gln Asp Arg Ala Ala Trp Gly Phe Gly Trp Asn Ala Gly Val Met
    210                 215                 220

Tyr Gln Phe Asn Glu Ala Asn Arg Ile Gly Leu Ala Tyr His Ser Lys
225                 230                 235                 240

Val Asp Ile Asp Phe Ala Asp Arg Thr Ala Thr Ser Phe Gly Lys Lys
                245                 250                 255
```

```
Asp Ile Val Ala Gly Lys Thr Gly Asn Leu Thr Phe Thr Leu Pro Asp
            260                 265                 270

Tyr Leu Glu Leu Ser Gly Phe His Gln Leu Thr Asp Lys Phe Ala Val
        275                 280                 285

His Tyr Ser Tyr Lys Tyr Thr His Trp Ser Arg Leu Thr Lys Leu His
    290                 295                 300

Ala Ser Tyr Glu Asn Gly Glu Lys Ala Phe Asp Lys Glu Leu Gln Tyr
305                 310                 315                 320

Ser Asn Asn Ser Arg Val Ala Leu Gly Ala Ser Tyr Asn Leu Asp Glu
                325                 330                 335

Lys Leu Thr Leu Arg Ala Gly Ile Ala Tyr Asp Gln Ala Ala Ser Arg
            340                 345                 350

His Gln Arg Ser Ala Ala Ile Pro Asp Thr Asp Arg Thr Trp Tyr Ser
        355                 360                 365

Leu Gly Gly Thr Tyr Lys Phe Thr Pro Asn Leu Ser Val Asp Leu Gly
    370                 375                 380

Tyr Ala Tyr Leu Lys Gly Lys Lys Val His Phe Lys Glu Val Gln Lys
385                 390                 395                 400

Ala Ala Gly Gly His Ile Thr Thr Ala Asn Tyr Thr Ser Gln Ala
                405                 410                 415

His Ala Asn Leu Tyr Gly Leu Asn Leu Asn Tyr Ser Phe
                420                 425

<210> SEQ ID NO 24
<211> LENGTH: 422
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: P48 (NT007)

<400> SEQUENCE: 24

Val Asn Gln Val Ala Ile Leu Gly Glu Glu Tyr Val Gly Met Arg Pro
1               5                   10                  15

Ser Met Lys Val Arg Glu Gly Asp Val Val Lys Lys Gly Gln Val Leu
            20                  25                  30

Phe Glu Asp Lys Lys Asn Pro Gly Val Ile Phe Thr Ala Pro Ala Ser
        35                  40                  45

Gly Thr Ile Thr Ala Ile Asn Arg Gly Glu Lys Arg Val Leu Gln Ser
    50                  55                  60

Val Val Ile Asn Val Glu Gly Asp Lys Ile Thr Phe Ala Lys Tyr
65                  70                  75                  80

Ser Thr Glu Gln Leu Asn Thr Leu Ser Ser Gln Val Lys Gln Asn
                85                  90                  95

Leu Ile Glu Ser Gly Leu Trp Thr Ala Leu Arg Thr Arg Pro Phe Ser
            100                 105                 110

Lys Val Pro Ser Ile Glu Ser Glu Ala Ser Ser Ile Phe Val Asn Ala
        115                 120                 125

Met Asp Thr Asn Pro Leu Ala Ala Asp Pro Ser Val Val Leu Lys Glu
    130                 135                 140

Tyr Ser Gln Asp Phe Thr Asn Gly Leu Thr Val Leu Ser Arg Leu Phe
145                 150                 155                 160

Pro Ser Lys Pro Leu His Leu Cys Lys Ala Gly Asp Ser Asn Ile Pro
                165                 170                 175
```

Thr Ala Asp Leu Glu Asn Leu Gln Ile His Asp Phe Thr Gly Val His
            180                 185                 190

Pro Ala Gly Leu Val Gly Thr His Ile His Phe Ile Asp Pro Val Gly
            195                 200                 205

Ile Gln Lys Thr Val Trp His Ile Asn Tyr Gln Asp Val Ile Ala Val
            210                 215                 220

Gly Lys Leu Phe Thr Thr Gly Glu Leu Tyr Ser Glu Arg Val Ile Ser
225                 230                 235                 240

Leu Ala Gly Pro Gln Val Lys Glu Pro Arg Leu Val Arg Thr Ile Ile
                245                 250                 255

Gly Ala Asn Leu Ser Gln Leu Thr Gln Asn Glu Leu Ser Ala Gly Lys
            260                 265                 270

Asn Arg Val Ile Ser Gly Ser Val Leu Cys Gly Gln Ile Ala Lys Asp
            275                 280                 285

Ser His Asp Tyr Leu Gly Arg Tyr Ala Leu Gln Val Ser Val Ile Ala
            290                 295                 300

Glu Gly Asn Glu Lys Glu Phe Phe Gly Trp Ile Met Pro Gln Ala Asn
305                 310                 315                 320

Lys Tyr Ser Val Thr Arg Thr Val Leu Gly His Phe Ser Lys Lys Leu
                325                 330                 335

Phe Asn Phe Thr Thr Ser Glu Asn Gly Gly Glu Arg Ala Met Val Pro
            340                 345                 350

Ile Gly Ser Tyr Glu Arg Val Met Pro Leu Asp Ile Leu Pro Thr Leu
            355                 360                 365

Leu Leu Arg Asp Leu Ile Val Gly Asp Thr Asp Gly Ala Gln Glu Leu
            370                 375                 380

Gly Cys Leu Glu Leu Asp Glu Asp Leu Ala Leu Cys Ser Phe Val
385                 390                 395                 400

Cys Pro Gly Lys Tyr Glu Tyr Gly Ser Ile Leu Arg Gln Val Leu Asp
                405                 410                 415

Lys Ile Glu Lys Glu Gly
            420

<210> SEQ ID NO 25
<211> LENGTH: 437
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: HtrA (NT006)

<400> SEQUENCE: 25

Thr Leu Pro Ser Phe Val Ser Glu Gln Asn Ser Leu Ala Pro Met Leu
1               5                   10                  15

Glu Lys Val Gln Pro Ala Val Val Thr Leu Ser Val Glu Gly Lys Ala
                20                  25                  30

Lys Gly Asp Ser Arg Ser Pro Phe Leu Asp Asp Ile Pro Glu Glu Phe
            35                  40                  45

Lys Phe Phe Phe Gly Asp Arg Phe Ala Glu Gln Phe Gly Gly Arg Gly
        50                  55                  60

Glu Ser Lys Arg Asn Phe Arg Gly Leu Gly Ser Gly Val Ile Ile Asn
65                  70                  75                  80

Ala Ser Lys Gly Tyr Val Leu Thr Asn Asn His Val Ile Asp Gly Ala
                85                  90                  95

Asp Lys Ile Thr Val Gln Leu Gln Asp Gly Arg Glu Phe Lys Ala Lys
            100                 105                 110

Leu Val Gly Lys Asp Glu Gln Ser Asp Ile Ala Leu Val Gln Leu Glu
        115                 120                 125

Lys Ser Ser Asn Leu Thr Glu Ile Lys Phe Ala Asp Ser Asp Lys Leu
    130                 135                 140

Arg Val Gly Asp Phe Thr Val Ala Ile Gly Asn Pro Phe Gly Leu Gly
145                 150                 155                 160

Gln Thr Val Thr Ser Gly Val Val Ser Ala Leu Gly Arg Ser Thr Gly
                165                 170                 175

Ser Asp Ser Gly Thr Tyr Glu Asn Tyr Ile Gln Thr Asp Ala Ala Val
            180                 185                 190

Asn Arg Gly Asn Ser Gly Gly Ala Leu Val Asn Leu Asn Gly Glu Leu
        195                 200                 205

Ile Gly Ile Asn Thr Ala Ile Ile Ser Pro Ser Gly Gly Asn Ala Gly
    210                 215                 220

Ile Ala Phe Ala Ile Pro Ser Asn Gln Ala Ser Asn Leu Val Gln Gln
225                 230                 235                 240

Ile Leu Glu Phe Gly Gln Val Arg Arg Gly Leu Leu Gly Ile Lys Gly
                245                 250                 255

Gly Glu Leu Asn Ala Asp Leu Ala Lys Ala Phe Asn Val Ser Ala Gln
            260                 265                 270

Gln Gly Ala Phe Val Ser Glu Val Leu Pro Lys Ser Ala Ala Glu Lys
        275                 280                 285

Ala Gly Leu Lys Ala Gly Asp Ile Ile Thr Ala Met Asn Gly Gln Lys
290                 295                 300

Ile Ser Ser Phe Ala Glu Met Arg Ala Lys Ile Ala Thr Thr Gly Ala
305                 310                 315                 320

Gly Lys Glu Ile Ser Leu Thr Tyr Leu Arg Asp Gly Lys Ser His Asp
                325                 330                 335

Val Lys Val Lys Leu Gln Ala Asp Asp Gly Ser Gln Leu Ser Ser Lys
            340                 345                 350

Thr Glu Leu Leu Ala Leu Asp Gly Ala Thr Leu Lys Asp Tyr Asp Thr
        355                 360                 365

Lys Gly Val Lys Gly Ile Glu Ile Thr Lys Ile Gln Pro Asn Ser Leu
370                 375                 380

Ala Ala Gln Arg Gly Leu Lys Ala Gly Asp Ile Ile Gly Ile Asn
385                 390                 395                 400

Arg Gln Met Ile Glu Asn Ile Arg Glu Leu Asn Lys Val Leu Glu Thr
                405                 410                 415

Glu Pro Ser Ala Ile Ala Leu Asn Ile Leu Arg Gly Asn Ser Asn Phe
            420                 425                 430

Tyr Leu Leu Val Gln
        435

<210> SEQ ID NO 26
<211> LENGTH: 144
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: PE (NT035)

<400> SEQUENCE: 26

Ser Ala Gln Ile Gln Lys Ala Glu Gln Asn Asp Val Lys Leu Ala Pro
1               5                   10                  15

Pro Thr Asp Val Arg Ser Gly Tyr Ile Arg Leu Val Lys Asn Val Asn
            20                  25                  30

Tyr Tyr Ile Asp Ser Glu Ser Ile Trp Val Asp Asn Gln Glu Pro Gln
            35                  40                  45

Ile Val His Phe Asp Ala Val Val Asn Leu Asp Lys Gly Leu Tyr Val
        50                  55                  60

Tyr Pro Glu Pro Lys Arg Tyr Ala Arg Ser Val Arg Gln Tyr Lys Ile
65                  70                  75                  80

Leu Asn Cys Ala Asn Tyr His Leu Thr Gln Val Arg Thr Asp Phe Tyr
                85                  90                  95

Asp Glu Phe Trp Gly Gln Gly Leu Arg Ala Ala Pro Lys Lys Gln Lys
            100                 105                 110

Lys His Thr Leu Ser Leu Thr Pro Asp Thr Thr Leu Tyr Asn Ala Ala
            115                 120                 125

Gln Ile Ile Cys Ala Asn Tyr Gly Lys Ala Phe Ser Val Asp Lys Lys
            130                 135                 140

<210> SEQ ID NO 27
<211> LENGTH: 197
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: P26 (NT010)

<400> SEQUENCE: 27

Met Lys Asn Ile Ala Lys Val Thr Ala Leu Ala Leu Gly Ile Ala Leu
1               5                   10                  15

Ala Ser Gly Tyr Ala Ser Ala Glu Glu Lys Ile Ala Phe Ile Asn Ala
            20                  25                  30

Gly Tyr Ile Phe Gln His His Pro Asp Arg Gln Ala Val Ala Asp Lys
            35                  40                  45

Leu Asp Ala Glu Phe Lys Pro Val Ala Glu Lys Leu Ala Ala Ser Lys
        50                  55                  60

Lys Glu Val Asp Lys Ile Ala Ala Arg Lys Lys Val Glu Ala
65                  70                  75                  80

Lys Val Ala Ala Leu Glu Lys Asp Ala Pro Arg Leu Arg Gln Ala Asp
                85                  90                  95

Ile Gln Lys Arg Gln Gln Glu Ile Asn Lys Leu Gly Ala Ala Glu Asp
            100                 105                 110

Ala Glu Leu Gln Lys Leu Met Gln Glu Gln Asp Lys Lys Val Gln Glu
            115                 120                 125

Phe Gln Ala Gln Asn Glu Lys Arg Gln Ala Glu Glu Arg Gly Lys Leu
            130                 135                 140

Leu Asp Ser Ile Gln Thr Ala Thr Asn Asn Leu Ala Lys Ala Lys Gly
145                 150                 155                 160

Tyr Thr Tyr Val Leu Asp Ala Asn Ser Val Val Phe Ala Val Glu Gly
            165                 170                 175

Lys Asp Ile Thr Glu Glu Val Leu Lys Ser Ile Pro Ala Ser Glu Lys
            180                 185                 190

Ala Gln Glu Lys Lys
            195

<210> SEQ ID NO 28
<211> LENGTH: 346
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: PHiD (NT080)

<400> SEQUENCE: 28

```
Cys Ser Ser His Ser Ser Asn Met Ala Asn Thr Gln Met Lys Ser Asp
1               5                   10                  15

Lys Ile Ile Ile Ala His Arg Gly Ala Ser Gly Tyr Leu Pro Glu His
            20                  25                  30

Thr Leu Glu Ser Lys Ala Leu Ala Phe Ala Gln Gln Ala Asp Tyr Leu
        35                  40                  45

Glu Gln Asp Leu Ala Met Thr Lys Asp Gly Arg Leu Val Val Ile His
    50                  55                  60

Asp His Phe Leu Asp Gly Leu Thr Asp Val Ala Lys Lys Phe Pro His
65                  70                  75                  80

Arg His Arg Lys Asp Gly Arg Tyr Tyr Val Ile Asp Phe Thr Leu Lys
                85                  90                  95

Glu Ile Gln Ser Leu Glu Met Thr Glu Asn Phe Glu Thr Lys Asp Gly
            100                 105                 110

Lys Gln Ala Gln Val Tyr Pro Asn Arg Phe Pro Leu Trp Lys Ser His
        115                 120                 125

Phe Arg Ile His Thr Phe Glu Asp Glu Ile Glu Phe Ile Gln Gly Leu
    130                 135                 140

Glu Lys Ser Thr Gly Lys Lys Val Gly Ile Tyr Pro Glu Ile Lys Ala
145                 150                 155                 160

Pro Trp Phe His His Gln Asn Gly Lys Asp Ile Ala Ala Glu Thr Leu
                165                 170                 175

Lys Val Leu Lys Lys Tyr Gly Tyr Asp Lys Lys Thr Asp Met Val Tyr
            180                 185                 190

Leu Gln Thr Phe Asp Phe Asn Glu Leu Lys Arg Ile Lys Thr Glu Leu
        195                 200                 205

Leu Pro Gln Met Gly Met Asp Leu Lys Leu Val Gln Leu Ile Ala Tyr
    210                 215                 220

Thr Asp Trp Lys Glu Thr Gln Glu Lys Asp Pro Lys Gly Tyr Trp Val
225                 230                 235                 240

Asn Tyr Asn Tyr Asp Trp Met Phe Lys Pro Gly Ala Met Ala Glu Val
                245                 250                 255

Val Lys Tyr Ala Asp Gly Val Gly Pro Gly Trp Tyr Met Leu Val Asn
            260                 265                 270

Lys Glu Glu Ser Lys Pro Asp Asn Ile Val Tyr Thr Pro Leu Val Lys
        275                 280                 285

Glu Leu Ala Gln Tyr Asn Val Glu Val His Pro Tyr Thr Val Arg Lys
    290                 295                 300

Asp Ala Leu Pro Glu Phe Phe Thr Asp Val Asn Gln Met Tyr Asp Ala
305                 310                 315                 320

Leu Leu Asn Lys Ser Gly Ala Thr Gly Val Phe Thr Asp Phe Pro Asp
                325                 330                 335

Thr Gly Val Glu Phe Leu Lys Gly Ile Lys
            340                 345
```

<210> SEQ ID NO 29
<211> LENGTH: 134
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: P6 (NT081)

<400> SEQUENCE: 29

Cys Ser Ser Ser Asn Asn Asp Ala Ala Gly Asn Gly Ala Ala Gln Thr
1               5                   10                  15

Phe Gly Gly Tyr Ser Val Ala Asp Leu Gln Gln Arg Tyr Asn Thr Val
            20                  25                  30

Tyr Phe Gly Phe Asp Lys Tyr Asp Ile Thr Gly Glu Tyr Val Gln Ile
        35                  40                  45

Leu Asp Ala His Ala Ala Tyr Leu Asn Ala Thr Pro Ala Ala Lys Val
    50                  55                  60

Leu Val Glu Gly Asn Thr Asp Glu Arg Gly Thr Pro Glu Tyr Asn Ile
65                  70                  75                  80

Ala Leu Gly Gln Arg Arg Ala Asp Ala Val Lys Gly Tyr Leu Ala Gly
                85                  90                  95

Lys Gly Val Asp Ala Gly Lys Leu Gly Thr Val Ser Tyr Gly Glu Glu
            100                 105                 110

Lys Pro Ala Val Leu Gly His Asp Glu Ala Ala Tyr Ser Lys Asn Arg
        115                 120                 125

Arg Ala Val Leu Ala Tyr
        130

<210> SEQ ID NO 30
<211> LENGTH: 433
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT013

<400> SEQUENCE: 30

Ser Glu Glu Asn Pro Ile Phe Ser Thr Ser Asp Ser Gly Glu Tyr His
1               5                   10                  15

Glu Leu Asn Thr Ser Pro Asn Lys Asn Ser Thr Ala Leu Gln Pro Asp
            20                  25                  30

Glu Asp Ala Thr Ser Tyr Asp Asp Glu Leu Gln Ala Lys Asp Asp Glu
        35                  40                  45

Val Asp Glu Val Lys Leu Ser Ser Asp Leu Gly Thr Leu Pro Gln
    50                  55                  60

His Ala Gln Asp Ala Leu Asn Gly Leu Leu Asp Ala Ala Asp Gln Ala
65                  70                  75                  80

Ile Arg Ile Thr Asp Gln Phe Ser Tyr Thr Val Thr Glu Gly Asp Thr
                85                  90                  95

Leu Lys Asp Val Leu Val Leu Ser Gly Leu Asp Ser Ser Val Gln
            100                 105                 110

Pro Leu Ile Lys Leu Asp Pro Glu Leu Ala His Leu Lys Ala Gly Gln
        115                 120                 125

Gln Phe Tyr Trp Ile Leu Asn Lys Asn Asp Asn Leu Glu Tyr Leu Asn

-continued

```
                130               135               140
Trp Leu Val Ser Glu Lys Glu Arg Ile Tyr Glu Arg Leu Glu Asp
145                 150                 155                 160

Gly Lys Phe Lys Arg Gln Val Ile Glu Lys Lys Ser Ile Trp Arg Lys
                165                 170                 175

Glu Val Leu Lys Gly Glu Ile Gln Asn Ser Leu Asn Ser Ser Leu Arg
                180                 185                 190

Glu Gln Gly Leu Asp Thr Arg Gln Ile Ser Gln Leu Ser Asn Ala Leu
                195                 200                 205

Gln Trp Gln Val Ser Leu Arg Lys Leu Lys Lys Gly Thr Gln Phe Ala
            210                 215                 220

Ile Leu Val Ser Arg Glu Tyr Leu Gly Asp Lys Leu Thr Gly Gln Gly
225                 230                 235                 240

Asn Val Glu Ala Leu Arg Ile Ser Ser Gly Lys Asn Tyr Tyr Ala
                245                 250                 255

Val Gln Ala Ala Asn Gly Arg Tyr Tyr Asn Gln Gln Gly Glu Thr Leu
                260                 265                 270

Gly Lys Gly Phe Ala Arg Tyr Pro Leu Gln Arg Gln Ala Arg Val Ser
                275                 280                 285

Ser Pro Phe Asn Pro Asn Arg Arg His Pro Val Thr Gly Arg Val Arg
            290                 295                 300

Pro His Lys Gly Val Asp Phe Ser Val Ser Gln Gly Thr Pro Val Ile
305                 310                 315                 320

Ala Pro Ala Asp Gly Thr Val Glu Lys Val Ala Tyr Gln Ala Gly Gly
                325                 330                 335

Ala Gly Arg Tyr Val Met Leu Arg His Gly Arg Glu Tyr Gln Thr Val
                340                 345                 350

Tyr Met His Leu Ser Lys Ser Leu Val Lys Ala Gly Gln Thr Val Lys
            355                 360                 365

Lys Gly Glu Arg Ile Ala Leu Ser Gly Asn Thr Gly Ile Ser Thr Gly
            370                 375                 380

Pro His Leu His Tyr Glu Phe Arg Ile Asn Gly Arg Ala Val Asn Pro
385                 390                 395                 400

Leu Thr Val Lys Leu Pro Gly Thr Ser Ser Gly Met Thr Ser Ala Glu
                405                 410                 415

Arg Lys Gln Phe Leu Val Arg Val Arg Glu Ala Glu Lys Met Leu Lys
                420                 425                 430

Pro
```

<210> SEQ ID NO 31
<211> LENGTH: 192
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT106

<400> SEQUENCE: 31

```
Ser Ser Asn Pro Glu Thr Leu Lys Ala Thr Asn Asp Ser Phe Gln Lys
1               5                   10                  15

Ser Glu Thr Ser Ile Pro His Phe Ser Pro Leu Ala Thr Gly Gly Val
                20                  25                  30

Gln Leu Pro Lys Ala Asp Asp Ala Tyr Ser Leu Pro Asn Ile Glu Val
            35                  40                  45
```

Lys Lys Gly Glu Asp Ile Asp Ile Arg Pro Pro Leu Ile Pro Leu Ala
          50                  55                  60

Ile Ile Gln Asn Ser Ile Thr Lys Phe Asp Gly Glu Arg Ser Leu Ile
65                  70                  75                  80

Val Tyr Pro Lys Gln Gln Ala Lys Leu Tyr Asn Leu Gln Gln Val Lys
                    85                  90                  95

Arg Leu Leu Lys Asp Glu Gly Ile Ser Ser Thr Thr Asp Gly Ser Ile
                100                 105                 110

Leu Thr Thr Asp Trp Ala Lys Thr Glu Arg Ile Gly Asp Lys Ser Ile
                115                 120                 125

Glu Ile Lys Tyr Gln Ile Glu Gln Val Met Thr Ala Asp Val Ser Val
130                 135                 140

Leu Thr Val Ser Ile Leu His Met Arg Arg Asp Gly Ile Ile Phe Thr
145                 150                 155                 160

Pro Asn Val Ser Asp Lys Gln Tyr Tyr Thr Ser Glu Arg Leu Asn Arg
                165                 170                 175

Ile Val Leu Thr Leu Thr Thr Ala Tyr Asn Lys Gln Leu Gln Asp Leu
                180                 185                 190

<210> SEQ ID NO 32
<211> LENGTH: 537
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT107

<400> SEQUENCE: 32

Gln Pro Asp Thr Gly Ser Leu Asn Arg Glu Leu Glu Gln Arg Arg Ile
1               5                   10                  15

Gln Pro Glu Ala Lys Pro Ser Gly Glu Leu Phe Asn Gln Ala Ala Lys
                20                  25                  30

Ser Pro Tyr Thr Ala Gln Tyr Lys Gln Glu Leu Lys Phe Pro Leu Thr
            35                  40                  45

Gln Val Gln Ile Leu Asp Arg Asn Asn Gln Glu Val Val Thr Asp Glu
50                  55                  60

Leu Ala His Ile Leu Lys Asn Tyr Val Gly Lys Glu Val Ser Leu Ser
65                  70                  75                  80

Asp Leu Ser Asn Leu Ala Asn Glu Ile Ser Glu Phe Tyr Arg Asn Asn
                85                  90                  95

Asn Tyr Leu Val Ala Lys Ala Ile Leu Pro Pro Gln Glu Ile Glu Gln
                100                 105                 110

Gly Thr Val Lys Ile Leu Leu Leu Lys Gly Asn Val Gly Glu Ile Arg
                115                 120                 125

Leu Gln Asn His Ser Ala Leu Ser Asn Lys Phe Val Ser Arg Leu Ser
            130                 135                 140

Asn Thr Thr Val Asn Thr Ser Glu Phe Ile Leu Lys Asp Glu Leu Glu
145                 150                 155                 160

Lys Phe Ala Leu Thr Ile Asn Asp Val Pro Gly Val Asn Ala Gly Leu
                165                 170                 175

Gln Leu Ser Ala Gly Lys Lys Val Gly Glu Ala Asn Leu Leu Ile Lys
            180                 185                 190

Ile Asn Asp Ala Lys Arg Phe Ser Tyr Val Ser Val Asp Asn Gln
            195                 200                 205

Gly Asn Lys Tyr Thr Gly Arg Tyr Arg Leu Ala Ala Gly Thr Lys Val
            210                 215                 220

Asn Asn Leu Thr Gly Trp Gly Asp Glu Leu Lys Leu Asp Leu Leu Ser
225                 230                 235                 240

Ser Asn Gln Ala Asn Leu Lys Asn Ala Arg Ile Asp Tyr Ser Ser Leu
                245                 250                 255

Ile Asp Gly Tyr Ser Thr Arg Phe Gly Val Thr Ala Asn Tyr Leu His
            260                 265                 270

Tyr Lys Leu Gly Gly Asn Phe Lys Ser Leu Gln Ser Gln Gly His Ser
        275                 280                 285

His Asn Leu Gly Ala Tyr Leu Leu His Pro Thr Ile Arg Thr Pro Asn
    290                 295                 300

Phe Arg Leu Ser Thr Lys Val Ser Phe Asn His Gln Asn Leu Thr Asp
305                 310                 315                 320

Glu Gln Gln Ala Val Thr Val Lys Gln Lys Arg Lys Ile Asn Ser Leu
                325                 330                 335

Thr Val Gly Ile Asp Gly Ser Trp Asn Leu Ile Lys Asp Gly Thr Thr
            340                 345                 350

Tyr Phe Ser Leu Ser Thr Leu Phe Gly Asn Leu Ala Asn Gln Thr Asn
        355                 360                 365

Glu Lys Lys His Asn Ala Lys Glu Asp Phe Gln Pro Gln Ser His Phe
    370                 375                 380

Thr Val Tyr Asn Tyr Arg Leu Ser His Glu Gln Ile Leu Pro Lys Ser
385                 390                 395                 400

Phe Ala Phe Asn Ile Gly Ile Asn Gly Gln Phe Ala Asp Lys Thr Leu
                405                 410                 415

Glu Ser Ser Gln Lys Met Leu Leu Gly Gly Leu Ser Gly Val Arg Gly
            420                 425                 430

His Gln Ala Gly Ala Ala Ser Val Asp Glu Gly His Leu Ile Gln Thr
        435                 440                 445

Glu Phe Lys His Tyr Leu Pro Val Phe Ser Gln Ser Val Leu Val Ser
    450                 455                 460

Ser Leu Phe Tyr Asp Tyr Gly Phe Gly Lys Tyr Tyr Lys Asn Ser Gln
465                 470                 475                 480

Ser Leu Ala Gln Ser Val Lys Asn Ser Val Lys Leu Gln Ser Val Gly
                485                 490                 495

Ala Gly Leu Ser Phe Ser Asp Ala Gly Ser Tyr Ala Ile Asn Val Ser
            500                 505                 510

Val Ala Lys Pro Leu Asp Asn Asn Ile Asp Asn Ala Asp Lys His Gln
        515                 520                 525

Phe Trp Leu Ser Met Ile Lys Thr Phe
    530                 535

<210> SEQ ID NO 33
<211> LENGTH: 345
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT108

<400> SEQUENCE: 33

Thr Ser Asn Ile Lys Asn Ile Gln Ile Pro Thr Thr Leu Asn Gly Ser
1               5                   10                  15

```
Asp Pro Gln Gln Phe Gly Ala Lys Tyr Thr Asn Arg Thr Tyr Gln Gln
            20                  25                  30

Ala Ala Leu Val Pro Val Ser Asn Ile Glu Asn Gln Ser Ala Val Ile
        35                  40                  45

Asn Gln Gly Asp Phe Leu Thr Gln Leu Ser Asn Ile Lys Asn Tyr Ser
    50                  55                  60

Ser Lys Leu Ser Thr Asn Phe Tyr Asp Asn Tyr Glu Lys Ile Thr Asn
65                  70                  75                  80

Trp Val Leu Ser Gly Ala Asn Ile Asn Glu Leu Thr Gln Phe Asn Ile
                85                  90                  95

His Pro Gln Ile Met Arg Gly Phe Asp Gly Tyr Gln Asn Val Leu Met
            100                 105                 110

Thr Gly Tyr Tyr Ser Pro Ile Leu Tyr Ala Arg His Thr Pro Gln Gly
        115                 120                 125

Gln Phe Lys Asn Pro Ile Tyr Arg Met Pro Val Lys Lys Arg Leu Ser
    130                 135                 140

Arg Ala Gln Ile Tyr Ala Gly Ala Leu Thr Gly Lys Arg Leu Glu Leu
145                 150                 155                 160

Ala Tyr Ser Asp Ser Met Leu Glu Asn Phe Leu Leu Gly Val Gln Gly
                165                 170                 175

Ser Gly Tyr Val Asp Phe Gly Asp Gly Asn Leu Asn Tyr Phe Ala Tyr
            180                 185                 190

Ala Gly Gln Asn Gly Tyr Pro Tyr Thr Ala Ile Gly Arg Leu Leu Val
        195                 200                 205

Glu Asp Gly Glu Ile Pro Lys Glu Lys Met Ser Ile Gln Ala Ile Arg
    210                 215                 220

Glu Trp Gly Asn Arg Asn Pro Ser Arg Val Gln Ser Leu Leu Glu Arg
225                 230                 235                 240

Asn Glu Ala Tyr Val Phe Phe Lys Asn Asp Pro Ser Gly Lys Val Lys
                245                 250                 255

Gly Ser Ala Gly Val Pro Leu Val Ala Met Ala Ser Val Ala Ser Asp
            260                 265                 270

Arg Asn Ile Ile Pro Ser Gly Ser Val Leu Leu Val Glu Val Pro Asp
        275                 280                 285

Ile Asp Asn Asn Gly Asn Trp Ile Gly Thr His Lys Leu His Leu Met
    290                 295                 300

Val Ala Leu Asp Val Gly Gly Ala Val Lys Gly His His Phe Asp Leu
305                 310                 315                 320

Tyr Arg Gly Ile Gly Ala Arg Ala Gly His Ile Ala Gly Leu Ser Lys
                325                 330                 335

His Tyr Gly Arg Val Trp Val Leu Arg
            340                 345

<210> SEQ ID NO 34
<211> LENGTH: 534
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT109

<400> SEQUENCE: 34

Ser Ser Asn Lys Tyr Asp Ala Glu Ala Ile Asn Ile Ser Gly Ser Leu
1               5                   10                  15
```

-continued

Arg Met Gln Ser Tyr Arg Leu Leu Tyr Glu Met Gln Glu Gln Pro Glu
            20                  25                  30

Ser Val Glu Thr Asn Leu Arg Arg Tyr His Ile Ser Leu His Ser Ser
            35                  40                  45

Ala Leu Leu Glu Val Gln Asn Gln Phe Phe Thr Pro Asn Val Leu Lys
 50                  55                  60

His Ser Tyr Gln Asn Ile Leu Gln Arg Trp Thr Asn Met Glu Lys Tyr
 65                  70                  75                  80

Ala Arg Gln Gln Asp Val Lys Asn Tyr Ser Lys Gln Leu Thr Asn Tyr
                85                  90                  95

Val Ala Asp Val Asp Tyr Phe Val Phe Glu Leu Gln Arg Phe Ser Glu
            100                 105                 110

Gln Lys Trp Ile Leu Gly Val Ser Val Leu Gly Phe Ala Met Leu Leu
            115                 120                 125

Ile Leu Leu Met Val Ser Tyr Val Ile Trp Tyr Thr Asn Arg Glu Val
            130                 135                 140

Val Lys Pro Leu His Leu Met Thr Lys Ala Ser Met Gln Val Gln Met
145                 150                 155                 160

Arg Gln Phe Asn His Ile Pro Leu Asp Thr Arg Lys Gln Asn Glu Leu
                165                 170                 175

Gly Thr Leu Ala Arg Val Phe Thr Gln Met Ser Thr Glu Leu Gly Gln
            180                 185                 190

Leu Tyr Ser Arg Leu Glu Glu Ala Val Asn Glu Lys Thr Gln Lys Leu
            195                 200                 205

Arg Gln Thr Asn Arg Thr Leu Ser Thr Leu Tyr Gln Ser Ala Gln Leu
            210                 215                 220

Leu Asn Thr Asn Thr Ile Asn Asp Lys Ile Leu Asn Gln Val Leu His
225                 230                 235                 240

Tyr Ile Phe Ile Ser Asp His Leu Asn Phe Val Lys Val Glu Val Met
                245                 250                 255

Gly Ala Glu His Trp Asp Ile Thr Leu Gly Lys Gln Asp Ala Asn Asn
            260                 265                 270

Glu Leu Gln Ile Glu Thr Leu Ser Val Asp Asn Glu Glu Leu Gly Val
            275                 280                 285

Leu Ser Trp Gln Ala Gly Leu Pro Cys Pro Asp Pro Arg Ile Met Gln
            290                 295                 300

Asn Leu Ala Gln Met Leu Ala Arg Ala Leu Tyr Phe His Lys Asn Leu
305                 310                 315                 320

Arg Gln Lys Glu Gln Ile Leu Leu Met Glu Glu Arg Ser Ile Ile Ala
                325                 330                 335

Arg Glu Leu His Asp Ser Leu Ala Gln Val Leu Ser Phe Leu Gln Ile
            340                 345                 350

Gln Leu Thr Leu Leu Lys His Asn Leu Lys Lys Glu Asp Glu Gln Ser
            355                 360                 365

Lys Glu Lys Ser Leu Ala Ile Ile Ala Asn Phe Glu Gln Ala Leu Ser
            370                 375                 380

Gly Gly Tyr Ala Gln Leu Arg Glu Leu Leu Ala Thr Phe Arg Leu Thr
385                 390                 395                 400

Ile Gln Glu Ala Asn Leu Gln Leu Ala Leu Lys Gln Val Ile Asp Ser
                405                 410                 415

Leu Arg Ser Gln Thr Thr Met Gln Met Asn Val Asn Cys Gln Leu Pro
            420                 425                 430

```
Ser Gln Ser Leu Asn Pro Gln Gln Leu Val His Val Leu Gln Ile Val
        435                 440                 445

Arg Glu Ala Thr Thr Asn Ala Ile Lys His Ser Gln Gly Thr Val Ile
450                 455                 460

Glu Ile Ser Ala Arg Ile Asn Ala Glu Gly Glu Tyr Glu Ile Leu Val
465                 470                 475                 480

Glu Asp Asp Gly Val Gly Ile Pro Asn Leu Glu Glu Pro Glu Gly His
                485                 490                 495

Tyr Gly Leu Asn Ile Met Ala Glu Arg Cys Arg Gln Leu Asn Ala Gln
                500                 505                 510

Leu His Ile His Arg Arg Glu Gln Gly Gly Thr Gln Val Lys Ile Thr
            515                 520                 525

Leu Pro His Thr Leu Tyr
    530
```

<210> SEQ ID NO 35
<211> LENGTH: 402
<212> TYPE: PRT
<213> ORGANISM: Unknown
<220> FEATURE:
<223> OTHER INFORMATION: Description of Unknown:
    Bacteria <Prokaryote> sequence
<220> FEATURE:
<223> OTHER INFORMATION: NT110

<400> SEQUENCE: 35

```
Ser Ser Arg Lys Leu Lys Leu Gln Ser Leu Ala Asn Lys Gly Asp Val
1               5                   10                  15

Arg Ala Leu Gln Val Leu Lys Leu Gln Glu His Pro Gly Arg Phe Ile
            20                  25                  30

Thr Val Val Gln Ile Leu Leu Asn Met Val Ala Ile Leu Gly Gly Gly
        35                  40                  45

Ile Gly Glu Ser Ala Leu Ser Pro Tyr Ile Ala Asp Ile Leu Asn Arg
    50                  55                  60

Ser Phe Glu Gly Ser Trp Ile Glu Pro Thr Ala Ser Thr Ile Ala Phe
65                  70                  75                  80

Ile Leu Val Thr Cys Leu Phe Ile Leu Phe Ala Asp Leu Ile Pro Lys
                85                  90                  95

Arg Ile Ala Ile Thr Tyr Pro Glu Met Val Ala Leu Ser Val Val Gly
            100                 105                 110

Ile Met Asn Phe Ser Met Tyr Val Phe Lys Pro Leu Val Trp Phe Phe
        115                 120                 125

Asp Thr Ile Ala Asn Val Phe Phe Arg Leu Phe Arg Ile Ser Thr Val
    130                 135                 140

Arg Glu Asp Gly Met Thr Ser Glu Asp Ile Phe Ala Val Val Glu Ala
145                 150                 155                 160

Gly Ala Glu Ala Gly Val Leu Lys Thr Gln Glu His Tyr Leu Ile Glu
                165                 170                 175

Asn Ile Phe Asp Met Gln Ala Arg Thr Val Thr Ser Thr Met Thr Thr
            180                 185                 190

Arg Glu Asn Ile Val Tyr Leu Asp Arg Thr Phe Ser Arg Gln Glu Val
        195                 200                 205

Met Asp Thr Leu Ser Arg Asp Ser His Ser Lys Ile Val Ile Cys Asp
    210                 215                 220

Asn Gly Leu Asp Lys Ile Leu Gly Tyr Ile Glu Ser His Thr Leu Leu
225                 230                 235                 240
```

```
Thr Met Tyr Leu Gln Asn Glu Asn Val Val Leu Thr Asp Pro Lys Leu
                245                 250                 255

Leu Arg Lys Ala Leu Phe Val Pro Asp Thr Leu Ser Leu Tyr Glu Val
            260                 265                 270

Leu Glu Leu Phe Lys Ser Thr Gly Glu Asp Phe Ala Ile Ile Val Asn
        275                 280                 285

Glu Tyr Ala Leu Val Val Gly Ile Val Thr Leu Asn Asp Val Met Ser
    290                 295                 300

Ile Val Met Gly Glu Leu Val Ser Asn Glu Glu Tyr Ile Val Ser
305                 310                 315                 320

Arg Asp Glu Asn Ser Trp Leu Ile Asp Gly Ala Thr Pro Leu Lys Glu
                325                 330                 335

Val Thr Arg Val Leu Asp Ile Ala Tyr Phe Pro Asp Glu Glu Asn Tyr
            340                 345                 350

Glu Thr Ile Ser Gly Phe Met Met Tyr Met Leu Arg Lys Ile Pro Lys
        355                 360                 365

Lys Thr Asp Ser Val Val Tyr Gly Lys Tyr Lys Phe Glu Val Ile Asp
    370                 375                 380

Thr Glu Asn Phe Lys Ile Asp Gln Ile Leu Val Ser Leu Val Lys Glu
385                 390                 395                 400

Gln Glu

<210> SEQ ID NO 36
<211> LENGTH: 265
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT111

<400> SEQUENCE: 36

Gln Asp Lys Asp Thr Glu Ala Lys Ile Lys Gln Leu Asn Gln Thr Val
1               5                   10                  15

Ala Gln Leu Ser Ala Glu Asn Thr Lys Leu Lys Glu Gln Ile Glu Lys
            20                  25                  30

Thr Val Pro Ala Ile Ile Val Glu Asn Asp Glu Ile Phe Asn Gln Ser
        35                  40                  45

Glu Ile Ile Lys His Pro Lys Ser Lys Glu Asp Tyr Gln Pro Glu Glu
    50                  55                  60

Thr Lys Ile Glu Tyr Ser Ile Ser Thr Ile Lys Thr Asn Ile Asp Trp
65                  70                  75                  80

Leu Asn Asp Leu Leu Trp Lys Lys Leu Thr Glu Asn Glu Glu Thr Lys
                85                  90                  95

Asn Ile Ser Arg Glu Gln Phe Val Ala Arg Tyr Gln Thr Ala Phe Glu
            100                 105                 110

Glu Asp Lys Lys Glu Ala Lys Glu Thr Pro Ser Phe Gly Ile Ser His
        115                 120                 125

Ser Ile Trp Thr Asn Phe Ile Gly Gln Lys Glu Lys Leu Ala Thr Phe
    130                 135                 140

Ala Ile Ser Phe Tyr Asp Tyr Glu Gly Gly Ala His Gly Ile Glu Gly
145                 150                 155                 160

Asn Arg Tyr Phe Thr Ile Asp Leu Thr Thr Arg His Ile Leu Thr Leu
                165                 170                 175

Asn Asp Leu Phe Asn Glu Lys Asp Leu Pro Lys Val Lys Thr Leu Leu
```

```
               180                 185                 190
Trp Glu Gln Tyr Asn Asn Ser Asn Lys Glu Tyr Glu Pro Ile Ile Glu
            195                 200                 205

Ala Asp Ser Phe Asn Leu Ser Asn Asn Ile Tyr Leu Asp Ser Lys Gly
        210                 215                 220

Val His Phe Ile Tyr Asp Val Tyr Glu Ile Ala Pro Tyr Ala Ala Gly
225                 230                 235                 240

Glu Gln Asp Leu Met Leu His Phe Gly Gln Leu Glu Glu Leu Phe Lys
                245                 250                 255

Pro Glu Phe Arg Gln Gly Asn Asp Ile
            260                 265
```

```
<210> SEQ ID NO 37
<211> LENGTH: 231
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT112

<400> SEQUENCE: 37
```

```
Ala Asn His Asn Ala Thr Lys Gln Ala Ser Glu Arg Asn Asp Ser Leu
1               5                   10                  15

Glu Asp Phe Asn Arg Thr Met Trp Lys Phe Asn Tyr Asn Val Ile Asp
            20                  25                  30

Arg Tyr Val Leu Glu Pro Ala Ala Lys Gly Trp Asn Asn Tyr Val Pro
        35                  40                  45

Lys Pro Ile Ser Ser Gly Leu Ala Gly Ile Ala Asn Asn Leu Asp Glu
50                  55                  60

Pro Val Ser Phe Ile Asn Arg Leu Ile Glu Gly Glu Pro Lys Lys Ala
65                  70                  75                  80

Phe Val His Phe Asn Arg Phe Trp Ile Asn Thr Val Phe Gly Leu Gly
                85                  90                  95

Gly Phe Ile Asp Phe Ala Ser Ala Ser Lys Glu Leu Arg Ile Asp Asn
            100                 105                 110

Gln Arg Gly Phe Gly Glu Thr Leu Gly Ser Tyr Gly Val Asp Ala Gly
        115                 120                 125

Thr Tyr Ile Val Leu Pro Ile Tyr Asn Ala Thr Thr Pro Arg Gln Leu
130                 135                 140

Thr Gly Ala Val Val Asp Ala Tyr Met Tyr Pro Phe Trp Gln Trp
145                 150                 155                 160

Val Gly Gly Pro Trp Ala Leu Val Lys Tyr Gly Val Gln Ala Val Asp
                165                 170                 175

Ala Arg Ala Lys Asn Leu Asn Asn Ala Glu Leu Leu Arg Gln Ala Gln
            180                 185                 190

Asp Pro Tyr Ile Thr Phe Arg Glu Ala Tyr Tyr Gln Asn Leu Gln Phe
        195                 200                 205

Lys Val Asn Asp Gly Lys Leu Val Glu Ser Lys Glu Ser Leu Pro Asp
    210                 215                 220

Asp Ile Leu Lys Glu Ile Asp
225                 230
```

```
<210> SEQ ID NO 38
<211> LENGTH: 341
<212> TYPE: PRT
```

<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT113

<400> SEQUENCE: 38

```
Ser Asn Ser Ser Asn Gln Gly Ile Asn Tyr Asp Glu Ala Phe Ala Lys
1               5                   10                  15

Asp Thr Gln Gly Leu Asp Ile Leu Thr Gly Gln Phe Ser His Asn Ile
            20                  25                  30

Asp Arg Ile Trp Gly Val Asn Glu Leu Leu Val Ala Ser Arg Lys Asp
        35                  40                  45

Tyr Val Lys Tyr Thr Asp Ser Phe Tyr Thr Arg Ser His Val Ser Phe
    50                  55                  60

Asp Glu Gly Asn Ile Val Ile Glu Thr Gln Gln Asp Leu Asn Arg Leu
65                  70                  75                  80

His Asn Ala Ile Val His Thr Leu Leu Met Gly Ala Asp Ala Lys Gly
                85                  90                  95

Ile Asp Leu Phe Thr Ser Gly Asp Val Pro Ile Ser Ser Arg Pro Phe
            100                 105                 110

Leu Leu Gly Gln Val Val Asp His Gly Gln Gln Ile Ala Asn Gln
        115                 120                 125

Val Ile Ala Ser Asn Phe Ala Thr Tyr Leu Ile Gln Asn Lys Leu Gln
    130                 135                 140

Thr Arg Arg Leu Gln Asn Gly His Thr Val Gln Phe Val Ser Val Pro
145                 150                 155                 160

Met Ile Ala Asn His Val Glu Val Arg Ala Arg Lys Tyr Leu Pro Leu
                165                 170                 175

Ile Arg Lys Ala Ala Gln Arg Tyr Gly Ile Asp Glu Ser Leu Ile Leu
            180                 185                 190

Gly Ile Met Gln Thr Glu Ser Ser Phe Asn Pro Tyr Ala Ile Ser Tyr
        195                 200                 205

Ala Asn Ala Ile Gly Leu Met Gln Val Val Pro His Thr Ala Gly Arg
    210                 215                 220

Asp Val Phe Ala Met Lys Gly Lys Gly Gly Gln Pro Ser Thr Arg Tyr
225                 230                 235                 240

Leu Tyr Asp Pro Ala Asn Ile Asp Ala Gly Val Ser Tyr Leu Trp
                245                 250                 255

Ile Leu Gln Asn Gln Tyr Leu Asp Gly Ile Thr Asn Pro Thr Ser Lys
            260                 265                 270

Arg Phe Ala Met Ile Ser Ala Tyr Asn Ser Gly Ala Gly Ala Val Leu
        275                 280                 285

Arg Val Phe Asp Asn Asp Lys Asp Thr Ala Ile Tyr Lys Ile Asn Gln
    290                 295                 300

Met Tyr Pro Glu Gln Val Tyr Arg Ile Leu Thr Thr Val His Pro Ser
305                 310                 315                 320

Ser Gln Ala Arg Asn Tyr Leu Leu Lys Val Asp Lys Ala Gln Lys Lys
                325                 330                 335

Phe Arg Val Arg Arg
            340
```

<210> SEQ ID NO 39
<211> LENGTH: 574
<212> TYPE: PRT

<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT114

<400> SEQUENCE: 39

```
Asp Ser Pro Asn Thr Ala Thr Ala Ser Ile Asn Leu Glu Gln Glu Lys
1               5                   10                  15

Gln Asn Trp Ala Ser Ile Gln His Gln Asp Tyr Leu Lys Arg Leu Lys
            20                  25                  30

Gln Arg Glu Val Phe Leu Gln Val Glu Gly Leu Leu Lys Ser Ala Val
        35                  40                  45

Lys Lys Gln Gln Phe Ser Glu Ala Ile Gln Asn Ile Thr Lys Thr Leu
    50                  55                  60

Ile Asp Ser Leu Gln Gly Tyr Pro Leu Gln Tyr Asp Leu Leu Ala Arg
65                  70                  75                  80

Phe Trp Glu Thr Lys Ile Ala Phe Leu Gln Asn Asp Asp Ile Gln Gly
                85                  90                  95

Lys Gln Gln Ala Ile Asn Glu Val Asn Ala Leu Val Gln Gln Asn Tyr
            100                 105                 110

Pro Phe Val Thr Pro Ala Phe Gln Ala Leu Leu Gln Lys Leu Ser Thr
        115                 120                 125

Leu Asn Glu Gln Gln Thr Ser Ala Thr Ser Asp Asn Ala Lys Glu Asn
    130                 135                 140

Asn Arg Val Gln Lys Glu Gln Asn Gln Val Glu Asn Pro Lys Gln Leu
145                 150                 155                 160

Ala Glu Ile Val Arg Lys Ser Asp Pro Asn Thr Leu Asp Lys Thr Val
                165                 170                 175

Leu Ile Asp Ala Phe Pro Arg Tyr Leu Lys Thr Leu Pro Glu Gln Met
            180                 185                 190

Asn Asn Leu Ser Phe Glu Ser Tyr Gln Lys Trp Ala Asn Thr Trp Gln
        195                 200                 205

Leu Ser Glu Asp Glu Ile Lys Gln Trp Lys Ile Ala Phe Leu Asn Arg
    210                 215                 220

Phe Phe Asp Asn Glu Asn Thr Asp Phe Gln Lys Trp Arg Asp Glu Gln
225                 230                 235                 240

Ile Arg Gln Leu Gln Thr Asp Asn Leu Thr Glu Arg Arg Leu Arg Met
                245                 250                 255

Ala Ile Trp Gln Lys Thr Glu Leu Thr Ser Trp Leu Asn Leu Leu Ser
            260                 265                 270

Ala Glu Ser Lys Ser Lys Gln Glu Trp Arg Tyr Trp Glu Ala Lys Gln
        275                 280                 285

Asp Ile Leu Lys Asn Thr Lys Lys Leu Thr Ala Leu Ser Lys Glu Arg
    290                 295                 300

Gly Phe Tyr Pro Met Leu Ala Thr Gln Leu Lys Gln Ala Tyr Gln
305                 310                 315                 320

Leu Asn Val Pro Ile Ala Ser Ser Phe Thr Gln Ala Glu Gln Leu Pro
                325                 330                 335

Phe Lys Gln Val Phe Ala Met Ile Thr Glu Leu Arg Glu Leu Gly Arg
            340                 345                 350

Asn Gly Leu Ala Lys Gln Arg Trp Arg Ile Leu Leu Asp Asn Val Asp
        355                 360                 365

Phe Thr Thr Gln Leu Lys Leu Ser Glu Tyr Ala Lys Asn Gln Gln Trp
```

```
            370                 375                 380
Phe Glu Leu Ala Val Asp Ala Ser Ile Val Ala Lys Ala Trp Gly Tyr
385                 390                 395                 400

Leu Ser Leu Arg Leu Pro Asn Ala Tyr Ser Glu Tyr Phe Asn Ala Ala
                405                 410                 415

Leu Gln Asn Leu Asn Ile Ser Lys Thr Phe Ala Met Ala Ile Ala Arg
                420                 425                 430

Gln Glu Ser Ala Trp Asn Pro Met Ala Gln Ser Ser Ala Asn Ala Arg
                435                 440                 445

Gly Leu Met Gln Leu Leu Pro Ser Thr Ala Lys Leu Thr Ala Glu Asn
                450                 455                 460

Asn Gln Leu Pro Tyr Gln Gly Glu Gln Asp Leu Phe Lys Pro Leu Asn
465                 470                 475                 480

Asn Ile Leu Leu Gly Thr Ala His Leu Asn Glu Leu Asn Gly Lys Tyr
                485                 490                 495

Pro Asn Asn Arg Ile Leu Ile Ala Ala Ala Tyr Asn Ala Gly Ala Asn
                500                 505                 510

Arg Val Glu Lys Trp Leu Ser Arg Ala Ser Gly Lys Leu Ala Leu Asp
                515                 520                 525

Glu Phe Val Ala Ser Ile Pro Phe Tyr Glu Thr Arg Gly Tyr Val Gln
                530                 535                 540

Asn Val Val Ala Tyr Asp Phe Tyr Gln Ile Leu Gln Asn Lys Glu
545                 550                 555                 560

Asn Pro Gln Ile Phe Ser Gln Glu Leu Asn Arg Leu Tyr
                565                 570

<210> SEQ ID NO 40
<211> LENGTH: 147
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT115

<400> SEQUENCE: 40

Gly Trp His Phe Gln Gln Ser Val Thr Met Pro Asn Glu Trp Arg Thr
1               5                   10                  15

Leu Ala Leu Glu Ser Asp Asp Ser Tyr Asn Asp Phe Thr Val Ile Met
                20                  25                  30

Arg Arg Lys Leu Gln Glu Asn Gln Val Asn Val Val Asn Leu Glu Gln
            35                  40                  45

Asn Ile Pro Ile Leu Arg Ile Asn Lys Gln Ile Thr Ser Asp Gln Val
50                  55                  60

Ala Ser Ile Phe Lys His Gly Arg Glu Ala Glu Lys Leu Leu Met Leu
65                  70                  75                  80

Glu Val Glu Ala Thr Phe Arg Leu Ala Asn Gly Glu Ser Tyr Pro Ile
                85                  90                  95

Asn Ala Lys Val Asn Arg Thr Phe Phe Asp Asn Ala Arg Ala Ala Leu
                100                 105                 110

Ala Lys Ser Glu Glu Arg Glu Val Ile Trp Asn Asp Met Arg Glu Gln
            115                 120                 125

Val Ala Arg Gln Leu Ile Val Lys Ile Ala Leu Gln Asn Gln Ile
        130                 135                 140

Lys Arg Lys
```

<210> SEQ ID NO 41
<211> LENGTH: 612
<212> TYPE: PRT
<213> ORGANISM: Unknown
<220> FEATURE:
<223> OTHER INFORMATION: Description of Unknown:
    Bacteria <Prokaryote> sequence
<220> FEATURE:
<223> OTHER INFORMATION: NT116

<400> SEQUENCE: 41

Ser Gly Gly Gly Ser Phe Asp Val Asp Val Ser Asn Pro Ser
1               5                   10                  15

Ser Ser Lys Pro Arg Tyr Gln Asp Asp Thr Ser Ser Arg Thr Lys
            20                  25                  30

Ser Asn Leu Glu Lys Leu Ser Ile Pro Ser Leu Gly Gly Met Lys
        35                  40                  45

Leu Val Ala Gln Asn Leu Ser Gly Asn Lys Glu Pro Ser Phe Leu Asn
    50                  55                  60

Glu Asn Gly Tyr Ile Ser Tyr Phe Ser Ser Pro Ser Thr Ile Glu Asp
65                  70                  75                  80

Asp Val Lys Asn Val Lys Thr Glu Asn Lys Ile His Thr Asn Pro Ile
                85                  90                  95

Gly Leu Glu Pro Asn Arg Ala Leu Gln Asp Pro Asn Leu Gln Lys Tyr
            100                 105                 110

Val Tyr Ser Gly Leu Tyr Tyr Ile Glu Asn Trp Lys Asp Phe Ser Lys
        115                 120                 125

Leu Ala Thr Glu Lys Lys Ala Tyr Ser Gly His Tyr Gly Tyr Ala Phe
    130                 135                 140

Tyr Tyr Gly Asn Lys Thr Ala Thr Asp Leu Pro Val Ser Gly Val Ala
145                 150                 155                 160

Thr Tyr Lys Gly Thr Trp Asp Phe Ile Thr Ala Thr Lys Tyr Gly Gln
                165                 170                 175

Asn Tyr Ser Leu Phe Ser Asn Ala Arg Gly Gln Ala Tyr Phe Arg Arg
            180                 185                 190

Ser Ala Thr Arg Gly Asp Ile Asp Leu Glu Asn Asn Ser Lys Asn Gly
        195                 200                 205

Asp Ile Gly Leu Ile Ser Glu Phe Ser Ala Asp Phe Gly Thr Lys Lys
    210                 215                 220

Leu Thr Gly Gln Leu Ser Tyr Thr Lys Arg Lys Thr Asp Ile Gln Gln
225                 230                 235                 240

Tyr Glu Lys Glu Lys Leu Tyr Asp Ile Asp Ala His Ile Tyr Ser Asn
                245                 250                 255

Arg Phe Arg Gly Lys Val Thr Pro Thr Lys Ser Thr Ser Asp Glu His
            260                 265                 270

Pro Phe Thr Ser Glu Gly Thr Leu Glu Gly Phe Tyr Gly Pro Asn
        275                 280                 285

Ala Glu Glu Leu Gly Gly Lys Phe Leu Ala Arg Asp Lys Arg Val Phe
    290                 295                 300

Gly Val Phe Ser Ala Lys Glu Thr Pro Glu Thr Lys Glu Lys Leu
305                 310                 315                 320

Ser Lys Glu Thr Leu Ile Asp Gly Lys Leu Ile Thr Phe Ser Thr Lys
                325                 330                 335

Thr Ala Asp Ala Thr Thr Ser Thr Thr Ala Ser Thr Thr Ala Asp Val

```
                    340                 345                 350
Lys Thr Asp Glu Lys Asn Phe Thr Thr Lys Asp Ile Ser Ser Phe Gly
                355                 360                 365

Glu Ala Asp Tyr Leu Leu Ile Asp Asn Tyr Pro Val Pro Leu Phe Pro
            370                 375                 380

Glu Gly Asp Thr Asp Asp Phe Val Thr Ser Lys His His Asp Ile Gly
385                 390                 395                 400

Asn Lys Thr Tyr Lys Val Glu Ala Cys Cys Lys Asn Leu Ser Tyr Val
                405                 410                 415

Lys Phe Gly Met Tyr Tyr Glu Asp Lys Glu Lys Asn Thr Asn Gln
            420                 425                 430

Thr Gly Gln Tyr His Gln Phe Leu Leu Gly Leu Arg Thr Pro Ser Ser
                435                 440                 445

Gln Ile Pro Val Thr Gly Asn Val Lys Tyr Leu Gly Ser Trp Phe Gly
            450                 455                 460

Tyr Ile Gly Asp Asp Lys Thr Ser Tyr Ser Thr Thr Gly Asn Lys Gln
465                 470                 475                 480

Gln Asp Lys Asn Ala Pro Ala Glu Phe Asp Val Asn Phe Asp Asn Lys
                485                 490                 495

Thr Leu Thr Gly Lys Leu Lys Arg Ala Asp Ser Gln Asn Thr Val Phe
            500                 505                 510

Asn Ile Glu Ala Thr Phe Lys Asn Gly Ser Asn Ala Phe Glu Gly Lys
            515                 520                 525

Ala Thr Ala Asn Val Val Ile Asp Pro Lys Asn Thr Gln Ala Thr Ser
            530                 535                 540

Lys Val Asn Phe Thr Thr Thr Val Asn Gly Ala Phe Tyr Gly Pro His
545                 550                 555                 560

Ala Thr Glu Leu Gly Gly Tyr Phe Thr Tyr Asn Gly Asn Asn Pro Thr
                565                 570                 575

Ala Thr Asn Ser Glu Ser Ser Ser Thr Val Pro Ser Pro Pro Asn Ser
            580                 585                 590

Pro Asn Ala Arg Ala Ala Val Val Phe Gly Ala Lys Arg Gln Val Glu
            595                 600                 605

Lys Thr Asn Lys
        610

<210> SEQ ID NO 42
<211> LENGTH: 350
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT117

<400> SEQUENCE: 42

Asn Thr Ile Ile Pro Asn Tyr Asn Thr Asp Ala His Leu Tyr Glu Phe
1               5                   10                  15

Thr Gln Thr Tyr Asp Leu Val Val Pro Lys Gly Ser Gln Gly Gln Thr
            20                  25                  30

Asn Leu Trp Val Pro Leu Pro Phe Asn Gly Glu Tyr Gln Gln Val Lys
        35                  40                  45

Ser Ile His Phe Glu Gly Asn Tyr Met Asn Ala Tyr Val Thr Glu Asn
    50                  55                  60

Asn Lys Tyr Gly Ala Lys Thr Leu Phe Ala Thr Trp Asp Lys Asp Ala
```

```
            65                  70                  75                  80
   Gln Lys Arg Asp Leu Lys Val Thr Met Val Ile Glu Thr Lys Asp Arg
                    85                  90                  95

Glu Pro Met Val Lys Gly Ala Leu Glu Asn Tyr Thr Pro Lys Asp
               100                 105                 110

Ile Gln Tyr Ser Val Asp Val Gln Glu Tyr Leu Lys Ala Thr Pro His
               115                 120                 125

Ile Lys Thr Asp Gly Ile Val Lys Glu Phe Ala Asp Lys Ile Leu Gly
   130                 135                 140

Lys Glu Thr Asn Pro Leu Lys Lys Ala Glu Leu Ile His His Trp Ile
   145                 150                 155                 160

Val Lys Asn Met Glu Arg Asp Asn Ser Val Leu Gly Cys Gly Asp Gly
                   165                 170                 175

Asp Val Glu Lys Ile Leu Thr Thr Gly Val Leu Gly Lys Cys Thr
               180                 185                 190

Asp Ile Asn Ser Val Phe Val Ala Leu Ala Arg Ala Ala Gly Ile Pro
               195                 200                 205

Ala Arg Glu Ile Phe Gly Ile Arg Leu Gly Thr Ala Glu Lys Met Gly
   210                 215                 220

Lys Tyr Ser Lys Gly Ala Phe Gly Ser Ala Asn Glu Gln Gly Ile Val
   225                 230                 235                 240

Asn Val Ser Gly Gly Gln His Cys Arg Ala Glu Phe Tyr Leu Ala Gly
                   245                 250                 255

Phe Gly Trp Val Pro Val Asp Ser Ala Asp Val Ala Lys Met Arg Leu
                   260                 265                 270

Ala Glu Lys Lys Ser Val Glu Asp Lys Asp Thr Gln Ala Val Ala Lys
                   275                 280                 285

Tyr Leu Phe Gly Asn Trp Glu Ala Asn Trp Val Gly Phe Asn His Ala
                   290                 295                 300

Arg Asp Phe Asp Leu Tyr Pro Gln Pro Glu Leu Ala Pro Ile Asn Asn
   305                 310                 315                 320

Phe Gly Tyr Pro Tyr Ala Glu Val Gly Gly Asp Pro Leu Asn Ser Phe
                   325                 330                 335

Asp Pro Lys Glu Phe Lys Tyr Asp Tyr Val Ser Lys Lys Leu
                   340                 345                 350

<210> SEQ ID NO 43
<211> LENGTH: 184
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT118

<400> SEQUENCE: 43

Trp Phe Tyr Ser Leu Asn Gln Glu Thr Ala Asp Leu Ser Glu Leu Val
   1               5                   10                  15

Lys Lys Pro Asp Ser Pro Asp Tyr Val Gly Tyr Lys Met Glu Thr Thr
                   20                  25                  30

Val Phe Ser Pro Glu Gly Lys Lys Gln Tyr Leu Ala Leu Ser Asp Lys
               35                  40                  45

Ile Glu His Tyr Thr Val Asn Glu Gln Thr Leu Phe Thr Ala Pro Leu
       50                  55                  60

Val Tyr Leu Tyr Pro Thr Thr Ser Asn Glu Lys Glu Gln Asn Pro Asn
```

```
            65                  70                  75                  80
Gln Asn Val Asp Phe Phe Ser Thr Gln Asn Trp Lys Leu Ser Ala Asn
                85                  90                  95

Gln Ala Arg Leu Thr Lys Asp Gln Ile Leu Tyr Leu Glu Gly Asn Val
            100                 105                 110

Val Val Gln Ser Leu Thr Ser Asp Ser Arg Leu Gln Arg Ile Glu Thr
        115                 120                 125

Glu Ser Ala Val Val Asn Leu Lys Thr Gln Asp Met Thr Ser Glu Thr
    130                 135                 140

Gln Val Lys Ile Lys Gly Lys Asn Phe Ser Ser Thr Gly Leu Lys Leu
145                 150                 155                 160

Val Gly Asn Leu Arg Gln Gln Val Ala Thr Leu Lys Glu Gln Val Lys
                165                 170                 175

Thr Tyr Tyr Glu Val Ser Lys Gln
            180

<210> SEQ ID NO 44
<211> LENGTH: 909
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT123

<400> SEQUENCE: 44

Gln Ser Leu Glu Leu Ser Pro Asn Asn Asp Leu Pro Phe Asp Pro Asn
1               5                   10                  15

Ile Gln His Gly Lys Leu Ser Asn Gly Leu Gln Tyr Phe Val Leu Lys
            20                  25                  30

Asn Thr Glu Pro Lys Glu Arg Val Tyr Ile Arg Leu Val Ile Asn Ala
        35                  40                  45

Gly Ser Met His Glu Asp Asp Gln Lys Gly Ile Ala His Leu Val
    50                  55                  60

Glu His Met Ala Phe Asn Gly Ser Lys Lys Tyr Pro Glu Asn Gln Ile
65                  70                  75                  80

Ile Asn Ala Leu Glu Lys Leu Gly Met Lys Phe Ala Arg Asp Ile Asn
                85                  90                  95

Ala Phe Thr Asp Phe Glu Asn Thr Val Tyr Thr Leu Asn Leu Asp Ser
            100                 105                 110

Asn Asn Gln Gln Lys Leu Glu Leu Ala Phe Asp Val Ile Asn Glu Trp
        115                 120                 125

Met Asn Asn Ile Thr Phe Leu Pro Lys Asp Val Asp Gly Glu Arg Gly
    130                 135                 140

Val Val Gln Glu Glu Trp Arg Arg Arg Leu Ser Pro Met Leu Arg Ile
145                 150                 155                 160

Gly Asn Lys Lys Ser Ala Ile Glu Met Ala Gly Ser Arg Tyr Val Leu
                165                 170                 175

Arg Asp Pro Ile Gly Asp Met Asp Ile Ile Lys Thr Ile Ser Ala Lys
            180                 185                 190

Arg Val Ala Asp Phe Tyr His Lys Trp Tyr Arg Pro Asp Asn Met Ser
        195                 200                 205

Val Ile Ile Val Gly Asp Ile Asp Thr Lys Gln Val Val Lys Leu Leu
    210                 215                 220

Lys Gln Asn Leu Ser Gln Glu Asn Pro Ile Thr Lys Thr Thr Leu Glu
```

```
                225                 230                 235                 240

Lys Ile Asp Phe Asn Ile Pro Leu Ile Asn Lys Trp Arg Leu Asp Ser
                        245                 250                 255

Ile Ser Glu Gln Gly Thr Thr Ile Pro Ser Ile Glu Leu Ser Phe Phe
                        260                 265                 270

Glu Asn Thr Ile Glu Thr Asn Thr Leu Ala Ser Tyr Lys Gln Glu Leu
                        275                 280                 285

Ile Gln Gln Ile Thr Thr Arg Leu Leu Asn Leu Arg Leu Gln Gln Trp
                        290                 295                 300

Glu Lys Glu Thr Glu Asn Gly Val Asp Ser Ala Asn Phe Tyr Arg Thr
        305                 310                 315                 320

His Leu Gly Lys Glu Thr Leu Gln Ser Ile Phe Ser Leu Gln Leu Ile
                        325                 330                 335

Asp Thr Gln Tyr Ser Lys Thr Ile Asp Lys Leu Phe Ala Phe Ile Ala
                        340                 345                 350

Ser Ile Lys Gln Gln Gly Phe Thr Gln Asn Glu Leu Asn Gly Glu Ile
                        355                 360                 365

Lys Arg Leu Thr Gln Leu Asn Glu Lys Gln Leu Asn Ile Arg Ser Gly
                        370                 375                 380

Ser Leu Lys Ile Ala Asp Asp Leu Ile Thr Ser Val Ala Asn Lys Gln
        385                 390                 395                 400

Val Val Leu Ser Val Asn Asp Arg Tyr Glu Leu Asn Lys Arg Phe Leu
                        405                 410                 415

Ser Gln Ile Thr Leu Ala Asp Leu Gln Arg Thr Leu Asn Gln Thr Leu
                        420                 425                 430

Ala Leu Lys Ala Lys Leu Leu Ile Thr Gln Pro Leu Pro Gln Lys
                        435                 440                 445

Ala Leu Pro Phe Asp Val Val Glu Ile Glu Thr Arg Trp Asn Asn Ala
                        450                 455                 460

Met Lys Met Gln Gln His Gln Trp Asp Glu Lys Lys Gln Ile Glu Lys
        465                 470                 475                 480

Leu Pro His Leu Thr Phe Asn Thr Gly Ser Leu Ser Gln Glu Lys Tyr
                        485                 490                 495

Trp Asp Arg Gly Asp Ile Tyr Glu Phe Arg Leu Ser Asn Gly Ser Lys
                        500                 505                 510

Leu Ile Tyr His Tyr Ser Asp Lys Thr Pro Asn Gln Val His Phe Arg
                        515                 520                 525

Ala Val Thr Gln Gly Gly Leu Arg Ser Ile Pro Asp Lys Asp Tyr His
                        530                 535                 540

Leu Leu Arg Ala Ala Val Ser Val Asp Glu Thr Gly Val Gly Glu
        545                 550                 555                 560

Leu Ser Leu Ser Ala Val Asn Gln Ile Phe Ser Arg Asp Pro Leu Val
                        565                 570                 575

Ile Ala Thr Val Ile Asp Asp Lys Gln Gly Phe Thr Gly Val Ser
                        580                 585                 590

Lys Pro Lys Asp Leu Glu Asn Leu Thr Leu Phe Arg Leu Lys Leu
                        595                 600                 605

Arg Ser Ser Pro Ile Ser Asp Leu Ala Leu Glu Lys Tyr Arg Arg Glu
                        610                 615                 620

Thr Arg Asp Tyr Phe Lys Gln Ile Asp Leu Glu Thr Gln Phe Met Gln
        625                 630                 635                 640

Ala Val Ser Lys Leu Arg Phe Pro Asn Ile Glu Thr Val Tyr Thr Gln
                        645                 650                 655
```

```
Lys Gln Ala Gln Gln Leu Ala Phe Asp Lys Asn Gln Leu Ser Asn Ala
            660                 665                 670

Tyr Gln Arg Tyr Ile Leu Asn Lys Thr Asp Phe Thr Tyr Phe Ile Ile
        675                 680                 685

Gly Asp Ile Glu Leu Asn Gln Val Lys Lys Leu Ala Glu Arg Tyr Leu
    690                 695                 700

Ala Ser Val Glu Ser Lys Thr Gln Ile Arg His Phe Val Pro Thr Ile
705                 710                 715                 720

Ile His Thr Pro Thr Gln Ser Phe Ile Met Asn Gly Leu Lys Glu Pro
                725                 730                 735

Arg Ala Asp Val Glu Ile Tyr Leu Thr Ala Asp Asn Thr Trp Arg Ala
            740                 745                 750

Glu Gln Lys Tyr Leu Phe Asn Ile Leu Ala Asp Ile Val Gln Glu Lys
        755                 760                 765

Leu Arg Leu Ile Leu Arg Glu Lys Val Ser Gly Val Tyr Ser Val Asn
    770                 775                 780

Ser Trp Phe Met Gln Asp Val His Thr Pro Gln Ile Glu Gly Lys Ile
785                 790                 795                 800

Glu Phe Ser Cys Asp Pro Lys Arg Val Glu Leu Thr His Leu Thr
                805                 810                 815

Asn Gln Val Leu Asp Asp Ile Val Lys Asn Gly Ile Asp Glu Asn Leu
            820                 825                 830

Leu Arg Lys Lys Leu Ala Glu Gln His Thr Gln Ile Arg Arg Glu Phe
        835                 840                 845

Asp Ser Leu Val Ser Val Ala Ser Ile Ile Glu Glu Ser Tyr Trp Gln
    850                 855                 860

Gln Asp Asn Pro Asp Ala Ile Tyr Thr Tyr Gln His Leu Asp Gln Leu
865                 870                 875                 880

Ala Thr Lys Ala Thr Ile Asp Ala Leu Ala Gln Lys Ala Leu Lys Lys
                885                 890                 895

Ser Gly Arg Phe Val Ser Val Leu Lys Ala Ala Thr Tyr
            900                 905

<210> SEQ ID NO 45
<211> LENGTH: 458
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT124

<400> SEQUENCE: 45

Trp Phe Thr Gly Lys Lys Ala Glu Glu Glu Tyr Leu His Gln Leu Lys
1               5                   10                  15

Gln Leu Asn Gln Leu Phe Thr Lys Thr Glu Ala Leu Glu Glu Ser Lys
            20                  25                  30

Ile Phe Tyr Lys Asn Ile Lys Phe Glu Arg Gly Leu Phe Ala Ser His
        35                  40                  45

Ile Gln Asp Gln Ile Glu Ile His Lys Ala Asn Glu Thr Ile Ile Ile
    50                  55                  60

Pro Leu Ser Ser Thr Leu Tyr His Gly Pro Leu Pro Leu Asp Arg Val
65                  70                  75                  80

Ala Lys Leu Asn Phe Val Pro Ala Ile Phe Ser Ser Gln Thr Leu Leu
                85                  90                  95
```

```
Gly Lys Asn Ala Thr Thr Gln Ala Phe Phe Asp Ile Thr Glu Ser Glu
                100                 105                 110
Lys Pro Leu Gln Leu Asn Phe Ala Met Asn Tyr Ser Leu Ser Gly Asn
            115                 120                 125
Ala Glu Leu Lys Leu Ala Ser Gly Gln Tyr His Asn Glu Gln Ser Lys
        130                 135                 140
Thr Asp Phe Asp Trp Ser Asn Val Val Leu Asn Ile Asp Leu Asn Gln
145                 150                 155                 160
Asn Thr Pro Asn Asn Tyr Val Leu Ser Val Asp Thr Phe Asn Ser Asn
                165                 170                 175
Ala Pro Asn His Ala Val Ser Thr Ala Ser Ser Ile Lys Ile Lys Asp
            180                 185                 190
Leu Val Val Gln Gly Ser Leu Gln Ser Thr Lys Trp Pro Phe Ile Tyr
        195                 200                 205
Ser Gly Asn Ile Asn Ser Lys Ile Gly Tyr Phe Glu Gln Asn Thr Glu
    210                 215                 220
Ser Pro Glu Thr Gly Glu Lys Phe Ser Leu Ile Gln Lys Asn Ser Gln
225                 230                 235                 240
Ala Asn Leu Thr Thr Gln Val Glu Gly Asp Thr Val Asn Ile Ile Asn
                245                 250                 255
Lys Thr Asn Leu Asp Glu Leu His Ile Asn Gly Asn Asn Leu Gly Lys
            260                 265                 270
Val Thr Asn Asn Val Glu Phe Asn His Ile Asp Gly Asn Ala Leu Gln
        275                 280                 285
Glu Leu Leu Asn Ile Leu Val Ala Ile Gly Lys Ala Asp Ser Asp Met
    290                 295                 300
Pro Leu Ser Lys Thr Leu Val Gln Lys Leu Gln Gln Ala Gly Met Ile
305                 310                 315                 320
Ile Ala Asn Asn Gln Pro Gln Ile Lys Phe Thr Pro Leu Ser Ile Ser
                325                 330                 335
Asp Glu Lys Gly Lys Val Ala Leu Asp Leu Asn Ile Ala Leu Val Pro
            340                 345                 350
Asn Pro Lys Phe Asp Leu Met Arg Ser Gly Leu Tyr Lys Gln Phe Lys
        355                 360                 365
Asp Phe Ser Ile Asn Phe Asp Val Asn Lys Glu Thr Ala Ile Ser Leu
    370                 375                 380
Leu Ser Lys Phe Val Pro Glu Asn Gln Lys Gln Asp Phe Val His Arg
385                 390                 395                 400
Leu Asn Glu Leu Val Thr Glu Gly Glu Val Asn Asp Ile Ile Val Asn
                405                 410                 415
Thr Asp Lys Thr Val Thr Leu Thr Leu Ala Leu Glu Asn Asn Asp Leu
            420                 425                 430
Lys Leu Asn Gly Lys Pro Ile Pro Glu Glu Gln Leu Lys Val Val Leu
        435                 440                 445
Phe Ile Leu Val Met Gly Gly Phe Gly Arg
    450                 455

<210> SEQ ID NO 46
<211> LENGTH: 6
<212> TYPE: PRT
<213> ORGANISM: Unknown
<220> FEATURE:
<223> OTHER INFORMATION: Description of Unknown:
      Bacteria <Prokaryote> sequence
<220> FEATURE:
```

<223> OTHER INFORMATION: Linker 1

<400> SEQUENCE: 46

Gly Ser Gly Gly Gly Gly
1               5

<210> SEQ ID NO 47
<211> LENGTH: 8
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: Linker 2

<400> SEQUENCE: 47

Gly Ser Gly Ser Gly Gly Gly Gly
1               5

<210> SEQ ID NO 48
<211> LENGTH: 17
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: Histidine Tag

<400> SEQUENCE: 48

Met Gly Ser Ser His His His His His His Glu Asn Leu Tyr Phe Gln
1               5                   10                  15

Gly

<210> SEQ ID NO 49
<211> LENGTH: 277
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT018 Variant from Fi176

<400> SEQUENCE: 49

Lys His Gly Gln Lys Arg Asp Asp Leu Asn Lys Ala Leu Tyr Phe Ser
1               5                   10                  15

Arg Leu Glu Glu Ile Glu Gln Asp Asn Ser Gln Gly Leu Val Glu Asn
            20                  25                  30

Val Glu Gln Leu Lys Gln Glu Leu Gln Lys Thr Leu Leu Asp Asp Val
        35                  40                  45

Pro Ser Lys Val Gln Glu Asn Val Asp Tyr Ser Gly Lys Ser Tyr Gly
    50                  55                  60

Lys Ile Trp Phe Val Ser Gly Val Leu Ala Leu Gly Ile Ile Ala Gly
65                  70                  75                  80

Ser Pro Tyr Phe Met Val Gly Ser Trp Gln Ala Glu Ser Met Leu Glu
                85                  90                  95

Gln Thr Tyr Ala Lys Leu Pro Tyr Phe Phe Asp Arg Met Lys Asp Glu
            100                 105                 110

Asp Lys Asn Pro Phe Ser Asp Thr Glu Met Gln Gln Phe Ser Thr Ala
        115                 120                 125

Leu Arg Ile Asp Leu Gln Lys Asn Pro Thr Asp Ala Lys Lys Trp Trp

```
            130                 135                 140
Met Leu Gly Gln Ile Gly Met Asn Leu Gly Asp Ala Arg Leu Ala Phe
145                 150                 155                 160

Asp Ser Tyr Gln Lys Ala Asn Lys Leu Glu Pro Asp Asn Val Gln Tyr
                165                 170                 175

Lys Leu Gly Tyr Ala Arg Ile Leu Met Phe Ser Glu Asp Ala Thr Asp
                180                 185                 190

Lys Leu Lys Gly Gly Asn Leu Leu Arg Glu Val Ile Arg Gln Glu His
                195                 200                 205

Thr Asn Ile Glu Ala Leu Ser Leu Leu Ala Phe Arg Tyr Phe Glu Thr
        210                 215                 220

Glu Asp Tyr Lys Met Ala Ala Val Thr Trp Ala Met Met Leu Arg Leu
225                 230                 235                 240

Met Pro Lys Asp Asp Glu Arg Val Pro Leu Ile Glu Lys Ser Ile Arg
                245                 250                 255

Thr Ala Arg Asp Ala Leu Glu Ala Gln Asn Glu Glu Lys Ser Lys Ser
                260                 265                 270

Ile Thr Pro Glu Lys
        275

<210> SEQ ID NO 50
<211> LENGTH: 160
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT024Variant from Fi176

<400> SEQUENCE: 50

Met Lys Thr Ile Asp Ile Thr Ala Asn Ser Lys Met Asp Asp Gln Ala
1               5                   10                  15

Arg Met Asn Leu Ala Gln Glu Phe Ala Asn Lys Gln Gln Trp Ser Ser
                20                  25                  30

Val Phe Asp Ile Met Tyr Pro Met Ala Leu Glu Gly Asn Thr Thr Ala
                35                  40                  45

Gln Ser Asn Leu Gly Met Leu Tyr Asn Leu Gly Arg Gly Thr Val Arg
        50                  55                  60

Asp Tyr Glu Lys Ala Tyr Trp Trp Phe Ser Glu Ala Ala Glu Lys Gly
65                  70                  75                  80

Ser Val Lys Gly Leu Asn Asn Leu Gly Val Met Tyr Leu Arg Gly Asp
                85                  90                  95

Tyr Val Lys Gln Asn Thr Glu Gln Ala Ile Lys Leu Phe Glu Arg Thr
                100                 105                 110

Ala Arg Ala Lys Asp Thr Asp Ala Met Met Met Leu Ser Asn Ile Tyr
        115                 120                 125

Arg Leu Gln Asn Gln Pro Glu Lys Ser Leu Glu Trp Leu Lys Lys Ala
        130                 135                 140

Ala Glu Leu Gly Asn Lys Glu Ala Lys Gln Arg Leu Ser Ser Gln Pro
145                 150                 155                 160

<210> SEQ ID NO 51
<211> LENGTH: 102
<212> TYPE: PRT
<213> ORGANISM: Unknown
<220> FEATURE:
<223> OTHER INFORMATION: Description of Unknown:
```

Bacteria <Prokaryote> sequence
<220> FEATURE:
<223> OTHER INFORMATION: NT032 Variant from Fi176

<400> SEQUENCE: 51

```
Gly Phe Asn Gly Asn Asn Ser Gln Gly Gly Phe Gln Gln Thr Ala Pro
1               5                   10                  15

Ala Ala Ile Ser Val Lys Gln Ala Leu Ser Ala Ala Asp Asn Ser Met
            20                  25                  30

Ile Thr Leu Val Gly Asn Ile Thr Gln Gln Ile Asp Asp Asp Glu Phe
        35                  40                  45

Trp Phe Thr Asp Gly Thr Gly Gln Ile Lys Ile Glu Ile Lys Lys Arg
    50                  55                  60

Val Trp Asn Gly Leu Asn Val Asp Ser Lys Asp Lys Val Lys Ile Tyr
65                  70                  75                  80

Gly Lys Leu Asp Asn Glu Ala Phe Glu Lys Ala Glu Leu Asp Val Leu
                85                  90                  95

Arg Val Glu Lys Ala Glu
            100
```

<210> SEQ ID NO 52
<211> LENGTH: 521
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT067 Variant from Fi176

<400> SEQUENCE: 52

```
Val Ile Val Pro Glu Gly Thr Gln Leu Asp Glu Lys Gln His Ile Val
1               5                   10                  15

Phe Asn Asn Gly Ala Glu Pro Gln Ser Phe Asp Pro His Lys Thr Glu
            20                  25                  30

Gly Val Pro Glu Ser Asn Val Ala Tyr Gln Leu Leu Glu Gly Leu Val
        35                  40                  45

Thr Ser Asp Ser Glu Gly Lys Leu Gln Pro Gly Val Ala Glu Ser Trp
    50                  55                  60

Glu Asn Thr Pro Asp Phe Lys Thr Trp Thr Phe His Leu Arg Lys Asp
65                  70                  75                  80

Ala Lys Trp Ser Asn Gly Asp Pro Val Thr Ala His Asp Phe Val Phe
                85                  90                  95

Ala Trp Arg Arg Leu Val Asp Pro Ala Thr Ala Ala Pro Tyr Ala Ser
            100                 105                 110

Tyr Leu Ser Tyr Leu Gln Val Glu Asn Ala Gln Asp Ile Ile Asp Gly
        115                 120                 125

Lys Lys Lys Pro Ala Glu Leu Gly Val Glu Ala Lys Asp Asp Tyr Thr
    130                 135                 140

Phe Val Val His Ala Ile Asn Pro Val Pro Tyr Ala Val Ser Leu Thr
145                 150                 155                 160

Thr His Gln Ser Leu Leu Pro Leu Pro Gln Lys Val Val Glu Lys Leu
                165                 170                 175

Gly Asp Ala Trp Val Lys Lys Glu Asn Tyr Val Gly Asn Gly Ala Tyr
            180                 185                 190

Lys Leu Ala Asn His Ile Ile Asn Glu Lys Ile Glu Phe Glu Arg Asn
        195                 200                 205
```

```
Pro Leu Tyr Trp Asn Asp Lys Glu Thr Val Ile Asn Ser Ala Thr Phe
    210                 215                 220

Leu Ala Ile Glu Asn Pro Ser Thr Asp Val Ala Arg Tyr Arg Ala Gly
225                 230                 235                 240

Asp Leu Asp Met Thr Ser Tyr Gly Leu Pro Pro Glu Gln Phe Ala Lys
            245                 250                 255

Leu Lys Lys Glu Leu Leu Gly Glu Val Tyr Val Thr Arg Thr Leu Gly
                260                 265                 270

Thr Tyr Ser Tyr Glu Leu Asn Asn Lys Lys Ala Pro Phe Asp Asn Val
            275                 280                 285

Asn Ile Arg Lys Ala Leu Asn Leu Ser Leu Asp Arg His Val Ile Thr
290                 295                 300

Asp Lys Val Leu Gly Gln Gly Gln Thr Pro Thr Tyr Val Phe Thr Pro
305                 310                 315                 320

Thr Tyr Ile Glu Glu Gly His Leu Ile Gln Gln Pro Ala Tyr Ser Lys
                325                 330                 335

Glu Pro Met Ala Gln Arg Asn Gly Glu Ala Ile Lys Leu Leu Glu Glu
            340                 345                 350

Ala Gly Tyr Ser Lys Ala Asn Pro Leu Lys Phe Ser Ile Leu Tyr Asn
                355                 360                 365

Thr Asn Glu Asn His Lys Lys Val Ala Ile Ala Ala Ala Ser Met Trp
    370                 375                 380

Lys Ala Asn Thr Lys Gly Leu Ile Asp Val Lys Leu Glu Asn Gln Glu
385                 390                 395                 400

Trp Lys Thr Tyr Ile Asp Ser Arg Arg Ala Gly Arg Tyr Asp Ala Ala
            405                 410                 415

Arg Ala Gly Trp Ser Ala Asp Tyr Asn Gln Ala Thr Thr Phe Gly Asn
                420                 425                 430

Tyr Phe Leu Ser Asn Ser Ser Asn Asn Thr Ala Lys Tyr Ala Asn Pro
        435                 440                 445

Glu Tyr Asp Lys Ala Met Ala Glu Ser Tyr Ala Ala Thr Asp Ala Glu
    450                 455                 460

Gly Arg Ala Lys Ala Tyr Ala Lys Ala Glu Glu Ile Leu Ala Lys Asp
465                 470                 475                 480

Tyr Gly Ile Val Pro Ile Phe Asn Tyr Val Asn Pro Arg Leu Val Lys
            485                 490                 495

Pro Tyr Val Lys Gly Tyr Ser Gly Lys Asp Pro Gln Asp His Ile Tyr
                500                 505                 510

Leu Arg Asn Leu Tyr Ile Ile Lys His
        515                 520

<210> SEQ ID NO 53
<211> LENGTH: 157
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT038 Variant from R2846

<400> SEQUENCE: 53

Lys Gln Asp Gly Ser Ala Asp Met Asp Lys Lys Val Lys Asn Gly Glu
1               5                   10                  15

Leu Val Lys Thr Lys Val Lys Leu Val Ser Ala Asn Gly Thr Asn Pro
            20                  25                  30
```

```
Val Lys Ile Ser Asn Val Ala Glu Gly Thr Glu Asp Thr Asp Ala Val
         35                  40                  45

Ser Phe Lys Gln Leu Lys Ala Leu Gln Asn Lys Gln Val Thr Leu Ser
 50                  55                  60

Ala Ser Asn Ala Tyr Ala Asn Gly Gly Ser Asp Ala Asp Val Gly Lys
 65                  70                  75                  80

Val Thr Gln Thr Leu Ser Asn Gly Leu Asn Phe Lys Phe Lys Ser Thr
                 85                  90                  95

Asp Gly Glu Leu Leu Asn Ile Lys Ala Asp Lys Asp Thr Val Thr Ile
            100                 105                 110

Thr Arg Ala Ser Gly Ala Asn Gly Ala Ala Thr Asp Ala Asp Lys
            115                 120                 125

Ile Lys Val Ala Ser Asp Gly Ile Ser Ala Gly Asn Lys Ala Val Lys
130                 135                 140

Asn Val Ala Ala Gly Glu Ile Ser Ala Thr Ser Thr Asp
145                 150                 155

<210> SEQ ID NO 54
<211> LENGTH: 252
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT001 Variant from Fi176

<400> SEQUENCE: 54

Lys Glu Asp Lys Lys Pro Glu Ala Ala Ala Pro Leu Lys Ile Lys
 1               5                  10                  15

Val Gly Val Met Ser Gly Pro Glu His Gln Val Ala Glu Ile Ala Ala
                 20                  25                  30

Lys Val Ala Lys Glu Lys Tyr Gly Leu Asp Val Gln Phe Val Glu Phe
             35                  40                  45

Asn Asp Tyr Ala Leu Pro Asn Glu Ala Val Ser Lys Gly Asp Leu Asp
 50                  55                  60

Ala Asn Ala Met Gln His Lys Pro Tyr Leu Asp Glu Asp Ala Lys Ala
 65                  70                  75                  80

Lys Asn Leu Asn Asn Leu Val Ile Val Gly Asn Thr Phe Val Tyr Pro
                 85                  90                  95

Leu Ala Gly Tyr Ser Lys Lys Ile Lys Asn Val Asn Glu Leu Gln Glu
            100                 105                 110

Gly Ala Lys Val Val Pro Asn Asp Pro Thr Asn Arg Gly Arg Ala
            115                 120                 125

Leu Ile Leu Leu Glu Lys Gln Gly Leu Ile Lys Leu Lys Asp Ala Asn
130                 135                 140

Asn Leu Leu Ser Thr Val Leu Asp Ile Val Glu Asn Pro Lys Lys Leu
145                 150                 155                 160

Asn Ile Thr Glu Val Asp Thr Ser Val Ala Ala Arg Thr Leu Asp Asp
                165                 170                 175

Val Asp Leu Ala Val Val Asn Asn Thr Tyr Ala Gly Gln Val Gly Leu
            180                 185                 190

Asn Ala Gln Asp Asp Gly Val Phe Val Glu Asp Lys Asp Ser Pro Tyr
            195                 200                 205

Val Asn Ile Ile Val Ser Arg Thr Asp Asn Lys Asp Ser Lys Ala Val
210                 215                 220
```

```
Gln Asp Phe Val Lys Ser Tyr Gln Thr Glu Glu Val Tyr Gln Glu Ala
225                 230                 235                 240

Gln Lys His Phe Lys Asp Gly Val Val Lys Gly Trp
                245                 250

<210> SEQ ID NO 55
<211> LENGTH: 243
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT016 Variant from Fi176

<400> SEQUENCE: 55

Ser Ser Gly Ser Lys Asp Val Glu Gln Ala Ser Val Asn Glu Leu Tyr
1               5                   10                  15

Thr Lys Gly Thr Thr Ser Leu Gln Glu Gly Ser Tyr Ser Glu Ala Ile
                20                  25                  30

Arg Tyr Leu Lys Ala Thr Thr Glu Arg Phe Pro Gly Ser Val Tyr Gln
            35                  40                  45

Glu Gln Ala Met Leu Asp Leu Ile Tyr Ala Asn Tyr Lys Thr Gln Asp
50                  55                  60

Tyr Thr Gln Val Leu Leu Met Val Asp Ser Phe Leu His Gln Phe Pro
65                  70                  75                  80

Gln Ser Pro Asn Gln Ala Tyr Ala Val Tyr Met Ala Gly Leu Thr Asn
                85                  90                  95

Ala Ala Thr Gly Asp Asn Phe Ile Gln Asp Phe Gly Ile Asp Arg
            100                 105                 110

Ala Thr Arg Glu Thr Thr Ser Met Arg Thr Ala Phe Ser Asn Phe Gln
        115                 120                 125

Asn Leu Val Arg Val Phe Pro Asn Ser Pro Tyr Ser Gln Asp Ala Leu
    130                 135                 140

Ala Arg Met Ala Tyr Ile Lys Asp Ala Leu Ala Arg His Glu Leu Glu
145                 150                 155                 160

Ile Ala Lys Phe Tyr Ala Lys Arg Lys Ala Trp Val Ala Val Ala Asn
                165                 170                 175

Arg Val Val Gly Met Leu Lys Gln Tyr Pro Asp Thr Lys Ala Thr Tyr
            180                 185                 190

Glu Gly Leu Phe Leu Met Gln Glu Ala Tyr Glu Lys Met Gly Leu Thr
        195                 200                 205

Ala Leu Ala Asn Asp Thr Gln Lys Ile Ile Asp Ala Asn Lys Asp Lys
    210                 215                 220

Thr Phe Ala Pro Ile Glu Lys Pro Asn Glu Pro Asp Leu Lys Val Pro
225                 230                 235                 240

Ala Val Lys

<210> SEQ ID NO 56
<211> LENGTH: 337
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT052 Variant from R2846

<400> SEQUENCE: 56
```

```
Asp Thr Leu Glu Gln Gln Phe Gln Gln Gly Leu Glu Ala Thr Lys Arg
1               5                   10                  15

Gly Asp Tyr Gln Thr Ala Phe Lys Leu Trp Leu Pro Leu Ala Glu Gln
            20                  25                  30

Gly Asn Ala Ser Ile Gln Phe Asn Leu Gly Leu Met Tyr Lys Lys Gly
            35                  40                  45

Gln Gly Ile Lys Gln Asp Asp Phe Glu Ala Val Lys Trp Tyr Arg Lys
50                  55                  60

Ala Ala Glu Gln Gly Val Ala Asp Ala Gln Leu Asn Leu Gly Asn Met
65                  70                  75                  80

Tyr Ala Lys Gly Leu Gly Val Lys Gln Asp Asp Val Glu Ala Val Lys
                85                  90                  95

Trp Tyr Arg Gln Ala Ala Glu Gln Gly Asn Ala Lys Ala Gln Phe Asn
            100                 105                 110

Leu Gly Leu Met Tyr Asp Asn Gly Arg Gly Val Lys Gln Asp Tyr Phe
            115                 120                 125

Glu Ala Val Lys Trp Phe Arg Lys Ala Ala Glu Gln Gly Tyr Ala Asp
            130                 135                 140

Ala Gln Phe Asn Leu Gly Asn Met Tyr Tyr Asn Gly His Gly Val Lys
145                 150                 155                 160

Gln Asp Asp Phe Glu Ala Val Lys Trp Tyr Arg Lys Ala Ala Glu Gln
                165                 170                 175

Gly Tyr Ala Asp Ala Gln Phe Asn Leu Gly Asn Met Tyr Tyr Asn Gly
            180                 185                 190

His Gly Val Lys Gln Asp Asp Phe Glu Ala Val Lys Trp Tyr Arg Lys
            195                 200                 205

Ala Ala Glu Gln Gly His Ala Lys Ala Gln Tyr Asn Leu Gly Asn Met
210                 215                 220

Tyr Ala Asn Gly Arg Gly Val Lys Gln Asp Tyr Phe Glu Ala Val Lys
225                 230                 235                 240

Trp Tyr Arg Lys Ala Ala Glu Gln Gly Tyr Ala Asp Ala Gln Ala Asn
                245                 250                 255

Leu Gly Ser Ala Tyr Ser Ala Gly His Gly Val Arg Gln Asp Tyr Ile
            260                 265                 270

Glu Ala Val Lys Trp Phe Lys Lys Ala Ala Glu Asn Gly Ser Ala Asp
            275                 280                 285

Gly Gln Phe Lys Leu Gly Leu Val Tyr Leu Ile Gly Gln Gly Ile Gln
            290                 295                 300

Lys Asp Arg Thr Leu Ala Lys Glu Trp Leu Gly Lys Ala Cys Asp Asn
305                 310                 315                 320

Gly Asn Gln Asn Gly Cys Glu Tyr Tyr Gly Glu Leu Asn Arg Gly Glu
                325                 330                 335

Arg
```

```
<210> SEQ ID NO 57
<211> LENGTH: 143
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT002 Variant from Fi176

<400> SEQUENCE: 57

Cys Ser Ser Phe Gln Asn Asp Asp Tyr Ala Met Asn Tyr Lys Gly Gln
```

```
              1               5                  10                 15
           Ile Gly Asp Pro Ile Met Ala Ile Ala Met Leu Ser Glu Gln Gln His
                           20                 25                 30
           Glu Trp Ala Gly Thr Pro Tyr Val Leu Gly Gly Val Ser Arg Arg Gly
                           35                 40                 45
           Val Asp Cys Ser Gly Phe Val Gln Lys Thr Phe Phe Asp Arg Phe Asn
            50                 55                 60
           Leu Arg Leu Pro Arg Ser Thr Val Glu Gln Ala Asn Tyr Gly Lys His
            65                 70                 75                 80
           Val Arg Lys Glu Asp Ile Gln Thr Gly Asp Leu Ile Phe Phe Lys Thr
                           85                 90                 95
           Gly Arg Gly Pro Asn Gly Tyr His Val Gly Ile Tyr Val Lys Glu Asp
                          100                105                110
           Lys Phe Leu His Ala Ser Thr Arg Gly Gly Val Val Tyr Ser Ser Met
                          115                120                125
           Asn Asn Pro Tyr Trp Ser Lys Ala Phe Trp Gln Val Arg Arg Ile
                          130                135                140
```

<210> SEQ ID NO 58
<211> LENGTH: 146
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT026 Variant from FI176

<400> SEQUENCE: 58

```
           Val Pro Leu Trp Lys Thr Asp Ser Pro Lys Thr Ile Leu Ala Lys Glu
            1               5                  10                 15
           Gln His Arg Leu Tyr Leu Phe Leu Arg Gln Ile Gln Ala Arg Ala Glu
                           20                 25                 30
           Asn Ser Ser Glu Val Trp Phe Leu Leu Ile Asn Arg Asn Leu Ala Thr
                           35                 40                 45
           Gln Gln Trp Cys Leu Thr Ala Gln Val Lys Asn Asn Gln Thr Cys Asp
            50                 55                 60
           Cys Leu Asn Pro Ile Asn Cys Pro Lys Glu Val Tyr Val His Phe Tyr
            65                 70                 75                 80
           Tyr Pro Tyr Phe Pro Asn Lys Thr Ile Ile Gln Ser His His Ile Tyr
                           85                 90                 95
           Pro Lys Glu Ile Thr Arg Phe Asp Gly Ile Arg Asn Thr Ile Val Thr
                          100                105                110
           Arg Cys Phe Ile Leu Gln Ala Glu Asn Glu Arg Thr Leu Phe Leu Phe
                          115                120                125
           Phe Asn Val Gly Ser Ile Arg Leu Lys Thr Asn Gln Phe Asp Ser Ala
                          130                135                140
           Cys Asn
           145
```

<210> SEQ ID NO 59
<211> LENGTH: 556
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT009Variant from Fi176

<400> SEQUENCE: 59

```
Glu Gln Thr Val Asp Ile Glu Val Gln Gly Ile Arg Gly Phe Arg Ala
1               5                   10                  15
Val Arg Asn Thr Asp Leu Asn Val Asn Leu Ile Asn Lys Glu Glu Met
            20                  25                  30
Asp Gly Ser Glu Arg Tyr Gln His Leu Val Thr Lys Ala Val Asp Arg
        35                  40                  45
Gly Leu Arg Val Phe Gly Tyr Tyr Asp Ser Ser Val Arg Phe Glu Arg
    50                  55                  60
Lys Gln Arg Gln Gly Lys Arg Asp Leu Leu Ile Ala His Val Thr Pro
65                  70                  75                  80
Gly Glu Pro Thr Lys Ile Ala Gly Thr Asp Val Gln Ile Glu Gly Glu
                85                  90                  95
Ala Ala Gln Asp Glu Asn Phe Asn Ala Leu Arg Lys Asn Leu Pro Lys
            100                 105                 110
Asp Gly Val Leu Val Glu His Gln Thr Tyr Asp Tyr Lys Thr Ala
        115                 120                 125
Ile Ser Arg Leu Ala Leu Asn Arg Gly Tyr Phe Asp Gly Glu Phe Lys
130                 135                 140
Ile Ser Arg Leu Glu Ile Ser Pro Glu Thr His Gln Ala Trp Trp Arg
145                 150                 155                 160
Met Leu Phe Asp Ser Gly Val Arg Tyr His Tyr Gly Asn Ile Thr Phe
                165                 170                 175
Ser His Ser Gln Ile Arg Asp Asp Tyr Leu Asn Asn Ile Leu Asn Ile
            180                 185                 190
Lys Ser Gly Asp Pro Tyr Leu Met Asn Asn Leu Ser Asp Leu Thr Ser
        195                 200                 205
Asp Phe Ser Ser Ser Asn Trp Phe Ser Ser Val Leu Val Gln Pro Asn
    210                 215                 220
Ile Asn His Lys Ser Lys Thr Val Asp Ile Glu Ile Leu Tyr Pro
225                 230                 235                 240
Arg Lys Lys Asn Ala Met Glu Leu Gly Val Gly Phe Asp Thr Asp Gly
                245                 250                 255
Gly Val His Gly Gln Ile Gly Trp Thr Lys Pro Trp Ile Asn Ser Arg
            260                 265                 270
Gly His Ser Leu Arg Ser Asn Leu Tyr Leu Ser Ala Pro Lys Gln Thr
        275                 280                 285
Leu Glu Ala Thr Tyr Arg Ile Pro Leu Leu Lys Asn Pro Leu Asn Tyr
    290                 295                 300
Tyr Tyr Asp Phe Ala Val Gly Trp Glu Gly Glu Lys Glu Asn Asp Thr
305                 310                 315                 320
Asn Thr Arg Ala Leu Thr Leu Ser Ala Leu Arg Tyr Trp Asn Asn Ala
                325                 330                 335
His Gly Trp Gln Tyr Phe Gly Gly Leu Arg Thr Arg Tyr Asp Ser Phe
            340                 345                 350
Thr Gln Ala Asp Ile Thr Asp Lys Thr Leu Leu Tyr Pro Thr Val
        355                 360                 365
Gly Phe Thr Arg Thr Arg Leu Arg Gly Ser Phe Ala Thr Trp Gly
    370                 375                 380
Asp Val Gln Lys Ile Thr Phe Asp Leu Ser Lys Arg Ile Trp Leu Ser
385                 390                 395                 400
Glu Ser Ser Phe Ile Lys Val Gln Ala Ser Ser Ala Trp Ile Arg Thr
```

```
                    405                 410                 415

Tyr Ala Glu Asn His Arg Ile Val Ala Arg Ala Glu Ile Gly Tyr Leu
                420                 425                 430

His Thr Lys Asp Ile Glu Lys Ile Pro Pro Thr Leu Arg Phe Phe Ala
            435                 440                 445

Gly Gly Asp Arg Ser Val Arg Gly Tyr Gly Tyr Lys Lys Ile Ala Pro
        450                 455                 460

Lys Asn Arg Asn Gly Lys Leu Val Gly Gly Ser Arg Leu Leu Thr Thr
465                 470                 475                 480

Ser Leu Glu Tyr Gln Tyr Gln Val Tyr Pro Asn Trp Trp Ala Ala Thr
                485                 490                 495

Phe Ala Asp Ser Gly Leu Ala Ala Asp Asn Tyr Thr Ala Lys Glu Leu
            500                 505                 510

Arg Tyr Gly Ala Gly Val Gly Val Arg Trp Ala Ser Pro Val Gly Ala
        515                 520                 525

Ile Lys Phe Asp Ile Ala Thr Pro Ile Arg Asp Lys Asp Asn Ser Lys
    530                 535                 540

Asn Ile Gln Phe Tyr Ile Gly Leu Gly Thr Glu Ile
545                 550                 555

<210> SEQ ID NO 60
<211> LENGTH: 126
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT025Variant from Fi176

<400> SEQUENCE: 60

Ile Ile Ala Ile Leu Ala Thr Ile Ala Ile Pro Ser Tyr Gln Asn Tyr
1               5                   10                  15

Thr Lys Lys Ala Ala Val Ser Glu Leu Leu Gln Ala Ser Ala Pro Tyr
            20                  25                  30

Lys Ala Asp Val Glu Leu Cys Val Tyr Ser Thr Asn Glu Thr Thr Asn
        35                  40                  45

Cys Thr Gly Gly Lys Asn Gly Ile Ala Ala Asp Ile Thr Thr Ala Lys
    50                  55                  60

Gly Tyr Val Lys Ser Val Thr Thr Ser Asn Gly Ala Ile Thr Val Lys
65                  70                  75                  80

Gly Asp Gly Thr Leu Ala Asn Met Glu Tyr Ile Leu Gln Ala Thr Gly
                85                  90                  95

Asn Ala Ala Thr Gly Val Thr Trp Thr Thr Thr Cys Lys Gly Thr Asp
            100                 105                 110

Ala Ser Leu Phe Pro Ala Asn Phe Cys Arg Ser Val Thr Lys
        115                 120                 125

<210> SEQ ID NO 61
<211> LENGTH: 162
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT028Variant from Fi176

<400> SEQUENCE: 61
```

```
Pro Arg Thr Val Ser His Gln Val Ile Ser Glu Asn Asp Asp Ile Gln
1               5                   10                  15

Leu Thr Gly Leu Ile Asn Asn Leu Glu Lys Asp Asn Arg Thr Gly Ile
            20                  25                  30

Phe His Lys Val Arg Thr Asn Arg Ser Ser Ala Leu Met Gly Asp Lys
        35                  40                  45

Ala Leu Ala Ser Val Tyr Asn Glu Trp Val Gly Thr Arg Tyr Arg Met
50                  55                  60

Gly Gly Thr Thr Lys Arg Gly Ile Asp Cys Ser Ala Phe Met Gln Thr
65                  70                  75                  80

Thr Phe Ser Glu Val Phe Gly Ile Glu Leu Pro Arg Ser Thr Ala Glu
            85                  90                  95

Gln Arg His Leu Gly Arg Lys Ile Asn Lys Ser Glu Leu Lys Lys Gly
        100                 105                 110

Asp Leu Val Phe Phe Arg Lys Asn Asn His Val Gly Val Tyr Ile Gly
            115                 120                 125

Asn Asn Gln Phe Met His Ala Ser Thr Gly Gln Gly Val Thr Ile Ser
        130                 135                 140

Ser Leu Asp Glu Lys Tyr Trp Ala Arg Thr Tyr Thr Gln Ser Arg Arg
145                 150                 155                 160

Ile Met
```

<210> SEQ ID NO 62
<211> LENGTH: 895
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT029 Variant from R2846

<400> SEQUENCE: 62

```
Ser Thr Pro Asp Leu Pro Gln Asn His Lys Ile Ile Thr Gly Thr Ala
1               5                   10                  15

Thr Val Ser His Thr Glu Asn Glu Met Thr Ile Lys Gln Thr Thr Pro
            20                  25                  30

Thr Thr Gln Ile Asn Trp Asp Ser Phe Asn Ile Gly Lys Asp Lys Glu
        35                  40                  45

Val Lys Phe Glu Gln Pro Ser Thr Ser Ala Val Ala Tyr Asn Arg Val
50                  55                  60

Thr Gly Gly Asn Ala Ser His Ile Gln Gly Lys Leu Thr Ala Asn Gly
65                  70                  75                  80

Lys Val Tyr Leu Ala Asn Pro Asn Gly Val Ile Ile Thr Lys Gly Ala
            85                  90                  95

Glu Ile Asn Val Ala Gly Leu Leu Ala Thr Thr Lys Asp Leu Glu Arg
        100                 105                 110

Ile Ser Glu Asn Gly Asn Thr Asn Thr Asn Lys Phe Thr Arg Lys Ala
        115                 120                 125

Lys Glu Gly Lys Val Leu Thr Glu Gly Gln Val Ile Asn Glu Gly Glu
        130                 135                 140

Ile Lys Ala Lys Asp Phe Val Val Leu Asn Gly Asp Glu Val Ile Asn
145                 150                 155                 160

Lys Gly Asn Ile Asn Val Glu Lys Asn Ser Thr Ile Asn Gly Glu Val
            165                 170                 175

Tyr Leu Ser Ser Ser Asn Asn Phe Thr Phe Thr Leu Ser Asp Ser Gly
```

```
            180                 185                 190
Ile Ser Val Ala Leu Glu Asp Asn Thr Val Gln Gly Ile Val Lys Asn
            195                 200                 205
Glu Gly Ile Val Lys Asn Glu Gly Ser Ile Lys Ala Gly Glu Ile Thr
            210                 215                 220
Leu Ser Ala Lys Gly Arg Lys Glu Ala Leu Asp Ser Leu Val Val Asn
225                 230                 235                 240
Asn Gly Val Leu Glu Ala Thr Lys Val Ser Asn Arg Lys Gly Lys Ile
            245                 250                 255
Val Leu Ser Ala Asp Asp Val Gln Leu Asn Asn Asn Ser Asp Ile Lys
            260                 265                 270
Gly Glu Ile Val Asn Phe Gly Thr Glu Val Thr Ser Asn Glu Asp Lys
            275                 280                 285
Lys Leu Lys Ile Thr Ser Gln Thr Gly Ser Lys Val Thr Ser Pro Lys
            290                 295                 300
Ile Asn Phe Lys Gly Lys Ser Val Asn Ile Lys Gly Asp Phe Gly Arg
305                 310                 315                 320
Glu Asp Asn Thr Thr Tyr Tyr Asp Asp Glu His Lys Lys Leu Lys Thr
                    325                 330                 335
Glu Val Asn Ile Asp Val Pro Asn Thr Glu Asn Ile Gln Ile Ala Asp
            340                 345                 350
Lys Asp Asn Ala Gly Thr Asp Ser Phe Ile Gln Thr Gly Ala Leu Ser
            355                 360                 365
Ser Leu Leu Ala Asn Asn Gly Lys Val Asn Leu Lys Gly Lys Asp Val
            370                 375                 380
Asn Ile Ser Gly Asn Ile Asn Ile Asn Ser Phe Arg Gly Thr Asp Ser
385                 390                 395                 400
Leu Leu Lys Leu Thr Asn Lys Gly His Ile Asn Ile Asn His Ala Asp
                    405                 410                 415
Ile His Ser Lys Gly Arg Leu Phe Phe Ile Thr Ser Leu Gln Asn Asp
            420                 425                 430
Val Asp Phe Gln Ser Asn Ile Thr Ile Thr Asp Ser Lys Ile Asn Leu
            435                 440                 445
Gly Asn Gly Ala Met Gly Leu Gly Arg Ser Val Asn Glu Asn Asp Leu
            450                 455                 460
Asp Arg Trp Arg Arg Thr Glu Tyr Ser Gln Arg Lys Lys Phe Asn Val
465                 470                 475                 480
Asn Met Arg Asn Val Val Phe Asp Gln Val Asp Asp Val Val Val Ala
                    485                 490                 495
Gly Gly Phe Lys Glu Val Asn Leu Asn Asn Ile Val Ala Thr Gly Gln
            500                 505                 510
Thr Asn Phe Tyr Ile Asp Gly Gly Val Ser Arg Asn Arg Asn Gly Val
            515                 520                 525
Ser Ser Lys Tyr Glu Tyr Gly Val Leu Asp Leu Asp Lys Arg Thr Gln
            530                 535                 540
Leu Ser Glu Leu Asp Gln Arg Arg Arg Trp Gly Tyr Tyr Pro Asp
545                 550                 555                 560
Leu Asp Leu Asp Met Asn Lys Ala Tyr Trp His Arg Phe Asp Met Phe
                    565                 570                 575
Ala Ser Lys Asn Thr Gly Arg Ser Thr Ile Lys Asp Thr Glu Ile Asn
            580                 585                 590
Ile Ser Asn Ser Lys Ile Asn Leu Lys Asn Gly Phe Val His Leu Leu
            595                 600                 605
```

Ala Glu Lys Ile Lys Leu Asp Asn Ser Lys Ile Asp Ile Thr Phe Asp
610                 615                 620

Lys Asp Asn Ser Gln Asp Ile Ser Thr Gln Ile Asn Arg Leu Gly Met
625                 630                 635                 640

Asn Gly Lys Val Ser Met Val Asn Ser His Ile Lys Ile Val Gly Asp
            645                 650                 655

Glu Lys Ile Asp Ile Ser Ala Lys Ala Pro Tyr Ala Thr Met Phe Leu
            660                 665                 670

Ile Gly Glu Leu Ile Gly Lys Ser Ser Ile Phe Val Lys Ser His
        675                 680                 685

Gln Gly Tyr Thr Phe Arg Thr Asp Gly Asp Thr Lys Ile Ala Gly Lys
    690                 695                 700

Asn Ser Lys Asp Leu Lys Ile Thr Ala Ile Asn Thr Gly Gly Arg
705                 710                 715                 720

Thr Gly Lys Glu Val Ile Ile Asn Gly Ala Pro Gly Ser Ile Asp Asn
                725                 730                 735

Asp Ala Asn Ile Ala Asn Met Ala Phe Thr Ile Gly Asp Asn Ala Asn
            740                 745                 750

Thr Lys Thr Thr Ile Glu Asn Ala Asp Ile Thr Ala Leu Ala Pro Asn
            755                 760                 765

Gly Gly Thr Ala Tyr Leu Ser Ser Lys Gly Val Glu Ile Glu Val Asn
770                 775                 780

Pro Asn Ser Asn Phe Thr Phe Phe Glu Leu Pro Arg Glu Lys Asn Phe
785                 790                 795                 800

Asn Gln Thr Lys Ile Asn Gly Asp Ser Thr Lys Leu Ser Glu Arg Gly
                805                 810                 815

Phe Ala Arg Leu Tyr Asp Lys Ile Asn Gly Val Arg Ala Ser Asn Leu
            820                 825                 830

Ser Ala Glu Gln Leu Asn Val Thr Asp Ser Ser Glu Lys Ile Ile Asn
            835                 840                 845

Thr Lys Leu Val Ser Ser Leu Asp Val Glu Lys Leu Val Ser Val Ala
850                 855                 860

Val Cys Asp Ala Gly Lys Gly Cys Glu Glu Gln Gln Phe Gly Asp Lys
865                 870                 875                 880

Gly Asn Asn Thr Lys Val Ser Val Gly Glu Leu Glu Ala Glu Gln
            885                 890                 895

<210> SEQ ID NO 63
<211> LENGTH: 183
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT031Variant from R2846

<400> SEQUENCE: 63

Met Lys Gly Lys Ile Thr Leu Phe Phe Thr Ala Leu Cys Phe Gly Leu
1               5                   10                  15

Thr Gly Cys Ile Ala Pro Pro Lys Gly Leu Glu Lys Glu Arg Phe Ser
            20                  25                  30

Ile Asn Ser Tyr Arg Glu Ile Ser Pro Gln Asp Leu Thr Cys His Cys
        35                  40                  45

Asn Thr Val Arg Leu Gly Gly Lys Ile Val Asn Thr Val Leu Ala
    50                  55                  60

```
Asn Gln Thr Lys Ile Glu Val Leu Ser Leu Pro Val Ser Ser Ile Ser
 65                  70                  75                  80

Gly Lys Pro Phe Val Glu Leu Gln Ser Asp Gly Arg Phe Ile Val Tyr
                 85                  90                  95

Phe Asn Gly Phe Val Glu Pro Glu Asn Leu Lys Glu Arg Tyr Ile Thr
            100                 105                 110

Val Gly Gly Gln Leu Thr Gly Thr Glu Lys Gly Lys Ile Glu Gln Ala
        115                 120                 125

Asp Tyr Thr Tyr Pro Val Val Gln Ala Asp Lys Tyr Arg Ile Trp Thr
    130                 135                 140

Leu Ser Thr Thr Tyr Asn Tyr Pro Thr Asp Asp Trp Asp Glu Asp
145                 150                 155                 160

Asp Trp Gly Phe Phe Arg Trp Arg His Arg Pro Trp Tyr Val Gln Pro
                165                 170                 175

Glu Ile His Tyr Tyr Leu Asn
            180

<210> SEQ ID NO 64
<211> LENGTH: 117
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT015Variant from Fi176

<400> SEQUENCE: 64

Ala Gln Asn Ala Asn Val Thr Thr Pro Gln Ala Gln Lys Met Gln Val
 1               5                  10                  15

Glu Lys Val Asp Lys Ala Leu Gln Lys Gly Glu Ala Asp Arg Tyr Leu
                 20                  25                  30

Cys Gln Asp Asp Lys Val Val Arg Val Val His Ala Thr His Lys Lys
             35                  40                  45

Tyr Lys Lys Asn Leu His Tyr Val Thr Val Thr Phe Gln Gly Val Ser
         50                  55                  60

Glu Lys Leu Thr Leu Met Ile Ser Glu Arg Gly Lys Asn Tyr Ala Asn
 65                  70                  75                  80

Ile Arg Trp Met Trp Gln Glu Arg Asp Asp Phe Ser Thr Leu Lys Thr
                 85                  90                  95

Asn Leu Gly Glu Ile Leu Ala Thr Gln Cys Val Ser Thr Ser Glu
            100                 105                 110

Arg Leu Ser Gly Gln
        115

<210> SEQ ID NO 65
<211> LENGTH: 134
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT023Variant from Fi176

<400> SEQUENCE: 65

Asn Thr Asp Ile Phe Ser Gly Asp Val Tyr Ser Ala Ser Gln Ala Lys
 1               5                  10                  15

Glu Ala Arg Ser Ile Thr Tyr Gly Thr Ile Val Ser Val Arg Pro Val
```

```
            20                  25                  30
Lys Ile Gln Ala Asp Asn Gln Gly Val Val Gly Thr Leu Gly Gly Gly
        35                  40                  45

Ala Leu Gly Gly Ile Ala Gly Ser Ala Ile Gly Gly Arg Gly Gln
    50                  55                  60

Ala Ile Ala Ala Val Val Gly Ala Ile Gly Gly Ala Ile Ala Gly Ser
65                  70                  75                  80

Lys Ile Glu Glu Lys Met Ser Gln Val Asn Gly Ala Glu Leu Val Ile
                85                  90                  95

Lys Lys Asp Asp Gly Gln Glu Ile Val Val Gln Lys Ala Asp Ser
            100                 105                 110

Ser Phe Val Ala Gly Arg Arg Val Arg Ile Val Gly Gly Ser Ser
        115                 120                 125

Leu Asn Val Ser Val Leu
        130

<210> SEQ ID NO 66
<211> LENGTH: 345
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT100 Variant from R2846

<400> SEQUENCE: 66

Met Asp Leu Gly Pro Ile Tyr Asn Thr Arg Asp Ile Asn Asp Gly Lys
1               5                   10                  15

Val Ile Asn Ile Asp Asn Pro Asn Tyr Thr Asn Pro Val Ala Ile Lys
                20                  25                  30

Lys Asn Glu Asn Asn Ala Tyr Gln Phe Asn His Leu Lys Thr Leu
            35                  40                  45

Gly Leu Tyr Ile Gln Asn Thr Thr Tyr Phe Thr Asp Asn Phe Ile Ile
        50                  55                  60

Thr Gly Gly Leu Arg Tyr Glu Tyr Phe Asp Gln Val Val Gly Arg Ser
65              70                  75                  80

Thr Leu Lys Asn Ile Arg Ser Gly Tyr Leu Ala Gln Lys Asp Gly Lys
                85                  90                  95

Leu Leu Tyr Gln Leu Gly Ser Val Tyr Lys Phe Thr Pro Asn Ile Ala
            100                 105                 110

Thr Phe Phe Asn His Ala Glu Ser Phe Arg Pro Gln Asn Asn Arg Thr
        115                 120                 125

Leu Ile Ile Asn Gly Glu Leu Pro Ala Glu Gln Gly Lys Ser Phe Glu
    130                 135                 140

Thr Gly Leu Lys Tyr Glu Asn Ala Tyr Leu Asn Ala Thr Val Ala Leu
145                 150                 155                 160

Phe Asn Ile Asn Lys Arg Asn Val Ala Glu Thr Val Asn Val Asn Gly
                165                 170                 175

Thr Asn Glu Leu Gln Ile Val Gly Lys Gln Arg Ser Arg Gly Ile Glu
            180                 185                 190

Phe Asp Leu Asn Gly Gln Leu Thr Asp Asn Leu Ser Ile Ala Ala Asn
        195                 200                 205

Tyr Thr Tyr Thr Lys Val Lys Asn Leu Glu Asn His Asn Asn Lys Leu
    210                 215                 220

Ala Val Gly Lys Gln Leu Ser Gly Val Pro Lys His Gln Ala Ser Leu
```

```
                225                 230                 235                 240

Phe Leu Ala Tyr Asn Ile Gly Glu Phe Asp Phe Gly Asn Ile Arg Val
                            245                 250                 255

Gly Gly Gly Ala Arg Tyr Leu Gly Ser Trp Tyr Ala Tyr Asn Asn Thr
                        260                 265                 270

Tyr Thr Lys Ala Tyr Lys Leu Pro Gln Ala Ile Val Tyr Asp Ala Phe
                        275                 280                 285

Ile Ala Tyr Asp Thr Lys Ile Ser Gly Lys Val Ser Phe Gln Leu
                290                 295                 300

Asn Gly Lys Asn Leu Ser Asn Lys Val Tyr Ser Pro Ser Thr Ser Gly
            305                 310                 315                 320

Asn Ala Ser Arg Thr Leu Ile Pro Val Ala Leu Gly Tyr Ala Arg Glu
                            325                 330                 335

Val Ile Leu Asn Thr Lys Ile Glu Phe
                        340                 345

<210> SEQ ID NO 67
<211> LENGTH: 505
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT066 variant from Fi176

<400> SEQUENCE: 67

Phe Lys Lys Ser Leu Ile Val Ala Ala Ser Phe Ala Ser Leu Ser Leu
            1               5                   10                  15

Phe Asn Ser Ala Thr Ala Glu Leu Val Tyr Lys Pro Leu Glu Gln Pro
                            20                  25                  30

Val Glu Pro Ala Lys Pro Asp Leu Lys Ile Glu Ser Val Asn Glu Lys
                        35                  40                  45

Phe Ala Glu Lys Tyr Pro Asn Gln Tyr Asn Ser Trp Arg Ser Thr Ala
                    50                  55                  60

Asn Gly Asp Gly Glu Asn Ile Ile Tyr Ala Asp Glu Glu Asn Pro Arg
            65                  70                  75                  80

Leu Ile Val Leu Trp Gly Gly Tyr Ala Phe Ala Lys Glu Tyr Asn Ala
                            85                  90                  95

Pro Arg Gly His Phe Tyr Ala Val Thr Asp Val Arg Asn Ile Leu Arg
                        100                 105                 110

Thr Gly Ala Pro Lys Thr Ala Asn Asp Gly Pro Gln Ala Met Ala Cys
                    115                 120                 125

Trp Thr Cys Lys Gly Pro Asp Val Pro Arg Leu Ile Ala Glu Trp Gly
                130                 135                 140

Glu Lys Asp Tyr Phe Asn Ala Lys Trp Ala Lys Gly Gly Pro Glu Ile
            145                 150                 155                 160

Val Asn Ser Ile Gly Cys Ala Asp Cys His Asp Thr Thr Ser Lys Asp
                            165                 170                 175

Phe Ala Glu Gly Lys Pro Ala Leu Arg Ile Ala Arg Pro His Ile Leu
                        180                 185                 190

Arg Ala Leu Asp Ala Leu Glu Lys Ala Thr Ala Glu Lys Asp Lys Ala
                    195                 200                 205

Glu Gly Arg Pro His Asn Asn Leu Ser Phe Asn Thr Ala Ala Arg Thr
                210                 215                 220

Glu Lys Arg Ala Glu Ile Cys Ala Asn Cys His Val Glu Tyr Tyr Phe
```

```
            225                 230                 235                 240
Ala Gly Asp Ile Lys Gln Val Thr Phe Pro Trp Asp Asn Gly Gln Thr
                245                 250                 255

Val Asp Asp Ile Glu Lys Tyr Tyr Asp Asp Ile Gly Phe Thr Asp Trp
                260                 265                 270

Thr His Ser Leu Ser Lys Ala Pro Met Leu Lys Ala Gln His Pro Asp
                275                 280                 285

Phe Glu Ile Trp Ser Leu Gly Met His Gly Lys Asn Gly Val Thr Cys
            290                 295                 300

Val Asp Cys His Met Pro Lys Val Gln Gly Ala Asp Gly Lys Val Tyr
305                 310                 315                 320

Thr Asp His Gln Ile Gln Asn Pro Phe Glu Ala Phe Asp His Thr Cys
                325                 330                 335

Ala Asn Cys His Asp Gln Ser Lys Glu Lys Leu Arg Asp Ile Val Thr
                340                 345                 350

Ser Arg Lys Lys Glu Val Lys Asp Val Met Gly Arg Leu Glu Asp Gln
            355                 360                 365

Val Val Lys Ala His Phe Glu Ala Lys Ala Ala Trp Asp Ala Gly Ala
370                 375                 380

Thr Lys Glu Glu Met Glu Ala Ala Leu Met Asp Ile Arg His Ala Gln
385                 390                 395                 400

Trp Arg Trp Asp Tyr Thr Ala Ala Ser His Gly Gly His Met His Ala
                405                 410                 415

Pro Glu Val Val Leu Arg Val Leu Ala Ser Gly Leu Asp Lys Val Ala
                420                 425                 430

Asp Ala Arg Thr Lys Leu Ala Val Ile Leu Thr Lys His Gly Val Lys
                435                 440                 445

Thr Pro Val Gln Ile Pro Asp Ile Ser Thr Ala Asp Lys Ala Trp Lys
            450                 455                 460

Val Met Gly Ile Asp Ile Glu Lys Glu Arg Lys Ala Lys Glu Glu Phe
465                 470                 475                 480

Leu Lys Thr Val Val Pro Gln Trp Glu Gln Gln Ala Arg Glu Lys Gly
                485                 490                 495

Leu Leu Val Asp Pro Pro Ala Gln Lys
            500                 505

<210> SEQ ID NO 68
<211> LENGTH: 6
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: His tag

<400> SEQUENCE: 68

His His His His His His
1               5

<210> SEQ ID NO 69
<211> LENGTH: 28
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT018 N-terminus
```

<400> SEQUENCE: 69

Met Asn Phe Thr Leu Ile Phe Ile Leu Thr Thr Leu Val Val Ala Leu
1               5                   10                  15

Ile Cys Phe Tyr Pro Leu Leu Arg Gln Phe Lys Ala
            20                  25

<210> SEQ ID NO 70
<211> LENGTH: 20
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT024 N-Terminus

<400> SEQUENCE: 70

Met Lys Leu Lys Leu Phe Phe His Ile Val Leu Leu Cys Phe Ser Leu
1               5                   10                  15

Pro Val Trp Ala
            20

<210> SEQ ID NO 71
<211> LENGTH: 19
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT032 N-terminus

<400> SEQUENCE: 71

Met Lys Lys Phe Ala Leu Ala Thr Ile Phe Ala Leu Ala Thr Thr Ser
1               5                   10                  15

Ala Phe Ala

<210> SEQ ID NO 72
<211> LENGTH: 20
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT067 N terminus

<400> SEQUENCE: 72

Met Gln His Lys Leu Leu Phe Ser Ala Ile Ala Leu Ala Leu Ser Tyr
1               5                   10                  15

Ser Val Gln Ala
            20

<210> SEQ ID NO 73
<211> LENGTH: 23
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT038 N-terminus

<400> SEQUENCE: 73

Met Pro Phe Gln Tyr Val Thr Glu Asp Gly Lys Thr Val Val Lys Val

```
                   1               5                  10                  15

Gly Asn Gly Tyr Tyr Glu Ala
                20

<210> SEQ ID NO 74
<211> LENGTH: 21
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT001 N-terminus

<400> SEQUENCE: 74

Met Lys Leu Lys Gln Leu Phe Ala Ile Thr Ala Ile Ala Ser Ala Leu
1               5                   10                  15

Val Leu Thr Gly Cys
                20

<210> SEQ ID NO 75
<211> LENGTH: 19
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT016 N-terminus

<400> SEQUENCE: 75

Met Arg Lys Ile Lys Ser Leu Ala Leu Leu Ala Val Ala Ala Leu Val
1               5                   10                  15

Ile Gly Cys

<210> SEQ ID NO 76
<211> LENGTH: 11
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT052 N-terminus

<400> SEQUENCE: 76

Met Leu Leu Phe Ile Leu Ser Ile Ala Trp Ala
1               5                   10

<210> SEQ ID NO 77
<211> LENGTH: 18
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT002 N-terminus

<400> SEQUENCE: 77

Met Lys Val Tyr Lys Ser Phe Leu Ile Ala Thr Ala Ser Leu Phe Leu
1               5                   10                  15

Phe Ala

<210> SEQ ID NO 78
<211> LENGTH: 24
```

```
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT026 N-terminus

<400> SEQUENCE: 78

Met Gln Lys Gly Met Thr Leu Val Glu Leu Leu Ile Gly Leu Ala Ile
1               5                   10                  15

Ile Ser Ile Val Leu Asn Phe Ala
            20

<210> SEQ ID NO 79
<211> LENGTH: 22
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT009 N-terminus

<400> SEQUENCE: 79

Met Asn Lys Thr Leu Leu Lys Leu Thr Ala Leu Phe Leu Ala Leu Asn
1               5                   10                  15

Cys Phe Pro Ala Phe Ala
            20

<210> SEQ ID NO 80
<211> LENGTH: 23
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT025 N-terminus

<400> SEQUENCE: 80

Met Lys Leu Thr Thr Gln Gln Thr Leu Lys Lys Gly Phe Thr Leu Ile
1               5                   10                  15

Glu Leu Met Ile Val Ile Ala
            20

<210> SEQ ID NO 81
<211> LENGTH: 21
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT028 N-terminus

<400> SEQUENCE: 81

Met Leu Lys Arg Ile Leu Val Ile Ile Gly Leu Ala Val Leu Ala Thr
1               5                   10                  15

Ala Cys Ser Asn Ala
            20

<210> SEQ ID NO 82
<211> LENGTH: 21
<212> TYPE: PRT
<213> ORGANISM: Unknown
<220> FEATURE:
```

<223> OTHER INFORMATION: Description of Unknown:
      Bacteria <Prokaryote> sequence
<220> FEATURE:
<223> OTHER INFORMATION: NT029 N-terminus

<400> SEQUENCE: 82

Met Tyr Lys Leu Asn Val Ile Ser Leu Ile Ile Leu Thr Thr Tyr Thr
1               5                   10                  15

Gly Ala Thr Tyr Ala
            20

<210> SEQ ID NO 83
<211> LENGTH: 18
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT031 N-terminus

<400> SEQUENCE: 83

Met Lys Gly Lys Ile Thr Leu Phe Phe Thr Ala Leu Cys Phe Gly Leu
1               5                   10                  15

Thr Gly

<210> SEQ ID NO 84
<211> LENGTH: 17
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT015 N-terminus

<400> SEQUENCE: 84

Met Leu Lys Lys Thr Ser Leu Ile Phe Thr Ala Leu Leu Leu Ala Gly
1               5                   10                  15

Cys

<210> SEQ ID NO 85
<211> LENGTH: 20
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT023 N-terminus

<400> SEQUENCE: 85

Met Lys Lys Thr Asn Met Ala Leu Ala Leu Leu Val Ala Phe Ser Val
1               5                   10                  15

Thr Gly Cys Ala
            20

<210> SEQ ID NO 86
<211> LENGTH: 30
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT100 N-terminus

```
<400> SEQUENCE: 86

Met Asp Leu Gly Pro Ile Tyr Asn Thr Arg Asp Ile Asn Asp Gly Lys
1               5                   10                  15

Val Ile Asn Ile Asp Asn Pro Asn Tyr Thr Asn Pro Val Ala
            20                  25                  30

<210> SEQ ID NO 87
<211> LENGTH: 26
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT040 N-terminus

<400> SEQUENCE: 87

Met Met Lys Thr Leu Leu Lys Gly Gln Thr Leu Leu Ala Leu Met Ile
1               5                   10                  15

Ser Leu Thr Leu Ser Ser Leu Leu Leu
            20                  25

<210> SEQ ID NO 88
<211> LENGTH: 18
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT048 N-terminus

<400> SEQUENCE: 88

Met Lys Ser Val Pro Leu Ile Thr Gly Gly Leu Ser Phe Leu Leu Ser
1               5                   10                  15

Ala Cys

<210> SEQ ID NO 89
<211> LENGTH: 22
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT124 N-terminus

<400> SEQUENCE: 89

Met Lys Lys Ser Lys Ile Ala Ala Gly Val Val Ile Ser Leu Ala Ala
1               5                   10                  15

Val Trp Cys Ala Gly Ala
            20

<210> SEQ ID NO 90
<211> LENGTH: 33
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT066 N-terminus

<400> SEQUENCE: 90

Met Lys Ile Tyr Leu Arg Phe Val Trp Ile Leu Ile Ile Ile Leu Asn
1               5                   10                  15
```

```
Phe Leu Leu Asn Leu Phe Ile Thr Thr Asn Gly Val Ile Ile Val Asn
            20                  25                  30
Ala

<210> SEQ ID NO 91
<211> LENGTH: 22
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT097 N-terminus

<400> SEQUENCE: 91

Met Lys Lys Phe Asn Gln Ser Ile Leu Ala Thr Ala Met Leu Leu Ala
1               5                   10                  15

Ala Gly Gly Ala Asn Ala
            20

<210> SEQ ID NO 92
<211> LENGTH: 25
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: P48 N-terminus

<400> SEQUENCE: 92

Met Ile Thr Ile Lys Lys Gly Leu Asp Leu Pro Ile Ala Gly Lys Pro
1               5                   10                  15

Ala Gln Val Ile His Ser Gly Asn Ala
            20                  25

<210> SEQ ID NO 93
<211> LENGTH: 26
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: HtrA N-terminus

<400> SEQUENCE: 93

Met Lys Lys Thr Arg Phe Val Leu Asn Ser Ile Ala Leu Gly Leu Ser
1               5                   10                  15

Val Leu Ser Thr Ser Phe Val Ala Gln Ala
            20                  25

<210> SEQ ID NO 94
<211> LENGTH: 16
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: PE N-terminus

<400> SEQUENCE: 94

Met Lys Lys Ile Ile Leu Thr Leu Ser Leu Gly Leu Leu Thr Ala Cys
1               5                   10                  15
```

```
<210> SEQ ID NO 95
<211> LENGTH: 18
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: PhiD N-terminus

<400> SEQUENCE: 95

Met Lys Leu Lys Thr Leu Ala Leu Ser Leu Leu Ala Ala Gly Val Leu
1               5                   10                  15

Ala Gly

<210> SEQ ID NO 96
<211> LENGTH: 19
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: P6 N-terminus

<400> SEQUENCE: 96

Met Asn Lys Phe Val Lys Ser Leu Leu Val Ala Gly Ser Val Ala Ala
1               5                   10                  15

Leu Ala Ala

<210> SEQ ID NO 97
<211> LENGTH: 42
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT013 N-terminus

<400> SEQUENCE: 97

Met Pro Val Gln His Val Lys Leu Ala Arg Asp Arg Arg Lys Lys Arg
1               5                   10                  15

Thr Tyr Ile Lys Val Gly Val Phe Phe Val Ala Ile Leu Leu Ile Leu
            20                  25                  30

Thr Gly Ile Leu Leu Thr Ile Lys Asp Lys
        35                  40

<210> SEQ ID NO 98
<211> LENGTH: 17
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT106 N-terminus

<400> SEQUENCE: 98

Met Lys Lys Ile Ile Leu Asn Leu Val Thr Ala Ile Ile Leu Ala Gly
1               5                   10                  15

Cys

<210> SEQ ID NO 99
<211> LENGTH: 28
```

```
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT107 N-terminus

<400> SEQUENCE: 99

Met Lys Met Arg Pro Arg Tyr Ser Val Ile Ala Ser Ala Val Ser Leu
1               5                   10                  15

Gly Phe Val Leu Ser Lys Ser Val Met Ala Leu Gly
            20                  25

<210> SEQ ID NO 100
<211> LENGTH: 24
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT108 N-terminus

<400> SEQUENCE: 100

Met Ser Val Cys Lys Pro Phe Trp Phe Lys Thr Phe Ser Ile Ser Ile
1               5                   10                  15

Ile Thr Ala Leu Leu Val Ser Cys
            20

<210> SEQ ID NO 101
<211> LENGTH: 30
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT109 N-terminus

<400> SEQUENCE: 101

Met Ile Met Glu Leu Phe His Thr Ile Leu Ala Ile Val Ala Leu Ile
1               5                   10                  15

Leu Ser Ser Ala Val Val Ser Ser Ala Glu Ile Ser Leu Ala
            20                  25                  30

<210> SEQ ID NO 102
<211> LENGTH: 30
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT110 N-terminus

<400> SEQUENCE: 102

Met Ile Met Glu Leu Phe His Thr Ile Leu Ala Ile Val Ala Leu Ile
1               5                   10                  15

Leu Ser Ser Ala Val Val Ser Ser Ala Glu Ile Ser Leu Ala
            20                  25                  30

<210> SEQ ID NO 103
<211> LENGTH: 19
<212> TYPE: PRT
<213> ORGANISM: Unknown
<220> FEATURE:
```

```
<223> OTHER INFORMATION: Description of Unknown:
      Bacteria <Prokaryote> sequence
<220> FEATURE:
<223> OTHER INFORMATION: NT111 N-terminus

<400> SEQUENCE: 103

Met Lys Lys Thr Leu Val Ala Ala Leu Ile Ser Ser Val Ile Leu Leu
1               5                   10                  15

Thr Gly Cys

<210> SEQ ID NO 104
<211> LENGTH: 19
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT112 N-terminus

<400> SEQUENCE: 104

Met Lys Thr Lys Val Ile Leu Thr Ala Leu Leu Ser Ala Ile Ala Leu
1               5                   10                  15

Thr Gly Cys

<210> SEQ ID NO 105
<211> LENGTH: 16
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT113 N-terminus

<400> SEQUENCE: 105

Met Lys Lys Tyr Leu Leu Leu Ala Leu Leu Pro Phe Leu Tyr Ala Cys
1               5                   10                  15

<210> SEQ ID NO 106
<211> LENGTH: 19
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT114 N-terminus

<400> SEQUENCE: 106

Met Lys Lys Val Ala Leu Ile Ser Leu Cys Ile Phe Thr Ala Leu Ser
1               5                   10                  15

Ala Phe Ala

<210> SEQ ID NO 107
<211> LENGTH: 35
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT115 N-terminus

<400> SEQUENCE: 107

Met Lys Tyr Leu His Phe Thr Arg Pro Thr Ile Lys Val Ile Phe Met
1               5                   10                  15
```

```
Ile Asn Ser Ile Lys Thr Leu Leu Leu Ile Ala Thr Leu Ala Ile Leu
            20                  25                  30

Ser Ala Cys
        35
```

<210> SEQ ID NO 108
<211> LENGTH: 18
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT116 N-terminus

<400> SEQUENCE: 108

```
Met Lys Ser Val Pro Leu Ile Thr Gly Gly Leu Ser Phe Leu Leu Ser
1               5                   10                  15

Ala Cys
```

<210> SEQ ID NO 109
<211> LENGTH: 19
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT117 N-terminus

<400> SEQUENCE: 109

```
Met Lys Lys Leu Ile Ala Val Ala Val Phe Ser Ala Cys Gly Ser Leu
1               5                   10                  15

Ala His Ala
```

<210> SEQ ID NO 110
<211> LENGTH: 18
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT118 N-terminus

<400> SEQUENCE: 110

```
Met Asn Ile Arg Trp Asn Val Ile Leu Gly Val Ile Ala Leu Cys Ala
1               5                   10                  15

Leu Ala
```

<210> SEQ ID NO 111
<211> LENGTH: 17
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT123 N-terminus

<400> SEQUENCE: 111

```
Met Lys Lys Thr Thr Ala Leu Phe Leu Leu Ile Phe Ser Leu Ile Ala
1               5                   10                  15

Cys
```

```
<210> SEQ ID NO 112
<211> LENGTH: 26
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: Immunostimulatory oligonucleotide

<400> SEQUENCE: 112

Ile Cys Ile Cys Ile Cys Ile Cys Ile Cys Ile Cys Ile Cys
 1               5                  10                  15

Ile Cys Ile Cys Ile Cys Ile Cys Ile Cys
            20                  25

<210> SEQ ID NO 113
<211> LENGTH: 11
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: Polycationicoligopeptide

<400> SEQUENCE: 113

Lys Leu Lys Leu Leu Leu Leu Leu Lys Leu Lys
 1               5                  10

<210> SEQ ID NO 114
<211> LENGTH: 122
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT119

<400> SEQUENCE: 114

Asp Thr Leu Glu Gln Gln Phe Gln Gln Gly Ser Glu Ala Thr Thr Arg
 1               5                  10                  15

Gly Asp Tyr Gln Thr Thr Phe Lys Phe Leu Leu Pro Leu Ala Glu Gln
            20                  25                  30

Gly Asn Ala Glu Ala Gln Leu Met Leu Gly Val Met Tyr Ala Arg Gly
        35                  40                  45

Ile Gly Val Lys Gln Asp Asp Phe Glu Ala Val Lys Trp Tyr Arg Gln
    50                  55                  60

Ala Ala Glu Gln Gly Tyr Ala Asn Ala Gln Ala Ile Leu Gly Phe Ser
65                  70                  75                  80

Tyr Leu Leu Gly Gln Ser Gly Val Gln Val Asn Lys Ser Leu Ala Lys
                85                  90                  95

Glu Trp Phe Gly Lys Ala Cys Asp Asn Gly Asp Gln Asn Gly Cys Glu
            100                 105                 110

Tyr Tyr Gly Lys Leu Asn Arg Gly Glu Leu
        115                 120

<210> SEQ ID NO 115
<211> LENGTH: 158
<212> TYPE: PRT
<213> ORGANISM: Unknown
<220> FEATURE:
<223> OTHER INFORMATION: Description of Unknown:
```

-continued

```
        Bacteria <Prokaryote> sequence
<220> FEATURE:
<223> OTHER INFORMATION: NT120

<400> SEQUENCE: 115

Asp Thr Leu Glu Gln Gln Phe Gln Gln Gly Leu Thr Ala Tyr Glu Gln
1               5                   10                  15

Ser Asn Tyr Gln Thr Ala Phe Lys Leu Trp Leu Pro Met Ala Glu Gln
            20                  25                  30

Gly Tyr Ala Lys Ala Gln Phe Asn Leu Gly Val Met Tyr Ala Lys Gly
        35                  40                  45

Gln Gly Val Lys Gln Asp Asp Phe Glu Ala Val Lys Trp Phe Arg Lys
    50                  55                  60

Ala Ala Glu Gln Gly Tyr Ala Glu Ala Lys Phe Asn Leu Gly His Met
65                  70                  75                  80

Tyr Ser Lys Gly Arg Gly Val Lys Gln Asp Asp Phe Glu Ala Val Asn
                85                  90                  95

Trp Tyr Arg Lys Ala Ala Glu Gln Gly Asp Ala Asp Ala Gln Ala Ile
            100                 105                 110

Leu Gly Phe Leu Tyr Leu Leu Gly Glu Arg Gly Val Gln Val Asn Lys
        115                 120                 125

Ser Leu Ala Lys Glu Trp Phe Gly Lys Ala Cys Asp Asn Gly Asn Gln
    130                 135                 140

Asn Gly Cys Glu Tyr Tyr Gly Lys Leu Asn Arg Gly Glu Leu
145                 150                 155

<210> SEQ ID NO 116
<211> LENGTH: 157
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT121

<400> SEQUENCE: 116

Asp Thr Leu Glu Gln Gln Phe Gln Gln Gly Leu Thr Ala Tyr Glu Gln
1               5                   10                  15

Ser Asn Tyr Gln Thr Ala Phe Lys Leu Trp Leu Pro Leu Ala Glu Gln
            20                  25                  30

Gly Asp Ala Asn Val Gln Phe Asn Leu Gly Val Met Tyr Ala Glu Gly
        35                  40                  45

Gln Gly Val Lys Gln Asp Asp Phe Glu Ala Val Lys Trp Tyr Arg Lys
    50                  55                  60

Ala Ala Glu Gln Gly Asp Ala Asn Ala Gln Ala Tyr Leu Gly Leu Ala
65                  70                  75                  80

Tyr Thr Glu Gly Arg Gly Val Arg Gln Asp Tyr Thr Glu Ala Val Lys
                85                  90                  95

Trp Phe Arg Lys Ala Ala Glu Gln Gly His Ala Asn Ala Gln Ala Ile
            100                 105                 110

Leu Gly Phe Ser Tyr Leu Leu Gly Lys Gly Val Gln Val Asn Lys Ser
        115                 120                 125

Leu Ala Lys Glu Trp Phe Gly Lys Ala Cys Asp Asn Gly Asp Gln Gly
    130                 135                 140

Gly Cys Lys Tyr Tyr Gly Lys Leu Asn Arg Gly Glu Arg
145                 150                 155
```

<210> SEQ ID NO 117
<211> LENGTH: 168
<212> TYPE: PRT
<213> ORGANISM: Unknown
<220> FEATURE:
<223> OTHER INFORMATION: Description of Unknown:
   Bacteria <Prokaryote> sequence
<220> FEATURE:
<223> OTHER INFORMATION: NT122

<400> SEQUENCE: 117

```
Phe Asp Lys Gln Glu Ala Lys Gln Lys Val Glu Asp Thr Lys Gln Thr
 1               5                  10                  15

Val Ala Ser Val Ala Ser Glu Thr Lys Asp Ala Ala Asn Thr Met
             20                  25                  30

Thr Glu Val Lys Glu Lys Ala Gln Gln Leu Ser Thr Asp Val Lys Asn
             35                  40                  45

Lys Val Ala Glu Lys Val Glu Asp Ala Lys Glu Val Ile Lys Ser Ala
 50                  55                  60

Thr Glu Thr Ala Ser Glu Lys Ala Thr Glu Ile Lys Glu Ala Val Ser
 65                  70                  75                  80

Glu Lys Ala Ser Glu Met Lys Glu Ala Ala Ser Glu Lys Ala Ser Glu
             85                  90                  95

Met Lys Glu Ala Ala Ser Glu Lys Ala Ser Glu Met Lys Glu Ala Ala
            100                 105                 110

Ser Glu Lys Ala Ser Glu Met Lys Glu Ala Ala Ser Glu Lys Ala Ser
            115                 120                 125

Glu Met Lys Glu Ala Ala Ser Glu Lys Val Gly Glu Met Lys Glu Lys
    130                 135                 140

Ala Thr Glu Met Lys Glu Ala Val Ser Glu Lys Ala Thr Gln Ala Val
145                 150                 155                 160

Asp Ala Val Lys Glu Ala Thr Lys
                165
```

<210> SEQ ID NO 118
<211> LENGTH: 26
<212> TYPE: PRT
<213> ORGANISM: Unknown
<220> FEATURE:
<223> OTHER INFORMATION: Description of Unknown:
   Bacteria <Prokaryote> sequence
<220> FEATURE:
<223> OTHER INFORMATION: NT119encoded N-terminus

<400> SEQUENCE: 118

```
Met Arg Phe Thr Lys Thr Leu Phe Thr Thr Ala Leu Leu Gly Ala Ser
 1               5                  10                  15

Ile Phe Ser Phe Gln Ser Thr Ala Trp Ala
             20                  25
```

<210> SEQ ID NO 119
<211> LENGTH: 26
<212> TYPE: PRT
<213> ORGANISM: Unknown
<220> FEATURE:
<223> OTHER INFORMATION: Description of Unknown:
   Bacteria <Prokaryote> sequence
<220> FEATURE:
<223> OTHER INFORMATION: NT120encoded N-terminus

<400> SEQUENCE: 119

```
Met Lys Leu Thr Lys Thr Leu Leu Thr Thr Ala Leu Phe Gly Ala Ser
```

```
                1               5                   10                  15

Val Phe Ser Phe Gln Ser Thr Ala Trp Ala
                20                  25

<210> SEQ ID NO 120
<211> LENGTH: 26
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT121encoded N-terminus

<400> SEQUENCE: 120

Met Lys Leu Thr Lys Thr Leu Leu Thr Thr Ala Leu Leu Gly Ala Ser
1               5                   10                  15

Val Phe Ser Phe Gln Ser Thr Ala Trp Ala
                20                  25

<210> SEQ ID NO 121
<211> LENGTH: 23
<212> TYPE: PRT
<213> ORGANISM: Unknown
<220> FEATURE:
<223> OTHER INFORMATION: Description of Unknown:
    Bacteria <Prokaryote> sequence
<220> FEATURE:
<223> OTHER INFORMATION: NT122encoded N-terminus

<400> SEQUENCE: 121

Met Glu Lys Ile Met Lys Lys Leu Thr Leu Ala Leu Val Leu Gly Ser
1               5                   10                  15

Ala Leu Ala Val Thr Gly Cys
                20

<210> SEQ ID NO 122
<211> LENGTH: 173
<212> TYPE: PRT
<213> ORGANISM: Unknown
<220> FEATURE:
<223> OTHER INFORMATION: Description of Unknown:
    Bacteria <Prokaryote> sequence
<220> FEATURE:
<223> OTHER INFORMATION: NT004

<400> SEQUENCE: 122

Ser Glu Glu Gln Val Gln Arg Asp Val Tyr Gln Ser Leu Asp Asp Cys
1               5                   10                  15

Leu Ala Asp Trp Lys Lys Ile Glu Leu Cys Glu Ala Asp Lys Asn Thr
                20                  25                  30

Glu Ser Thr Gln Lys Thr Glu Thr Thr Pro Gln Gln Gly Leu Gly Leu
        35                  40                  45

Asn Ile Arg Asp Asn Gly Asn Ala Glu Ser Ala Val Lys Asn Pro Ala
    50                  55                  60

Glu Asn Asn Val Gln Ala Asn Gln Ser Glu Asn Asn Ala Glu Ser Thr
65                  70                  75                  80

Thr Lys Ala Glu Ser Thr Asp Pro Ser Leu Gly Ala Ala Ile Ala Gly
                85                  90                  95

Gly Val Met Gly Tyr Leu Ala Ala Arg Ala Ile Ser Ser Phe Leu Gly
            100                 105                 110

Pro Ser Tyr His Pro Gly Asn Arg Ala Val Thr Thr Pro Thr Gly Gln
        115                 120                 125
```

```
Val Val Gln Pro Gln Thr Asn Arg Ser Val Gly Lys Pro Met Leu Val
    130                 135                 140

Lys Gly Asn Ala Gly Ser Met Asn Ser Lys Pro Val Ser Arg Gly Gly
145                 150                 155                 160

Phe Ser Ser Pro Asn Asn Thr His Arg Ser Ser Gly Gly
                165                 170
```

<210> SEQ ID NO 123
<211> LENGTH: 171
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT014

<400> SEQUENCE: 123

```
Val Ala Ala Val Ile Gly Gly Gly Ala Val Ala Ala Lys Val Ala Thr
1               5                   10                  15

Asp Pro Arg Thr Thr Gly Thr Gln Ile Asp Asp Glu Thr Leu Glu Phe
                20                  25                  30

Lys Val Glu Asn Ala Val Glu Lys Asp Ala Gln Ile Lys Ala Glu Gly
            35                  40                  45

Arg Val Asn Ala Val Ser Tyr Asn Gly Arg Val Leu Leu Ile Gly Gln
        50                  55                  60

Val Pro Asn Ser Asp Val Lys Asp Thr Ala Thr Ala Leu Ala Lys Gly
65                  70                  75                  80

Val Lys Gly Val Asn Glu Val Tyr Asn Glu Leu Thr Val Ser Ser Lys
                85                  90                  95

Ile Ser Phe Ala Gln Ile Ser Lys Asp Ser Trp Leu Thr Thr Gln Val
            100                 105                 110

Lys Ser Lys Met Phe Val Asp Gly Arg Val Lys Ala Thr Asp Val Lys
        115                 120                 125

Val Ile Ser Glu Asn Gly Glu Val Phe Leu Leu Gly Asn Val Thr Gln
    130                 135                 140

Ser Gln Ala Asn Ala Ala Asp Ile Ala Ser Lys Ile Ser Gly Val
145                 150                 155                 160

Lys Lys Val Ile Lys Val Phe Lys Tyr Leu Asp
                165                 170
```

<210> SEQ ID NO 124
<211> LENGTH: 387
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT022

<400> SEQUENCE: 124

```
Thr Ser Asn Phe Pro Ala Pro Ile Ser Asp Ala Asp Gly Asn Leu Ser
1               5                   10                  15

Pro Ser Val Ile Gln Ser Val Asn Gly Ser Asn Val Gly Gly Ala Trp
                20                  25                  30

Gln Pro Glu Ile Gln Lys Asn Ser Leu Pro Thr Thr Gly Asn Met Val
            35                  40                  45

Thr Pro Gln Pro Asn Phe Gln Pro Ile Asn Gln Gln Pro Thr Met Pro
```

```
            50                  55                  60
Thr Ala Pro Ala Gln Pro Ala Phe Gln Pro Ser Pro Lys Thr Val Val
 65                  70                  75                  80

Ser Ala Pro Thr Val Gln Thr Lys Thr Val Thr Lys Thr Val Ala Asp
                 85                  90                  95

Cys Val Asp Gly Gln His Ile Asn Ile Pro Arg Asn Pro Asn Thr Asn
            100                 105                 110

Val Pro Asp Tyr Ser Lys Ile Ser Lys Gly Ser Tyr Lys Gly Asn Thr
        115                 120                 125

Tyr Lys Val Asn Lys Gly Asp Thr Met Phe Leu Ile Ala Tyr Leu Ala
    130                 135                 140

Gly Ile Asp Val Lys Glu Leu Ala Ala Leu Asn Asn Leu Ser Glu Pro
145                 150                 155                 160

Tyr Asn Leu Ser Leu Gly Gln Val Leu Lys Ile Ser Asn Cys Ser Thr
                165                 170                 175

Lys Thr Val Thr Thr Thr Val Ser Val Lys Gln Pro Ala Val Thr Thr
            180                 185                 190

Ser Thr Ala Thr Pro Val Lys Pro Ala Val Thr Tyr Thr Pro Gly Ala
        195                 200                 205

Asn Gly Thr Gln Ile Gly Ser Asp Gly Thr Ile Ile Gly Pro Ile Lys
    210                 215                 220

Ser Glu Ala Gly Thr Ser Pro Ser Val Pro Val Ala Thr Ser Ser Thr
225                 230                 235                 240

Gln Val Thr Ser Ser Val Asn Asn Ala Asn Ser Thr Pro Ile Asn Ser
                245                 250                 255

Asn Val Val Ala Pro Ile Ala Ser His Val Val Trp Gln Trp Pro Thr
            260                 265                 270

Ser Gly Asn Ile Ile Gln Gly Phe Ser Ser Thr Asp Gly Gly Asn Lys
        275                 280                 285

Gly Ile Asp Ile Ser Gly Ser Arg Gly Gln Ala Val Lys Ala Ala Ala
    290                 295                 300

Ala Gly Arg Ile Val Tyr Ala Gly Asn Ala Leu Arg Gly Tyr Gly Asn
305                 310                 315                 320

Leu Ile Ile Ile Lys His Asn Asp Asp Phe Leu Ser Ala Tyr Ala His
                325                 330                 335

Asn Asp Lys Ile Leu Val Ala Asp Gln Gln Glu Val Lys Ala Gly Gln
            340                 345                 350

Asp Ile Ala Lys Met Gly Ser Ser Gly Thr Asn Thr Val Lys Leu His
        355                 360                 365

Phe Glu Ile Arg Tyr Lys Gly Lys Ser Val Asp Pro Val Arg Tyr Leu
    370                 375                 380

Pro Arg His
385

<210> SEQ ID NO 125
<211> LENGTH: 20
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT004 N-terminus

<400> SEQUENCE: 125

Met Lys Lys Lys Asn Gln Ile Leu Val Ser Leu Ser Ile Val Ala Leu
```

-continued

```
                 1               5                  10                 15

Leu Gly Gly Cys
            20

<210> SEQ ID NO 126
<211> LENGTH: 22
<212> TYPE: PRT
<213> ORGANISM: Unknown
<220> FEATURE:
<223> OTHER INFORMATION: Description of Unknown:
      Bacteria <Prokaryote> sequence
<220> FEATURE:
<223> OTHER INFORMATION: NT014 N-terminus

<400> SEQUENCE: 126

Met Thr Leu Ser Pro Leu Lys Lys Leu Ala Ile Leu Leu Gly Ala Thr
1               5                   10                  15

Ile Phe Leu Gln Gly Cys
            20

<210> SEQ ID NO 127
<211> LENGTH: 22
<212> TYPE: PRT
<213> ORGANISM: Unknown
<220> FEATURE:
<223> OTHER INFORMATION: Description of Unknown:
     Bacteria <Prokaryote> sequence
<220> FEATURE:
<223> OTHER INFORMATION: NT022 N-terminus

<400> SEQUENCE: 127

Met Thr Leu Ser Pro Leu Lys Lys Leu Ala Ile Leu Leu Gly Ala Thr
1               5                   10                  15

Ile Phe Leu Gln Gly Cys
            20

<210> SEQ ID NO 128
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: NT061

<400> SEQUENCE: 128

Glu Glu Arg Val Val Ala Thr Val Asp Gly Ile Pro Ile Leu Glu Ser
1               5                   10                  15

Gln Val Arg Ala Asn Met Gly Lys Lys Gly Asp Arg Gln Ser Ala Leu
            20                  25                  30

Asp Lys Ile Ile Asp Asp Leu Leu Val Gln Lys Ala Ile Gln Glu Ser
        35                  40                  45

Gly Val Lys Ile Asp Pro Arg Glu Ile Asp Arg Val Val Glu Asp Thr
    50                  55                  60

Ala Ala Arg Asn Gly Leu Thr Tyr Gly Gln Phe Leu Asp Ala Leu Asp
65                  70                  75                  80

Tyr Gln Gly Ile Ser Leu Asn Thr Phe Arg Gln Gln Ile Ala Asn Gln
                85                  90                  95

Met Val Met Gly Ala Val Arg Asn Lys Ala Ile Gln Glu Ser Ile Asp
            100                 105                 110

Val Thr Arg Glu Glu Val Val Ala Leu Gly Gln Lys Met Leu Asp Glu
        115                 120                 125
```

Ala Lys Ser Gln Gly Thr Ala Gln Lys Val Thr Gly Lys Glu Tyr Glu
            130                 135                 140

Val Arg His Ile Leu Leu Lys Leu Asn Pro Leu Leu Asn Asp Ala Gln
145                 150                 155                 160

Ala Lys Lys Gln Leu Ala Lys Ile Arg Ser Asp Ile Ile Ala Gly Lys
                165                 170                 175

Thr Thr Phe Ala Asp Ala Ala Leu Lys Tyr Ser Lys Asp Tyr Leu Ser
            180                 185                 190

Gly Ala Asn Gly Gly Ser Leu Gly Tyr Ala Phe Pro Glu Thr Tyr Ala
                195                 200                 205

Pro Gln Phe Ala Gln Thr Val Met Lys Ser Lys Gln Gly Val Ile Ser
210                 215                 220

Ala Pro Phe Lys Thr Glu Phe Gly Trp His Ile Leu Glu Val Thr Gly
225                 230                 235                 240

Val Ser Asp Gly Asp Leu Thr Ala Glu Ala Tyr Thr Gln Lys Ala Tyr
                245                 250                 255

Glu Arg Leu Val Asn Thr Gln Leu Gln Asp Ala Thr Asn Asp Trp Val
            260                 265                 270

Lys Ala Leu Arg Lys Arg Ala Asn Ile Gln Tyr Phe Asn Lys
            275                 280                 285

<210> SEQ ID NO 129
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: NT061 N-terminus

<400> SEQUENCE: 129

Met Lys Met Lys Lys Phe Ile Leu Lys Ser Phe Leu Leu Ala Thr Leu
1               5                   10                  15

Gly Cys Val Ala Phe Thr Ser Met Ala Gln Ala
            20                  25

<210> SEQ ID NO 130
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: NT017

<400> SEQUENCE: 130

Gly Leu Leu Ile Phe Ser Pro Val Ser Gln Ser Ser Asp Leu Asn Gln
1               5                   10                  15

Ile Gln Lys Gln Ile Lys Gln Gln Glu Ser Lys Ile Glu Lys Gln Lys
            20                  25                  30

Arg Glu Gln Ala Lys Leu Gln Ala Asn Leu Lys Lys His Glu Ser Lys
        35                  40                  45

Ile Asn Thr Val Glu Gly Glu Leu Leu Glu Thr Glu Ile Ser Leu Lys
    50                  55                  60

Glu Ile Arg Lys Gln Ile Ala Asp Ala Asp Lys Gln Phe Lys Gln Leu
65                  70                  75                  80

Glu Lys Gln Glu Arg Glu Gln Lys Ala Arg Leu Ala Lys Gln Met Asp
                85                  90                  95

```
Ile Ile Tyr Arg Ser Gly Ile Asn Pro Ser Leu Ile Glu Arg Met Phe
            100                 105                 110

Ala Gln Asp Pro Thr Lys Ala Glu Arg Met Lys Val Tyr Tyr Gln His
        115                 120                 125

Leu Asn Gln Val Arg Ile Glu Met Ile Asp Asn Leu Lys Ala Thr Gln
    130                 135                 140

Ala Gln Ile Ala Val Gln Lys Glu Ala Ile Leu Ala Gln Gln Lys Asn
145                 150                 155                 160

His Arg Asn Gln Leu Ser Thr Gln Lys Gln Gln Gln Ala Leu Gln
                165                 170                 175

Lys Ala Gln Gln Glu His Gln Ser Thr Leu Asn Glu Leu Asn Lys Asn
        180                 185                 190

Leu Ala Leu Asp Gln Asp Lys Leu Asn Ala Leu Lys Ala Asn Glu Gln
    195                 200                 205

Ala Leu Arg Gln Glu Ile Gln Arg Ala Glu Gln Ala Ala Arg Glu Gln
        210                 215                 220

Glu Lys Arg Glu Arg Glu Ala Leu Ala Gln Arg Gln Lys Ala Glu Glu
225                 230                 235                 240

Lys Arg Thr Ser Lys Pro Tyr Gln Pro Thr Val Gln Glu Arg Gln Leu
                245                 250                 255

Ile Asn Ser Thr Ser Gly Leu Gly Ala Ala Lys Lys Gln Tyr Ser Leu
            260                 265                 270

Pro Val Ser Gly Ser Ile Leu His Thr Phe Gly Ser Ile Gln Ala Gly
        275                 280                 285

Glu Val Arg Trp Lys Gly Met Val Ile Gly Ala Ser Ala Gly Thr Pro
    290                 295                 300

Val Lys Ala Ile Ala Ala Gly Arg Val Ile Leu Ala Gly Tyr Leu Asn
305                 310                 315                 320

Gly Tyr Gly Tyr Met Val Ile Val Lys His Gly Glu Thr Asp Leu Ser
                325                 330                 335

Leu Tyr Gly Phe Asn Gln Ala Val Ser Val Lys Val Gly Gln Leu Val
            340                 345                 350

Ser Ala Gly Gln Val Ile Ala Gln Val Gly Asn Thr Gly Glu Ile Ser
        355                 360                 365

Arg Ser Ala Leu Tyr Phe Gly Ile Ser Arg Lys Gly Thr Pro Val Asn
    370                 375                 380

Pro Ala Gly Trp Val Arg
385                 390

<210> SEQ ID NO 131
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: NT017 N-terminus

<400> SEQUENCE: 131

Met Leu Arg Phe Gly Val Asn Gln Lys Thr Ser Leu Leu Thr Ala
1               5                   10                  15

Leu Leu Ser Cys
                20
```

ANTIGENS AND ANTIGEN COMBINATIONS

CROSS-REFERENCE TO RELATED APPLICATIONS

This application is the U.S. National Phase of International Application No. PCT/EP2013/058459, filed Apr. 24, 2013 and published in English, which claims the benefit of and priority to GB provisional application No. 1207385.4, filed on 26 Apr. 2012 and EP application number NO. EP12199079.0 filed on 21 Dec. 2012, the complete contents of both hereby incorporated herein by reference for all purposes.

SEQUENCE LISTING

The instant application contains a Sequence Listing which has been submitted electronically in ASCII format and is hereby incorporated by reference in its entirety. Said ASCII copy, created on Mar. 20, 2015, is named PAT054802-US-PCT_SL.txt and is 224,185 bytes in size.

TECHNICAL FIELD

This invention is in the field of *Haemophilus influenzae* immunology and vaccinology, in particular non-typeable *H. influenzae* (NTHI). The invention provides antigen polypeptides and combinations of antigen polypeptides for raising antibodies and immune responses and against *H. influenzae* strains. The invention also provides compositions containing such antigens, and the use thereof as vaccines or medicaments against *H. influenzae*. The invention also provides immunogenic compositions containing such antigens used alone or in combination or used together with other vaccines. The invention also provides methods for raising immune responses against *H. influenzae*, and methods for the treatment and prevention of infections by *H. influenzae*.

BACKGROUND ART

*Haemophilus influenzae* is a small, non-motile, Gram-negative coccobacillus. It is a respiratory pathogen that causes a wide spectrum of human infections, including: asymptomatic colonization of the upper respiratory tract (i.e. carriage); infections that extend from colonized mucosal surfaces to cause otitis media (inflammation of the middle ear), bronchitis, conjunctivitis, sinusitis, urinary tract infections and pneumonia; and invasive infections, such as bacteremia, septic arthritis, epiglottitis, pneumonia, empyema, pericarditis, cellulitis, osteomyelitis and meningitis. *H. influenzae* was the first bacterium for which a complete genome sequence was published [1].

*H. influenzae* strains are either capsulated (typeable) or non-capsulated (non-typeable), and there are six major serological types of capsulated strains (a to f). 95% of *H. influenzae*-caused invasive diseases are caused by *H. influenzae* type b ('Hib') strains. The most serious manifestation of Hib disease is meningitis, but the introduction in the 1980s of vaccines based on conjugated Hib capsular saccharides has hugely reduced incidence of this disease.

Although Hib infections can now be controlled by vaccination, other pathogenic *H. influenzae* strains remain a risk. For instance, non-typeable *H. influenzae* (NTHI) is responsible for otitis media (OM), particularly chronic and acute OM. While OM is rarely associated with mortality, it is associated with significant morbidity. Hearing loss is the most common complication of OM, with behavioural, educational and language development delays being additional consequences of early onset OM with effusion. Acute OM is the most common bacterial infection in children in the USA. The non-typeable *H. influenzae* biogroup aegyptius causes epidemic conjunctivitis and Brazilian purpuric fever (BPF) [2], with BPF having a mortality of up to 70%.

To date, antibiotics are the main tool against the spectrum of clinical entities known collectively as OM, but widespread use of antibiotics for OM has met with controversy due to the emergence of multiple-antibiotic resistant microorganisms. Progress towards a vaccine is slow due to an incomplete understanding of both the pathogenesis of OM and the immune response to it.

The genome sequence of the serotype d strain KW20 [1,3] has been useful for understanding basic *H. influenzae* biology, but it has not been so useful in countering pathogenic *H. influenzae* strains, as serotype d strains are generally not pathogens. Polypeptides from pathogenic non-typeable *H. influenzae* have been identified and investigated as vaccine candidates. Reference 4 discloses immunogenic polypeptides from a pathogenic non-typeable *H. influenzae* strain.

However, there remains a need for providing a vaccine that protects against a broad spectrum of *Haemophilus influenzae* strains. *H. influenzae* is a versatile microorganism with an improved ability to adapt to new niches and to cause a broad spectrum of disease. Fitness, virulence and colonization factors can change in order to allow the microorganism to adapt to different tissues and hosts. Therefore, potential antigens are subject to high selective pressure and, as a result, may have sequence variability among different strains.

Thus there remains a need to identify further and improved antigens for use in non-typeable *Haemophilus influenzae* vaccines, and in particular for vaccines which are useful against multiple NTHI-caused pathologies.

The database of genomes available at ncbi.nlm.nih.gov under genomes listed pathogenic and non-pathogenic *Haemophilus influenzae* genomes with as few as 2,500 proteins to as many as 4,000 proteins. However, such listings do not identify which are conserved across a significant fraction of the pathogenic NTHI, what are the conserved regions in the proteins that are so conserved, or which proteins among the thousands of potential proteins can be used in a vaccine to produce a sufficient immune response to protect against pathogenic NTHI which requires screening large numbers of proteins to identify the best candidates.

It is an object of the invention to provide further and better antigens and/or combinations which are efficacious in raising immune responses against different strains of *H. influenzae*, for use in the development of vaccines for preventing and/or treating infections caused by *H. influenzae* pathogens, in particular non-typeable *H. influenzae*. In particular, it is an object to provide polypeptides and combinations of polypeptides for use in improved immunogenic compositions and vaccines for preventing and/or in treating such infections, and in particular acute otitis media and chronic obstructive pulmonary disease (COPD). The polypeptides may also be useful for diagnostic purposes, and as targets for antibiotics.

DISCLOSURE OF THE INVENTION

Present invention describes non-typeable *Haemophilus influenzae* (NTHI) polypeptides that are useful for immunisation, for use either alone or in combination. These polypeptides may be combined with other NTHI polypeptides as well as. The antigens are useful in NTHI vaccines but may also be used as components in vaccines for immunising against multiple pathogens.

By using two parallel approaches, namely reverse vaccinology and proteomic analysis of outer membrane vesicles (OMVs) it has been possible to identify antigens which are conserved amongst 86 different NTHI strains. Reverse vaccinology uses in silico analysis to identify proteins conserved in the genomes of different NTHI strains and potentially surface-exposed. The second approach is instead focused on the identification of antigens by analysing mass spectrometry of the proteins contained in the outer membrane vesicles produced by NTHI.

The genome of a NTHI strain includes about 1800 genes. The inventors have identified 274 conserved antigens from 15 complete genomes plus 39 strains selected on the basis of geographical distribution and 32 strains derived from an otitis media Finnish collection which are all currently publicly available. From these 274 the inventors have selected 53 polypeptides of particular interest. These antigens were selected from the strain NP86-028, with the exception of CGSHiGG_00130 being selected from PittG, CGSHiGG_02400 selected from PittG, gi-145633184 selected from 3655 strain and gi-145628236 selected from 22.1-21 strain.

Amongst the group of 53 antigens the following further selection has been generated considering immunogenicity and conservation criteria:

A set of 26 antigens referred herein as "the first antigen group"

A set of 6 antigens referred herein as "the second antigen group"

A set of 21 antigens referred herein as "the third antigen group"

Most preferred set of antigens is referred to herein as 'the first antigen group'. Thus the invention provides an immunogenic composition comprising at least one antigen, preferably comprising one or more (i.e. 1, 2, 3, 4, 5, 6 or more) antigens selected from the group consisting of: (1) NTHI0915 (NT018), (2) NTHI1416 (NT024), (3) NTHI2017 (NT032), (4) CGSHiGG_02400 (NT038), (5) NTHI1292 (NT067), (6) NTHI0877 (NT001), (7) NTHI0266 (NT016), (8) CGSHiGG_00130 (NT052), (9) NTHI1627 (NT002), (10) NTHI1109 (NT026), (11) NTHI0821 (NT009), (12) NTHI0409 (NT025), (13) NTHI1954 (NT028), (14) NTHI0371 (NT029), (15) NTHI0509 (NT031), (16) NTHI0449 (NT015), (17) NTHI1473 (NT023), (18) gi-145633184 (NT100), (19) NTHI1110 (NT040), (20) gi-46129075 (NT048), (21) gi-145628236 (NT053), (22) NTHI1230 (NT066), (23) NTHI0522 (NT097), (24) NT004, (25) NT014, (26) NT022. These antigens show a positive bactericidal activity as shown in Table III and Table IV.

Within the first antigen group, preferred antigens are selected from a subset of any of (1) NTHI0915 (NT018) antigen, (2) NTHI1416 (NT024) antigen, (3) NTHI2017 (NT032) antigen, (4) CGSHiGG_02400 (NT038), (5) NTHI1292 antigen (NT067), (6) NTHI0877 (NT001) antigen, (8) NT052 antigen, (24) NT004 antigen, (25) NT014 antigen, (26) NT022 antigen, (7) NTHI0266 NT016 antigen. These antigens are all showing a good level of purification as shown in Table II and immunogenicity efficacy is reported in tables III and IV.

Particularly preferred antigens were NT067, NT014, NT016, NT022.

Thus the invention provides an immunogenic composition comprising one or more (i.e. 1, 2, 3, 4, 5, 6 or more) antigens selected from the group consisting from the "first antigen group".

The inventors have also identified the following 6 polypeptides: (24) P48 (NTHI0254 also defined as NT007), (25) HtrA (NTHI1905 also defined as NT006), (26) PE (NTHI0267 also defined as NT035), (27) P26 (NTHI0501 also defined as NT010), (28) PHiD (NTHI0811 also defined as NT080), (29) P6 (NTHI0501, also defined as NT081). This set of 6 antigens is referred to herein as 'the second antigen group'.

The inventors have also identified the following 22 polypeptides: (30) NTHI0532 (NT013), (31) NTHI0363 (NT106), (32) NTHI0370 (NT107), (33) NTHI0205 (NT108), (34) NTHI0374 (NT109), (35) NTHI0579 (NT110), (36) NTHI0837 (NT111), (37) NTHI0849 (NT112), (38) NTHI0921 (NT113), (39) NTHI0995 (NT114), (40) NTHI1091 (NT115), (41) NTHI1169 (NT116), (42) NTHI1208 (NT117), (43) NTHI1318 (NT118), (44) NTHI1796 (NT123), (45) NTHI1930 (NT124), (46) NTHI1565 (NT119), (47) NTHI1569 (NT120), (48) NTHI1571 (NT121), (49) NTHI1667 (NT122), (50) NTHI0588 (NT061), (51) NTHI0915 (NT017). This set of 22 antigens is referred to herein as 'the third antigen group'.

In one embodiment, a composition includes at least one antigen (i.e. 1, 2, 3, 4, 5, 6 or more) selected from the first antigen group and/or at least one antigen (i.e. 1, 2, 3, 4, 5, 6 or more) selected from the second antigen group and/or at least one antigen (i.e. 1, 2, 3, 4, 5, 6 or more) selected from the third antigen group. Antigens from the first antigen group can be selected from the most preferred subset of antigens.

Preferably the invention provides an immunogenic composition comprising one antigen selected from any of the first antigen group or second antigen group or third antigen group.

Thus the invention also provides an immunogenic composition comprising a combination of antigens, said combination comprising two or more (i.e. 2, 3, 4, 5, 6 or more) antigens selected from the group consisting of the "first antigen group" and/or the "second antigen group" and/or the "third antigen group".

Where a composition includes an antigen from the "second antigen group", it is preferred that the composition should also include (i) at least one further antigen from the "second antigen group" or (ii) at least one antigen from the "first antigen group" or the "third antigen group". Thus the invention would not encompass a composition including as its sole antigenic component a single antigen from the "second antigen group". Where a composition includes two or more antigens from the "second antigen group", it is preferred that the composition should include at least one antigen which is not (a) a P48 antigen (b) a HtrA antigen (c) a PE antigen or (d) a P26 antigen. Thus in some embodiments the invention does not encompass combinations only of P48, HtrA, PE and/or P26. Similarly, in some embodiments the invention does not encompass hybrid antigens which include 'X' moieties only from P48, HtrA, PE and/or P26.

Within the 11 preferred antigens of the first antigen group there are 55 possible pairs of different antigens. All such pairs are disclosed herein and are part of the invention. Thus the invention provides an immunogenic composition comprising a pair of antigens, wherein said pair is one of said 55 pairs.

In one embodiment, a composition includes at least one antigen (i.e. 1, 2, 3, 4, 5, 6 or more) selected from the first antigen group and/or at least one antigen (i.e. 1, 2, 3, 4, 5, 6 or more) selected from the second antigen group, and/or at least one antigen (i.e. 1, 2, 3, 4, 5, 6 or more) selected from the third antigen group.

In all cases, antigens from the first antigen group can be advantageously selected from the most preferred subset of any of (1) NTHI0915 (NT018), (2) NTHI1416 (NT024), (3) NTHI2017 (NT032), (4) CGSHiGG_02400 (NT038), (5) NTHI1292 (NT067), (6) NTHI0877 (NT001), (8) NT052, (24) NT004, (25) NT014, (26) NT022, (7) NT016.

The invention also provides an immunogenic composition comprising a combination of antigens, said combination comprising two or more (i.e. 2, 3, 4 or 5) antigens selected from the group consisting of: (1) NTHI0915 (NT018), (2) NTHI1416 (NT024), (3) NTHI2017 (NT032), (4) CGSHiGG_02400 (NT038), (5) NTHI1292 (NT067), (6) NTHI0877 (NT001), (8) NT052, (24) NT004, (25) NT014, (26) NT022, (7) NT016. The composition can also include an adjuvant e.g. an adjuvant comprising an oil-in-water emulsion or an aluminium salt.

Reference 5 discusses non-typeable H. influenzae antigens, inter alia as candidates for potential use in vaccines. References 6 to 10, are concerned, individually, with non-typeable H. influenzae polypeptides P48, HtrA, PE and P26, respectively, and inter alia with their immunogenic potential. Reference 5 also mentions HtrA, PE and P26 individually amongst a larger number of vaccine candidates, and e.g. reference 10 is concerned with polypeptide PE. However, these antigens, belonging to the "second antigen group" and were not described for use in combination. It has now surprisingly been found that a combination of one or more of these antigens (second antigen group) with at least one of the antigen listed in the "first antigen group" is particularly suitable for generating a protective immune response against non-typeable H. influenzae, and thus the above-mentioned objects of the invention.

Advantageous combinations of the invention are those in which two or more antigens act synergistically. Thus the protection against NTHI pathogen achieved by their combined administration exceeds that expected by mere addition of their individual protective efficacy.

First Antigen Group

NT018 Antigen

The "NT018" antigen is annotated as TPR repeat-containing protein and also as cytochrome c maturation heme lyase subunit CcmH2. It has been annotated as NTHI0915 in the strain 86-028NP.

Said sequence is highly conserved amongst all the strains analyzed and is predicted to be a membrane-bound metallopeptidase. NT018 is surface exposed as shown in Table III. NT018 has been cloned and expressed from another non-typeable strain, Fi176, which is a strain isolated form the Finland otitis media collection.

Useful NT018 antigens can elicit an antibody (e.g. when administered to a human) that recognises SEQ ID NO: 1 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 1; and/or (b) comprising a fragment of at least 'n' consecutive amino acids of SEQ ID NO: 1, wherein 'n' is 7 or more (e.g. 8, 10, 12, 14, 16, 18, 20, 25, 30, 35, 40, 50, 60, 70, 80, 90, 100, 150, 200, 250 or more). These NT018 proteins include variants of SEQ ID NO: 1, such as SEQ ID NO: 49 which has been cloned and expressed and tested in immunogenicity (Table III, IV). Preferred fragments of (b) comprise an epitope from SEQ ID NO: 1. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25, 26, 27, 28 or more) from the N-terminus of SEQ ID NO: 1 while retaining at least one epitope of SEQ ID NO: 1. Other fragments omit one or more protein domains.

A NT018 antigen of the invention can be expressed with its native 28 N-terminal amino acids of NT018 (MNFTLI-FILTTLVVALICFYPLLRQFKA; SEQ ID NO: 69) or can be expressed with an alternative N-terminal sequence e.g. with a simple N-terminus methionine, or Met-Ala-, or a leader peptide which targets or traffics the expressed protein in a desired fashion.

NT024 Antigen

The "NT024" antigen is annotated as "hypothetical protein" and has been annotated as NTHI1416 in the genome 86-028NP. This antigen has been cloned and expressed from Fi176 strain.

Useful NT024 antigens can elicit an antibody (e.g. when administered to a human) that recognises SEQ ID NO: 2 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 2; and/or (b) comprising a fragment of at least 'n' consecutive amino acids of SEQ ID NO: 2 wherein 'n' is 7 or more (e.g. 8, 10, 12, 14, 16, 18, 20, 25, 30, 35, 40, 50, 60, 70, 80, 90, 100, 150, 200, 250 or more). These NT024 proteins include variants of SEQ ID NO: 2, such as SEQ ID NO: 50 cloned from strain Fi176. Preferred fragments of (b) comprise an epitope from SEQ ID NO: 2. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 2 while retaining at least one epitope of SEQ ID NO: 2. Other fragments omit one or more protein domains.

A NT024 antigen of the invention can be expressed with the native 20 N-terminal amino acids of NT024 (MKLKLFFHIVLLCFSLPVWA; SEQ ID NO: 70) or can be expressed with an alternative N-terminal sequence e.g. with a simple N-terminus methionine, or Met-Ala-, or a leader peptide which targets or traffics the expressed protein in a desired fashion.

NT032 Antigen

The "NT032" antigen is annotated as "hypothetical protein" and has been annotated as NTHI2017 in the genome 86-028NP. Domain most conserved amongst strains tested is described as "Bacterial OB fold (BOF) protein". This antigen has been cloned and expressed from Fi176 strain.

Useful NT032 antigens can elicit an antibody (e.g. when administered to a human) that recognises SEQ ID NO: 3 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 3; and/or (b) comprising a fragment of at least 'n' consecutive amino acids of SEQ ID NO: 3, wherein 'n' is 7 or more (e.g. 8, 10, 12, 14, 16, 18, 20, 25, 30, 35, 40, 50, 60, 70, 80, 90, 100, 150, 200, 250 or more). These NT032 proteins include variants of SEQ ID NO: 3, such as SEQ ID NO: 51 cloned from Fi176 strain. Preferred fragments of (b) comprise an epitope from SEQ ID NO: 3. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 3 while retaining at least one epitope of SEQ ID NO: 3. Other fragments omit one or more protein domains.

A NT032 antigen of the invention can be expressed with the native 19 N-terminal amino acids of NT032 (MKKFA-LATIFALATTSAFA; SEQ ID NO: 71) or can be expressed with an alternative N-terminal sequence e.g. with a simple N-terminus methionine, or Met-Ala-, or a leader peptide which targets or traffics the expressed protein in a desired fashion.

NT067 Antigen

The "NT067" antigen is annotated as ABC transporter protein and it has been proposed its hypothetical function as periplasmic oligopeptide-binding protein OppA. In the strain 86-028NP has been annotated as NTHI1292. This antigen has been cloned and expressed from Fi176 strain.

Useful NT067 antigens can elicit an antibody (e.g. when administered to a human) that recognises SEQ ID NO: 5 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 5; and/or (b) comprising a fragment of at least 'n' consecutive amino acids of SEQ ID NO: 5, wherein 'n' is 7 or more (e.g. 8, 10, 12, 14, 16, 18, 20, 25, 30, 35, 40, 50, 60, 70, 80, 90, 100, 150, 200, 250 or more). These NT067 proteins include variants of SEQ ID NO: 5, such as SEQ ID NO: 52 cloned from Fi176 strain. Preferred fragments of (b) comprise an epitope from SEQ ID NO: 5. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 5 while retaining at least one epitope of SEQ ID NO: 5. Other fragments omit one or more protein domains.

A NT067 antigen of the invention can be expressed with the native 20 N-terminal amino acids of NT067 (MQHKLL-FSAIALALSYSVQA; SEQ ID NO: 72) or can be expressed with an alternative N-terminal sequence e.g. with a simple N-terminus methionine, or Met-Ala-, or a leader peptide which targets or traffics the expressed protein in a desired fashion.

NT038 Antigen

This antigen is known as Hia (*Haemophilus influenzae* adhesin) protein [11] and has been identified in the strain CGSHiGG_02400 as a 282 aa in length, however it is a truncated form of Hia (616 aa) as originally described in the strain 86-028NP or in other NTHi strains. This antigen has been cloned from R2846 strain.

Useful NT038 antigens can elicit an antibody (e.g. when administered to a human) that recognises SEQ ID NO: 4 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 4; and/or (b) comprising a fragment of at least 'n' consecutive amino acids of SEQ ID NO: 4, wherein 'n' is 7 or more (e.g. 8, 10, 12, 14, 16, 18, 20, 25, 30, 35, 40, 50, 60, 70, 80, 90, 100, 150, 200, 250 or more). These NT038 proteins include variants of SEQ ID NO: 4, such as SEQ ID NO: 53, which is lacking the first 23 native N-terminal amino acids and 102 amino acids at the C-terminal. Preferred fragments of (b) comprise an epitope from SEQ ID NO: 4. Other preferred fragments lack one or more amino acids (e.g. 1, 2, 3, 4, 5, 6, 7, 8, 9, 10, 15, 20, 25 or more) from the C-terminus (even up to 102aa) and/or one or more amino acids (e.g. 1, 2, 3, 4, 5, 6, 7, 8, 9, 10, 15, 20, 23, 25 or more) from the N-terminus of SEQ ID NO: 4 while retaining at least one epitope of SEQ ID NO: 4. Other fragments omit one or more protein domains.

A NT038 antigen of the invention can be expressed with the native 23 N-terminal amino acids of NT038 (MP-FQYVTEDGKTVVKVGNGYYEA; SEQ ID NO: 73) or can be expressed with an alternative N-terminal sequence e.g. with a simple N-terminus methionine, or Met-Ala-, or a leader peptide which targets or traffics the expressed protein in a desired fashion.

NT001 Antigen

This antigen has been annotated as NTHI0877 in the genome 86-028NP and is known as D-methionine-binding lipoprotein MetQ. MetD is an ABC transporter encoding a DL methionine uptake system. This antigen has been previously disclosed as BASB202 (28 Kda) [12, 13], and its use as vaccine against NTHI has been proposed. This antigen shares 99.63% alignment ID with an homologue antigen as described in Ref (4) and it has been found well conserved amongst all the strains considered in the present invention. In present invention it is cloned and expressed from Fi176 strain.

Useful NT001 antigens can elicit an antibody (e.g. when administered to a human) that recognises SEQ ID NO: 6 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 6; and/or (b) comprising a fragment of at least 'n' consecutive amino acids of SEQ ID NO: 6, wherein 'n' is 7 or more (e.g. 8, 10, 12, 14, 16, 18, 20, 25, 30, 35, 40, 50, 60, 70, 80, 90, 100, 150, 200, 250 or more). These NT001 proteins include variants of SEQ ID NO: 4, such as SEQ ID NO: 54. Preferred fragments of (b) comprise an epitope from SEQ ID NO: 6. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 21, 25 or more) from the N-terminus of SEQ ID NO: 6 while retaining at least one epitope of SEQ ID NO: 6. Other fragments omit one or more protein domains.

A NT001 antigen of the invention can be expressed with the native 21 N-terminal amino acids of NT001 (MKLKQL-FAITAIASALVLTGC; SEQ ID NO: 74) or can be expressed with an alternative N-terminal sequence e.g. with a simple N-terminus methionine, or Met-Ala-, or a leader peptide which targets or traffics the expressed protein in a desired fashion.

NT016 Antigen

This antigen has been annotated as NTHI0266 in the strain 86-028NP and described as Hypothetical lipoprotein. This antigen has been cloned and expressed from Fi176 strain.

Useful NT016 antigens can elicit an antibody (e.g. when administered to a human) that recognises SEQ ID NO: 7 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 7; and/or (b) comprising a fragment of at least 'n' consecutive amino acids of SEQ ID NO: 7, wherein 'n' is 7 or more (e.g. 8, 10, 12, 14, 16, 18, 20, 25, 30, 35, 40, 50, 60, 70, 80, 90, 100, 150, 200, 250 or more). These NT016 proteins include variants of SEQ ID NO: 7, such as SEQ ID NO: 55. Preferred fragments of (b) comprise an epitope from SEQ ID NO: 7. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 19, 20, 25 or more) from the N-terminus of SEQ ID NO: 7 while retaining at least one epitope of SEQ ID NO: 7. Other fragments omit one or more protein domains.

A NT016 antigen of the invention can be expressed with the native 16 N-terminal amino acids of NT016 (MRKIK-SLALLAVAALVIGC; SEQ ID NO: 75) or can be expressed with an alternative N-terminal sequence e.g. with a simple N-terminus methionine, or Met-Ala-, or a leader peptide which targets or traffics the expressed protein in a desired fashion.

NT052 Antigen

This antigen has been annotated as CGSHiGG_00130 from PittGG strain. It is part of Sell-domain containing protein families. It has been cloned from R2846 strain and the cloned sequence is reported as SEQ ID NO: 8. Despite the sequence cloned from R2846 is sharing only 64.16% identity over the sequence as annotated CGSHiGG_00130, it has been shown that there are conserved Sell domains which are repeated along the sequence which are useful to provide an efficacious antigenicity. Consensus for this repeats is SEQ ID NO: EAVKWYRKAAEQ.

Useful NT052 antigens can elicit an antibody (e.g. when administered to a human) that recognises SEQ ID NO: 8 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 8; and/or (b) comprising a fragment of at least 'n' consecutive amino acids of SEQ ID NO: 8, wherein 'n' is 7 or more (e.g. 8, 10, 12, 14, 16, 18, 20, 25, 30, 35, 40, 50, 60, 70, 80, 90, 100, 150, 200, 250 or more). These NT052 proteins include variants of SEQ ID NO: 8, such as SEQ ID NO: 56. Preferred fragments of (b) comprise an epitope from SEQ ID NO: 8. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 11, 15, 20, 25 or more) from the N-terminus of SEQ ID NO: 8 while retaining at least one epitope of SEQ ID NO: 8. Other fragments omit one or more protein domains.

A NT052 antigen of the invention can be expressed with the native 11 N-terminal amino acids of NT052 (MLLFIL-SIAWA; SEQ ID NO: 76) or can be expressed with an alternative N-terminal sequence e.g. with a simple N-terminus methionine, or Met-Ala-, or a leader peptide which targets or traffics the expressed protein in a desired fashion.

NT002 Antigen

This antigen has been annotated as NTHI1627 in 86-026NP strain and as lipoprotein. It has been cloned and expressed from Fi176 strain.

Useful NT002 antigens can elicit an antibody (e.g. when administered to a human) that recognises SEQ ID NO: 9 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 9; and/or (b) comprising a fragment of at least 'n' consecutive amino acids of SEQ ID NO: 9, wherein 'n' is 7 or more (e.g. 8, 10, 12, 14, 16, 18, 20, 25, 30, 35, 40, 50, 60, 70, 80, 90, 100, 150, 200, 250 or more). These NT002 proteins include variants of SEQ ID NO: 9, such as SEQ ID NO: 57. Preferred fragments of (b) comprise an epitope from SEQ ID NO: 9. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 9 while retaining at least one epitope of SEQ ID NO: 9. Other fragments omit one or more protein domains.

A NT002 antigen of the invention can be expressed with the native 18 N-terminal amino acids of NT002 (MKVYKS-FLIATASLFLFA; SEQ ID NO: 77) or can be expressed with an alternative N-terminal sequence e.g. with a simple N-terminus methionine, or Met-Ala-, or a leader peptide which targets or traffics the expressed protein in a desired fashion.

A NT002 antigen of the invention can be a lipoprotein e.g. lipidated at a N-terminus cysteine.

NT026 Antigen

This antigen has been annotated as hypothetical protein NTHI1109 in 86-026NP strain. It has been predicted to be a cytoplasmic membrane protein. It has been cloned and expressed from Fi176 strain.

Useful NT026 antigens can elicit an antibody (e.g. when administered to a human) that recognises SEQ ID NO: 10 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 10; and/or (b) comprising a fragment of at least 'n' consecutive amino acids of SEQ ID NO:10 wherein 'n' is 7 or more (e.g. 8, 10, 12, 14, 16, 18, 20, 25, 30, 35, 40, 50, 60, 70, 80, 90, 100, 150, 200, 250 or more). These NT026 proteins include variants of SEQ ID NO: 10, such as SEQ ID NO: 58, cloned from Fi176 strain. Preferred fragments of (b) comprise an epitope from SEQ ID NO: 10. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 10 while retaining at least one epitope of SEQ ID NO: 10. Other fragments omit one or more protein domains.

A NT026 antigen of the invention can be expressed with the native 24 N-terminal amino acids of NT026 (MQKG-MTLVELLIGLAIISIVLNFA; SEQ ID NO: 78) or can be expressed with an alternative N-terminal sequence e.g. with a simple N-terminus methionine, or Met-Ala-, or a leader peptide which targets or traffics the expressed protein in a desired fashion.

NT009 Antigen

This antigen has been annotated as NTHI0821in 86-026NP strain and is part of OMP85 family protein. It is located in the outer membrane of the bacteria. It has been cloned and expressed from Fi176 strain.

Useful NT009 antigens can elicit an antibody (e.g. when administered to a human) that recognises SEQ ID NO: 11 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 11; and/or (b) comprising a fragment of at least 'n' consecutive amino acids of SEQ ID NO: 11, wherein 'n' is 7 or more (e.g. 8, 10, 12, 14, 16, 18, 20, 25, 30, 35, 40, 50, 60, 70, 80, 90, 100, 150, 200, 250 or more). These NT009 proteins include variants of SEQ ID NO: 11, such as SEQ ID NO: 59 cloned from Fi176. Preferred fragments of (b) comprise an epitope from SEQ ID NO: 11. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 22, 25 or more) from the N-terminus of SEQ ID NO: 11 while retaining at least one epitope of SEQ ID NO: 11. Other fragments omit one or more protein domains.

A NT009 antigen of the invention can be expressed with the native 22 N-terminal amino acids of NT009 (MNK- TLLKLTALFLALNCFPAFA; SEQ ID NO: 79) or can be expressed with an alternative N-terminal sequence e.g. with a simple N-terminus methionine, or Met-Ala-, or a leader peptide which targets or traffics the expressed protein in a desired fashion.

NT025 Antigen

This antigen has been annotated as NTHI0409 in 86-026NP strain and belongs to the type IV pilin subunit protein family. It has been cloned and expressed from Fi176 strain.

Useful NT025 antigens can elicit an antibody (e.g. when administered to a human) that recognises SEQ ID NO: 12 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 12; and/or (b) comprising a fragment of at least 'n' consecutive amino acids of SEQ ID NO: 12, wherein 'n' is 7 or more (e.g. 8, 10, 12, 14, 16, 18, 20, 25, 30, 35, 40, 50, 60, 70, 80, 90, 100, 150, 200, 250 or more). These NT025 proteins include variants of SEQ ID NO: 12, such as SEQ ID NO: 60 as cloned from Fi176. Preferred fragments of (b) comprise an epitope from SEQ ID NO: 12. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 23, 25 or more) from the N-terminus of SEQ ID NO: 12 while retaining at least one epitope of SEQ ID NO: 12. Other fragments omit one or more protein domains.

A NT025 antigen of the invention can be expressed with the native 23 N-terminal amino acids of NT025 (MKLTTQQTLKKGFTLIELMIVIA; SEQ ID NO: 80) or can be expressed with an alternative N-terminal sequence e.g. with a simple N-terminus methionine, or Met-Ala-, or a leader peptide which targets or traffics the expressed protein in a desired fashion.

NT028 Antigen

This antigen has been annotated as NTHI1954 in 86-026NP strain and as lipoprotein NlpC. It has been cloned and expressed from Fi176 strain.

Useful NT028 antigens can elicit an antibody (e.g. when administered to a human) that recognises SEQ ID NO: 13 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 13; and/or (b) comprising a fragment of at least 'n' consecutive amino acids of SEQ ID NO: 13, wherein 'n' is 7 or more (e.g. 8, 10, 12, 14, 16, 18, 20, 25, 30, 35, 40, 50, 60, 70, 80, 90, 100, 150, 200, 250 or more). These NT028 proteins include variants of SEQ ID NO: 13, such as SEQ ID NO: 61 as cloned from Fi176. Preferred fragments of (b) comprise an epitope from SEQ ID NO: 13. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 13 while retaining at least one epitope of SEQ ID NO: 13. Other fragments omit one or more protein domains.

A NT028 antigen of the invention can be expressed with the native 21 N-terminal amino acids of NT028 (MLKRILVIIGLAVLATACSNA; SEQ ID NO: 81) or can be expressed with an alternative N-terminal sequence e.g. with a simple N-terminus methionine, or Met-Ala-, or a leader peptide which targets or traffics the expressed protein in a desired fashion.

A NT028 antigen of the invention can be a lipoprotein e.g. lipidated at a N-terminus cysteine.

NT029 Antigen

This antigen has been annotated as NTHI0371 in 86-026NP strain and as heme/hemopexin binding protein A, belonging to the outer membrane protein family. It has been cloned and expressed from R2846 strain.

Useful NT029 antigens can elicit an antibody (e.g. when administered to a human) that recognises SEQ ID NO: 14 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 14; and/or (b) comprising a fragment of at least 'n' consecutive amino acids of SEQ ID NO: 14, wherein 'n' is 7 or more (e.g. 8, 10, 12, 14, 16, 18, 20, 25, 30, 35, 40, 50, 60, 70, 80, 90, 100, 150, 200, 250 or more). These NT029 proteins include variants of SEQ ID NO: 14, such as SEQ ID NO 62 cloned from R2846 strain. Preferred fragments of (b) comprise an epitope from SEQ ID NO: 14. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 14 while retaining at least one epitope of SEQ ID NO: 14. Other fragments omit one or more protein domains.

A NT029 antigen of the invention can be expressed with the native 21 N-terminal amino acids of NT029 (MYKLNVISLIILTTYTGATYA; SEQ ID NO: 82) or can be expressed with an alternative N-terminal sequence e.g. with a simple N-terminus methionine, or Met-Ala-, or a leader peptide which targets or traffics the expressed protein in a desired fashion.

NT031 Antigen

This antigen has been annotated as starvation inducible outer membrane lipoprotein NTHI0509 in 86-026NP strain. It has been cloned and expressed from R2846 strain.

Useful NT031 antigens can elicit an antibody (e.g. when administered to a human) that recognises SEQ ID NO: 15 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 15; and/or (b) comprising a fragment of at least 'n' consecutive amino acids of SEQ ID NO: 15, wherein 'n' is 7 or more (e.g. 8, 10, 12, 14, 16, 18, 20, 25, 30, 35, 40, 50, 60, 70, 80, 90, 100, 150, 200, 250 or more). These NT031 proteins include variants of SEQ ID NO: 15, such as SEQ ID NO: 63 cloned and expressed from R2846 strain. Preferred fragments of (b) comprise an epitope from SEQ ID NO: 15. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 18, 20, 25 or more) from the N-terminus of SEQ ID NO: 15 while retaining at least one epitope of SEQ ID NO: 15. Other fragments omit one or more protein domains.

A NT031 antigen of the invention can be expressed with the native 18 N-terminal amino acids of NT031 (MKGKITLFFTALCFGLTG; SEQ ID NO: 83) or can be expressed with an alternative N-terminal sequence e.g. with a simple N-terminus methionine, or Met-Ala-, or a leader peptide which targets or traffics the expressed protein in a desired fashion.

A NT031 antigen of the invention can be a lipoprotein e.g. lipidated at a N-terminus cysteine.

NT015 Antigen

This antigen has been annotated as opacity associated protein OapB NTHI0449 in 86-026NP strain. It has been cloned and expressed from Fi176 strain.

Useful NT015 antigens can elicit an antibody (e.g. when administered to a human) that recognises SEQ ID NO: 16 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 16; and/or (b) comprising a fragment of at least 'n' consecutive amino acids of SEQ ID NO: 16, wherein 'n' is 7 or more (e.g. 8, 10, 12, 14, 16, 18, 20, 25, 30, 35, 40, 50, 60, 70, 80, 90, 100, 150, 200, 250 or more). These NT015 proteins include variants of SEQ ID NO: 16, such as SEQ ID NO: 64 cloned and expressed from Fi176. Preferred fragments of (b) comprise an epitope from SEQ ID NO: 16. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 16 while retaining at least one epitope of SEQ ID NO: 16. Other fragments omit one or more protein domains.

A NT015 antigen of the invention can be expressed with the native 17 N-terminal amino acids of NT015 (MLKKT-SLIFTALLLAGC; SEQ ID NO: 84) or can be expressed with an alternative N-terminal sequence e.g. with a simple N-terminus methionine, or Met-Ala-, or a leader peptide which targets or traffics the expressed protein in a desired fashion.

NT023 Antigen

This antigen has been annotated as outer membrane lipoprotein PCP, NTHI1473 in 86-026NP strain. It has been cloned and expressed from Fi176 strain.

Useful NT023 antigens can elicit an antibody (e.g. when administered to a human) that recognises SEQ ID NO: 17 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 17; and/or (b) comprising a fragment of at least 'n' consecutive amino acids of SEQ ID NO: 17, wherein 'n' is 7 or more (e.g. 8, 10, 12, 14, 16, 18, 20, 25, 30, 35, 40, 50, 60, 70, 80, 90, 100, 150, 200, 250 or more). These NT023 proteins include variants of SEQ ID NO: 17, such as SEQ ID NO: 65 cloned and expressed from strain Fi176. Preferred fragments of (b) comprise an epitope from SEQ ID NO: 17. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 17 while retaining at least one epitope of SEQ ID NO: 17. Other fragments omit one or more protein domains.

A NT023 antigen of the invention can be expressed with the native 20 N-terminal amino acids of NT023 (MKKT-NMALALLVAFSVTGCA; SEQ ID NO: 85) or can be expressed with an alternative N-terminal sequence e.g. with a simple N-terminus methionine, or Met-Ala-, or a leader peptide which targets or traffics the expressed protein in a desired fashion.

A NT023 antigen of the invention can be a lipoprotein e.g. lipidated at a N-terminus cysteine.

NT100 Antigen

This antigen has been annotated as "putative hydroxamate-type ferric siderophore receptor" and in NCBI as gi-145633184 from strain 3655. It has been cloned from R246 strain.

Useful NT100 antigens can elicit an antibody (e.g. when administered to a human) that recognises SEQ ID NO: 18 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 18; and/or (b) comprising a fragment of at least 'n' consecutive amino acids of SEQ ID NO: 18, wherein 'n' is 7 or more (e.g. 8, 10, 12, 14, 16, 18, 20, 25, 30, 35, 40, 50, 60, 70, 80, 90, 100, 150, 200, 250 or more). These NT100 proteins include variants of SEQ ID NO: 18, such as SEQ ID NO: 66. Preferred fragments of (b) comprise an epitope from SEQ ID NO: 18. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 18 while retaining at least one epitope of SEQ ID NO: 18. Other fragments omit one or more protein domains.

A NT100 antigen of the invention can be expressed with the native 30 N-terminal amino acids of NT100 (MDLGPI-YNTRDINDGKVINIDNPNYTNPVA; SEQ ID NO: 86) or can be expressed with an alternative N-terminal sequence e.g. with a simple N-terminus methionine, or Met-Ala-, or a leader peptide which targets or traffics the expressed protein in a desired fashion.

NT040 Antigen

This antigen has been annotated as hypothetical protein NTHI1110 in 86-026NP strain. It has been cloned and expressed from R2846 strain Useful NT040 antigens can elicit an antibody (e.g. when administered to a human) that recognises SEQ ID NO: 19 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 19; and/or (b) comprising a fragment of at least 'n' consecutive amino acids of SEQ ID NO: 19, wherein 'n' is 7 or more (e.g. 8, 10, 12, 14, 16, 18, 20, 25, 30, 35, 40, 50, 60, 70, 80, 90, 100, 150, 200, 250 or more). These NT040 proteins include variants of SEQ ID NO: 19. Preferred fragments of (b) comprise an epitope from SEQ ID NO: 19. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 19 while retaining at least one epitope of SEQ ID NO: 19. Other fragments omit one or more protein domains.

A NT040 antigen of the invention can be expressed with the native 26 N-terminal amino acids of NT040 (MMK-TLLKGQTLLALMISLTLSSLLLL; SEQ ID NO: 87) or can be expressed with an alternative N-terminal sequence e.g. with a simple N-terminus methionine, or Met-Ala-, or a leader peptide which targets or traffics the expressed protein in a desired fashion.

NT048 Antigen

This antigen has been annotated as NTHI1169 in strain 86-028NP. It has been cloned and expressed from R2846 strain.

Useful NT048 antigens can elicit an antibody (e.g. when administered to a human) that recognises SEQ ID NO: 20 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 20; and/or (b) comprising a fragment of at least 'n' consecutive amino acids of SEQ ID NO: 20, wherein 'n' is 7 or more (e.g. 8, 10, 12, 14, 16, 18, 20, 25, 30, 35, 40, 50, 60, 70, 80, 90, 100, 150, 200, 250 or more). These NT048 proteins include variants of SEQ ID NO: 20. Preferred fragments of (b) comprise an epitope from SEQ ID NO: 20. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 20 while retaining at least one epitope of SEQ ID NO: 20. Other fragments omit one or more protein domains.

A NT048 antigen of the invention can be expressed with the native 18 N-terminal amino acids of NT048 (MKSVPLITGGLSFLLSAC; SEQ ID NO: 88) or can be expressed with an alternative N-terminal sequence e.g. with a simple N-terminus methionine, or Met-Ala-, or a leader peptide which targets or traffics the expressed protein in a desired fashion.

NT053 Antigen

The antigen has been annotated as gi-145628236 in R2846 strain and cloned from said strain.

Useful NT053 antigens can elicit an antibody (e.g. when administered to a human) that recognises SEQ ID NO: 21 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 21; and/or (b) comprising a fragment of at least 'n' consecutive amino acids of SEQ ID NO: 21, wherein 'n' is 7 or more (e.g. 8, 10, 12, 14, 16, 18, 20, 25, 30, 35, 40, 50, 60, 70, 80, 90, 100, 150, 200, 250 or more). These NT053 proteins include variants of SEQ ID NO: 21. Preferred fragments of (b) comprise an epitope from SEQ ID NO: 21. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 21 while retaining at least one epitope of SEQ ID NO: 21. Other fragments omit one or more protein domains.

A NT053 antigen of the invention can be expressed with the native N-terminal Met of NT053 or can be expressed with an alternative N-terminal sequence e.g. with Met-Ala-, or a leader peptide which targets or traffics the expressed protein in a desired fashion.

NT066 Antigen

The antigen has been annotated as NTHI1230 in NP86-028 strain and localized in the periplasm of the bacteria. It has been cloned and expressed from Fi176 strain.

Useful NT066 antigens can elicit an antibody (e.g. when administered to a human) that recognises SEQ ID NO: 22 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 22; and/or (b) comprising a fragment of at least 'n' consecutive amino acids of SEQ ID NO: 22, wherein 'n' is 7 or more (e.g. 8, 10, 12, 14, 16, 18, 20, 25, 30, 35, 40, 50, 60, 70, 80, 90, 100, 150, 200, 250 or more). These NT066 proteins include variants of SEQ ID NO: 22, such as SEQ ID NO: 67. Preferred fragments of (b) comprise an epitope from SEQ ID NO: 22. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25, 27, 30, 33 or more) from the N-terminus of SEQ ID NO: 22 while retaining at least one epitope of SEQ ID NO: 22. Other fragments omit one or more protein domains.

A NT066 antigen of the invention can be expressed with the native 33 N-terminal amino acids of NT066 (MKIYLRFVWILIIILNFLLNLFITTNGVIIVNA; SEQ ID NO: 90) or can be expressed with an alternative N-terminal sequence e.g. with a simple N-terminus methionine, or Met-Ala-, or a leader peptide which targets or traffics the expressed protein in a desired fashion.

NT097 Antigen

The antigen has been annotated as NTHI0522 in NP86-028 strain and described as long-chain fatty acid FadL like transporter protein predicted to be present in the outer membrane milieu. It has been cloned and expressed from R2846 strain.

Useful NT097 antigens can elicit an antibody (e.g. when administered to a human) that recognises SEQ ID NO: 23 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 23; and/or (b) comprising a fragment of at least 'n' consecutive amino acids of SEQ ID NO: 23, wherein 'n' is 7 or more (e.g. 8, 10, 12, 14, 16, 18, 20, 25, 30, 35, 40, 50, 60, 70, 80, 90, 100, 150, 200, 250 or more). These NT097 proteins include variants of SEQ ID NO: 23. Preferred fragments of (b) comprise an epitope from SEQ ID NO: 23. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 22, 25 or more) from the N-terminus of SEQ ID NO: 23 while retaining at least one epitope of SEQ ID NO: 23. Other fragments omit one or more protein domains.

A NT097 antigen of the invention can be expressed with the native 22 N-terminal amino acids of NT097 (MKKFNQSILATAMLLAAGGANA; SEQ ID NO: 91) or can be expressed with an alternative N-terminal sequence e.g. with a simple N-terminus methionine, or Met-Ala-, or a leader peptide which targets or traffics the expressed protein in a desired fashion.

NT004 Antigen

The antigen has been annotated as hypothetical protein CGSHiGG_08215 from strain PittGG in the outer membrane milieu. It has been cloned and expressed from Fi 176 strain.

Useful NT004 antigens can elicit an antibody (e.g. when administered to a human) that recognises SEQ ID NO: 122 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 122; and/or (b) comprising a fragment of at least 'n' consecutive amino acids of SEQ ID NO: 122, wherein 'n' is 7 or more (e.g. 8, 10, 12, 14, 16, 18, 20, 25, 30, 35, 40, 50, 60, 70, 80, 90, 100, 150, 200, 250 or more). These NT004 proteins include variants of SEQ ID NO: 122. Preferred fragments of (b) comprise an epitope from SEQ ID NO: 122. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 22, 25 or more) from the N-terminus of SEQ ID NO: 122 while retaining at least one epitope of SEQ ID NO: 122. Other fragments omit one or more protein domains.

A NT004 antigen of the invention can be expressed with the native 20 N-terminal amino acids of NT004 (MKKKNQILVSLSIVALLGGC; SEQ ID NO: 125) or can be expressed with an alternative N-terminal sequence e.g. with a simple N-terminus methionine, or Met-Ala-, or a leader peptide which targets or traffics the expressed protein in a desired fashion.

NT014 Antigen

The antigen has been annotated as hypothetical protein HI1658 from strain Rd KW20. It has been cloned and expressed from Fi176 strain.

Useful NT014 antigens can elicit an antibody (e.g. when administered to a human) that recognises SEQ ID NO: 123 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 123; and/or (b) comprising a fragment of at least 'n' consecutive amino acids of SEQ ID NO: 123, wherein 'n' is 7 or more (e.g. 8, 10, 12, 14, 16, 18, 20, 25, 30, 35, 40, 50, 60, 70, 80, 90, 100, 150, 200, 250 or more). These NT014 proteins include variants of SEQ ID NO: 123. Preferred fragments of (b) comprise an epitope from SEQ ID NO: 123. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 22, 25 or more) from the N-terminus of SEQ ID NO: 123 while retaining at least one epitope of SEQ ID NO: 123. Other fragments omit one or more protein domains.

A NT014 antigen of the invention can be expressed with the native 22 N-terminal amino acids of NT014 (MTLSPLKKLAILLGATIFLQGC; SEQ ID NO: 126) or can be expressed with an alternative N-terminal sequence e.g. with a simple N-terminus methionine, or Met-Ala-, or a leader peptide which targets or traffics the expressed protein in a desired fashion.

NT022 Antigen

The antigen has been annotated as NTHI0830 from strain NP86-028 and identified to be a possible outer membrane antigenic lipoprotein B. It has been cloned and expressed from Fi176 strain. It has been also found to contain a LytM catalytic domain and to be surface exposed and secreted.

Useful NT022 antigens can elicit an antibody (e.g. when administered to a human) that recognises SEQ ID NO: 124 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 124; and/or (b) comprising a fragment of at least 'n' consecutive amino acids of SEQ ID NO: 124, wherein 'n' is 7 or more (e.g. 8, 10, 12, 14, 16, 18, 20, 25, 30, 35, 40, 50, 60, 70, 80, 90, 100, 150, 200, 250 or more). These NT022 proteins include variants of SEQ ID NO: 124. Preferred fragments of (b) comprise an epitope from SEQ ID NO: 124. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 22, 25 or more) from the N-terminus of SEQ ID NO: 124 while retaining at least one epitope of SEQ ID NO: 124. Other fragments omit one or more protein domains.

A NT022 antigen of the invention can be expressed with the native 18 N-terminal amino acids of NT022 (MKKSFLLLPLSLVVLSAC; SEQ ID NO: 127) or can be expressed with an alternative N-terminal sequence e.g. with a simple N-terminus methionine, or Met-Ala-, or a leader peptide which targets or traffics the expressed protein in a desired fashion.

Second Antigen Group

Antigen P48

The P48 polypeptide has been annotated in the literature as a Na(+)-translocating NADH-quinone reductase subunit A. For reference purposes, a full-length amino acid sequence of P48 is given as SEQ ID NO: 24 herein.

Preferred P48 polypeptides for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 24, e.g. 90% identity or more, or 95% identity or more, or 99% identity or more; and/or (b) comprising a fragment of at least 'n' consecutive amino acids of SEQ ID NO: 24, wherein 'n' is 7 or more (e.g. 8, 10, 12, 14, 16, 18, 20, 25, 30, 35, 40, 50, 60, 70, 80, 90, 100, 150, 200, 250 or more; e.g. 20 or more; or e.g. 50 or more; or e.g. 80 or more). These P48 polypeptides include variants of SEQ ID NO: 24. Preferred fragments of (b) comprise an epitope from SEQ ID NO: 24. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 24 while retaining at least one epitope of SEQ ID NO: 24. Other fragments omit one or more protein domains.

A P48 antigen of the invention ideally does not have the native 25 N-terminal amino acids of P48 (MITIKKGLDLPIAGKPAQVIHSGNA; SEQ ID NO: 92) and so it should be expressed with an alternative N-terminal sequence e.g. with a simple N-terminus methionine, or Met-Ala-, or a leader peptide which targets or traffics the expressed protein in a desired fashion.

According to the invention, the P48 antigen may advantageously be combined with one or more (e.g. 1, 2 or 3) of antigens HtrA, PE, P26, PHiD antigen and/or P6 as described herein, in particular, e.g. with HtrA.

Antigen HtrA

The HtrA polypeptide has been annotated in the literature as a periplasmic serine protease do/HhoA-like precursor, and has been described as a heat-shock protein or chaperone. For reference purposes, a full-length amino acid sequence of HtrA is given as SEQ ID NO: 25 herein.

Preferred HtrA polypeptides for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 25, e.g. 90% identity or more, or 95% identity or more, or 99% identity or more; and/or (b) comprising a fragment of at least 'n' consecutive amino acids of SEQ ID NO: 25, wherein 'n' is 7 or more (e.g. 8, 10, 12, 14, 16, 18, 20, 25, 30, 35, 40, 50, 60, 70, 80, 90, 100, 150, 200, 250 or more; e.g. 20 or more; or e.g. 50 or more; or e.g. 80 or more). These HtrA polypeptides include variants of SEQ ID NO: 25. Preferred fragments of (b) comprise an epitope from SEQ ID NO: 25. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 25 while retaining at least one epitope of SEQ ID NO: 25. Other fragments omit one or more polypeptide domains.

A HtrA antigen of the invention ideally does not have the native 26 N-terminal amino acids of HtrA (MKKTRFVLNSIALGLSVLSTSFVAQA; SEQ ID NO: 93) and so it should be expressed with an alternative N-terminal sequence e.g. with a simple N-terminus methionine, or Met-Ala-, or a leader peptide which targets or traffics the expressed protein in a desired fashion.

According to the invention, the HtrA antigen may advantageously be combined with one or more (e.g. 1, 2, or 3) of antigens P48, PE, P26, P6 and/or PHiD, in particular, e.g. with P48.

Antigen PE

The PE polypeptide has been annotated as Lipoprotein—Vitronectin binding protein, or as binding IgD and acting as an adhesion to type 2 alveolar cells. For reference purposes, a full-length amino acid sequence of PE is given as SEQ ID NO: 26 herein.

Preferred PE polypeptides for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 26, e.g. 90% identity or more, or 95% identity or more, or 99% identity or more; and/or (b) comprising a fragment of at least 'n' consecutive amino acids of SEQ ID NO: 26, wherein 'n' is 7 or more (e.g. 8, 10, 12, 14, 16, 18, 20, 25, 30, 35, 40, 50, 60, 70, 80, 90, 100, 150 or more; e.g. 20 or more; or e.g. 50 or more; or e.g. 80 or more). These PE polypeptides include variants of SEQ ID NO: 26. Preferred fragments of (b) comprise an epitope from SEQ ID NO: 26. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 26 while retaining at least one epitope of SEQ ID NO: 26. Other fragments omit one or more polypeptide domains.

A PE antigen of the invention ideally does not have the native 16 N-terminal amino acids of PE (MKKI-ILTLSLGLLTAC; SEQ ID NO: 94) and so it should be expressed with an alternative N-terminal sequence e.g. with a simple N-terminus methionine, or Met-Ala-, or a leader peptide which targets or traffics the expressed protein in a desired fashion.

According to the invention, the PE antigen may advantageously be combined with one or more (e.g. 1, 2 or 3) of antigens P48, HtrA, P26, P6 and/or PHiD as described herein.

Antigen P26

The P26 polypeptide is also known as outer membrane protein 26. It has been annotated as a member of the Skp family of proteins, whose putative function is translocation of outer membrane proteins [5]. For reference purposes, a full-length amino acid sequence of P26 is given as SEQ ID NO: 27 herein.

Preferred P26 polypeptides for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 27, e.g. 90% identity or more, or 95% identity or more, or 99% identity or more; and/or (b) comprising a fragment of at least 'n' consecutive amino acids of SEQ ID NO: 27, wherein 'n' is 7 or more (e.g. 8, 10, 12, 14, 16, 18, 20, 25, 30, 35, 40, 50, 60, 70, 80, 90, 100, 150 or more; e.g. 20 or more; or e.g. 50 or more; or e.g. 80 or more). These P26 polypeptides include variants of SEQ ID NO:27. Preferred fragments of (b) comprise an epitope from SEQ ID NO: 27. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 27 while retaining at least one epitope of SEQ ID NO: 27. Other fragments omit one or more protein domains.

According to the invention, the P26 antigen may advantageously be combined with one or more (e.g. 1, 2, or 3) of the antigens P48, HtrA, PE, PHiD and/or P6 as described herein, in particular with either or all of P48, HtrA and or PE as described herein.

PHiD Antigen

PHiD antigen is known also as "protein D" and has been used primarily as carrier protein in glycoconjugate NTHi vaccine approaches [95]. This antigen has been cloned and expressed from Fi176 strain.

Preferred PHiD polypeptides for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 28, e.g. 90% identity or more, or 95% identity or more, or 99% identity or more; and/or (b) comprising a fragment of at least 'n' consecutive amino acids of SEQ ID NO: 28, wherein 'n' is 7 or more (e.g. 8, 10, 12, 14, 16, 18, 20, 25, 30, 35, 40, 50, 60, 70, 80, 90, 100, 150 or more; e.g. 20 or more; or e.g. 50 or more; or e.g. 80 or more). These PHiD polypeptides include variants of SEQ ID NO: 28. Preferred fragments of (b) comprise an epitope from SEQ ID NO: 28. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 28 while retaining at least one epitope of SEQ ID NO: 28. Other fragments omit one or more protein domains.

A PhiD antigen of the invention can be expressed with the native 18 N-terminal amino acids of PhiD (MKLKT-LALSLLAAGVLAG; SEQ ID NO: 95) or can be expressed with an alternative N-terminal sequence e.g. with a simple N-terminus methionine, or Met-Ala-, or a leader peptide which targets or traffics the expressed protein in a desired fashion.

According to the invention, the PHiD antigen may advantageously combined with one or more (e.g. 1, 2, or 3) of any of the antigens P48, HtrA, PE, P26, and/or P6 as described herein.

A PhiD antigen of the invention can be a lipoprotein e.g. lipidated at a N-terminus cysteine.

P6 Antigen

P6 antigen is known also as OMP 6 (Outer membrane protein 6) [14]. This antigen was cloned and expressed from Fi176 strain.

Preferred P6 polypeptides for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 29, e.g. 90% identity or more, or 95% identity or more, or 99% identity or more; and/or (b) comprising a fragment of at least 'n' consecutive amino acids of SEQ ID NO: 29, wherein 'n' is 7 or more (e.g. 8, 10, 12, 14, 16, 18, 20, 25, 30, 35, 40, 50, 60, 70, 80, 90, 100, 150 or more; e.g. 20 or more; or e.g. 50 or more; or e.g. 80 or more). These P6 polypeptides include variants of SEQ ID NO: 29. Preferred fragments of (b) comprise an epitope from SEQ ID NO: 29. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 29 while retaining at least one epitope of SEQ ID NO: 29. Other fragments omit one or more protein domains.

A P6 antigen of the invention can be expressed with the native 19 N-terminal amino acids of P6 (MNKFVKSLL- VAGSVAALAA; SEQ ID NO: 96) or can be expressed with an alternative N-terminal sequence e.g. with a simple N-terminus methionine, or Met-Ala-, or a leader peptide which targets or traffics the expressed protein in a desired fashion.

According to the invention, the P6 antigen may advantageously combined with one or more (e.g. 1, 2, or 3) of any of the antigens P48, HtrA, PE, P26, and/or PHiD as described herein.

A P6 antigen of the invention can be a lipoprotein e.g. lipidated at a N-terminus cysteine.

Third Antigen Group
NT013 Antigen

The "NT013" antigen is annotated as TPR repeat-containing protein and also as cytochrome c maturation heme lyase subunit CcmH2. It has been released as NTHI0532 in the strain 86-028NP. NT013 has been annotated as belonging to the metalloprotease protein family and it has a LytM catalytic domain.

Useful NT013 antigens can elicit an antibody (e.g. when administered to a human) that recognises SEQ ID NO: 30 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 30; and/or (b) comprising a fragment of at least 'n' consecutive amino acids of SEQ ID NO: 30, wherein 'n' is 7 or more (e.g. 8, 10, 12, 14, 16, 18, 20, 25, 30, 35, 40, 50, 60, 70, 80, 90, 100, 150, 200, 250 or more). These NT013 proteins include variants of SEQ ID NO: 30. Preferred fragments of (b) comprise an epitope from SEQ ID NO: 30. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 30 while retaining at least one epitope of SEQ ID NO: 30. Other fragments omit one or more protein domains.

A NT013 antigen of the invention can be expressed with the native 42 N-terminal amino acids of NT013 (MPVQHVKLARDRRKKRTYIKVGVFFVAILLILT-GILLTIKDK; SEQ ID NO: 97) or can be expressed with an alternative N-terminal sequence e.g. with a simple N-terminus methionine, or Met-Ala-, or a leader peptide which targets or traffics the expressed protein in a desired fashion.

NT106 Antigen

The "NT106" antigen is annotated as lipoprotein and has been released as NTHI0363 in the genome 86-028NP.

Useful NT106 antigens can elicit an antibody (e.g. when administered to a human) that recognises SEQ ID NO: 31 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 31; and/or (b) comprising a fragment of at least 'n' consecutive amino acids of SEQ ID NO: 31, wherein 'n' is 7 or more (e.g. 8, 10, 12, 14, 16, 18, 20, 25, 30, 35, 40, 50, 60, 70, 80, 90, 100, 150, 200, 250 or more). These NT106 proteins include variants of SEQ ID NO: 31. Preferred fragments of (b) comprise an epitope from SEQ ID NO: 31. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 31 while retaining at least one epitope of SEQ ID NO: 31. Other fragments omit one or more protein domains.

A NT106 antigen of the invention can be expressed with the native 17 N-terminal amino acids of NT106 (MKKI-ILNLVTAIILAGC; SEQ ID NO: 98) or can be expressed with an alternative N-terminal sequence e.g. with a simple N-terminus methionine, or Met-Ala-, or a leader peptide which targets or traffics the expressed protein in a desired fashion.

A NT106 antigen of the invention can be a lipoprotein e.g. lipidated at a N-terminus cysteine.

NT107 Antigen

The "NT107" antigen is annotated as "Heme/hemopexin-binding protein B" and has been released as NTHI0370 in the genome 86-028NP.

Useful NT107 antigens can elicit an antibody (e.g. when administered to a human) that recognises SEQ ID NO: 32 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 32; and/or (b) comprising a fragment of at least 'n' consecutive amino acids of SEQ ID NO: 32, wherein 'n' is 7 or more (e.g. 8, 10, 12, 14, 16, 18, 20, 25, 30, 35, 40, 50, 60, 70, 80, 90, 100, 150, 200, 250 or more). These NT107 proteins include variants of SEQ ID NO: 32. Preferred fragments of (b) comprise an epitope from SEQ ID NO: 32. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 32 while retaining at least one epitope of SEQ ID NO: 32. Other fragments omit one or more protein domains.

A NT107 antigen of the invention can be expressed with the native 28 N-terminal amino acids of NT107 (MKMR-PRYSVIASAVSLGFVLSKSVMALG; SEQ ID NO: 99) or can be expressed with an alternative N-terminal sequence e.g. with a simple N-terminus methionine, or Met-Ala-, or a leader peptide which targets or traffics the expressed protein in a desired fashion.

NT108 Antigen

The "NT108" antigen is annotated as murein transglycosylase A lipoprotein. In the strain 86-028NP has been annotated as NTHI0205.

Useful NT108 antigens can elicit an antibody (e.g. when administered to a human) that recognises SEQ ID NO: 33 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 33; and/or (b) comprising a fragment of at least 'n' consecutive amino acids of SEQ ID NO: 33, wherein 'n' is 7 or more (e.g. 8, 10, 12, 14, 16, 18, 20, 25, 30, 35, 40, 50, 60, 70, 80, 90, 100, 150, 200, 250 or more). These NT108 proteins include variants of SEQ ID NO: 33. Preferred fragments of (b) comprise an epitope from SEQ ID NO: 33. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 33 while retaining at least one epitope of SEQ ID NO: 33. Other fragments omit one or more protein domains.

A NT108 antigen of the invention can be expressed with the native 24 N-terminal amino acids of NT108 (MSVCK-PFWFKTFSISIITALLVSC; SEQ ID NO: 100) or can be expressed with an alternative N-terminal sequence e.g. with a simple N-terminus methionine, or Met-Ala-, or a leader peptide which targets or traffics the expressed protein in a desired fashion.

A NT108 antigen of the invention can be a lipoprotein e.g. lipidated at a N-terminus cysteine.

NT109 Antigen

This antigen is annotated as nitrate/nitrite sensor protein NarQand has been identified as NTHI0374 in the strain 86-028NP and found to be conserved in the strains analysed.

Useful NT109 antigens can elicit an antibody (e.g. when administered to a human) that recognises SEQ ID NO: 34 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 34; and/or (b) comprising a fragment of at least 'n' consecutive amino acids of SEQ ID NO: 34, wherein 'n' is 7 or more (e.g. 8, 10, 12, 14, 16, 18, 20, 25, 30, 35, 40, 50, 60, 70, 80, 90, 100, 150, 200, 250 or more). These NT109 proteins include variants of SEQ ID NO: 34. Preferred fragments of (b) comprise an epitope from SEQ ID NO: 34. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 34 while retaining at least one epitope of SEQ ID NO: 34. Other fragments omit one or more protein domains.

A NT109 antigen of the invention can be expressed with the native 33 N-terminal amino acids of NT109 (MYTK-GSVSTRIAKYLFIILIVAGVISSLSLAIM; SEQ ID NO: 101) or can be expressed with an alternative N-terminal sequence e.g. with a simple N-terminus methionine, or Met-Ala-, or a leader peptide which targets or traffics the expressed protein in a desired fashion.

NT110 Antigen

This antigen has been annotated as NTHI0579 in the genome 86-028NP and is known as putative haemolysis TlyC. IT has been found associated to the outer membrane.

Useful NT110 antigens can elicit an antibody (e.g. when administered to a human) that recognises SEQ ID NO: 35.

Preferred fragments of (b) comprise an epitope from SEQ ID NO: 35. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 35 while retaining at least one epitope of SEQ ID NO: 35. Other fragments omit one or more protein domains.

A NT110 antigen of the invention can be expressed with the native 30 N-terminal amino acids of NT110 (MIMELFHTILAIVALILSSAVVSSAEISLA; SEQ ID NO: 102) or can be expressed with an alternative N-terminal sequence e.g. with a simple N-terminus methionine, or Met-Ala-, or a leader peptide which targets or traffics the expressed protein in a desired fashion.

NT111 Antigen

This antigen has been annotated as NTHI0837 in the strain 86-028NP and described as putative lipoprotein.

Useful NT111 antigens can elicit an antibody (e.g. when administered to a human) that recognises SEQ ID NO: 36 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 36; and/or (b) comprising a fragment of at least 'n' consecutive amino acids of SEQ ID NO: 36, wherein 'n' is 7 or more (e.g. 8, 10, 12, 14, 16, 18, 20, 25, 30, 35, 40, 50, 60, 70, 80, 90, 100, 150, 200, 250 or more). These NT111 proteins include variants of SEQ ID NO: 36. Preferred fragments of (b) comprise an epitope from SEQ ID NO: 36. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 36 while retaining at least one epitope of SEQ ID NO: 36. Other fragments omit one or more protein domains.

A NT111 antigen of the invention can be expressed with the native 19 N-terminal amino acids of NT111 (MKK-TLVAALISSVILLTGC; SEQ ID NO: 103) or can be expressed with an alternative N-terminal sequence e.g. with a simple N-terminus methionine, or Met-Ala-, or a leader peptide which targets or traffics the expressed protein in a desired fashion.

A NT110 antigen of the invention can be a lipoprotein e.g. lipidated at a N-terminus cysteine.

NT112 Antigen

This antigen has been annotated as NTHI0849 from NP86-028strain. It is annotated as VacJ lipoprotein.

Useful NT112 antigens can elicit an antibody (e.g. when administered to a human) that recognises SEQ ID NO: 37 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 37; and/or (b) comprising a fragment of at least 'n' consecutive amino acids of SEQ ID NO: 37, wherein 'n' is 7 or more (e.g. 8, 10, 12, 14, 16, 18, 20, 25, 30, 35, 40, 50, 60, 70, 80, 90, 100, 150, 200, 250 or more). These NT112 proteins include variants of SEQ ID NO: 37. Preferred fragments of (b) comprise an epitope from SEQ ID NO: 37. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 37 while retaining at least one epitope of SEQ ID NO: 37. Other fragments omit one or more protein domains.

A NT112 antigen of the invention can be expressed with the native 19 N-terminal amino acids of NT112 (MKTK-VILTALLSAIALTGC; SEQ ID NO: 104) or can be expressed with an alternative N-terminal sequence e.g. with a simple N-terminus methionine, or Met-Ala-, or a leader peptide which targets or traffics the expressed protein in a desired fashion.

A NT112 antigen of the invention can be a lipoprotein e.g. lipidated at a N-terminus cysteine.

NT113 Antigen

This antigen has been annotated as NTHI0921 in 86-026NP strain and as lipoprotein.

Useful NT113 antigens can elicit an antibody (e.g. when administered to a human) that recognises SEQ ID NO: 38 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 38; and/or (b) comprising a fragment of at least 'n' consecutive amino acids of SEQ ID NO: 38, wherein 'n' is 7 or more (e.g. 8, 10, 12, 14, 16, 18, 20, 25, 30, 35, 40, 50, 60, 70, 80, 90, 100, 150, 200, 250 or more). These NT113 proteins include variants of SEQ ID NO: 38.

Preferred fragments of (b) comprise an epitope from SEQ ID NO: 38. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 38 while retaining at least one epitope of SEQ ID NO: 38. Other fragments omit one or more protein domains.

A NT113 antigen of the invention can be expressed with the native 16 N-terminal amino acids of NT113 (MKKYLL- LALLPFLYAC; SEQ ID NO: 105) or can be expressed with an alternative N-terminal sequence e.g. with a simple N-terminus methionine, or Met-Ala-, or a leader peptide which targets or traffics the expressed protein in a desired fashion.

A NT113 antigen of the invention can be a lipoprotein e.g. lipidated at a N-terminus cysteine.

NT114 Antigen

This antigen has been annotated as soluble lytic murein transglycosylase protein and as NTHI0995 in 86-026NP strain.

Useful NT114 antigens can elicit an antibody (e.g. when administered to a human) that recognises SEQ ID NO: 39 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 39; and/or (b) comprising a fragment of at least 'n' consecutive amino acids of SEQ ID NO: 39, wherein 'n' is 7 or more (e.g. 8, 10, 12, 14, 16, 18, 20, 25, 30, 35, 40, 50, 60, 70, 80, 90, 100, 150, 200, 250 or more). These NT114 proteins include variants of SEQ ID NO: 39. Preferred fragments of (b) comprise an epitope from SEQ ID NO: 39. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 39 while retaining at least one epitope of SEQ ID NO: 39. Other fragments omit one or more protein domains.

A NT114 antigen of the invention can be expressed with the native 19 N-terminal amino acids of NT114 (MKKVALISLCIFTALSAFA; SEQ ID NO: 106) or can be expressed with an alternative N-terminal sequence e.g. with a simple N-terminus methionine, or Met-Ala-, or a leader peptide which targets or traffics the expressed protein in a desired fashion.

NT115 Antigen

This antigen has been annotated as NTHI1091 in 86-026NP strain and as putative LptE lipoprotein. It is located in the extracellular milieu.

Useful NT115 antigens can elicit an antibody (e.g. when administered to a human) that recognises SEQ ID NO: 40 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 40; and/or (b) comprising a fragment of at least 'n' consecutive amino acids of SEQ ID NO: 40, wherein 'n' is 7 or more (e.g. 8, 10, 12, 14, 16, 18, 20, 25, 30, 35, 40, 50, 60, 70, 80, 90, 100, 150, 200, 250 or more). These NT115 proteins include variants of SEQ ID NO: 40. Preferred fragments of (b) comprise an epitope from SEQ ID NO: 40. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 40 while retaining at least one epitope of SEQ ID NO: 40. Other fragments omit one or more protein domains.

A NT115 antigen of the invention can be expressed with the native 35 N-terminal amino acids of NT115 (MKYLHETRPTIKVIEMINSIKTLLLIATLAILSAC; SEQ ID NO: 107) or can be expressed with an alternative N-terminal sequence e.g. with a simple N-terminus methionine, or Met-Ala-, or a leader peptide which targets or traffics the expressed protein in a desired fashion.

A NT115 antigen of the invention can be a lipoprotein e.g. lipidated at a N-terminus cysteine.

NT116 Antigen

This antigen has been described as NTHI1169 in 86-026NP strain and belongs to the transferrin-binding protein family.

Useful NT116 antigens can elicit an antibody (e.g. when administered to a human) that recognises SEQ ID NO: 41 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 41; and/or (b) comprising a fragment of at least 'n' consecutive amino acids of SEQ ID NO: 41, wherein 'n' is 7 or more (e.g. 8, 10, 12, 14, 16, 18, 20, 25, 30, 35, 40, 50, 60, 70, 80, 90, 100, 150, 200, 250 or more). These NT116 proteins include variants of SEQ ID NO: 41. Preferred fragments of (b) comprise an epitope from SEQ ID NO: 41. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 41 while retaining at least one epitope of SEQ ID NO: 41. Other fragments omit one or more protein domains.

A NT116 antigen of the invention can be expressed with the native 18 N-terminal amino acids of NT116 (MKSVPLITGGLSFLLSAC; SEQ ID NO: 108) or can be expressed with an alternative N-terminal sequence e.g. with a simple N-terminus methionine, or Met-Ala-, or a leader peptide which targets or traffics the expressed protein in a desired fashion.

NT117 Antigen

This antigen has been annotated as NTHI1208 in 86-026NP strain and putative transglutaminase. It has been located in the outer membrane.

Useful NT117 antigens can elicit an antibody (e.g. when administered to a human) that recognises SEQ ID NO: 42 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 42; and/or (b) comprising a fragment of at least 'n' consecutive amino acids of SEQ ID NO: 42, wherein 'n' is 7 or more (e.g. 8, 10, 12, 14, 16, 18, 20, 25, 30, 35, 40, 50, 60, 70, 80, 90, 100, 150, 200, 250 or more). These NT117 proteins include variants of SEQ ID NO: 42 Preferred fragments of (b) comprise an epitope from SEQ ID NO: 42 Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 42 while retaining at least one epitope of SEQ ID NO: 42. Other fragments omit one or more protein domains.

A NT117 antigen of the invention can be expressed with the native 19 N-terminal amino acids of NT117 (MKKLIAVAVFSACGSLAHA; SEQ ID NO: 109) or can be expressed with an alternative N-terminal sequence e.g. with a simple N-terminus methionine, or Met-Ala-, or a leader peptide which targets or traffics the expressed protein in a desired fashion.

NT118 Antigen

This antigen has been annotated as NTHI1318 in 86-026NP strain and as hypothetical protein.

Useful NT118 antigens can elicit an antibody (e.g. when administered to a human) that recognises SEQ ID NO: 43 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 43; and/or (b)

comprising a fragment of at least 'n' consecutive amino acids of SEQ ID NO: 43, wherein 'n' is 7 or more (e.g. 8, 10, 12, 14, 16, 18, 20, 25, 30, 35, 40, 50, 60, 70, 80, 90, 100, 150, 200, 250 or more). These NT118 proteins include variants of SEQ ID NO: 43. Preferred fragments of (b) comprise an epitope from SEQ ID NO: 43. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 43 while retaining at least one epitope of SEQ ID NO: 43. Other fragments omit one or more protein domains.

A NT118 antigen of the invention can be expressed with the native 18 N-terminal amino acids of NT118 (MNIRWN-VILGVIALCALA; SEQ ID NO: 110) or can be expressed with an alternative N-terminal sequence e.g. with a simple N-terminus methionine, or Met-Ala-, or a leader peptide which targets or traffics the expressed protein in a desired fashion.

NT119 Antigen

This antigen has been annotated as NTHI1565 hypothetical protein in 86-028NP strain.

Useful NT119 antigens can elicit an antibody (e.g. when administered to a human) that recognises SEQ ID NO: 114 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 114; and/or (b) comprising a fragment of at least 'n' consecutive amino acids of SEQ ID NO: 114, wherein 'n' is 7 or more (e.g. 8, 10, 12, 14, 16, 18, 20, 25, 30, 35, 40, 50, 60, 70, 80, 90, 100, 150, 200, 250 or more). These NT119 proteins include variants of SEQ ID NO: 114. Preferred fragments of (b) comprise an epitope from SEQ ID NO: 114. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 114 while retaining at least one epitope of SEQ ID NO: 114. Other fragments omit one or more protein domains.

A NT119 antigen of the invention can be expressed with the native 26 N-terminal amino acids of NT119 (MRFTK-TLFTTALLGASIFSFQSTAWA; SEQ ID NO: 118) or can be expressed with an alternative N-terminal sequence e.g. with a simple N-terminus methionine, or Met-Ala-, or a leader peptide which targets or traffics the expressed protein in a desired fashion.

NT120 Antigen

This antigen has been annotated as NTHI1569 hypothetical protein in 86-028NP strain.

Useful NT120 antigens can elicit an antibody (e.g. when administered to a human) that recognises SEQ ID NO: 115 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 115; and/or (b) comprising a fragment of at least 'n' consecutive amino acids of SEQ ID NO: 115, wherein 'n' is 7 or more (e.g. 8, 10, 12, 14, 16, 18, 20, 25, 30, 35, 40, 50, 60, 70, 80, 90, 100, 150, 200, 250 or more). These NT120 proteins include variants of SEQ ID NO: 115. Preferred fragments of (b) comprise an epitope from SEQ ID NO: 115. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 115 while retaining at least one epitope of SEQ ID NO: 115. Other fragments omit one or more protein domains.

A NT120 antigen of the invention can be expressed with the native 26 N-terminal amino acids of NT120 (MKLTK-TLLTTALFGASVFSFQSTAWA; SEQ ID NO: 119) or can be expressed with an alternative N-terminal sequence e.g. with a simple N-terminus methionine, or Met-Ala-, or a leader peptide which targets or traffics the expressed protein in a desired fashion.

NT121 Antigen

This antigen has been annotated as NTHI1571 hypothetical protein in 86-028NP strain.

Useful NT121 antigens can elicit an antibody (e.g. when administered to a human) that recognises SEQ ID NO: 116 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 116; and/or (b) comprising a fragment of at least 'n' consecutive amino acids of SEQ ID NO: 116, wherein 'n' is 7 or more (e.g. 8, 10, 12, 14, 16, 18, 20, 25, 30, 35, 40, 50, 60, 70, 80, 90, 100, 150, 200, 250 or more). These NT121 proteins include variants of SEQ ID NO: 116. Preferred fragments of (b) comprise an epitope from SEQ ID NO: 116. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 116 while retaining at least one epitope of SEQ ID NO: 116. Other fragments omit one or more protein domains.

A NT121 antigen of the invention can be expressed with the native 26 N-terminal amino acids of NT121 (MKLTK-TLLTTALLGASVFSFQSTAWA; SEQ ID NO: 120) or can be expressed with an alternative N-terminal sequence e.g. with a simple N-terminus methionine, or Met-Ala-, or a leader peptide which targets or traffics the expressed protein in a desired fashion.

NT122 Antigen

This antigen has been annotated as NTHI1667 hypothetical protein in 86-028NP strain.

Useful NT122 antigens can elicit an antibody (e.g. when administered to a human) that recognises SEQ ID NO: 117 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 117; and/or (b) comprising a fragment of at least 'n' consecutive amino acids of SEQ ID NO: 117, wherein 'n' is 7 or more (e.g. 8, 10, 12, 14, 16, 18, 20, 25, 30, 35, 40, 50, 60, 70, 80, 90, 100, 150, 200, 250 or more). These NT122 proteins include variants of SEQ ID NO: 117. Preferred fragments of (b) comprise an epitope from SEQ ID NO: 117. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 117 while retaining at least one epitope of SEQ ID NO: 117. Other fragments omit one or more protein domains.

A NT122 antigen of the invention can be expressed with the native 23 N-terminal amino acids of NT122 (MEKIM-KKLTLALVLGSALAVTGC; SEQ ID NO: 121) or can be expressed with an alternative N-terminal sequence e.g. with a simple N-terminus methionine, or Met-Ala-, or a leader peptide which targets or traffics the expressed protein in a desired fashion.

NT123 Antigen

This antigen has been annotated as zinc protease NTHI1796 in 86-026NP strain.

Useful NT123 antigens can elicit an antibody (e.g. when administered to a human) that recognises SEQ ID NO: 44 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 44; and/or (b) comprising a fragment of at least 'n' consecutive amino acids of SEQ ID NO: 44, wherein 'n' is 7 or more (e.g. 8, 10, 12, 14, 16, 18, 20, 25, 30, 35, 40, 50, 60, 70, 80, 90, 100, 150, 200, 250 or more). These NT123 proteins include variants of SEQ ID NO: 44. Preferred fragments of (b) comprise an epitope from SEQ ID NO: 44. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 44 while retaining at least one epitope of SEQ ID NO: 44. Other fragments omit one or more protein domains.

A NT123 antigen of the invention can be expressed with the native 17 N-terminal amino acids of NT123 (MKKT-TALFLLIFSLIAC; SEQ ID NO: 111) or can be expressed with an alternative N-terminal sequence e.g. with a simple N-terminus methionine, or Met-Ala-, or a leader peptide which targets or traffics the expressed protein in a desired fashion.

NT124 Antigen

This antigen has been annotated as hypothetical protein NTHI1930 in 86-026NP strain.

Useful NT124 antigens can elicit an antibody (e.g. when administered to a human) that recognises SEQ ID NO: 45 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 45; and/or (b) comprising a fragment of at least 'n' consecutive amino acids of SEQ ID NO: 45, wherein 'n' is 7 or more (e.g. 8, 10, 12, 14, 16, 18, 20, 25, 30, 35, 40, 50, 60, 70, 80, 90, 100, 150, 200, 250 or more). These NT124 proteins include variants of SEQ ID NO: 45. Preferred fragments of (b) comprise an epitope from SEQ ID NO: 45. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 45 while retaining at least one epitope of SEQ ID NO: 45. Other fragments omit one or more protein domains.

A NT124 antigen of the invention can be expressed with the native 22 N-terminal amino acids of NT124 (MKKSKI-AAGVVISLAAVWCAGA; SEQ ID NO: 89) or can be expressed with an alternative N-terminal sequence e.g. with a simple N-terminus methionine, or Met-Ala-, or a leader peptide which targets or traffics the expressed protein in a desired fashion.

NT061 Antigen

This antigen has been annotated as survival protein SurA-like protein NTHI0588 in 86-026NP strain.

Useful NT061 antigens antigens can elicit an antibody (e.g. when administered to a human) that recognises SEQ ID NO: 128 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 128; and/or (b) comprising a fragment of at least 'n' consecutive amino acids of SEQ ID NO: 128, wherein 'n' is 7 or more (e.g. 8, 10, 12, 14, 16, 18, 20, 25, 30, 35, 40, 50, 60, 70, 80, 90, 100, 150, 200, 250 or more). These NT061 proteins include variants of SEQ ID NO: 128. Preferred fragments of (b) comprise an epitope from SEQ ID NO: 128. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 128 while retaining at least one epitope of SEQ ID NO: 128. Other fragments omit one or more protein domains.

A NT061 antigen of the invention can be expressed with the native 27 N-terminal amino acids of NT061 (MKMK-KFILKSFLLATLGCVAFTSMAQA; SEQ ID NO: 129) or can be expressed with an alternative N-terminal sequence e.g. with a simple N-terminus methionine, or Met-Ala-, or a leader peptide which targets or traffics the expressed protein in a desired fashion.

NT017 Antigen

This antigen has been annotated as survival protein SurA-like protein NTHI0915 in 86-026NP strain.

Useful NT017 antigens antigens can elicit an antibody (e.g. when administered to a human) that recognises SEQ ID NO: 130 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 130; and/or (b) comprising a fragment of at least 'n' consecutive amino acids of SEQ ID NO: 130, wherein 'n' is 7 or more (e.g. 8, 10, 12, 14, 16, 18, 20, 25, 30, 35, 40, 50, 60, 70, 80, 90, 100, 150, 200, 250 or more). These NT017 proteins include variants of SEQ ID NO: 130. Preferred fragments of (b) comprise an epitope from SEQ ID NO: 130. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 130 while retaining at least one epitope of SEQ ID NO: 130. Other fragments omit one or more protein domains.

A NT017 antigen of the invention can be expressed with the native 20 N-terminal amino acids of NT017 (MLRF-GVNQKTSLLLTALLSC; SEQ ID NO: 131) or can be expressed with an alternative N-terminal sequence e.g. with a simple N-terminus methionine, or Met-Ala-, or a leader peptide which targets or traffics the expressed protein in a desired fashion.

Hybrid Polypeptides

The polypeptides used with the invention may be expressed individually or independently on separate polypeptide chains. Alternatively, two or more of the polypeptides used with the invention may also be expressed as a single polypeptide chain (a 'hybrid' polypeptide). Hybrid polypeptides can be represented by the formula NH$_2$-A-{-X-L-}$_n$-B-COOH, wherein: A is an optional N-terminal amino acid sequence; B is an optional C-terminal amino acid sequence; n is an integer of 2 or more (e.g. 2, 3, 4, 5, 6, etc.); wherein at least one of the X, is an amino acid sequence of an antigen of the invention (as described above); and L is an optional linker amino acid sequence. According to the invention, for example, each X, may comprise the amino acid sequences of an antigen selected from the group consisting of: (1) NTHI0915 (NT018), (2) NTHI1416 (NT024), (3) NTHI2017 (NT032), (4) CGSHiGG_02400 (NT038, but this is not amongst preferred), (5) NTHI1292 (NT067), (6) NTHI0877 (NT001), (7) NTHI0266 (NT016), (8) CGSHiGG_00130 (NT052), (9) NTHI1627 (NT002), (10) NTHI1109 (NT026), (11) NTHI0821 (NT009), (12) NTHI0409 (NT025), (13) NTHI1954 (NT028), (14)

NTHI0371 (NT029), (15) NTHI0509 (NT031), (16) NTHI0449 (NT015), (17) NTHI1473 (NT023), (18) gi-145633184 (NT100), (19) NTHI1110 (NT040), (20) gi-46129075 (NT048), (21) gi-145628236 (NT053), (22) NTHI1230 (NT066), (23) NTHI0522 (NT097), (24) P48 (NTHI0254 also defined as NT007), (25) HtrA (NTHI1905 also defined as NT006), (26) PE (NTHI0267 also defined as NT035), (27) P26 (NTHI0501 also defined as NT010), (28) PHiD (NTHI0811 also defined as NT080), (29) P6 (NTHI0501, also defined as NT081), (30) NT013, (31) NT106, (32) NT107, (33) NT108, (34) NT109, (35) NT110, (36) NT111, (37) NT112, (38) NT113, (39) NT114, (40) NT115, (41) NT116, (42) NT117, (43) NT118, (44) NT119, (45) NT120, (46) NT121, (47), NT122, (48) NT123, (49) NT124; (50) NT004; (51) NT014; (52) NT022 (also annotated as NTHI0830); (53) NT016 (also annotated as NTHI0266).

According to the invention, the $X_n$ may comprise the amino acid sequences of two or more antigens selected from the group consisting of any of the antigen listed in the "First antigen group" and any of the antigen listed in the "Second antigen group". Each $X_n$ may be an amino acid sequence of an antigen of an antigen combination of the invention (as described above). In certain embodiments, n is 2. When n is 2, any combination of two of the antigens as described above may also be used in accordance with the invention. When n is 3, for example, any combination of the invention of three antigens as described above may be used. Generally, two or more of the $X_n$ may be the same antigens or, when n is 2, 3, or 4, each $X_n$ may be a different antigen. When two or more of the $X_n$ are sequences of the same antigen), said two or more $X_n$ may have the same polypeptide sequence or a different polypeptide sequence, e.g., may be different variants or fragments of the given antigen, as described above.

Where these antigens are defined in terms of (a) having 50% or more identity (e.g. 60%, 65%, 70%, 75%, 80%, 85%, 90%, 91%, 92%, 93%, 94%, 95%, 96%, 97%, 98%, 99%, 99.5% or more) to a given sequence; and/or (b) comprising a fragment of at least 'n' consecutive amino acids of a given sequence, wherein 'n' is 7 or more (e.g. 8, 10, 12, 14, 16, 18, 20, 25, 30, 35, 40, 50, 60, 70, 80, 90, 100, 150, 200, 250 or more), the level of identity in (a) and the value of 'n' in (b) may be the same for each X.

The leader peptide sequence in the wild-type form of each -X- moiety may be included or omitted in the hybrid protein. In some embodiments, the leader peptides will be deleted except for that of the -X- moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of {-X-L-}, linker amino acid sequence -L- may be present or absent. For instance, when n=2 the hybrid may be $NH_2$-$X_1$-$L_1$-$X_2$-$L_2$-COOH, $NH_2$-$X_1$-$X_2$-COOH, $NH_2$-$X_1$-$L_1$-$X_2$-COOH, $NH_2$-$X_1$-$X_2$-$L_2$-COOH, etc. Linker amino acid sequence(s) -L- will typically be short (e.g. 20 or fewer amino acids i.e. 20, 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising $Gly_n$ where n=2, 3, 4, 5, 6, 7, 8, 9, 10 or more), and histidine tags (i.e. $His_n$ where n=3, 4, 5, 6, 7, 8, 9, 10 or more). Other suitable linker amino acid sequences will be apparent to those skilled in the art. A useful linker is GSGGGG (SEQ ID NO:46) or GSGSGGGG (SEQ ID NO:47), with the Gly-Ser dipeptide being formed from a BamHI restriction site, thus aiding cloning and manipulation, and the $(Gly)_4$ tetrapeptide being a typical poly-glycine linker. Other suitable linkers, particularly for use as the final $L_n$, are a Leu-Glu dipeptide.

-A- is an optional N-terminal amino acid sequence. This will typically be short (e.g. 40 or fewer amino acids i.e. 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. $His_n$ where n=3, 4, 5, 6, 7, 8, 9, 10 or more) such as SEQ ID NO: 48. Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine e.g. Met-Ala-Ser, or a single Met residue.

-B- is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. $His_n$ where n=3, 4, 5, 6, 7, 8, 9, 10 or more, such as SEQ ID NO: 68), or sequences which enhance protein stability. Other suitable C-terminal amino acid sequences will be apparent to those skilled in the art.

Strains and Variants

Antigens are defined above by reference to naming conventions from the literature e.g. the "NTHI" numbering (from the genome of strain 86-028NP) or CGSHiGG numbering (from the genome of strain PittGG). Such conventions are explained in more detail in reference 15 (particularly Table 1). Table V herein relates the existing nomenclature to the "NT" nomenclature used herein. Thus an exemplary amino acid and nucleotide sequence for any of the antigens of the invention can easily be found in public sequence databases for the indicated strains (together with additional information, such as functional annotations), but the invention is not limited to sequences from the 86-028NP, 3655 or PittGG strains. Genome sequences of several other NTHI strains are available (again, see Table 1 of reference 15). Standard search and alignment techniques can be used to identify in any of these (or other) further genome sequences the homolog of any particular sequence given herein. Moreover, the available sequences can be used to design primers for amplification of homologous sequences from other strains. Thus the invention is not limited to these specific strains, but rather encompasses such variants and homologs from other NTHI strains, as well as non-natural variants. In general, suitable variants of a particular SEQ ID NO include its allelic variants, its polymorphic forms, its homologs, its orthologs, its paralogs, its mutants, etc. For instance, SEQ ID Nos: 49, 52, 54, 55, 57-59, 64, 65 & 67 include mutations as described below.

Thus, for instance, polypeptides used with the invention may, compared to the SEQ ID NO herein, include one or more (e.g. 1, 2, 3, 4, 5, 6, 7, 8, 9, etc.) amino acid substitutions, such as conservative substitutions (i.e. substitutions of one amino acid with another which has a related side chain). Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are some-times classified jointly as aromatic amino acids. In general, substitution of single amino acids within these families does not have a major effect on the biological activity. The polypeptides may also include one or more (e.g. 1, 2, 3, 4, 5, 6, 7, 8, 9, etc.) single amino acid deletions relative to the SEQ ID NO sequences. The polypeptides may also include one or more (e.g. 1, 2, 3, 4, 5, 6, 7, 8, 9, etc.) insertions (e.g. each of 1, 2, 3, 4 or 5 amino acids) relative to the SEQ ID NO sequences.

Similarly, a polypeptide used with the invention may comprise an amino acid sequence that:
(a) is identical (i.e. 100% identical) to a sequence disclosed in the sequence listing;
(b) shares sequence identity (e.g. 80%, 85%, 90%, 91%, 92%, 93%, 94%, 95%, 96%, 97%, 98%, 99%, 99.5% or more) with a sequence disclosed in the sequence listing;
(c) has 1, 2, 3, 4, 5, 6, 7, 8, 9 or 10 (or more) single amino acid alterations (deletions, insertions, substitutions), which may be at separate locations or may be contiguous, as compared to the sequences of (a) or (b); and/or
(d) when aligned with a particular sequence from the sequence listing using a pairwise alignment algorithm, each moving window of x amino acids from N-terminus to C-terminus (such that for an alignment that extends top amino acids, where p>x, there are p−x+1 such windows) has at least x·y identical aligned amino acids, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer. The preferred pairwise alignment algorithm is the Needleman-Wunsch global alignment algorithm [16], using default parameters (e.g. with Gap opening penalty =10.0, and with Gap extension penalty =0.5, using the EBLOSUM62 scoring matrix). This algorithm is conveniently implemented in the needle tool in the EMBOSS package [17].

Where hybrid polypeptides are used, the individual antigens within the hybrid (i.e. individual -X- moieties) may be from one or more strains. Where n=2, for instance, $X_2$ may be from the same strain as $X_1$ or from a different strain. Where n=3, the strains might be (i) $X_1=X_2=X_3$ (ii) $X_1=X_2\neq X_3$ (iii) $X_1\neq X_2=X_3$ (iv) $X_1\neq_2\neq_3$ or (v) $X_1=X_3\neq X_2$, etc.

Within group (c), deletions or substitutions may be at the N-terminus and/or C-terminus, or may be between the two termini. Thus a truncation is an example of a deletion. Truncations may involve deletion of up to 40 (or more) amino acids at the N-terminus and/or C-terminus. N-terminus truncation can remove leader peptides e.g. to facilitate recombinant expression in a heterologous host. C-terminus truncation can remove anchor sequences e.g. to facilitate recombinant expression in a heterologous host.

In general, when an antigen comprises a sequence that is not identical to a NTHI sequence from the sequence listing (e.g. when it comprises a sequence listing with <100% sequence identity thereto, or when it comprises a fragment thereof) it is preferred in each individual instance that the antigen can elicit an antibody which recognises the respective NTHI sequence from the sequence listing.

Mutant Bacteria

The present invention, also provides a NTHi bacterium in which one or more of the antigens of the invention has/have been knocked out [18]. Techniques for producing knockout bacteria are well known, and knockout of genes from NTHi strains have been reported i.e. in Ref. 19. A knockout mutation may be situated in the coding region of the gene or may lie within its transcriptional control regions (e.g. within its promoter). A knockout mutation will reduce the level of mRNA encoding the antigen to <1% of that produced by the wild-type bacterium, preferably <0.5%, more preferably <0.1%, and most preferably to 0%.

The invention also provides a NTHI bacterium in which one or more of the antigens of the invention has a mutation which inhibits its activity. The gene encoding the antigen will have a mutation that changes the encoded amino acid sequence or abolishes its expression. Mutation may involve deletion, substitution, and/or insertion, any of which may be involve one or more amino acids.

One embodiment provides deletions of one or more genes codying for antigens of the invention.

It was known in E. coli that two components of the division machinery with LytM domains (EnvC and N1pD) are direct regulators of the cell wall hydrolases (amidases) responsible for cell separation (AmiA, AmiB and AmiC) [20]. It is also known that LytM metalloproteases in E. coli are absolutely required for daughter cell separation.

In one embodiment, the present invention provides NTHI genes codifying for polypeptides that have the LytM catalytic domain. Generally metalloproteases are identified as containing HxH and HxxxD aminoacid domains in their catalytic domains. Preferably, these one or more genes are codifying for any one of NT013, NT022 or NT017.

The present invention describes that the mutation or deletion of one or more genes encoding for polypeptides having in common the LytM catalytic domain results in a drastic change in the bacterial cell division and bacterial phenotype.

Inventors have also shown that said mutation or deletion results in the release of vesicles known as OMVs or outer membrane vesicles, whereas the same wild type NTHi strains do not normally release OMVs.

In one particularly preferred embodiment it is described that by deleting NT013 and/or NT022 not only the bacterial cell division is affected, but there is also a surprising production and release of outer membrane vesicles (OMVs) in NTHI strains, that normally do not release OMVs.

Preferred embodiments provide NTHI strains wherein the deletions of one or more genes codying for anyone of NT013 or NT022 or NT017. For instance, the genes deleted can be substituted with an antibiotic resistance cassette, such as the erytromycin resistance cassette. It has been found that all the above mentioned polypeptides have in common a LytM catalytic domain and are all metalloproteases.

It has been also found that the LytM domain in NT013 and NT022 is conserved. NT013 catalytic active site is represented by the following aminoacid motifs -HKGD- and -HLH- at the C-terminal portion. of NT022 catalytic active site is represented by the following aminoacid motifs -NKGID- and -KLH- at the C-terminal.

The invention also provides a bacterium, such as a NTHi bacterium, which hyper-expresses an antigen of the invention.

The invention also provides a bacterium, such as a NTHi bacterium, that constitutively expresses an antigen of the invention. The invention also provides a E. coli comprising at least a gene encoding an antigen of the invention, wherein the gene is under the control of an inducible promoter.

OMV Based Vaccine

Gram-negative bacteria are separated from the external medium by two successive layers of membrane structures. These structures, referred to as the cytoplasmic membrane and the outer membrane (OM), differ both structurally and functionally. The outer membrane plays an important role in the interaction of pathogenic bacteria with their respective hosts. Consequently, the surface exposed bacterial molecules represent important targets for the host immune response, making outer-membrane components attractive candidates in providing vaccine, diagnostic and therapeutics reagents.

Mutant bacteria of the invention are particularly useful for preparing bacterial outer membrane vesicles which include NTHi antigens (e.g. antigens of the invention), and which can be used as immunogens.

The invention also provides a bacterium, such as a NTHi bacterium, which hyper-expresses at least one antigen of the invention preferably by overproducing OMVs.

Up-regulation can be used to increase the levels of useful NTHi proteins in OMVs.

A method for producing a NTHi bacterium overproducing OMVs of the invention is also provided, which method comprises genetically modifying a Gram-negative bacterial strain by one or more of the following processes: (a) engineering the strain to downregulate expression of one or more Tol genes; and (b) mutating one or more gene(s) encoding a protein comprising a peptidoglycan-associated site to attenuate the peptidoglycan-binding activity of the protein(s); (c) by mutation or deletion of one or more genes encoding for polypeptides having in common the LytM catalytic domain. In one particularly preferred embodiment, the NTHi might not express active NT013, NT022 genes and/or any of Tol genes [19], [18].

The invention also provides a process for preparing a NTHi vesicle, comprising a step of treating a NTHi bacterium of the invention such that its outer membrane forms vesicles.

The invention also provides a process for preparing a NTHi vesicle, comprising a step of culturing a NTHi bacterium of the invention under conditions in which its outer membrane spontaneously sheds vesicles.

The invention also provides a NTHi bacterium which overproduces OMVs and which also hyperexpresses the antigens of the present invention.

Polypeptides Used with the Invention

Polypeptides used with the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.).

Polypeptides used with the invention can be prepared by various means (e.g. recombinant expression, purification from cell culture, chemical synthesis, etc.). Recombinantly-expressed proteins are preferred, particularly for hybrid polypeptides.

Polypeptides used with the invention are preferably provided in purified or substantially purified form i.e. substantially free from other polypeptides (e.g. free from naturally-occurring polypeptides), particularly from other *H. influenzae* or host cell polypeptides, and are generally at least about 50% pure (by weight), and usually at least about 90% pure i.e. less than about 50%, and more preferably less than about 10% (e.g. 5%) of a composition is made up of other expressed polypeptides. Thus the antigens in the compositions are separated from the whole organism with which the molecule is expressed.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labelling component. Also included are, for example, polypeptides containing one or more analogues of an amino acid (including, for example, unnatural amino acids, etc.), as well as other modifications known in the art. Polypeptides can occur as single chains or associated chains.

Polypeptides used with the invention may comprise a sequence -P-Q- or -Q-P-, wherein: -P- is an amino acid sequence as defined above and -Q- is not a sequence as defined above i.e. may be provided as fusion proteins. Where the N-terminus codon of -P- is not ATG, but this codon is not present at the N-terminus of a polypeptide, it will be translated as the standard amino acid for that codon rather than as a Met. Where this codon is at the N-terminus of a polypeptide, however, it will be translated as Met. Examples of -Q- moieties include, but are not limited to, histidine tags (i.e. $His_n$ where n=3, 4, 5, 6, 7, 8, 9, 10 or more e.g. SEQ ID NO: 68), maltose-binding protein, or glutathione-S-transferase (GST).

Polypeptides used with the invention may comprise sequence -P-Q- or -Q-P when initially expressed as a nascent protein, but in some embodiments the -Q- moiety may be absent from the protein at its point of use e.g. a leader peptide might be post-translationally cleaved.

A useful N-terminus sequence for expression is SEQ ID NO: 48.

Although expression of the polypeptides used with the invention may take place in a *H. influenzae*, the invention will usually use a heterologous host for expression (recombinant expression). The heterologous host may be prokaryotic (e.g. a bacterium) or eukaryotic. It may be *E.coli*, but other suitable hosts include *Bacillus subtilis*, *Vibrio cholerae*, *Salmonella typhi*, *Salmonella typhimurium*, *Neisseria lactamica*, *Neisseria cinerea*, *Mycobacteria* (e.g. *M.tuberculosis*), yeasts, etc. Compared to the wild-type *H. influenzae* genes encoding polypeptides of the invention, it is helpful to change codons to optimise expression efficiency in such hosts without affecting the encoded amino acids.

Polypeptides used with the invention may be synthesised by a process comprising a step of synthesising at least part of the polypeptide by chemical means.

Nucleic Acids

The invention also provides nucleic acids (e.g. combinations of nucleic acids, vectors, or vector combinations), encoding polypeptides used with the invention, combinations of polypeptides or hybrid polypeptides of the invention. It also provides nucleic acid comprising a nucleotide sequence that encodes one or more (e.g., 2, 3 or 4) polypeptides or hybrid polypeptides of the antigen combinations of the invention. A nucleic acid may be, e.g., a vector (e.g. a cloning or expression vector).

Nucleotide sequences encoding polypeptides of the one or more (at least one) antigen and antigen combinations of the invention are either known (see e.g. references 6-9) or may be designed according to the genetic code. Thus, in the context of the present invention, such a nucleotide sequence may encode one or more of: (1) NTHI0915 (NT018), (2) NTHI1416 (NT024), (3) NTHI2017 (NT032), (4) CGSHiGG_02400 (NT038), (5) NTHI1292 (NT067), (6) NTHI0877 (NT001), (7) NTHI0266 (NT016), (8) CGSHiGG_00130 (NT052), (9) NTHI1627 (NT002), (10) NTHI1109 (NT026), (11) NTHI0821 (NT009), (12) NTHI0409 (NT025), (13) NTHI1954 (NT028), (14) NTHI0371 (NT029), (15) NTHI0509 (NT031), (16)

NTHI0449 (NT015), (17) NTHI1473 (NT023), (18) gi-145633184 (NT100), (19) NTHI1110 (NT040), (20) gi-46129075 (NT048), (21) gi-145628236 (NT053), (22) NTHI1230 (NT066), (23) NTHI0522 (NT097) or a P48 antigen (such as SEQ ID NO: 24); an HtrA antigen (such as SEQ ID NO: 25); a PE antigen (such as SEQ ID NO: 26); P26 antigen (such as SEQ ID NO: 27); a PHiD antigen (such as SEQ ID NO: 28); a P6 antigen (such as SEQ ID NO: 29), (24) NT004, (25) NT014, (26) NT022 or one or more antigens from the "third antigen group" or may encode an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more, e.g. 90% identity or more, or 95% identity or more, or 99% identity or more, to any of above mentioned polypeptides; and/or (b) comprising a fragment of at least 'n' consecutive amino acids of any of said polypeptides: 1, wherein 'n' is 7 or more (e.g. 8, 10, 12, 14, 16, 18, 20, 25, 30, 35, 40, 50, 60, 70, 80, 90, 100, 150, 200, 250 or more; e.g. 20 or more; or e.g. 50 or more; or e.g. 80 or more).

The invention also provides nucleic acid which can hybridize to these nucleic acids. Hybridization reactions can be performed under conditions of different "stringency". Conditions that increase stringency of a hybridization reaction of widely known and published in the art (e.g. page 752 of reference 121). Examples of relevant conditions include (in order of increasing stringency): incubation temperatures of 25° C., 37° C., 50° C., 55° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or de-ionized water. Hybridization techniques and their optimization are well known in the art (e.g. see refs, 21, 22 & 123).

A nucleic acid may hybridize to a target under low stringency conditions; in other embodiments it hybridizes under intermediate stringency conditions; in preferred embodiments, it hybridizes under high stringency conditions. An exemplary set of low stringency hybridization conditions is 50° C. and 10×SSC. An exemplary set of intermediate stringency hybridization conditions is 55° C. and 1×SSC. An exemplary set of high stringency hybridization conditions is 68° C. and 0.1×SSC.

The invention includes nucleic acid comprising sequences complementary to these sequences (e.g. for antisense or probing, or for use as primers).

Nucleic acid according to the invention can take various forms (e.g. single-stranded, double-stranded, vectors, primers, probes, labelled etc.). Nucleic acids of the invention may be circular or branched, but will generally be linear. Unless otherwise specified or required, any embodiment of the invention that utilizes a nucleic acid may utilize both the double-stranded form and each of two complementary single-stranded forms which make up the double-stranded form. Primers and probes are generally single-stranded, as are antisense nucleic acids.

Nucleic acids encoding antigens described herein are preferably provided in purified or substantially purified form i.e. substantially free from other nucleic acids (e.g. free from naturally-occurring nucleic acids), particularly from other H. influenzae or host cell nucleic acids, generally being at least about 50% pure (by weight), and usually at least about 90% pure. Nucleic acids of the invention are preferably H. influenzae nucleic acids.

Nucleic acids encoding antigens described herein may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

Nucleic acids may be attached to a solid support (e.g. a bead, plate, filter, film, slide, microarray support, resin, etc.). Nucleic acids may be labelled e.g. with a radioactive or fluorescent label, or a biotin label. This is particularly useful where the nucleic acid is to be used in detection techniques e.g. where the nucleic acid is a primer or as a probe.

The term "nucleic acid" includes in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the invention includes mRNA, tRNA, rRNA, ribozymes, DNA, cDNA, recombinant nucleic acids, branched nucleic acids, plasmids, vectors, probes, primers, etc. Where nucleic acid of the invention takes the form of RNA, it may or may not have a 5' cap.

Nucleic acids encoding antigens described herein may be part of a vector i.e. part of a nucleic acid construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, "viral vectors" which is designed to result in the production of a recombinant virus or virus-like particle, or "shuttle vectors", which comprise the attributes of more than one type of vector. Preferred vectors are plasmids. A "host cell" includes an individual cell or cell culture which can be or has been a recipient of exogenous nucleic acid. Host cells include progeny of a single host cell, and the progeny may not necessarily be completely identical (in morphology or in total DNA complement) to the original parent cell due to natural, accidental, or deliberate mutation and/or change. Host cells include cells transfected or infected in vivo or in vitro with nucleic acid of the invention.

The term "complement" or "complementary" when used in relation to nucleic acids refers to Watson-Crick base pairing. Thus the complement of C is G, the complement of G is C, the complement of A is T (or U), and the complement of T (or U) is A. It is also possible to use bases such as I (the purine inosine) e.g. to complement pyrimidines (C or T).

Nucleic acids encoding antigens described herein can be used, for example: to produce polypeptides; as hybridization probes for the detection of nucleic acid in biological samples; to generate additional copies of the nucleic acids; to generate ribozymes or antisense oligonucleotides; as single-stranded DNA primers or probes; or as triple-strand forming oligonucleotides.

The invention provides a process for producing nucleic acid encoding antigens described herein, wherein the nucleic acid is synthesised in part or in whole using chemical means.

The invention provides vectors comprising nucleotide sequences encoding antigens described herein (e.g. cloning or expression vectors) and host cells transformed with such vectors.

For certain embodiments of the invention, nucleic acids are preferably at least 7 nucleotides in length (e.g. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 90, 100, 110, 120, 130, 140, 150, 160, 170, 180, 190, 200, 225, 250, 275, 300 nucleotides or longer).

For certain embodiments of the invention, nucleic acids are preferably at most 500 nucleotides in length (e.g. 450, 400, 350, 300, 250, 200, 150, 140, 130, 120, 110, 100, 90, 80, 75, 70, 65, 60, 55, 50, 45, 40, 39, 38, 37, 36, 35, 34, 33, 32, 31, 30, 29, 28, 27, 26, 25, 24, 23, 22, 21, 20, 19, 18, 17, 16, 15 nucleotides or shorter).

Immunogenic Compositions and Medicaments

Immunogenic compositions of the invention may be useful as vaccines. Vaccines according to the invention may either be prophylactic (i.e. to prevent infection) or therapeutic (i.e. to treat infection), but will typically be prophylactic.

Compositions may thus be pharmaceutically acceptable. They will usually include components in addition to the antigens e.g. they typically include one or more pharmaceutical carrier(s) and/or excipient(s). A thorough discussion of such components is available in reference 118.

Compositions will generally be administered to a mammal in aqueous form. Prior to administration, however, the composition may have been in a non-aqueous form. For instance, although some vaccines are manufactured in aqueous form, then filled and distributed and administered also in aqueous form, other vaccines are lyophilised during manufacture and are reconstituted into an aqueous form at the time of use. Thus a composition of the invention may be dried, such as a lyophilised formulation.

The composition may include preservatives such as thiomersal or 2-phenoxyethanol. It is preferred, however, that the vaccine should be substantially free from (i.e. less than 5 μg/ml) mercurial material e.g. thiomersal-free. Vaccines containing no mercury are more preferred. Preservative-free vaccines are particularly preferred.

To improve thermal stability, a composition may include a temperature protective agent. Further details of such agents are provided below.

To control tonicity, it is preferred to include a physiological salt, such as a sodium salt. Sodium chloride (NaCl) is preferred, which may be present at between 1 and 20 mg/ml e.g. about 10±2 mg/ml NaCl. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Human vaccines are typically administered in a dosage volume of about 0.5 ml, although a half dose (i.e. about 0.25 ml) may be administered to children.

Immunogenic compositions of the invention can also comprise one or more immunoregulatory agents. Preferably, one or more of the immunoregulatory agents include one or more adjuvants. The adjuvants may include a TH1 adjuvant and/or a TH2 adjuvant, further discussed below.

Adjuvants which may be used in compositions of the invention include, but are not limited to:

mineral salts, such as aluminium salts and calcium salts, including hydroxides (e.g. oxyhydroxides), phosphates (e.g. hydroxyphosphates, orthophosphates) and sulphates, etc. [e.g. see chapters 8 & 9 of ref. 23];

oil-in-water emulsions, such as squalene-water emulsions, including MF59 (5% Squalene, 0.5% Tween 80, and 0.5% Span 85, formulated into submicron particles using a microfluidizer) (Chapter 10 of ref. 23; see also refs. 24-26, and chapter 12 of ref. 27], complete Freund's adjuvant (CFA) and incomplete Freund's adjuvant (IFA);

saponin formulations [chapter 22 of ref. 23], such as QS21 [28] and ISCOMs [chapter 23 of ref. 23];

virosomes and virus-like particles (VLPs) [29-35];

bacterial or microbial derivatives, such as non-toxic derivatives of enterobacterial lipopolysaccharide (LPS), Lipid A derivatives [36, 37], immunostimulatory oligonucleotides [38-43], such as IC-31™ [44] (deoxynucleotide comprising 26-mer sequence 5'-(IC)$_{13}$-3' (SEQ ID NO: 112) and polycationic polymer peptide comprising 11-mer amino acid sequence KLKLLLLLKLK (SEQ ID NO: 113) and ADP-ribosylating toxins and detoxified derivatives thereof [45-54];

human immunomodulators, including cytokines, such as interleukins (e.g. IL-1, IL-2, IL-4, IL-5, IL-6, IL-7, IL-12 [55, 56], interferons (e.g. interferon-γ), macrophage colony stimulating factor, and tumor necrosis factor;

bioadhesives and mucoadhesives, such as chitosan and derivatives thereof, esterified hyaluronic acid microspheres [57] or mucoadhesives, such as cross-linked derivatives of poly(acrylic acid), polyvinyl alcohol, polyvinyl pyrollidone, polysaccharides and carboxymethylcellulose [58];

microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.);

liposomes [Chapters 13 & 14 of ref. 23, ref. 59-61];

polyoxyethylene ethers and polyoxyethylene esters [62];

PCPP formulations [63 and 64];

muramyl peptides, including N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE); and imidazoquinolone compounds, including Imiquamod and its homologues (e.g. "Resiquimod 3M") [65 and 66].

Immunogenic compositions and vaccines of the invention may also comprise combinations of aspects of one or more of the adjuvants identified above. For example, the following adjuvant compositions may be used in the invention: (1)

a saponin and an oil-in-water emulsion [67]; (2) a saponin (e.g. QS21)+a non-toxic LPS derivative (e.g. 3dMPL) [68]; (3) a saponin (e.g. QS21)+a non-toxic LPS derivative (e.g. 3dMPL)+a cholesterol; (4) a saponin (e.g. QS21)+3dMPL+ IL-12 (optionally + a sterol) [69]; (5) combinations of 3dMPL with, for example, QS21 and/or oil-in-water emulsions [70]; (6) SAF, containing 10% squalne, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+ a non-toxic derivative of LPS (such as 3dMPL).

Other substances that act as immunostimulating agents are disclosed in chapter 7 of ref. 23.

The use of an aluminium hydroxide and/or aluminium phosphate adjuvant is particularly preferred, and antigens are generally adsorbed to these salts. Calcium phosphate is another preferred adjuvant. Other preferred adjuvant combinations include combinations of Th1 and Th2 adjuvants such as CpG & alum or resiquimod & alum. A combination of aluminium phosphate and 3dMPL may be used (this has been reported as effective in pneumococcal immunisation [71]). The use of an MF59 adjuvant is preferred, in particular in case of IM (intramuscular) or IP (Intraperitoneal) immunization.

The compositions of the invention may elicit both a cell mediated immune response as well as a humoral immune response. This immune response will preferably induce long lasting (e.g. neutralising) antibodies and a cell mediated immunity that can quickly respond upon exposure to NTHI.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class I molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-γ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A TH1 immune response may include one or more of an increase in CTLs, an increase in one or more of the cytokines associated with a TH1 immune response (such as IL-2, IFN-γ, and TNF-β, an increase in activated macrophages, an increase in NK activity, or an increase in the production of IgG2a. Preferably, the enhanced TH1 immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminium salts are preferred TH2 adjuvants for use in the invention.

Preferably, the invention includes a composition comprising a combination of a TH1 adjuvant and a TH2 adjuvant. Preferably, such a composition elicits an enhanced TH1 and an enhanced TH2 response, i.e., an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response.

The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

*H. influenzae* infections can affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. Such kits may comprise one or more antigens in liquid form and one or more lyophilised antigens.

Where a composition is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Where more than one antigen is included in a composition then two antigens may be present at the same dose as each other or at different doses.

As mentioned above, a composition may include a temperature protective agent, and this component may be particularly useful in adjuvanted compositions (particularly those containing a mineral adjuvant, such as an aluminium salt). As described in reference 72, a liquid temperature protective agent may be added to an aqueous vaccine composition to lower its freezing point e.g. to reduce the freezing point to below 0° C. Thus the composition can be stored below 0° C., but above its freezing point, to inhibit thermal breakdown. The temperature protective agent also permits freezing of the composition while protecting mineral salt adjuvants against agglomeration or sedimentation after freezing and thawing, and may also protect the composition at elevated temperatures e.g. above 40° C. A starting aqueous vaccine and the liquid temperature protective agent may be mixed such that the liquid temperature protective agent forms from 1-80% by volume of the final mixture. Suitable temperature protective agents should be safe for human administration, readily miscible/soluble in water, and should not damage other components (e.g. antigen and adjuvant) in the composition. Examples include glycerin, propylene glycol, and/or polyethylene glycol (PEG). Suitable PEGs may have an average molecular weight ranging from 200-20,000 Da. In a preferred embodiment, the polyethylene glycol can have an average molecular weight of about 300 Da ('PEG-300').

Compositions of the invention may be formed by mixing (i) an aqueous composition comprising two or more (e.g. 1, 2, 3, 4) antigen(s) of the antigen combinations of the invention with (ii) a temperature protective agent. The mixture may then be stored e.g. below 0° C., from 0-20° C., from 20-35° C., from 35-55° C., or higher. It may be stored in liquid or frozen form. The mixture may be lyophilised. The composition may alternatively be formed by mixing (i) a dried composition comprising two or more (e.g. 1, 2, 3, 4) antigen(s) of the antigen combinations of the invention, with (ii) a liquid composition comprising the temperature protective agent. Thus component (ii) can be used to reconstitute component (i).

Methods of Treatment, and Administration of the Vaccine

The invention also provides a method for raising an immune response in a mammal comprising the step of administering an effective amount of a composition of the invention, or one or more steps of administering at least one or more (e.g. 1, 2, 3, 4, 5, 6, 7, 8, 9 or 10) antigens of the invention. The immune response is preferably protective and preferably involves antibodies and/or cell-mediated immunity. The method may raise a booster response.

The invention also provides at least one or more antigens of the invention for combined use as a medicament e.g. for use in raising an immune response in a mammal.

The invention also provides the use of at least one or more antigens of the invention in the manufacture of a medicament for raising an immune response in a mammal.

In the methods and uses of the invention, at least one or more (e.g. 1, 2, 3, 4) antigens of the invention may be administered simultaneously, separately or sequentially.

By raising an immune response in the mammal by these uses and methods, the mammal can be protected against *H. influenzae* infection. The invention is effective against *H. influenzae* of various different serotypes, but can be particularly useful in protecting against disease resulting from infection by non-typeable *H. influenzae* (NTHI). In accordance with the invention, an infection may be associated with a disease or condition selected from, for instance, otitis media (including acute otitis media), bronchitis, conjunctivitis, sinusitis, a urinary tract infection, pneumonia, bacteremia, septic arthritis, epiglottitis, pneumonia, empyema, pericarditis, cellulitis, osteomyelitis, lower respiratory tract infection or meningitis. The invention is particularly useful for treating or preventing inflammation of the middle ear or for treating or preventing COPD diseases, by eliciting an immune response that prevents bacteria from moving from the throat to the middle ear via the eustachian tube, where the middle ear is then colonised.

The invention also provides a kit comprising a first component and a second component wherein neither the first component nor the second component is a composition of the invention as described above, but wherein the first component and the second component can be combined to provide a composition of the invention as described above. The kit may further include a third component comprising one or more of the following: instructions, syringe or other delivery device, adjuvant, or pharmaceutically acceptable formulating solution.

The invention also provides a delivery device pre-filled with an immunogenic composition of the invention.

The mammal is preferably a human, e.g. human patient. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc. A mammal (e.g. human, e.g. a patient) may either be at risk from the disease themselves or may be a pregnant female, e.g. woman ('maternal immunisation').

One way of checking efficacy of therapeutic treatment involves monitoring *H. influenzae* infection after administration of the compositions of the invention. One way of checking efficacy of prophylactic treatment involves monitoring immune responses, systemically (such as monitoring the level of IgG1 and IgG2a production) and/or mucosally (such as monitoring the level of IgA production), against the antigens in the compositions of the invention after administration of the composition. Immunogenicity of compositions of the invention can be determined by administering them to test subjects (e.g. children 12-16 months age, or animal models such as a chinchilla model [73]) and then determining standard parameters including ELISA titres (GMT) of IgG. These immune responses will generally be determined around 4 weeks after administration of the composition, and compared to values determined before administration of the composition. Where more than one dose of the composition is administered, more than one post-administration determination may be made. Typically, antigen-specific serum antibody responses are determined post-immunisation but pre-challenge whereas antigen-specific mucosal antibody responses are determined post-immunisation and post-challenge.

Another way of assessing the immunogenicity of the compositions of the present invention is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within antigens.

The efficacy of vaccine compositions can also be determined in vivo by immunization studies in animal models of *H. influenzae* infection, e.g., guinea pigs Chinchillas, or mice, with the vaccine compositions. One such model is described in reference 74.

Other useful animal model to be used to determine in vivo the efficacy of vaccine compositions of the invention is described in reference 75.

Compositions of the invention will generally be administered directly to a patient. Direct delivery may be accomplished by parenteral injection (e.g. subcutaneously, intraperitoneally, intravenously, intramuscularly, or to the interstitial space of a tissue), or mucosal, such as by rectal, oral, (e.g. tablet, spray), vaginal, topical, transdermal or transcutaneous, intranasal, ocular, aural, pulmonary or other mucosal administration.

The invention may be used to elicit systemic and/or mucosal immunity, preferably to elicit an enhanced systemic and/or mucosal immunity.

Preferably the enhanced systemic and/or mucosal immunity is reflected in an enhanced TH1 and/or TH2 immune response. Preferably, the enhanced immune response includes an increase in the production of IgG1 and/or IgG2a and/or IgA.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines prepared according to the invention may be used to treat both children and adults. Thus a human patient may be less than 1 year old, 1-5 years old, 5-15 years old, 15-55 years old, or at least 55 years old. Preferred patients for receiving the vaccines are the elderly (e.g. $\geq 50$ years old, $\geq 60$ years old, and preferably $\geq 65$ years), the young (e.g. $\leq 5$ years old), hospitalised patients, healthcare workers, armed service and military personnel, pregnant women, the chronically ill, or immunodeficient patients. The vaccines are not suitable solely for these groups, however, and may be used more generally in a population.

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, etc.

Mucosal Immunisation

The invention provides the antigens, antigen combinations, and compositions of the invention for mucosal immunisation. E.g., the invention provides an immunogenic composition comprising (i) a polypeptide antigen combination of the invention, and (ii) a bacterial ADP-ribosylating toxin and or detoxified derivative thereof. The invention also provides a method for raising an immune response in a mammal comprising the step of administering an effective amount of such an immunogenic composition to the mammal. The composition is preferably administered via mucosa (to a mucosal surface) e.g. it may be administered intranasal.

The toxin of component (ii) may be, for example, derived from *E.coli* heat labile enterotoxin ("LT"). The derivative may have a detoxifying mutation in its A subunit e.g. it may be LT-K63 or LT-R72. In particular it may be LT-K63. In other embodiments, it is not LT-K63.

Intranasal administration of antigens or compositions of the invention and a LT-K63 adjuvant is preferred. This may decrease the *H. influenzae* bacterial load in the nasopharynx, lungs and blood, and increase survival rate of infected mammals.

Further Antigenic Components of Compositions of the Invention

The invention also provides compositions further comprising at least one further non-typeable *H. influenzae* antigen.

The invention also provides compositions further comprising at least one antigen that is not a non-typeable *H. influenzae* antigen.

In particular, the invention also provides a composition comprising one or more polypeptides of the invention and one or more of the following further antigens:

an antigen from *N. meningitidis* serogroup A, B, C, W135 and/or Y.

a saccharide or polypeptide antigen from *Streptococcus pneumoniae* [e.g. 76, 77, 78].

an antigen from hepatitis A virus, such as inactivated virus [e.g. 79, 80].

an antigen from hepatitis B virus, such as the surface and/or core antigens [e.g. 80, 81].

a diphtheria antigen, such as a diphtheria toxoid [e.g. chapter 3 of ref. 82] or the $CRM_{197}$ mutant [e.g. 83].

a tetanus antigen, such as a tetanus toxoid [e.g. chapter 4 of ref. 82].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 84 & 85].

a whole cellular pertussis antigen a saccharide antigen from *Haemophilus influenzae* B [e.g. 86].

polio antigen(s) [e.g. 87, 88] such as IPV.

measles, mumps and/or rubella antigens [e.g. chapters 9, 10 & 11 of ref. 82].

influenza antigen(s) [e.g. chapter 19 of ref. 82], such as the haemagglutinin and/or neuraminidase surface proteins.

an antigen from *Moraxella catarrhalis* [e.g. 89].

an protein antigen from *Streptococcus agalactiae* (group B streptococcus) [e.g. 90, 91].

a saccharide antigen from *Streptococcus agalactiae* (group B streptococcus).

an antigen from *Streptococcus pyogenes* (group A streptococcus) [e.g. 91, 92, 93].

an antigen from *Staphylococcus aureus* [e.g. 94].

an antigen from Respiratory Syncytial Virus, e.g. a recombinant protein F [e.g. 142]

a vaccine composition comprising diphtheria (D), tetanus (T), pertussis (acellular, component) (Pa), hepatitis B (rDNA) (HBV), poliomyelitis (inactivated) (IPV) and *Haemophilus influenzae* type b (Hib) conjugate vaccine (adsorbed), e.g. Infanrix-hexa The composition may comprise one or more of these further antigens. Combinations with a RSV vaccine and/or with a DTPa-containing vaccine are of particular interest.

Toxic protein antigens may be detoxified where necessary (e.g. detoxification of pertussis toxin by chemical and/or genetic means [85]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. Carrier proteins for the conjugates include diphtheria toxin, tetanus toxin, the *N. meningitidis* outer membrane protein [95], synthetic peptides [96,97], heat shock proteins [98,99], pertussis proteins [100,101], protein D from *H. influenzae* [102], cytokines [103], lymphokines [103], streptococcal proteins, hormones [103], growth factors [103], toxin A or B from *C. difficile* [104], iron-uptake proteins [105], etc. A preferred carrier protein is the CRM197 mutant of diphtheria toxin [106].

Antigens in the composition will typically be present at a concentration of at least 1 µg/ml each. In general, the concentration of any given antigen will be sufficient to elicit an immune response against that antigen.

As an alternative to using proteins antigens in the immunogenic compositions of the invention, nucleic acid (preferably DNA e.g. in the form of a plasmid) encoding the antigen may be used.

Antigens are preferably adsorbed to an aluminium salt.

Antibodies

Antibodies against antigens according to the invention can be used for passive immunisation [107]. Thus the invention provides antibodies specific to antigens of the invention for use in therapy. These antibodies may be used singly or in combination. The invention also provides and immunogenic and pharmaceutical compositions comprising such antibodies.

The antibodies can be used in medicine and in therapy e.g. for passive immunisation against NTHI, or for clearing a NTHI infection. The invention also provides the use of such antibodies in the manufacture of a medicament. The invention also provides a method for treating a mammal comprising the step of administering an effective amount of an antibody of the invention. As described above for immunogenic compositions, these methods and uses allow a mammal to be protected against NTHI infections. In particular, antibodies of the invention may be used in methods of treating or preventing infections by NTHI, comprising the step of administering to the mammal an effective amount of an antibody as described herein, or a composition comprising such an antibody.

The term "antibody" includes intact immunoglobulin molecules (like palivizumab), as well as fragments thereof which are capable of binding a NTHI antigen. These include hybrid (chimeric) antibody molecules [108, 109]; F(ab')2 and F(ab) fragments and Fv molecules; non-covalent heterodimers [110, 111]; single-chain Fv molecules (sFv) [112]; dimeric and trimeric antibody fragment constructs; minibodies [113, 114]; humanized antibody molecules [115-117]; and any functional fragments obtained from such molecules, as well as antibodies obtained through non-conventional processes such as phage display. Preferably, the antibodies are monoclonal antibodies. Methods of obtaining monoclonal antibodies are well known in the art. Humanised or fully-human antibodies are preferred. Antibodies and antibody combinations of the invention may be purified or isolated.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 118-125, etc.

Where the invention concerns an "epitope", this epitope may be a B-cell epitope and/or a T-cell epitope. Such epitopes can be identified empirically (e.g. using PEPSCAN [126,127] or similar methods), or they can be predicted (e.g. using the Jameson-Wolf antigenic index [128], matrix-based approaches [129], MAPITOPE [130], TEPITOPE [131, 132], neural networks [133], OptiMer & EpiMer [134, 135], ADEPT [136], Tsites [137], hydrophilicity [138], antigenic index [139] or the 10 methods disclosed in references 140-144, etc.). Epitopes are the parts of an antigen that are recognised by and bind to the antigen binding sites of antibodies or T-cell receptors, and they may also be referred to as "antigenic determinants".

Where an antigen "domain" is omitted, this may involve omission of a signal peptide, of a cytoplasmic domain, of a transmembrane domain, of an extracellular domain, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref. 22. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 145.

MODES FOR CARRYING OUT THE INVENTION

Overview

Figure 1A:
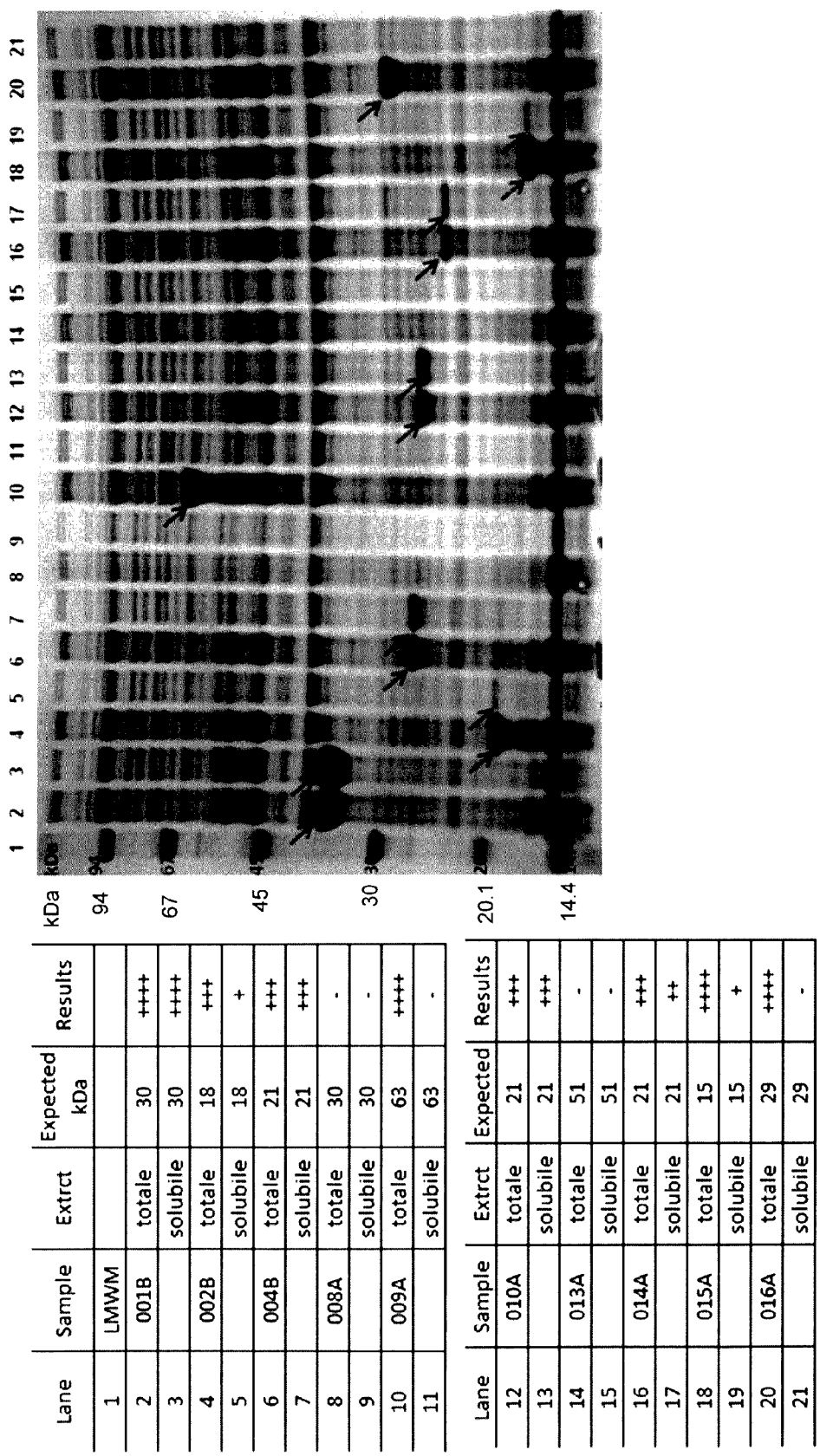
FIG. 1 shows a mini-induction confirming strong expression of the antigens in BL21 (DE3)T1$^r$ cells. (a): (LMWM: molecular weight standard markers)

Antigens list all of them which were identified as conserved in a comparative analysis performed by the inventors of at least 86 different NTHI strains, were cloned and expressed. The proteins were purified and used to immunize mice. Antisera from the immunized mice were used to verify surface localization and protective capability of the proteins used in immunization (Table III and/or Table IV). The results show that immunization NT052, NT024, NT032, NT001, NT067, NT004, NT014, NT022, NT016 is highly protective against NTHI and they showed higher or at least comparable bacterial killing activity SBA (Serum bactericidal assay) titers even compared with the "second antigen group".

Strains and Variants

Inventors found that genes encoding NT022, NT016, NT014, NT018, NT024, NT032, NT067 and NT001 were present and conserved in all 86 genome sequences analysed.

The encoded NT018 sequences were 95-100% identical across the panel composed by the 15 complete genomes and the 32 strains from the Finnish otitis collection. The encoded NT024 sequences were 90-100% identical in the panel composed by the 15 complete genomes and the 32 strains from the Finnish otitis collection.

The encoded NT032 sequences were 95-100% identical in the panel composed by the 15 complete genomes and the 32 strains from the Finnish otitis collection; the encoded NT067 sequences were 95-100% identical in the panel composed by the 15 complete genomes and the 32 strains from the Finnish otitis collection. The encoded NT001 sequences were 95-100% identical in the panel composed by the 15 complete genomes and the 32 strains from the Finnish otitis collection.

Conservation in the encoded amino acid sequences are shown in Table I.

TABLE I

| antigen conservation (% identity) amongst Haemophilus genomes and strains | | | | | |
|---|---|---|---|---|---|
| | Antigen | | | | |
| | NT018 | NT024 | NT032 | NT067 | NT001 |
| % | 95-100 | 90-100 | 95-100 | 95-100 | 95-100 |

For expression purposes, antigens belonging to the "first antigen group" and/or "second antigen group" were cloned from either strain Fi176 which is one strain isolated from a Finnish collection of strains obtained from patients with otitis media or from strain R2846 [146]. Most of the antigen selected and further tested in animal model are also found to be well conserved amongst strains, e.g. NT016, NT067, NT022, NT014.

In some cases mutations have been introduced into the wild-type sequences. These mutations are underlined in the sequence listing for NT018, NT067, NT001, NT016, NT002, NT026, NT009, NT015, NT023 and NT066 (see SEQ ID NOs: 49, 52, 54, 55, 57-59, 64, 65 & 67).

Cloning and Expression of NTHI Recombinant Proteins

Cloning and expression of antigens can be performed by standard methods [121].

ORFs for antigens from NTHI strain Fi176 or R2846 were PCR-amplified using specific oligonucleotides and NTHI chromosomal DNA as template. Resulting PCR products were cloned in pET15b (Novagen) using the PIPE method [147], consisting in the PCR amplification of the cloning vector (V-PCR) and in the39 PCR amplification of the insert (I-PCR). Then, 1 µl of V-PCR and 1 µl of I-PCR are mixed and transformed in chemically competent HK100 cells [148]. I-PCR reactions were set up containing 1 µM each of the forward and reverse primers, 1× Cloned Pfu DNA Polymerase Reaction Buffer, 2.5 units of Pfu Turbo DNA polymerase (Stratagene), 200 µM of each dNTP (Invitrogen) and 50 ng of genomic DNA template. The reactions were conducted as follows: initial denaturation for 2 min at 95° C., then 25 cycles of 95° C. for 30 s, 55 ° C. for 45 s, and 68° C. for 3 min followed by a final cool down to 4° C. V-PCR reactions were identical to the I-PCR reactions but the steps at 68° C. were lasting 14 min and 2 ng of pET15b plasmid were used as DNA template. Correct transformants where selected by PCR screening and DNA plasmid sequencing of the vector-insert junctions. The correct plasmid were then prepared from selected HK100 clones and used to transform BL21(DE3)T1$^r$ cells (Sigma) in order to allow protein expression.

Figure 1B:
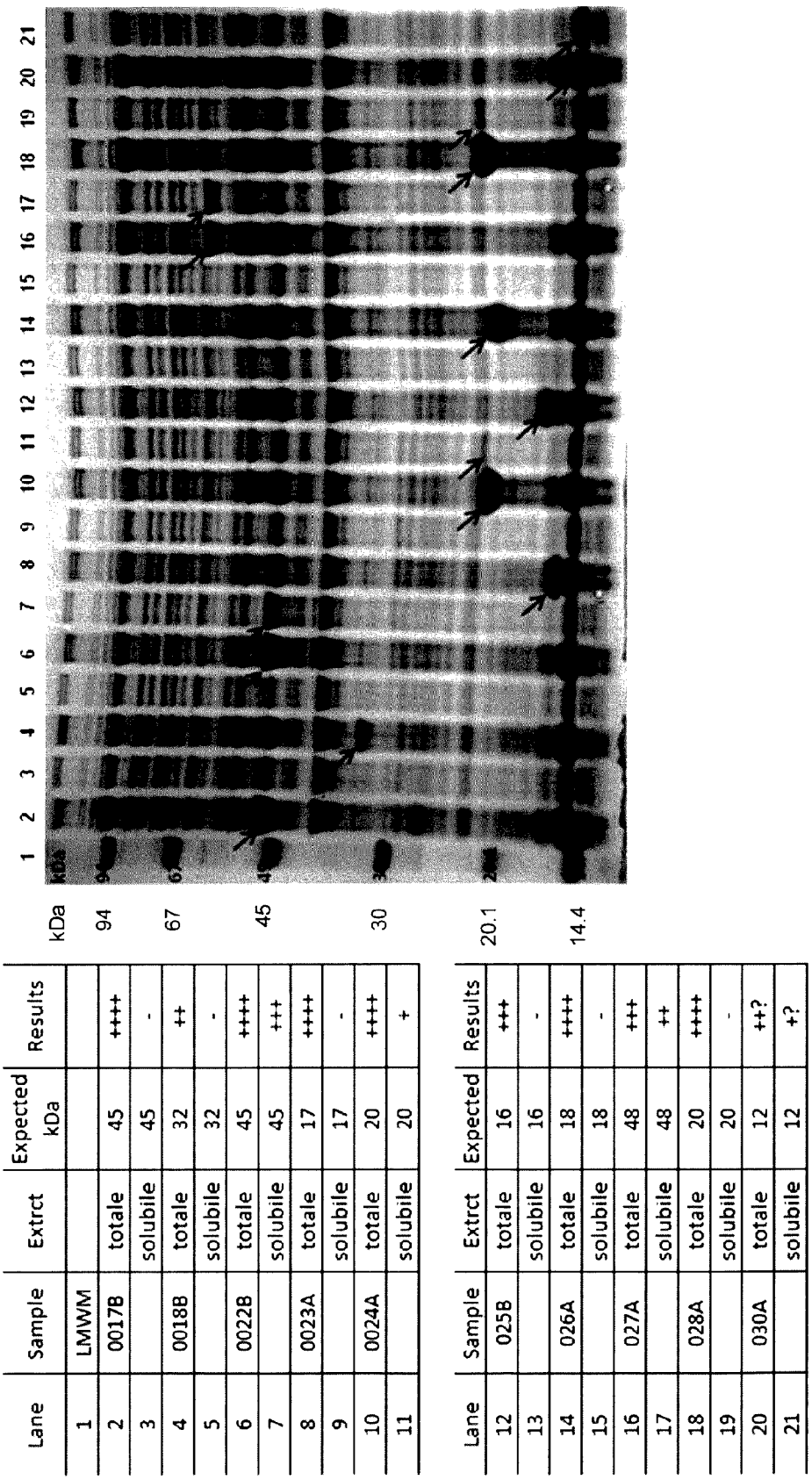
Figure 1C:
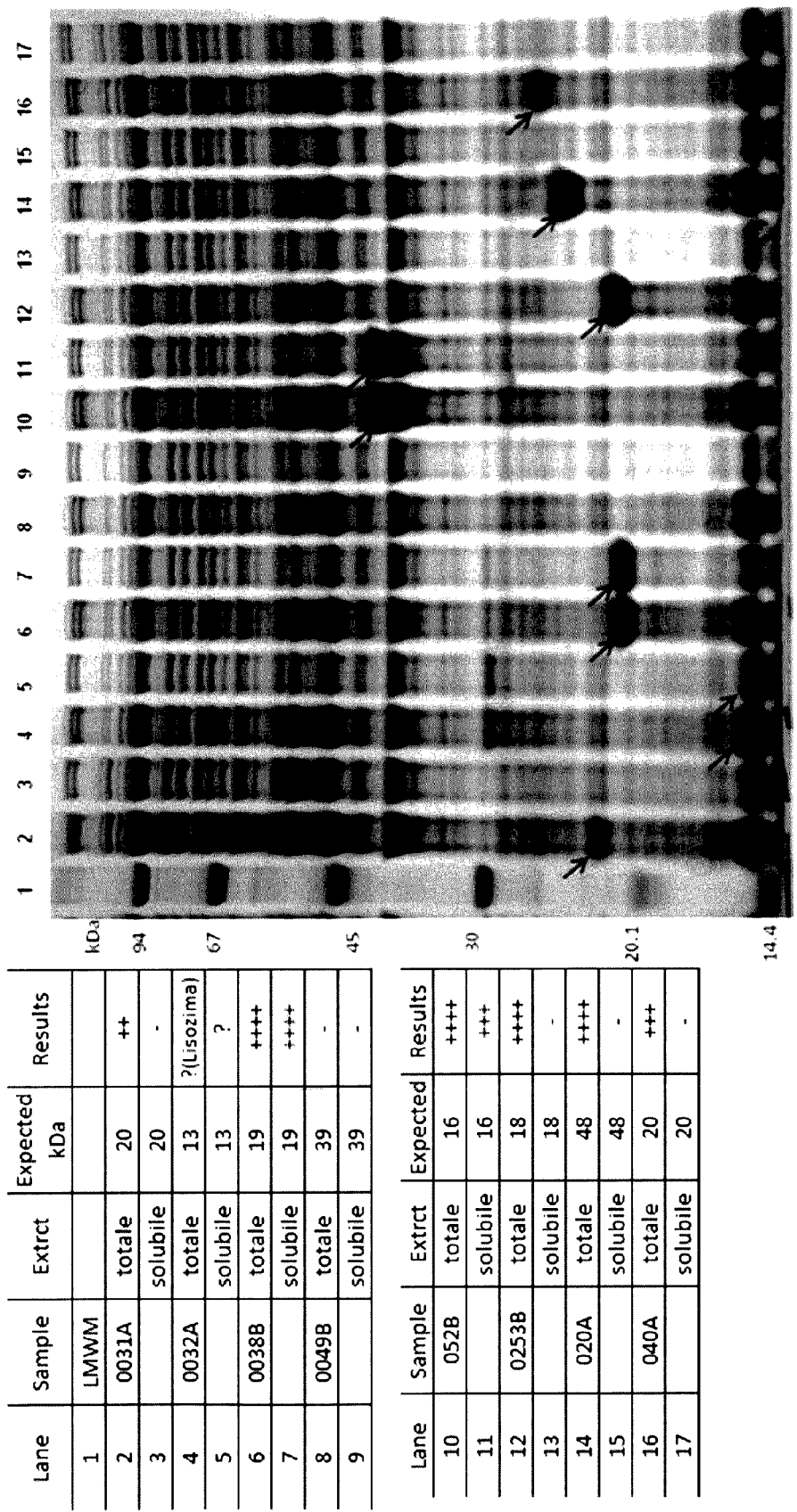

To express cloned proteins, BL21(DE3)T1$^r$ clones containing pET15b constructs were grown in LB medium containing 100 µg/ml Ampicilin at 37° C. until $OD_{600}$=0.5. Protein expression was then induced by adding 1 mM IPTG and growing at the same temperature for additional 3 hrs. Conventional protein extractions and SDS-Page were performed to check protein expression. FIG. 1 shows a mini-induction confirming good expression of the antigens.

Protein Purification

Proteins were purified by the following general procedure: BL21(DE3)T1 wet biomass is suspended in lysis buffer and clarified by centrifugation. For purification of soluble protein ( ) supernatants after lysis are applied on His Multitrap HP 50 µl NiSepharose High Performance 96 well plates. For insoluble protein (HtrA, PE and P48), pellets containing the unsoluble fraction after lysis are solubilised with 6M Guanidine-HCl and re-centrifuged, and the supernatants applied to His Multitrap HP 50 ml NiSepharose High Performance 96 well plates.

Flow-through is collected and all wells washed with buffer containing 20 mM imidazole. His fusion proteins are then eluted with 250 mM imidazole. The procedure is performed using a vacuum system. Purified antigens are used in the immunisation schemes described herein.

The following protocol was followed:
1) Resuspend BL21(DE3)T1 pellet (1 g) in 1.5 ml B-PER™ (PIERCE) buffer, add 15 µl of lysozyme, 7.5 µl DNAse and 3 µl of $MgCl_2$ 1 M
2) Incubate for 30 min for lysis
3) Centrifuge at 20000 rpm at 4° C. for 30 minute; for purification of any insoluble protein, solubilise pellets containing the unsoluble fraction after lysis with 6M Guanidine-HCl and re-centrifuge
4) Recover supernatant and filter (pore of 0.8 µm).
5) Use His Multitrap HP 50 µl NiSepharose High Performance 96wells, connected to a vacuum system
Buffer A: 50 mM NaPPi, 300 mM NaCl, pH8
Buffer B: 50 mM NaPPi, 300 mM NaCl, 250 mM Imidazole, pH8
Buffer C: 50 mM NaPPi, 300 mM NaCl, 20 mM Imidazole, pH8
  1st Step: remove ethanol from the plate.
  2nd Step: wash the plate with 400 µl of milliQ H2O.
  3rd Step: equilibrate the plate with 400 µl A of Buffer A
  4th Step: load 600 µl of starting material for each protein in one of the 12 columns. If the volume is larger, repeat until all the material is fully loaded.
  Recover the flow through.
  5th Step: Wash Step: 4 washes with 400 µl of Buffer C. Discard the flow through.
  6th Step: Elution: 2×300 µl Buffer B (2 elution steps).
  Activate vacuum 15 minutes after adding the buffer.

1 µl of total extract, 1 µl of starting material, 1 µl of flow through and 10 µl of elution volume (for each protein) are analysed by SDS-PAGE.

For insoluble protein, buffer B is replaced by 10 mM tris, 50 mM $Na_2HPO_4$, 8 M urea, 250 mM imidazole, 40% glycerol.

LAL Test

The LAL test is a test that measures the endotoxin concentration in a vaccine sample using the endosafe®-PTS™ Charles River technology.

Test Technology

The PTS utilizes LAL kinetic chromogenic methodology to measure color intensity directly related to the endotoxin concentration in a sample. Each cartridge contains precise amounts of licensed LAL reagent, chromogenic substrate, and control standard endotoxin (CSE). The cartridges are manufactured according to rigid quality control procedures to ensure test accuracy and product stability.

TABLE II

Purification of preferred antigens

| Internal ID | Annotation | kDa (expected) | kDa (SE estimated) | Soluble | densitometry | Purity % RP-HPLC | SE-UPLC | SE-HPLC | | LAL Test EU/µg |
|---|---|---|---|---|---|---|---|---|---|---|
| nt001 | NTHI0877 | 30 | 36 | yes | 97 | 84 | | | monomer | 0.47 |
| nt018 | NTHI0915 | 34 | 46 | yes | 80 | 88 | | | monomer | 0.18 |
| nt024 | NTHI1416 | 20 | 20 | yes | 81 | 85 | 97 | | monomer | 3.77 |
| nt032 | NTHI2017 | 13 | 16 | yes | 91 | 76 | | | monomer | 0.82 |
| nt067 | NTHI1292 | 60 | 50 | yes | 88 | 78 | | | monomer | 0.06 |
| nt052 | CGSHiGG_00130 | 34 | 46 | yes | 88 | 88 | | | monomer | 0.18 |
| nt004 | CGSHiGG_08215 | 20 | 34 | yes | 95 | | 95 | | monomer | 0.09 |
| nt014 | HI1658 | 20 | 17 | yes | 89 | | 87 | | monomer | 0.10 |
| nt022 | NTHI0830 | 43 | 77 | yes | 93 | | 93 | | monomer | 0.10 |
| nt016 | NTHI0266 | 29 | 30 | yes | 98% | | | | monomer | 0.13 |

Immunisation of Mice and Production of Antisera

Five weeks old CD1 mice (8 for each antigen) were immunized by 3 intraperitoneal injections (every two weeks) of 10 micrograms of purified protein antigens with Freund's adjuvant (200 microliters per mouse) or with Alum (aluminium hydroxide adjuvant; 2 mg/ml). Sera were collected two weeks after the third injection and stocked at −20° C. Controls were injected with Freund's adjuvant only or alum only.

FACS Analysis

Figure 2:
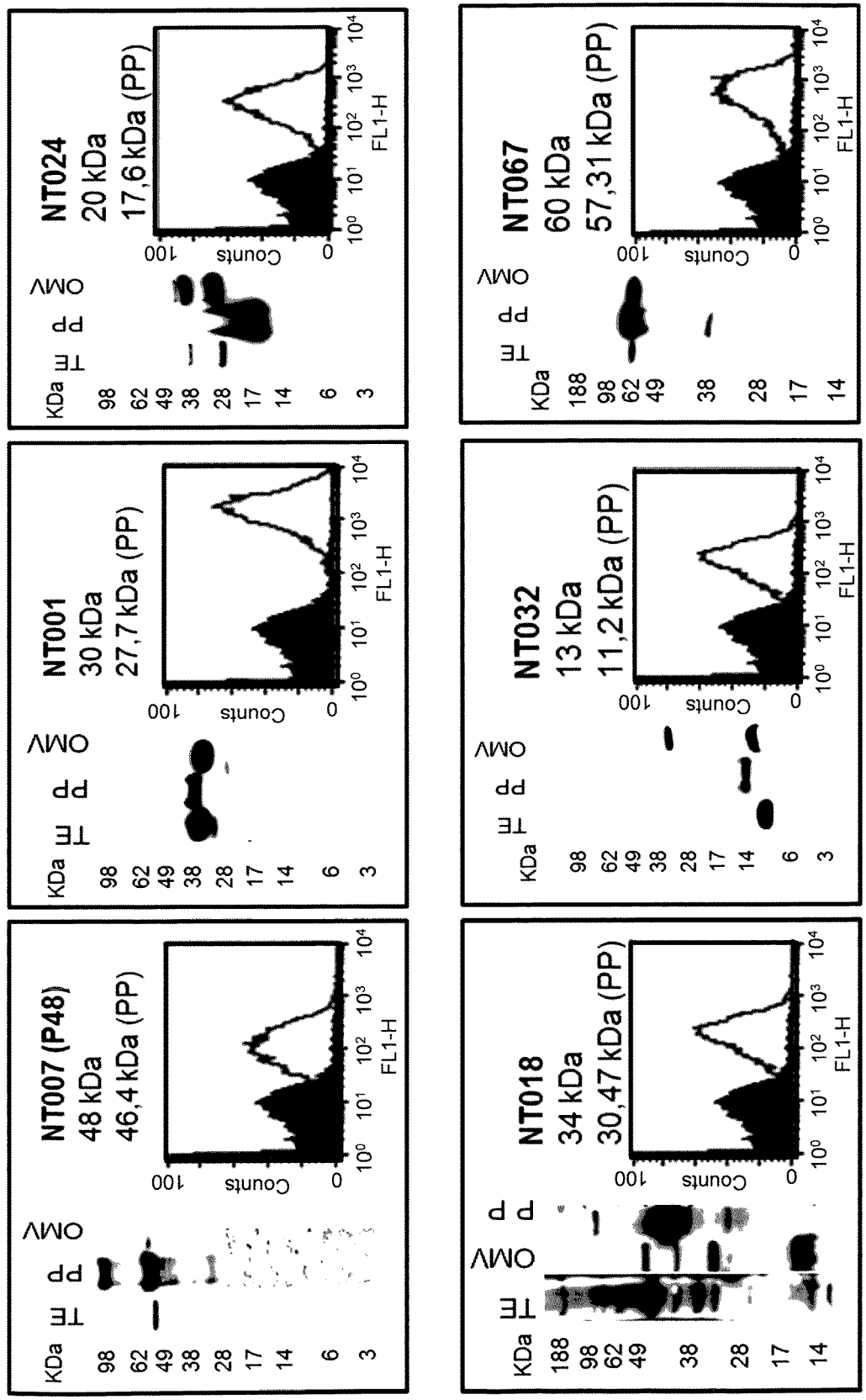
FIG. 2 shows various results for NT001, NT007, NT018, NT024, NT032 and NT067. Similar expression results were obtained with the other preferred antigens, such as NT052, NT004, NT014, NT016 or NT022. Each panel shows western blot and FACS data. The western blots were performed using mouse sera, and lanes show reactivity with total bacterial extracts ("TE"), with vesicles prepared from NTHI outer membranes ("OMV"), or with purified recombination protein ("PP"). The FACS analyses follow incubation of inactivated bacteria with sera from mice immunized with various antigen compositions using only alum as negative control; pre-immune serum negative controls are shown as solid areas, and surface expression signal obtained with sample serum is shown as a single line.

A surface labeling assay by FACS was performed in order to examine the surface exposure of the selected antigens and the levels of expression in different strains. NTHI were incubated with sera derived from mice immunized with recombinant proteins or negative controls, and analysed by FACS. The results are shown in FIG. 2. In FIG. 2, pre-immune serum negative controls are shown as solid areas, and the signal obtained with sample serum is shown as a single line. The results of FACS analyses of antigens P48, HtrA, PE, and P26 demonstrate that each of these antigens is exposed on the surface of the bacterium and thus accessible to antibody binding.

The following materials and methods were used in this analysis:

Materials
1. 96 U-bottom well plates.
2. Blocking and Washing Buffer: PBS containing 1% (w/v) BSA.
3. Goat anti-mouse IgG-Fluorescein IsoThio Cyanate FITC.
4. PBS containing 0.5% (v/v) para-formaldehyde: dilute a stock solution of 4% (v/v) para-formaldehyde in PBS to 0.5% (v/v) fresh before the assay and filter sterilize (0.22 µm filter).
5. PBS containing 1% (w/v) BSA. To prepare this solution, dissolve 1% (w/v) BSA in PBS, making at least 100 ml for each strain. Filter-sterilize the solution (0.22 µm filter) and prepare fresh for use.
6. FACScan tubes (Becton Dickson).
7. FACScalibur flow cytometer (Becton Dickinson).

Methods
1. Grow NTHI until an OD$\lambda_{600}$ nm value of 0.5 is reached, then transfer 1 ml of culture to a sterile 1.5 ml Eppendorf tube and centrifuge at 13000 g in a microcentrifuge for 3 minutes to pellet the bacteria. Discard the supernatant and suspend the pellet suspended in 1 ml of PBS containing 1% (w/v) BSA. Finally, dilute the bacterial suspension 1/50 in PBS containing 1% (w/v) BSA.
2. Add 50 µl samples of sera diluted in Blocking Buffer (at 1/100, 1/200 and 1/400) in a 96 well plate. Include positive controls, such as anti-OMV antisera,
3. Add 50 µl of bacterial cells to each well and store the plate at 4 C° for 2 h.
4. Centrifuge the cells for 5 minutes at 3500 g, discard the supernatant and wash the cells by adding 200 µl/well of Washing Buffer.
5. Add 50 µl of a 1/100 dilution of FITC-conjugated goat anti-mouse Ig to each well and store the plate at 4° C. for 1 h.
6. Centrifuge the cells at 3500 g for 5 min and wash the pellet with 200 µl/well of PBS.
7. Repeat the centrifugation step, discard the supernatant and add 200 µl/well of PBS containing 0.5% (v/v) para-formaldehyde, in order to fix the cells.
8. Transfer the fixed samples to individual FACScan tubes and analyse by flow cytometry, following the equipment manufacturer's instructions.

Serum Bactericidal Assay (SBA)

Antisera derived from mice immunized with recombinant proteins were tested in a serum bactericidal assay, to verify the presence of functional antibodies able to induce killing of NTHI. Pre-immune sera and sera from mice injected only with adjuvant were used as negative controls. NTHI (strain 176) culture (BHI+NAD and Haemin) was incubated at 37° C. with shaking, until OD595 nm was 0.25-0.27. The bacterial cells were diluted in D-PBS buffer at the working dilution 1:50000. Sera were inactivated at 56° for 30 minutes and then serially diluted in D-PBS in a 96-well U-bottom plate (see FIG. 3). Columns 11 and 12 of the plate shown in FIG. 3 contain negative controls to assess the growth of the bacteria and to detect any non-complement mediated killing. Bacteria and a source of complement (Rabbit 7504, Cedarlane) were added to each well except in the complement control wells which received heat-inactivated complement.

Figure 3:
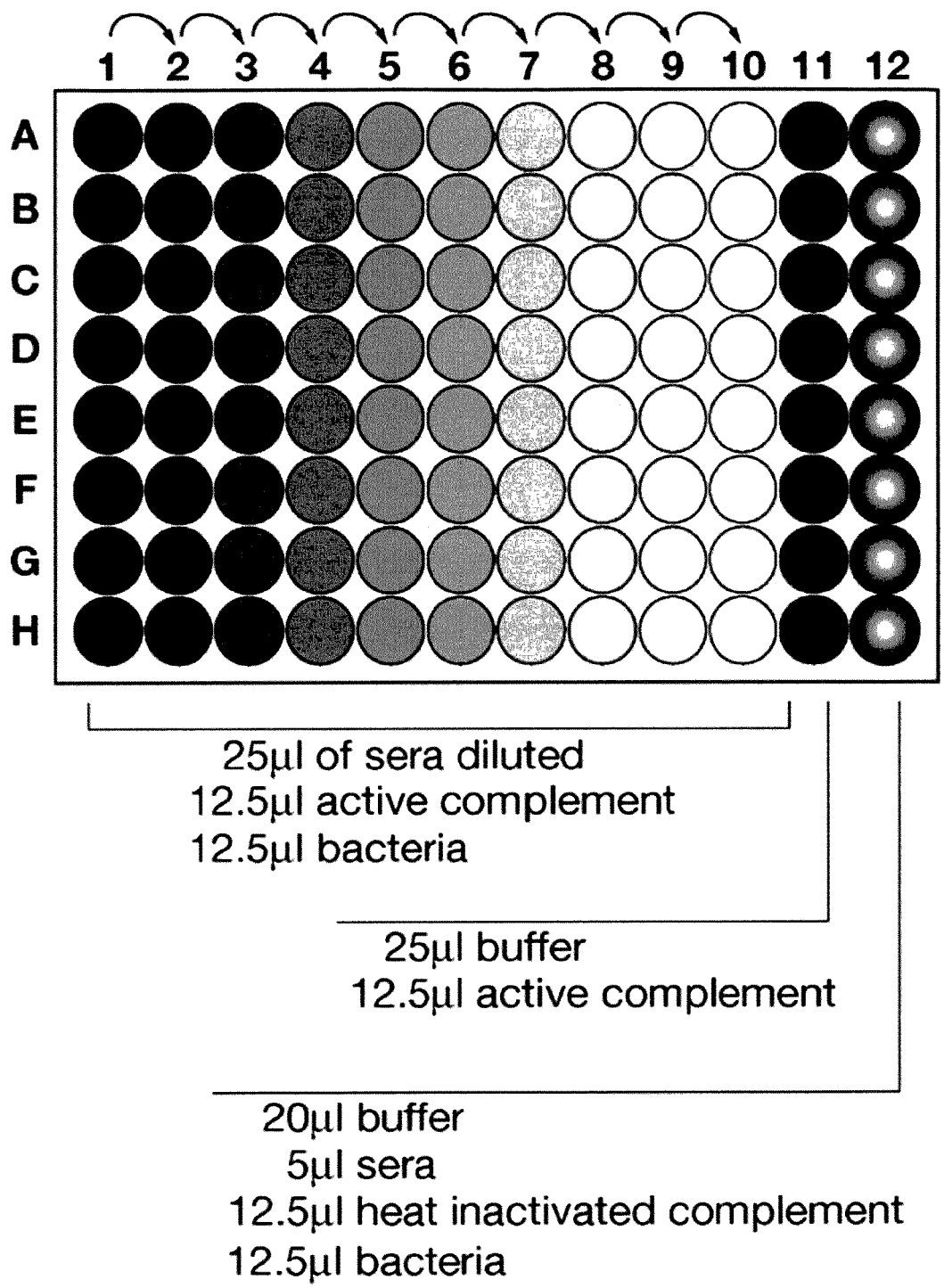
FIG. 3 shows the layout on a 96 well plate of a serum bactericidal assay to verify the capacity of antisera against antigens of the invention to kill NTHI.

As shown in FIG. 3, wells in columns 1-10 contain 25 µl diluted sera, 12.5 µl active complement, and 12.5 µl bacteria. Wells in column 11 contain 25 µl buffer, 12.5 µl active complement, and 12.5 µl bacteria. Wells in column 12 contain 25 µl buffer, 5 µl sera, 12.5 µl heat inactivated complement, and 12.5 µl bacteria.

10 µl of the time zero (TO) assay controls (column 11-12) were plated on agar chocolate plate (Biomerieux) by the spot and tilt method. Plates were incubated at 37° C., ON. The assay microtiter plates were incubated for 1 hour at 37° C. After this period (T60) 7 µl of each well were plated as spot on an agar chocolate plate (each well was plated in duplicate). The number of colonies (colony forming units, CFU) was counted using a colony counter or manually. A bactericidal effect was considered to be observed when the number of colonies was lower than 50% of T=0.

An overview of the results is provided in the following Table III and Table IV.

TABLE III

Immunogenicity results

| Internal ID | Annotation | SEq ID NOs | kDa | SBA TITER Freund's adjuvant (176 wt) | FACS |
|---|---|---|---|---|---|
| NT001 | NTHI0877 | SEQ ID NO: 6 or SEQ ID NO: 54 | 30 | 2048-8192 | +++++ |
| NT016 | NTHI0266 | SEQ ID NO: 7 or SEQ ID NO: 55 | 29 | 2048-8192 | +++++ |
| NT024 | NTHI1416 | SEQ ID NO: 2 or SEQ ID NO: 50 | 20 | 2048-8192 | ++ |
| NT032 | NTHI2017 | SEQ ID NO: 3 or SEQ ID NO: 51 | 13 | 2048-8192 | + |
| NT018 | NTHI0915 | SEQ ID NO: 1 or SEQ ID NO: 49 | 34 | 2048-4096 | + |
| NT038 | CGSHiGG_02400 | SEQ ID NO: 4 or SEQ ID NO: 50 | 22 | 2048-4096 | ++ |
| NT052 | CGSHiGG_00130 | SEQ ID NO: 8 or SEQ ID NO: 56 | 44 | 2048-4096 | ++ |
| NT067 | NTHI1292 | SEQ ID NO: 5 or SEQ ID NO: 52 | 60 | 2048 | ++ |
| NT002 | NTHI1627 | SEQ ID NO: 9 or SEQ ID NO: 57 | 18 | 1024-2048 | +++ |
| NT026 | NTHI1109 | SEQ ID NO: 10 or SEQ ID NO: 58 | 19 | 4096-8192 | ++++ |
| NT009 | NTHI0821 | SEQ ID NO: 11 or SEQ ID NO: 59 | 64 | 4096 | +++ |
| NT025 | NTHI0409 | SEQ ID NO: 12 or SEQ ID NO: 60 | 17 | 4096 | ++++ |
| NT028 | NTHI1954 | SEQ ID NO: 13 SEQ ID NO: 61 | 20 | 4096 | +++ |
| NT029 | NTHI0371 | SEQ ID NO: 14 SEQ ID NO: 62 | 101 | 4096 | +++ |
| NT031 | NTHI0509 | SEQ ID NO: 15 SEQ ID NO: 63 | 20 | 4096 | + |
| NT015 | NTHI0449 | SEQ ID NO: 16 SEQ ID NO: 64 | 15 | 2048-4096 | ++ |
| NT023 | NTHI1473 | SEQ ID NO: 17 SEQ ID NO: 65 | 17 | 2048-4096 | ++ |

TABLE III-continued

Immunogenicity results

| Internal ID | Annotation | SEq ID NOs | kDa | SBA TITER Freund's adjuvant (176 wt) | FACS |
|---|---|---|---|---|---|
| NT100 | gi145633184 | SEQ ID NO: 18 SEQ ID NO: 66 | 34 | 2048-4096 | + |
| NT040 | NTHI1110 | SEQ ID NO: 19 | 26 | 1024-2048 | + |
| NT048 | gi-46129075 | SEQ ID NO: 20 | 71 | 1024-2048 | + |
| NT053 | gi145628236 | SEQ ID NO: 21 | 17 | 1024-2048 | + |
| NT066 | NTHI1230 | SEQ ID NO: 22 SEQ ID NO: 67 | 59 | 1024-2048 | + |
| NT097 | NTHI0522 | SEQ ID NO: 23 | 50 | 1024-2048 | ++ |
| NT006 (HtrA) | NTHI1905 | SEQ ID NO: 25 | 51 | 2048 | ++++ |
| NT035 (PE) | NTHI0267 | SEQ ID NO: 26 | 18 | 512-1024 | ++ |
| NT080 (PHiD) | NTHI0811 | SEQ ID NO: 28 | | 512 | |
| NT081 (P6) | NTHI0501 | SEQ ID NO: 29 | | 512 | |
| NT010 (P26) | NTHI1083 | SEQ ID NO: 27 | 22 | 128-512 | +++ |
| NT007 (P48) | NTHI0254 | SEQ ID NO: 24 | 48 | 8192-16384 | +++++ |
| Unrelated antigen | | | | 16 | + |
| Freund's Adj. alone | | | | 512/1024 | |

These results show that antigens selected are highly effective in killing NTHI pathogens. In particular NT018, NT001, NT024, NT032, NT067, NT016 all show particularly strong protective effects.

TABLE IV

Immunization experiments using compositions comprising NTHI antigens and Alum

| Protein Antigen | Purity | SBA (Freund) | SBA (Alum) | FACS Freund | FACS alum | Solubility |
|---|---|---|---|---|---|---|
| NT001 | 97% | 2048-8192 | 512-1024 | +++++ | +++ | Yes |
| NT024 | 94% | 2048-8192 | 1024 | ++ | +++ | Yes |
| NT038 | 97% | 2048-4096 | 64 | ++ | − | Yes |
| NT018 | 80% | 2048-4096 | 512-1024 | + | +++ | Yes |
| NT032 | 99% | 2048-8192 | 64-128 | + | + | Yes |
| NT067 | 88% | 2048 | 512-2048 | ++ | +++ | Yes |
| NT025 | 94% | 4096 | 128-256 | ++++ | + | No |
| NT026 | 64% | 4096-8192 | 64 | ++++ | − | No |
| NT028 | 81% | 4096 | 128-256 | +++ | ++ | No |
| NT029 | 52% | 4096 | 128 | +++ | ++ | Yes |
| NT023 | 80% | 2048-4096 | 256-512 | ++ | + | Yes |
| NT015 | 78% | 2048-4096 | 128-256 | ++ | + | No |
| NT031 | 90% | 4096 | 128 | + | + | No |
| NT100 | 81% | 2048-4096 | 512 | + | + | Yes |
| NT081 (P6) | 88% | 2048 | 256 | + | + | No |
| NT080 (PHiD) | 92% | 1024 | 128 | + | + | Yes |
| NT006 (HtrA) | 57% | 2048 | 256 | ++++ | ++++ | |
| NT007 (P48) | 79% | 8192-16384 | 256-512 | +++++ | +++++ | |
| NT052 | 88% | 2048-4096 | 512-1024 | + | +++ | Yes |
| NT014 | 87% | 1024 | 512-1024 | ++ | ++ | Yes |
| NT004 | 95% | 256-512 | 128-256 | ++ | + | Yes |
| NT022 | 93% | 64-256 | 1024 | +++ | + | Yes |
| NT016 | 98% | 2048-8192 | 128 | +++ | ++++ | Yes |
| NT106 | 82% | Not tested | 64-128 | ++ | +++ | Yes |
| NT113 | 92% | Not tested | 128 | ++ | +++ | Yes |
| NT061 | 83% | Not tested | 128 | +++ | +++ | Yes |
| Freund's | | 512 | NA | | | |
| Alum | | NA | 4-8 | | | |

These results further confirmed that antigens selected are highly effective in killing NTHI pathogens also when used in immunogenic compositions with alum as adjuvant.

In particular NT016, NT052, NT018, NT001, NT024, NT032, NT067, NT014, NT022 all confirm particularly strong protective effects as measured in serum bactericidal assay (SBA).

Particularly preferred antigens were NT067, NT014, NT016, NT022. These antigens have been also tested in an in vivo animal model according to the protocol described in Ref. 75.

In vivo Vaccine Efficacy Testing

Individual antigens as listed in Table IV can be tested for their ability to protect against an otitis media (OM) infection using an in vivo model such as Junbo and Jeff mouse mutants [75].

The vaccine efficacy in the in vivo protection experiment is performed using 3 administrations (at day 0, 21, 35) of 10 micrograms/mouse of purified recombinant protein antigens formulated with or without adjuvant, followed by intranasal inoculation with selected NTHI pathogenic strains.

10 Pre-immune sera, post-immunization sera, and terminal sera 7 days post-NTHI inoculation are collected and stored at −80° C. Controls are immunized with adjuvant or with an unrelated antigen as control. Middle ear bulla and nasopharyngeal (NP) washes samples are collected and plated to determine NTHi numbers; bulla infection and nasopharingeal carriage rates, and bulla NTHi titres are then calculated.

It will be understood that the invention is described above by way of example only and modifications may be made whilst remaining within the scope and spirit of the invention.

TABLE V

Nomenclature cross-reference with representative strains

| SEQ ID NOs | Name | 86-028NP NTHI_# | 3655 Strain | PittG Strain |
|---|---|---|---|---|
| 1 or 49 | NT018 | NTHI0915 | | |
| 2 or 50 | NT024 | NTHI1416 | | |
| 3 or 51 | NT032 | NTHI2017 | | |
| 4 or 53 | NT038 | | | CGSHiGG_02400 |
| 5 or 52 | NT067 | NTHI1292 | | |
| 6 or 54 | NT001 | NTHI0877 | | |
| 7 or 55 | NT016 | NTHI0266 | | |

TABLE V-continued

Nomenclature cross-reference with representative strains

| SEQ ID NOs | Name | 86-028NP NTHI_# | 3655 Strain | PittG Strain |
|---|---|---|---|---|
| 8 or 56 | NT052 | | | CGSHiGG_00130 |
| 9 or 57 | NT002 | NTHI1627 | | |
| 10 or 58 | NT026 | NTHI1109 | | |
| 11 or 59 | NT009 | NTHI0821 | | |
| 12 or 60 | NT025 | NTHI0409 | | |
| 13 or 61 | NT028 | NTHI1954 | | |
| 14 or 62 | NT029 | NTHI0371 | | |
| 15 or 63 | NT031 | NTHI0509 | | |
| 16 or 64 | NT015 | NTHI0449 | | |
| 17 or 65 | NT023 | NTHI1473 | | |
| 18 or 66 | NT100 | | gi-145633184 | |
| 19 | NT040 | NTHI1110 | | |
| 20 | NT048 | | gi-46129075 | |
| 21 | NT053 | | gi-145628236 | |
| 22 or 67 | NT066 | NTHI1230 | | |
| 23 | NT097 | NTHI0522 | | |
| 24 | NT007 | P48 | | |
| 25 | NT006 | HtrA | | |
| 26 | NT035 | PE | | |
| 27 | NT010 | P26 | | |
| 28 | NT080 | PHiD | | |
| 29 | NT081 | P6 | | |
| 30 | NT013 | NTHI0532 | | |
| 31 | NT106 | NTHI0363 | | |
| 32 | NT107 | NTHI0370 | | |
| 33 | NT108 | NTHI0205 | | |
| 34 | NT109 | NTHI0374 | | |
| 35 | NT110 | NTHI0579 | | |
| 36 | NT111 | NTHI0837 | | |
| 37 | NT112 | NTHI0849 | | |
| 38 | NT113 | NTHI0921 | | |
| 39 | NT114 | NTHI0995 | | |
| 40 | NT115 | NTHI1091 | | |
| 41 | NT116 | NTHI1169 | | |
| 42 | NT117 | NTHI1208 | | |
| 43 | NT118 | NTHI1318 | | |
| 44 | NT123 | NTHI1796 | | |
| 45 | NT124 | NTHI1930 | | |
| 114 | NT119 | NTHI1565 | | |
| 115 | NT120 | NTHI1569 | | |
| 116 | NT121 | NTHI1571 | | |
| 117 | NT122 | NTHI1667 | | |
| 122 | NT004 | | | CGSHiGG_08215 |
| 123 | NT014 | | gi-145629254 | |
| 124 | NT022 | NTHI0830 | | |
| 128 | NT061 | NTHI0588 | | |
| 130 | NT017 | NTHI0915 | | |

REFERENCES

[1] Fleischmann et al. (1995) *Science* 269:496-512.
[2] Li et al. (2003) *Mol Microbiol* 47:1101-1111.
[3] GenBank accession NC_000907.
[4] WO2005/111066
[5] Murphy et al. Current Infectious Disease report (2009) 11:177-182.
[6] Webb DC et al.—Investigation of the potential of a 48 kDa protein as a vaccine candidate for infection against nontypable *Haemophilus influenzae*. Vaccine. 2007 May 16;25(20):4012-9.
[7] Hallström T et al.—Nontypeable *Haemophilus influenzae* protein E binds vitronectin and is important for serum resistance. J Immunol. 2009 August 15;183(4):2593-601.
[8] Loosmore S M et al.—The *Haemophilus influenzae* HtrA protein is a protective antigen. Infect Immun. 1998 Mar; 66(3):899-906.
[9] Kyd J M et al.—Potential of a novel protein, OMP26, from nontypeable *Haemophilus influenzae* to enhance pulmonary clearance in a rat model. Infect Immun. 1998 May;66(5):2272-8.
[10] Ronander E, The Journal of Infectious Diseases (2009): 199 p522-530
[11] WO00/55191.
[12] WO02/24729.
[13] Chanyangam M. et al., (1991) *Infection and Immunity*, Vol. 59 (2), 600-608
[14] Munson R.S.; Granoff D.M (1985) *Infection and Immunity* 49 (3):544 - 549
[15] Hogg et al. (2007) *Genome Biology* 8:R103.
[16] Needleman & Wunsch (1970) *J. Mol. Biol.* 48, 443-453.
[17] Rice et al. (2000) *Trends Genet* 16:276-277.
[18] Bernadac A., et al. (1998) Journal of Bacteriology 180 (18) : 4872-4878
[19] WO2002/062378
[20] Uehara T. et al., The EMBO Journal (2010) 29, 1412-1422
[21] U.S. Pat. No. 5,707,829
[22] *Current Protocols in Molecular Biology* (F. M. Ausubel et al. eds., 1987) Supplement 30.
[23] *Vaccine Design*(1995) eds. Powell & Newman. ISBN: 030644867X. Plenum.
[24] WO90/14837.
[25] Podda & Del Giudice (2003) *Expert Rev Vaccines* 2:197-203.
[26] Podda (2001) *Vaccine* 19: 2673-2680.
[27] *Vaccine Adjuvants: Preparation Methods and Research Protocols* (Volume 42 of *Methods in Molecular Medicine* series). ISBN: 1-59259-083-7. Ed. O'Hagan.
[28] U.S. Pat. No, 5,057,540.
[29] Niikura et al. (2002) *Virology* 293:273-280.
[30] Lenz et al. (2001) *J Immunol* 166:5346-5355.
[31] Pinto et al. (2003) *J Infect Dis* 188:327-338.
[32] Gerber et al. (2001) *J Virol* 75:4752-4760.
[33] WO03/024480.
[34] WO03/024481.
[35] Gluck et al. (2002) *Vaccine* 20:B10-B16.
[36] Meraldi et al. (2003) *Vaccine* 21:2485-2491.
[37] Pajak et al. (2003) *Vaccine* 21:836-842.
[38] Krieg (2003) *Nature Medicine* 9:831-835.
[39] McCluskie et al. (2002) *FEMS Immunology and Medical Microbiology* 32:179-185.
[40] W098/40100.
[41] U.S. Pat. No. 6,207,646.
[42] U.S. Pat. No. 6,239,116.
[43] U.S. Pat. No. 6,429,199.
[44] Schellack et al. (2006) *Vaccine* 24:5461-72.
[45] Johnson et al. (1999) *Bioorg Med Chem Lett* 9:2273-2278.
[46] Evans et al. (2003) *Expert Rev Vaccines* 2:219-229.
[47] Beignon et al. (2002) *Infect Immun* 70:3012-3019.
[48] Pizza et al. (2001) *Vaccine* 19:2534-2541.
[49] Pizza et al. (2000) *Int J Med Microbiol* 290:455-461.
[50] Scharton-Kersten et al. (2000) *Infect Immun* 68:5306-5313.
[51] Ryan et al. (1999) *Infect Immun* 67:6270-6280.
[52] Partidos et al. (1999) *Immunol Lett* 67:209-216.
[53] Peppoloni et al. (2003) *Expert Rev Vaccines* 2:285-293.
[54] Pine et al. (2002) *J Control Release* 85:263-270.
[55] WO99/40936.
[56] WO99/44636.
[57] Singh et al] (2001) *J Cont Release* 70:267-276.
[58] WO99/27960.
[59] U.S. Pat. No. 6,090,406.
[60] U.S. Pat. No. 5,916,588.
[61] EP-A-0626169.
[62] WO99/52549.
[63] Andrianov et al. (1998) *Biomaterials* 19:109-115.

[64] Payne et al. (1998) *Adv Drug Delivery Review* 31:185-196.
[65] Stanley (2002) *Clin Exp Dermatol* 27:571-577.
[66] Jones (2003) *Curr Opin Investig Drugs* 4:214-218.
[67] WO99/11241.
[68] WO94/00153.
[69] WO98/57659.
[70] European patent applications 0835318, 0735898 and 0761231.
[71] Ogunniyi et al. (2001) *Infect Immun* 69:5997-6003.
[72] WO2006/110603.
[73] Mason et al. (2003) *Infect Immun* 71:3454-3462.
[74] Zwijnenburg et al. (2001) *J Infect Dis* 183:1143-6.
[75] Cheeseman M. T. et al. (2011) *PLoS Genetics* 7 (10) : e1002336.
[76] Watson (2000) *Pediatr Infect Dis J*19:331-332.
[77] Rubin (2000) *Pediatr Clin North Am* 47:269-285, v.
[78] Jedrzejas (2001) *Microbiol Mol Biol Rev* 65:187-207.
[79] Bell (2000) *Pediatr Infect Dis J* 19:1187-1188.
[80] Iwarson (1995) *APMIS* 103:321-326.
[81] Gerlich et al. (1990) *Vaccine* 8 Suppl:S63-68 & 79-80.
[82] *Vaccines*(1988) eds. Plotkin & Mortimer. ISBN 0-7216-1946-0.
[83] Del Guidice et al. (1998) *Molecular Aspects of Medicine* 19:1-70.
[84] Gustafsson et al. (1996) *N. Engl. J. Med.* 334:349-355.
[85] Rappuoli et al. (1991) *TIBTECH* 9:232-238.
[86] Costantino et al. (1999) *Vaccine* 17:1251-1263.
[87] Sutter et al. (2000) *Pediatr Clin North Am* 47:287-308.
[88] Zimmerman & Spann (1999) *Am Fam Physician* 59:113-118, 125-126.
[89] McMichael (2000) *Vaccine* 19 Suppl 1:S101-107.
[90] Schuchat (1999) *Lancet* 353(9146):51-6.
[91] WO02/34771.
[92] Dale (1999) *Infect Dis Clin North Am* 13:227-43, viii.
[93] Ferretti et al. (2001) *PNAS USA* 98: 4658-4663.
[94] Kuroda et al. (2001) *Lancet* 357(9264):1225-1240; see also pages 1218-1219.
[95] EP-A-0372501
[96] EP-A-0378881
[97] EP-A-0427347
[98] WO93/17712
[99] WO94/03208
[100] WO98/58668
[101] EP-A-0471177
[102] WO00/56360
[103] WO91/01146
[104] WO00/61761
[105] WO01/72337
[106] *Research Disclosure*, 453077 (January 2002)
[107] Brandt et al. (2006) *J Antimicrob Chemother.* 58(6): 1291-4. Epub 2006 Oct. 26
[108] Winter et al., (1991) *Nature* 349:293-99
[109] U.S. Pat. No. 4,816,567.
[110] Inbar et al., (1972) *Proc. Natl. Acad. Sci. U.S.A.* 69:2659-62.
[111] Ehrlich et al., (1980) *Biochem* 19:4091-96.
[112] Huston et al., (1988) *Proc. Natl. Acad. Sci. U.S.A.* 85:5897-83.
[113] Pack et al., (1992) *Biochem* 31, 1579-84.
[114] Cumber et al., (1992) *J. Immunology* 149B, 120-26.
[115] Riechmann et al., (1988) *Nature* 332, 323-27.
[116] Verhoeyan et al., (1988) *Science* 239, 1534-36.
[117] GB 2,276,169.
[118] Gennaro (2000) *Remington: The Science and Practice of Pharmacy.* 20th edition, ISBN: 0683306472.
[119] *Methods In Enzymology* (S. Colowick and N. Kaplan, eds., Academic Press, Inc.)
[120] *Handbook of Experimental Immunology*, Vols. I-IV (D. M. Weir and C. C. Blackwell, eds, 1986, Blackwell Scientific Publications)
[121] Sambrook et al. (2001) *Molecular Cloning: A Laboratory Manual,* 3rd edition (Cold Spring Harbor Laboratory Press).
[122] *Handbook of Surface and Colloidal Chemistry* (Birdi, K. S. ed., CRC Press, 1997)
[123] Ausubel et al. (eds) (2002) *Short protocols in molecular biology,* 5th edition (Current Protocols).
[124] *Molecular Biology Techniques: An Intensive Laboratory Course,* (Ream et al., eds., 1998, Academic Press)
[125] *PCR (Introduction to Biotechniques Series),* 2nd ed. (Newton & Graham eds., 1997, Springer Verlag)
[126] Geysen et al. (1984) *PNAS USA* 81:3998-4002.
[127] Carter (1994) *Methods Mol Biol* 36:207-23.
[128] Jameson, B A et al. 1988, *CABIOS* 4(1):181-186.
[129] Raddrizzani & Hammer (2000) *Brief Bioinform* 1(2): 179-89.
[130] Bublil et al. (2007) *Proteins* 68(1):294-304.
[131] De Lalla et al. (1999) *J. Immunol.* 163:1725-29.
[132] Kwok et al. (2001) *Trends Immunol* 22:583-88.
[133] Brusic et al. (1998) *Bioinformatics* 14(2):121-30
[134] Meister et al. (1995) *Vaccine* 13(6):581-91.
[135] Roberts et al. (1996) *AIDS Res Hum Retroviruses* 12(7):593-610.
[136] Maksyutov & Zagrebelnaya (1993) *Comput Appl Biosci* 9(3):291-7.
[137] Feller & de la Cruz (1991) *Nature* 349(6311):720-1.
[138] Hopp (1993) *Peptide Research* 6:183-190.
[139] Welling et al. (1985) *FEBS Lett.* 188:215-218.
[140] Davenport et al. (1995) *Immunogenetics* 42:392-297.
[141] Tsurui & Takahashi (2007) *J Pharmacol Sci.* 105(4): 299-316.
[142] Tong et al. (2007) *Brief Bioinform.* 8(2):96-108.
[143] Schirle et al. (2001) *J Immunol Methods.* 257(1-2):1-16.
[144] Chen et al. (2007) *Amino Acids* 33(3):423-8.
[145] Smith & Waterman (1981) *Adv. Appl. Math.* 2: 482-489.
[146] Lundström et al. (2008) *Biochemistry,* 47 (22) :6025-38 Structural analysis of the lipopolysaccharide from nontypeable *Haemophilus influenzae* strain R2846.
[147] Klock, H. E., et al. (2008). *Proteins* 71:982-994
[148] Klock, H. E., et al. (2005) *J. Struct. Funct. Genomics* 6, 89-94

The invention claimed is:

1. An immunogenic composition comprising:
   an effective amount of an adjuvant;
   at least one isolated or recombinant polypeptide antigen from non-typeable *Haemophilus influenza* selected from a group consisting of: NTHI1292 (NT067) and NT113, and
   at least one isolated or recombinant polypeptide antigen from non-typeable *Haemophilus influenza* selected from the group consisting of: NTHI0267 (NT035) and NTHI0409 (NT025).

2. The composition of claim 1 wherein,
   said NT067 antigen is a polypeptide that comprises an amino acid sequence: (a) having 80% or more identity to SEQ ID NO: 5 or to SEQ ID NO: 52; and/or (b) that is a fragment of at least 10 consecutive amino acids, and comprises an epitope, of SEQ ID NO: 5 or SEQ ID NO: 52.

3. The immunogenic composition according to claim 1, further comprising at least one polypeptide selected from the group consisting of: (24) P48 (NTHI0254 also defined as NT007), (25) HtrA (NTHI1905 also defined as NT006), (26) PE (NTHI0267 also defined as NT035), (27) P26 (NTHI0501 also defined as NT010), (28) PHiD (NTHI0811 also defined as NT080), and (29) P6 (NTHI0501, also defined as NT081).

4. The composition of claim 1, further comprising at least one vaccine antigen that is not a non-typeable *H. influenzae* antigen selected from the group consisting of:
   an antigen from *N. meningitidis* serogroup A, B, C, W135, or Y, or a combination thereof;
   a saccharide or polypeptide antigen from *Streptococcus pneumonia*;
   an antigen from hepatitis A virus;
   an antigen from hepatitis B virus;
   a diphtheria antigen;
   a tetanus antigen;
   an antigen from *Bordetella pertussis*;
   a whole cellular pertussis antigen;
   a saccharide antigen from *Haemophilus influenzae* B;
   a polio antigen;
   a measles, mumps, or rubella antigen, or a combination thereof;
   an influenza antigen;
   an antigen from *Moraxella catarrhalis*;
   an antigen from Respiratory Syncytial Virus;
   a vaccine composition comprising diphtheria (D), tetanus (T), pertussis (acellular, component) (Pa), hepatitis B (rDNA) (HBV), poliomyelitis (inactivated) (IPV) and *Haemophilus influenzae* type b (Hib) conjugate vaccine (adsorbed); and,
   a combination of any of the foregoing.

5. The composition of claim 1 which further comprises one or more pharmaceutically acceptable carriers, diluents, or a combination thereof.

6. A vaccine comprising the composition of claim 1.

7. A method for raising an immune response against a non-typeable *H influenza*, comprising the step of administering to a mammal an effective amount of the composition of claim 1.

8. A method for raising an immune response against a non-typeable *H influenza*, comprising the step of administering to a mammal an effective amount of the composition of claim 3.

9. The immunogenic composition according to claim 1, further comprising at least one isolated or recombinant polypeptide antigen from non-typeable *Haemophilus influenza*, selected from a group consisting of: (8) CGSHiGG_00130 (NT052), (1) NTHI_0915 (NT018), (2) NTHI1416 (NT024), (3) NTHI12017 (NT032), (4) CGSHiGG 02400 (NT038), (6) NTHI0877 (NT001), (7) NTHI0266 (NT016), (9) NTHI1627 (NT002), (10) NTHI1109 (NT026), (11) NTHI0821 (NT009), (12) NTHI0409 (NT025), (13) NTHI1954 (NT028), (14) NTHI0371 (NT029), (15) NTHI0509 (NT031), (16) NTHI0449 (NT015), (17) NTHI1473 (NT023), (18) gi-145633184 (NT100), (19) NTHI1110 (NT040), (20) gi-46129075 (NT048), (21) gi-145628236 (NT053), (22) NTHI1230 (NT066), (23) NTHI0522 (NT097), (24) NT004, (25) NT014, (26) NT022, (30) NT013, (31) NT106, (32) NT107, (33) NT108, (34) NT109, (35) NT110, (36) NT111, (37) NT112, (39) NT114, (40) NT115, (41) NT116, (42) NT117, (43) NT118, (44) NT123, (45) NT124, (46) NT119, (47) NT120, (48) NT121, (49) NT122, and (50) NT061.

* * * * *